United States Patent
Sharp et al.

(10) Patent No.: US 11,957,696 B2
(45) Date of Patent: *Apr. 16, 2024

(54) ABIRATERONE PRODRUGS

(71) Applicant: Propella Therapeutics, Inc., Pittsboro, NC (US)

(72) Inventors: Matthew J. Sharp, Apex, NC (US); William R. Moore, Jr., Pittsboro, NC (US)

(73) Assignee: PROPELLA THERAPEUTICS, INC., Pittsboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/670,712

(22) Filed: Feb. 14, 2022

(65) Prior Publication Data

US 2022/0265681 A1 Aug. 25, 2022

Related U.S. Application Data

(60) Provisional application No. 63/149,550, filed on Feb. 15, 2021.

(51) Int. Cl.
*A61K 31/58* (2006.01)
*A61K 45/06* (2006.01)

(52) U.S. Cl.
CPC .............. *A61K 31/58* (2013.01); *A61K 45/06* (2013.01)

(58) Field of Classification Search
CPC ................................. A61K 45/06; A61K 31/58
See application file for complete search history.

(56) References Cited

U.S. PATENT DOCUMENTS

| | | | |
|---|---|---|---|
| 5,604,213 A | 2/1997 | Barrie et al. | |
| 5,618,807 A | 4/1997 | Barrie et al. | |
| 8,338,588 B2 | 12/2012 | Hunt | |
| 8,822,438 B2 | 9/2014 | Auerbach et al. | |
| 9,353,145 B2 | 5/2016 | Derrien et al. | |
| 9,359,395 B2 | 6/2016 | Casebier | |
| 9,889,144 B2 | 2/2018 | Murphy et al. | |
| 9,937,259 B2 | 4/2018 | Sun | |
| 10,087,212 B2 | 10/2018 | Xing et al. | |
| 10,292,990 B2 | 5/2019 | Nemeth et al. | |
| 10,792,292 B2 * | 10/2020 | Sharp | A61K 47/44 |
| 11,559,534 B2 * | 1/2023 | Sharp | A61K 31/58 |
| 2009/0124587 A1 | 5/2009 | Auerbach et al. | |
| 2011/0129423 A1 | 6/2011 | Frincke | |
| 2011/0312916 A1 | 12/2011 | Casebier | |
| 2014/0011992 A1 | 1/2014 | Perez et al. | |
| 2015/0337003 A1 | 11/2015 | Koziol et al. | |
| 2017/0216443 A1 | 8/2017 | Sun | |
| 2019/0040098 A1 | 2/2019 | Wang et al. | |
| 2019/0151458 A1 | 5/2019 | Ciufolini et al. | |
| 2019/0315797 A1 | 10/2019 | Sun et al. | |
| 2020/0237784 A1 | 7/2020 | Wang et al. | |
| 2020/0281945 A1 | 9/2020 | Sharp et al. | |

FOREIGN PATENT DOCUMENTS

| | | | |
|---|---|---|---|
| CA | 3133620 A1 | 9/2020 | |
| CN | 101044155 A | 9/2007 | |
| CN | 102686600 A | 9/2012 | |
| CN | 104017045 A | 9/2014 | |
| CN | 105646637 A | 6/2016 | |
| CN | 106977577 A | 7/2017 | |
| CN | 113929727 A | 1/2022 | |
| EA | 25518 B9 | 10/2017 | |
| EP | 3610876 A1 | 2/2020 | |
| RU | 2013132766 A | 1/2015 | |
| RU | 2015144285 A | 4/2017 | |
| WO | WO2013158644 A2 | 10/2013 | |
| WO | WO2013159225 A1 | 10/2013 | |
| WO | WO2014009434 A1 | 1/2014 | |
| WO | WO-2014111815 A2 * | 7/2014 | ............. A61K 31/58 |
| WO | WO2014111815 A2 | 7/2014 | |
| WO | WO2014145813 A1 | 9/2014 | |
| WO | WO2015038649 A1 | 3/2015 | |
| WO | WO2015134464 A2 | 9/2015 | |
| WO | WO2015143004 A1 | 9/2015 | |
| WO | WO2016044701 A1 | 3/2016 | |
| WO | WO2016050116 A1 | 4/2016 | |
| WO | WO2016082792 A1 | 6/2016 | |
| WO | WO2017106957 A1 | 6/2017 | |
| WO | WO2020180942 A1 | 9/2020 | |
| WO | WO2022051330 A1 | 3/2022 | |
| WO | WO2022174134 A1 | 8/2022 | |
| WO | WO2023/038933 A1 | 3/2023 | |

OTHER PUBLICATIONS

Handbook of Pharmaceutical Excipients, 5th edition 2006. (Year: 2006).*
Zytiga® (abiraterone acetate) tablets Prescribing Information, the Food and Drug Administration, 2018.
Larsen, S. W. and Larsen, C., "Critical Factors Influencing the In Vivo Performance of Long-acting Lipophilic Solutions—Impact on In Vitro Release Method Design," AAPS J., 11(4):762-770 (2009).
Minto, C. F., et al., "Pharmacokinetics and Pharmacodynamics of Nandrolone Esters in Oil Vehicle: Effects of Ester, Injection Site and Injection Volume," J Pharmacol Exp Ther., 281(1):93-102 (1997).
Tanaka, T., et al., "Intramuscular Absorption of Drugs from Oily Solutions in the Rat," Chem Pharm Bull., 22(6):1275-1284 (1974).
Chang, S.-C. and Lee, V. H. L., "Influence of chain length on the in vitro hydrolysis of model ester prodrugs by ocular esterases," Current Eye Research, 2(10):651-656 (1982).

(Continued)

*Primary Examiner* — Bahar Craigo
*Assistant Examiner* — Manahil Mirghani Ali Abdalhameed
(74) *Attorney, Agent, or Firm* — NIXON & VANDERHYE, PC

(57) ABSTRACT

Sustained-release abiraterone prodrug formulations, methods, and kits for parenteral administration to a subject having a sex hormone-dependent benign or malignant disorder such as prostate cancer, an androgen receptor driven cancer, a syndrome due to androgen excess, and/or a syndrome due to glucocorticoid excess such as hypercortisolemia.

21 Claims, 24 Drawing Sheets

(56) References Cited

OTHER PUBLICATIONS

Forsdahl, G., et al., "Detection of testosterone esters in blood," Drug Testing and Analysis, 7(11-12):983-989 (2015).

Avitia, J., et al., "A Phase 1 Study of PRL-02, a Long-Acting IM Depot Injection of Abiraterone Decanoate in Patients with Prostate Cancer," Presented at the 2022 ESMO Congress, Sep. 9-13, 2022, Paris, France, Propella Therapeutics, Inc.

Moore, W., et al., "Abiraterone decanoate (PRL-02): Pharmacology of a single intramuscular (IM) depot injection compared to oral abiraterone acetate (AA) in intact male rats (Abstract #160)," 2022 Genitourinary Cancers Symposium, Propella Therapeutics, Inc. (Feb. 17, 2022).

Propella Therapeutics Corporate Presentation at the 11th Annual LifeSci Partners Corporate Access Event (Jan. 5-7, 2022), 26 pages, last accessed at https://propellatx.com/category/presentations/ on Mar. 27, 2023.

Warneke, T., et al., "Abstract 337037: A Phase 1/2a, Open-label, Multicenter Study of Intramuscular Abiraterone Decanoate (PRL-02) Depot in Patients with Advanced Prostate Cancer (NCT04729114)," ASCO Poster, Propella Therapeutics, Inc. (Jun. 4, 2021).

Pouton, C. W., "Formulation of self-emulsifying drug delivery systems," Advanced Drug Delivery Reviews, 25:47-58 (1997).

Presentation at the MedInvest Oncology Conference (Dec. 7-10, 2021): Propella Therapeutics Corporate Presentation, 26 pages, last accessed at https://propellatx.com/category/presentations/ on Mar. 27, 2023.

U.S. Appl. No. 17/635,106, filed Feb. 14, 2022, Sharp et al., related application.

U.S. Appl. No. 18/098,798, filed Jan. 19, 2023, Sharp et al., related application.

"A phase 1 /2a, open-label, multicenter study of intramuscular (IM) abiraterone decanoate (PRL-02) depot in patients with advanced prostate cancer (NCT04729114). Journal of Clinical Oncology", Jan. 1, 2021, XP093051039, Retrieved from the Internet: URL:https://ascopubs.org/doi/10.1200/JC0.2021.39.15_suppl.TPS5090.

"Abiraterone decanoate (AD): Potent and long-acting activity of a novel intramuscular (IM) abiraterone prodrug depot in a castrate monkey model. Journal of Clinical Oncology", Jan. 1, 2021, XP2805809, Retrieved from the Internet: URL:https://ascopubs.org/doi/10.1200/JC0.2021.39.6_suppl.78.

"Abiraterone decanoate (PRL-02): Pharmacology of a single intramuscular (IM) depot injection compared to oral abiraterone acetate (AA) in intact male rats. Journal of Clinical Oncology", Feb. 16, 2022, XP9544705, Retrieved from the Internet: URL:https://ascopubs.org/doi/10.1200/JC0.2022.40.6_suppl.160.

Benoist GE, Hendriks RJ, Mulders PF, Gerritsen WR, Somford DM, Schalken JA, van Oort IM, Burger DM, van Erp NP (Nov. 2016). "Pharmacokinetic Aspects of the Two Novel Oral Drugs Used for Metastatic Castration- Resistant Prostate Cancer: Abiraterone Acetate and Enzalutamide". Clin Pharmacokinet.

Potter, et al. "Novel Steroidal Inhibitors of Human Cytochrome P45017.alpha.-Hydroxylase-C17,20-lyase): Potential Agents for the Treatment of Prostatic Cancer", Journal of Medicinal Chemistry, 1995, 38 (13), 2463-2471 DOI: 10.1021/jm00013a022.

\* cited by examiner

| Index | Angle | d Value | Rel. Intensity |
|---|---|---|---|
| 0 | 4.411 | 20.01401 | 11.7 % |
| 1 | 6.625 | 13.33076 | 100.0 % |
| 2 | 9.092 | 9.71850 | 5.0 % |
| 3 | 9.288 | 9.51378 | 5.2 % |
| 4 | 11.075 | 7.98287 | 9.3 % |
| 5 | 11.739 | 7.53258 | 4.7 % |
| 6 | 14.812 | 5.97581 | 13.6 % |
| 7 | 16.406 | 5.39887 | 16.3 % |
| 8 | 18.078 | 4.90295 | 18.4 % |
| 9 | 20.644 | 4.29897 | 4.0 % |
| 10 | 21.589 | 4.11295 | 13.2 % |
| 11 | 22.230 | 3.99577 | 20.2 % |
| 12 | 24.015 | 3.70272 | 4.8 % |
| 13 | 33.709 | 2.65671 | 2.9 % |
| 14 | 35.895 | 2.49980 | 5.3 % |
| 15 | 38.241 | 2.35164 | 17.3 % |

FIG. 2D (Cont.)

| Index | Angle | d Value | Rel. Intensity |
|---|---|---|---|
| 0 | 4.918 | 17.95206 | 9.3 % |
| 1 | 6.282 | 14.05860 | 17.2 % |
| 2 | 8.117 | 10.88401 | 12.0 % |
| 3 | 8.662 | 10.20011 | 17.0 % |
| 4 | 9.791 | 9.02605 | 13.3 % |
| 5 | 11.068 | 7.98747 | 5.8 % |
| 6 | 11.832 | 7.47368 | 12.4 % |
| 7 | 12.595 | 7.02226 | 10.6 % |
| 8 | 14.504 | 6.10203 | 100.0 % |
| 9 | 15.310 | 5.78288 | 23.5 % |
| 10 | 15.902 | 5.56869 | 17.2 % |
| 11 | 17.341 | 5.10980 | 58.1 % |
| 12 | 18.011 | 4.92118 | 48.3 % |
| 13 | 18.669 | 4.74918 | 84.5 % |
| 14 | 20.933 | 4.24029 | 83.4 % |
| 15 | 21.518 | 4.12641 | 23.3 % |
| 16 | 22.197 | 4.00166 | 30.8 % |
| 17 | 22.818 | 3.89420 | 34.4 % |

FIG. 2G (Cont.)

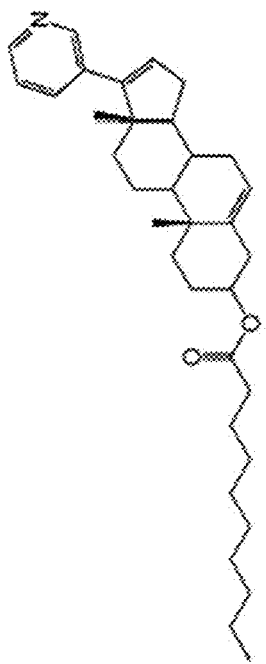

| Test or Property | Test Result | |
|---|---|---|
| Appearance | White solid | |
| Infrared Spectroscopy | Spectrum is in agreement with reference material | |
| Impurities by High Performance Liquid Chromatography (HPLC) Report all impurities ≥ 0.05 wt% | Impurity (RRT) / ID | Result (wt%) |
| | RRT 1.19 (Ethyl Prasterone Decanoate) | 0.42 |
| Purity by HPLC | 99.6 wt% | |
| Residual Solvents by Gas Chromatography | Solvent | Amount Found |
| | Acetone | Not Detected (LOD = 3 ppm) |
| | Acetonitrile | Not Detected (LOD = 8 ppm) |
| | Dichloromethane | 181 ppm |
| Powder X-ray Diffraction | Crystalline | |
| Sulfated Ash (Residue on Ignition) | < 0.05 wt% | |
| Karl Fischer Moisture | 0.12 wt% | |
| Triethylamine by Ion Chromatography | < 986 ppm | |
| Microbial Enumeration by USP <61> | Total Aerobic Microbial Count (TAMC): < 50 CFU/g Total Combined Yeasts and Molds Count (TYMC): < 50 CFU/g | |
| Bacterial Endotoxins by USP <85>[1] | < 51.4 EU/g | |

Assigned Purity: 99.4 wt%

RRT = Relative Retention Time   LOD = Limit of Detection

Assigned Purity = 100% - (% HPLC Impurities + % KF Moisture + % Residual solvents)
= 100% - (0.42% + 0.12% + 0.0181%) = 99.44 wt%

FIG. 3

ABIRATERONE PRODRUGS

This application claims the benefit of U.S. Provisional Application No. 63/149,550, filed Feb. 15, 2021, the content of which is incorporated herein by reference in its entirety.

The present disclosure relates generally to novel prodrugs of abiraterone and long-acting, depot-based parenteral formulations of abiraterone prodrugs. The disclosure is subject to a wide range of applications, such as for intramuscular (IM) injection to a patient suffering from an androgen or estrogen hormone-dependent benign or malignant disorder or androgen receptor driven cancer, including various cancers (such as prostate cancer, bladder cancer, hepatocellular carcinoma, lung cancer, breast cancer, and ovarian cancer, etc.), and for the treatment of non-oncologic syndromes due to the overproduction of androgens (including both classical and nonclassical congenital adrenal hyperplasia, endometriosis, polycystic ovary syndrome, precocious puberty, hirsutism, etc.) or due to the overproduction of glucocorticoids, typically cortisol in conditions such as Cushing's syndrome or Cushing's disease.

BACKGROUND

Abiraterone ((3β)-17-(pyridin-3-yl) androsta-5, 16-dien-3-ol; CAS #: 154229-19-3); Formula: $C_{24}H_{31}NO$; Mol. Weight: 349.5 g/mol) is an inhibitor of CYP17A1 (which is a member of the cytochrome P450 superfamily of enzymes that catalyze the synthesis of cholesterol, steroids and other lipids and are involved in drug metabolism). CYP17A1 has both 17α-hydroxylase activity and 17,20-lyase activity. Abiraterone potently and selectively inhibits both CYP17A1 17α-hydroxylase and 17,20-lyase enzyme activities. The 17α-hydroxylase activity of CYP17A1 is required for the generation of glucocorticoids such as cortisol. However, both the hydroxylase and 17,20-lyase activities of CYP17A1 are required for the production of androgenic (e.g., androstenedione, testosterone, and dihyrotestosterone) and estrogenic (estrone, estradiol. estratriol) steroids through the conversion of 17α-hydroxypregnenolone to the sex steroid precursor, dehydroepiandrosterone, see FIG. 1. Thus, abiraterone interferes with the synthesis of androgens and estrogens in the gonads (primarily in the testes and overies) and extra-gonadally (e.g., in the adrenals and in the tumors themselves).

Though abiraterone itself is poorly absorbed, it can be administered orally as an abiraterone acetate prodrug. Abiraterone acetate is also poorly absorbed, but can be converted to abiraterone in the gut, which is poorly absorbed into the bloodstream following the cleavage of the acetate prodrug. Abiraterone acetate ((3β)-17-(3-Pyridyl)androsta-5, acetate; CAS #154229-18-2) is approved in the United States for treatment of castration resistant or castration sensitive prostate cancer under the brand name Zytiga®. Abiraterone acetate is now also available globally.

It is known that orally administered abiraterone acetate prodrug is not significantly absorbed by the gastrointestinal tract (and little prodrug can be detected in blood plasma). Instead, it has been shown that abiraterone acetate is hydrolyzed to abiraterone in the intraluminal environment resulting in generation of abiraterone supersaturation, which is responsible for creating the strong driving force for abiraterone absorption (Stappaerts et al., *Eur. J. Pharmaceutics Biopharmaceutics* 90:1, 2015).

Because abiraterone blocks the normal physiologic production of steroids by the adrenal glands, its prodrug formulation is commonly prescribed with administration of a low dose of a steroid to prevent adrenal insufficiency. Indeed, Zytiga® (250 mg tablets) is approved in the United States only in combination with prednisone for the treatment of patients with metastatic castration resistant prostate cancer (CRPC) and patients with metastatic castration-sensitive prostate cancer (CSPC). The prescribing information provided with Zytiga® recommends oral administration of 1,000 mg (4×250 mg tablets) once daily in combination with prednisone (5 mg) administered orally twice daily for CRPC patients or once daily for CSPC patients. In Europe, the use of Zytiga® is approved only in combination with either prednisone or prednisolone.

Because the administration of abiraterone acetate with food increases the absorption of abiraterone acetate (and, therefore, has the potential to result in increased and highly variable exposures, which can potentially cause various side effects including cardiovascular side effects and/or hepatotoxicity etc., the prodrug should be consumed on an empty stomach at least one hour before, or two hours after, a meal. Indeed, the prescribing information for Zytiga® states it must be taken on an empty stomach, and no food should be consumed for at least two hours before oral dosing and at least one hour after oral dosing.

The prescribing information explains that for a daily oral dose of 1,000 mg of Zytiga® in patients with metastatic CRPC, abiraterone's steady-state $C_{max}$ values were 226±178 ng/mL (mean±SD) and its area under the curve (AUC) values were 1173±690 ng·hr/mL (mean±SD). A single-dose (1,000 mg) cross-over study of Zytiga® in healthy subjects found that systemic exposure of abiraterone was increased when Zytiga® was administered with food. Specifically, abiraterone's $C_{max}$ and AUC values were approximately 7- and 5-fold higher, respectively, when Zytiga® was administered with a low-fat meal (7% fat, 300 calories) and approximately 17- and 10-fold higher, respectively, when Zytiga® was administered with a high-fat meal (57% fat, 825 calories).

The currently approved solid dosage oral form of the prodrug abiraterone acetate has several disadvantages. For example, it has very low bioavailability that necessitates a large daily pill burden for patients (4×250 mg tablets once daily). In addition, it causes highly variable blood levels in patients due to the combination of low bioavailability and a large food effect. Further, as abiraterone is rapidly cleared, this approved dosing regimen results in a daily $C_{min}$ of abiraterone, which is believed to be associated with a loss of therapeutic effect in metastatic CRPC patients.

Non-oral modes of administration (for example, parenteral routes) have been explored for other classes of drugs. However, to date, there are no sustained-release injectable prodrug formulations of abiraterone.

SUMMARY

The present disclosure generally relates to novel abiraterone prodrugs, long-acting abiraterone prodrug formulations, and methods of using the same, for example, in treating a subject having a sex hormone-dependent benign or malignant disorder, an androgen receptor driven cancer, and/or a syndrome due to androgen and/or glucocorticoid excess, see also U.S. Pat. No. 10,792,292 B2, issued to Propella Therapeutics, Inc. on Oct. 6, 2020 and U.S. Provisional Application No. 63/073,502, filed Sep. 2, 2020, the content of each of which is herein incorporated by reference in its entirety.

The novel abiraterone prodrugs can typically be a fatty acid ester of abiraterone, which upon cleavage, releases abiraterone and a safe and degradable fatty acid component.

Compared to oral abiraterone acetate formulation, the novel abiraterone prodrugs and formulations herein are a breakthrough in that they provide increased bioavailability, elimination of the food effect, reduced pill burden, less frequent dosing frequency, and sustained effective blood plasma levels of abiraterone, e.g., continuous plasma exposures above daily $C_{min}$ levels observed for oral administration of abiraterone acetate, for example, for at least one week, typically, for at least two weeks and up to ten weeks or more following administration of the abiraterone prodrug formulation. Further, pharmacokinetics and pharmacodynamics studies of representative abiraterone prodrugs demonstrate that the novel abiraterone prodrugs and formulations are suitable for dosing once a week, once a month, once every two months, once every three months, or even less frequently, for treating a subject having a sex hormone-dependent benign or malignant disorder, an androgen receptor driven cancer, a syndrome due to androgen excess and/or a syndrome due to glucocorticoid excess. This feature alone represents a significant improvement over the currently marketed Zytiga® tablets, which require a large daily pill burden for patients (4×250 mg tablets once daily).

As detailed herein, the present disclosure further shows that administering abiraterone prodrugs, such as abiraterone decanoate, can achieve a sustained reduction of serum androgen levels without the need to castrate the subject or administer to the subject another drug in an amount effective in reducing serum androgen levels. The present disclosure also shows that administering abiraterone prodrugs are generally well tolerated. For example, no liver toxicity was observed from intramuscular administration of abiraterone decanoate at the tested doses. In addition, the present disclosure provides novel parenteral formulations of abiraterone prodrugs, in particular, abiraterone decanoate formulations, which can be better suited for pharmaceutical development. The compositions and methods described herein fulfill a long-felt and unmet need by providing an alternative to oral formulations that suffer from (1) low bioavailability, (2) interactions with ingested food, (3) delivery of highly variable blood levels of parent drug with the possibility of reduced efficacy and increased side effects, (4) requirement of daily dosing and high pill burden, (5) requirement of castration, and (6) poor patient compliance due to required abstinence from food within hours of administration, high pill burden, and the need for complementary daily administration of prednisone or prednisolone with a conflicting dosing schedule as it is to be taken with food.

In some embodiments, the present disclosure provides the following:

[1] A method of treating a sex hormone dependent or androgen receptor driven cancer in a subject in need thereof, such as a non-castrated subject in need thereof, the method comprising administering, typically, parenterally administering, to the subject a therapeutically effective amount of a pharmaceutical composition comprising an abiraterone prodrug (e.g., an abiraterone lipophilic ester).

[2] The method of [1], wherein the subject is not treated with a gonadotropin-releasing hormone agonist and/or antagonist in an amount effective to reduce serum testosterone level in the subject.

[3] The method of [1], wherein the subject is not treated with a drug selected from buserelin, leuprolide, deslorelin, fertirelin, histrelin, gonadorelin, lecirelin, goserelin, nafarelin, peforelin and triptorelin.

[4] The method of [1] or [3], wherein the subject is not treated with a drug selected from abarelix, cetrorelix, degarelix, ganirelix, elagolix, linzagolixa, and relugolix.

[5] The method any one of [1]-[4], wherein the subject is sensitive to or otherwise intolerant with a gonadotropin-releasing hormone antagonist and/or agonist.

[6] The method of any one of [1]-[5], wherein the subject is not treated with a glucocorticoid replacement therapy.

[7] The method of any one of [1]-[6], wherein the abiraterone prodrug comprises abiraterone decanoate, or a pharmaceutically acceptable salt thereof,

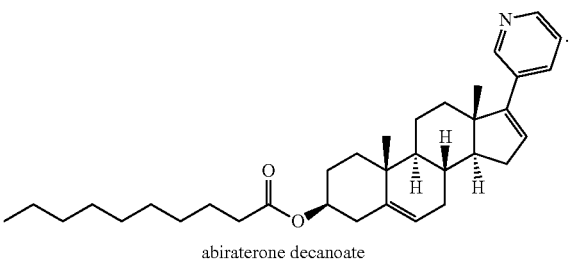

abiraterone decanoate

[8] The method of any one of [1]-[7], wherein the pharmaceutical composition comprises the abiraterone prodrug and a pharmaceutically acceptable carrier.

[9] The method of [8], wherein the pharmaceutically acceptable carrier comprises a pharmaceutically acceptable oil and optionally a further pharmaceutically acceptable solvent.

[10] The method of [9], wherein the pharmaceutically acceptable oil comprises a triglyceride (e.g., long and/or medium chain triglycerides), and the further pharmaceutically acceptable solvent, if present, comprises an alcohol, ester, and/or acid solvent.

[11] The method of [9] or [10], wherein the pharmaceutically acceptable oil is selected from vegetable oil, castor oil, corn oil, sesame oil, cottonseed oil, peanut oil, poppy seed oil, tea seed oil, and soybean oil, and the further pharmaceutically acceptable solvent, if present, comprises benzyl alcohol, benzyl benzoate, or a combination thereof.

[12] The method of any one of [8]-[11], wherein the pharmaceutically acceptable carrier comprises corn oil, benzyl alcohol, and benzyl benzoate.

[13] The method of any one of [1]-[12], wherein the pharmaceutical composition comprises, for each milliliter, (a) abiraterone decanoate in its basic form, in an amount of about 100 mg to about 300 mg (e.g., about 100 mg, about 120 mg, about 150 mg, about 180 mg, about 200 mg or about 250 mg); (b) benzyl alcohol in an amount of about 50 mg to about 150 mg (e.g., about 75 mg, about 100 mg, or about 125 mg); (c) benzyl benzoate in an amount of about 100 mg to about 300 mg (e.g., about 100 mg, about 150 mg, about 200 mg, or about 250 mg); and (d) corn oil, q.s. to 1 milliliter.

[14] The method of any one of [1]-[13], wherein the pharmaceutical composition is characterized as having a viscosity of less than 0.1 Pa*s, such as about 0.05 Ps*s or lower.

[15] The method of any one of [1]-[14], wherein the pharmaceutical composition is characterized as having a glide force of about 1-10 N when measured using a

[16] The method of any one of [1]-[15], wherein the pharmaceutical composition is characterized as having no more than 1000 particles having a size of 10 m or greater, and no more than 300 particles having a size of 25 m or greater, when measured according to USP <788> and/or <789>.

[17] The method of any one of [1]-[16], wherein the pharmaceutical composition is characterized as having less than 100 EU/ml, such as less than 25 EU/ml of bacterial endotoxins measured according to USP <85>.

[18] The method of any one of [1]-[17], wherein the subject has not undergone a prostatectomy.

[19] The method of any one of [1]-[18], wherein the subject is further treated with a radiation therapy.

[20] The method of any one of [1]-[19], wherein the sex hormone dependent or androgen receptor driven cancer is androgen receptor positive salivary duct carcinoma, or androgen receptor positive glioblastoma multiforme.

[21] The method of any one of [1]-[19], wherein the sex hormone dependent or androgen receptor driven cancer is prostate cancer.

[22] The method of [21], wherein the prostate cancer is a localized prostate cancer, e.g., a high risk localized prostate cancer.

[23] The method of [21], wherein the prostate cancer is a metastatic castration-sensitive prostate cancer, non-metastatic castration-sensitive prostate cancer, non-metastatic castration-resistant prostate cancer, or metastatic castration-resistant prostate cancer.

[24] The method of [21], wherein the prostate cancer is a newly diagnosed high risk metastatic hormone sensitive prostate cancer.

[25] The method of [21], wherein the prostate cancer is a metastatic CRPC, wherein the subject is asymptomatic or mildly symptomatic after failure of androgen deprivation therapy in whom chemotherapy is not yet clinically indicated.

[26] The method of [21], wherein the prostate cancer is a metastatic CRPC, wherein the subject's disease has progressed on or after a taxane-based chemotherapy regimen, such as docetaxel-based or cabazitaxel-based chemotherapy regimen.

[27] The method of [21], wherein the prostate cancer is a refractory prostate cancer.

[28] The method of any one of [1]-[5] and [7]-[27], further comprising administering to the subject one or more agents selected from hydrocortisone, prednisone, prednisolone, methylprednisolone, and dexamethasone.

[29] The method of any one of [1]-[28], further comprising administering to the subject a poly ADP ribose polymerase (PARP) inhibitor, e.g., niraparib, rucaparib, olaparib, talazoparib, veliparib, and fluzoparib.

[30] The method of any one of [1]-[29], further comprising administering to the subject a $1^{st}$-generation androgen receptor antagonist, e.g., proxalutamide, bicalutamide, flutamide, nilutamide, topilutamide.

[31] The method of any one of [1]-[30], further comprising administering to the subject a $2^{nd}$-generation androgen receptor antagonist (e.g., apalutamide, darolutamide or enzalutamide).

[32] The method of any one of [1]-[31], further comprising administering to the subject a $3^{rd}$ generation androgen receptor antagonist (such as an N-terminal domain inhibitor) or an androgen receptor degrader molecule, alone or in combination with one or more $1^{st}$ generation or $2^{nd}$ generation androgen receptor antagonists.

[33] The method of any one of [1]-[32], further comprising administering to the subject a chemotherapeutic agent, such as a taxane based chemotherapeutic agent (e.g., docetaxel, cabazitaxel, paclitaxel, etc.) or platinum based chemotherapeutic agent (e.g., cisplatin, carboplatin, oxaliplatin, etc.).

[34] The method of any one of [1]-[33], further comprising administering to the subject an immunotherapy, such as administering Sipuleucel-T, an immune checkpoint inhibitor (e.g., anti-PD-1 antibody such as pembrolizumab or nivolumab, or anti-PD-L1 antibody such as avelumab or atezolizumab), or an anti-CTLA-4 antibody (e.g., ipilimumab), etc.

[35] The method of any one of [1]-[34], further comprising administering to the subject a bispecific T-cell engager (BiTE) therapy, such as blinatumomab or solitomab.

[36] The method of any one of [1]-[35], further comprising administering to the subject a kinase inhibitor, e.g., sunitinib, dasatinib, cabozantinib, erdafitinib, dovitinib, capivasertib, onvansertib, ipatasertib, afuresertib, alisertib, apitolisib, opaganib, etc.

[37] The method of any one of [1]-[36], further comprising administering to the subject a bone protecting agent (e.g., denosumab, zolendronic acid), and wherein the subject is characterized as having prostate cancer (e.g., CRPC) with bone metastasis.

[38] The method of any one of [1]-[37], further comprising administering to the subject a therapeutic agent selected from 1) an anti-IL23 targeting monoclonal antibody, e.g., tildrakizumab; 2) a selenium, such as sodium selenite; 3) an EZH2 inhibitor, e.g., CPI-1205, GSK2816126, or tazemetostat; 4) a CDK4/6 inhibitor, e.g., palbociclib, ribociclib, abemaciclib; 6) a bromodomain and extra-terminal domain (BET) inhibitor, e.g., CCS1477, INCB057643, alobresib, ZEN-3694, or molibresib (GSK525762); 7) an anti-CD105 antibody, e.g., TRC105 or carotuximab; 8) niclosamide; 9) an A2A receptor antagonist, e.g., AZD4635; 10) a PI3K inhibitor, e.g., AZD-8186, buparlisib, or dactolisib; 11) a further non-steroidal CYP17A1 inhibitor, e.g. seviteronel; 12) an antiprogestogen, e.g., onapristone; 13) navitoclax; 14) an HSP90 inhibitor, e.g., onalespib (AT13387); 15) an HSP27 inhibitor, e.g., OGX-427; 16) a 5-alpha-reductase inhibitor, e.g., dutasteride; 17) metformin; 18) AMG-386; 19) dextromethorphan; 20) theophylline; 21) hydroxychloroquine; and 22) lenalidomide.

[39] The method of any one of [1]-[38], further comprising administering to the subject one or more kinase modulators selected from FLT-3 (FMS-like tyrosine kinase) inhibitors, AXL (anexelekto) inhibitors (e.g., Gilteritinib), CDK (cyclin dependent kinase) inhibitors, such as CDK1, 2, 4, 5, 6, 7, or 9 inhibitors, retinoblastoma (Rb) inhibitors, protein kinase B (AKT) inhibitors, SRC inhibitors, IkappaB kinase 1 (IKK1) inhibitors, PIM-1 modulators, Lemur tyrosine kinase 2 (LMTK2) modulators, Lyn inhibitors, Aurora A inhibitors, ANPK (a nuclear protein kinase) inhibitors, extracellular-signal regulated kinase (ERK) modulators, c-jun N-terminal kinase (JNK) modulators, Big MAP kinase (BMK) modulators, p38 mitogen-activated protein kinases (MAPK) modulators, and combinations thereof.

[40] The method of any one of [1]-[39], wherein the subject is chemotherapy naïve or hormone therapy naïve prior to being administered the pharmaceutical composition.

[41] The method of any one of [1]-[40], wherein the administering of the pharmaceutical composition provides an effective amount of abiraterone in the subject to achieve a sustained reduction of serum testosterone level to (1) about 50 ng/dL or below when the subject is a non-castrated subject, or (2) about 1 ng/dL or below when the subject is a castrated subject, within 15 days of the first administration of the abiraterone prodrug.

[42] A method of reducing serum testosterone level in a subject in need thereof, the method comprising parenterally administering to the subject a pharmaceutical composition comprising an abiraterone prodrug (e.g., an abiraterone lipophilic ester), wherein the administering provides an effective amount of abiraterone to achieve a sustained reduction of serum testosterone level to (1) about 50 ng/dL or below when the subject is a non-castrated subject, or (2) about 1 ng/dL or below when the subject is a castrated subject, within 15 days of the first administration of the abiraterone prodrug.

[43] The method of [42], wherein the subject is a non-castrated subject.

[44] The method of [42] or [43], wherein the subject is not treated with a gonadotropin-releasing hormone antagonist and/or agonist in an amount effective to reduce serum testosterone level in the subject.

[45] The method of [42] or [43], wherein the subject is not treated with a drug selected from buserelin, leuprolide, deslorelin, fertirelin, histrelin, gonadorelin, lecirelin, goserelin, nafarelin, peforelin and triptorelin.

[46] The method of [42], [43] or [45], wherein the subject is not treated with a drug selected from abarelix, cetrorelix, degarelix, ganirelix, elagolix, linzagolixa, and relugolix.

[47] The method of any one of [42]-[46], wherein the subject is sensitive to or otherwise intolerant with a gonadotropin-releasing hormone antagonist and/or agonist.

[48] The method of any one of [42]-[47], wherein the abiraterone prodrug comprises abiraterone decanoate, or a pharmaceutically acceptable salt thereof,

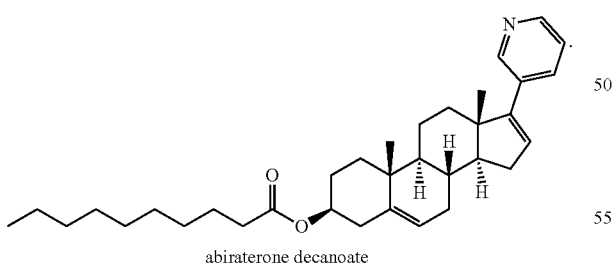

abiraterone decanoate

[49] The method of any one of [42]-[48], wherein the pharmaceutical composition comprises the abiraterone prodrug and a pharmaceutically acceptable carrier.

[50] The method of [49], wherein the pharmaceutically acceptable carrier comprises a pharmaceutically acceptable oil and optionally a further pharmaceutically acceptable solvent.

[51] The method of [50], wherein the pharmaceutically acceptable oil comprises a triglyceride (e.g., long and/or medium chain triglycerides), and the further pharmaceutically acceptable solvent, if present, comprises an alcohol, ester, and/or acid solvent.

[52] The method of [50] or [51], wherein the pharmaceutically acceptable oil is selected from vegetable oil, castor oil, corn oil, sesame oil, cottonseed oil, peanut oil, poppy seed oil, tea seed oil, and soybean oil, and the further pharmaceutically acceptable solvent, if present, comprises benzyl alcohol, benzyl benzoate, or a combination thereof.

[53] The method of any one of [49]-[52], wherein the pharmaceutically acceptable carrier comprises corn oil, benzyl alcohol, and benzyl benzoate.

[54] The method of any one of [42]-[53], wherein the pharmaceutical composition comprises, for each milliliter, (a) abiraterone decanoate in its basic form, in an amount of about 100 mg to about 300 mg (e.g., about 100 mg, about 120 mg, about 150 mg, about 180 mg, about 200 mg or about 250 mg); (b) benzyl alcohol in an amount of about 50 mg to about 150 mg (e.g., about 75 mg, about 100 mg, or about 125 mg); (c) benzyl benzoate in an amount of about 100 mg to about 300 mg (e.g., about 100 mg, about 150 mg, about 200 mg, or about 250 mg); and (d) corn oil, q.s. to 1 milliliter.

[55] The method of any one of [42]-[54], wherein the pharmaceutical composition is characterized as having a viscosity of less than 0.1 Pa*s, such as about 0.05 Ps*s or lower.

[56] The method of any one of [42]-[55], wherein the pharmaceutical composition is characterized as having a glide force of about 1-10 N when measured using a 21 G, 1.5 inch needle, and/or about 2-15 N when measured using a 23 G, 1.5 inch needle, and/or about 30-150 N when measured using a 27 G, 1.5 inch needle.

[57] The method of any one of [42]-[56], wherein the pharmaceutical composition is characterized as having no more than 1000 particles having a size of 10 m or greater, and no more than 300 particles having a size of 25 m or greater, when measured according to USP <788> and/or <789>.

[58] The method of any one of [42]-[57], wherein the pharmaceutical composition is characterized as having less than 100 EU/ml, such as less than 25 EU/ml of bacterial endotoxins measured according to USP <85>.

[59] The method of any one of [42]-[58], wherein the subject is characterized as having a sex hormone dependent cancer or androgen receptor driven cancer.

[60] The method of any one of [42]-[59], wherein the subject is characterized as having androgen receptor positive salivary duct carcinoma, or androgen receptor positive glioblastoma multiforme.

[61] The method of any one of [42]-[59], wherein the subject is characterized as having prostate cancer.

[62] The method of [61], wherein the prostate cancer is a localized prostate cancer, e.g., a high risk localized prostate cancer.

[63] The method of any one of [42]-[62], wherein the subject has not undergone a prostatectomy.

[64] The method of any one of [42]-[63], wherein the subject is further treated with a radiation therapy.

[65] The method of any one of [1]-[64], wherein the pharmaceutical composition is administered through an intramuscular injection, intradermal injection, or subcutaneous injection.

[66] The method of any one of [1]-[65], wherein the pharmaceutical composition is administered to the subject once a week or once in more than a week.

[67] The method of any one of [1]-[66], wherein the pharmaceutical composition is administered to the subject once a month or once in more than a month, such as once every two months or once every three months.

[68] The method of any one of [1]-[67], wherein the pharmaceutical composition is administered to the subject with or without food.

[69] The method of any one of [1]-[68], wherein the administering provides (a) a blood plasma concentration of abiraterone above 1.0 ng/ml for a period of at least two weeks from a single dose; (b) a single dose or steady state $C_{max}$ of abiraterone between about 5 ng/ml and about 300 ng/ml; or (c) both (a) and (b).

[70] The method of any one of [1]-[69], wherein the subject suffers from hepatic impairment, such as moderate to severe hepatic impairment (Child-Pugh Class B or C), prior to the administering of the abiraterone prodrug

[71] A pharmaceutical composition comprises, for each milliliter, (a) abiraterone decanoate in its basic form, in an amount of about 100 mg to about 300 mg (e.g., about 100 mg, about 120 mg, about 150 mg, about 180 mg, about 200 mg or about 250 mg); (b) benzyl alcohol in an amount of about 50 mg to about 150 mg (e.g., about 75 mg, about 100 mg, or about 125 mg); (c) benzyl benzoate in an amount of about 100 mg to about 300 mg (e.g., about 100 mg, about 150 mg, about 200 mg, or about 250 mg); and (d) corn oil, q.s. to 1 milliliter, wherein abiraterone decanoate has the following structure:

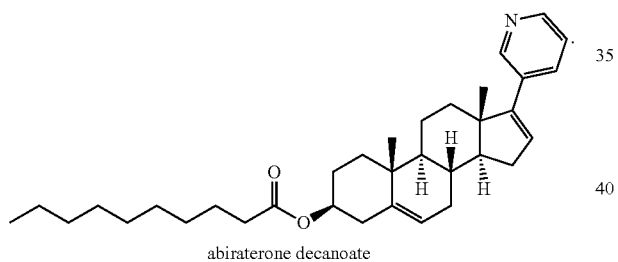

abiraterone decanoate

[72] The pharmaceutical composition of [71], comprising for each milliliter, (a) abiraterone decanoate in its basic form, in an amount of about 180 mg; (b) benzyl alcohol in an amount of about 50 mg to about 150 mg (e.g., about 75 mg, about 100 mg, or about 125 mg); (c) benzyl benzoate in an amount of about 100 mg to about 300 mg (e.g., about 100 mg, about 150 mg, about 200 mg, or about 250 mg); and (d) corn oil, q.s. to 1 milliliter.

[73] The pharmaceutical composition of [71], comprising for each milliliter, (a) abiraterone decanoate in its basic form, in an amount of about 200 mg; (b) benzyl alcohol in an amount of about 50 mg to about 150 mg (e.g., about 75 mg, about 100 mg, or about 125 mg); (c) benzyl benzoate in an amount of about 100 mg to about 300 mg (e.g., about 100 mg, about 150 mg, about 200 mg, or about 250 mg); and (d) corn oil, q.s. to 1 milliliter.

[74] The pharmaceutical composition of any one of [71]-[73], wherein the weight ratio of benzyl alcohol to benzyl benzoate in the pharmaceutical composition ranges from about 2:1 to about 1:5 (e.g., about 1:1 to 1:3, such as about 1:2).

[75] The pharmaceutical composition of any one of [71]-[74], wherein the abiraterone decanoate is substantially pure, e.g., characterized as having a purity by weight of at least 95%, preferably, at least 98%, such as about 98.5%, about 99%, about 99.5%, or higher.

[76] The pharmaceutical composition of any one of [71]-[75], wherein the abiraterone decanoate is characterized as having less than 1% (e.g., less than 0.5% by weight, such as less than 0.3%, less than 0.2%, or less than 0.1%) by weight of ethyl prasterone decanoate having the formula:

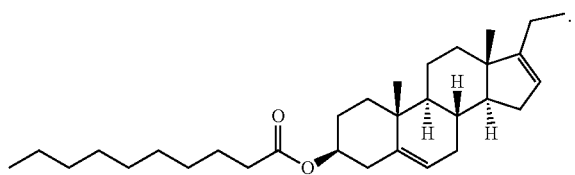

[77] The pharmaceutical composition of any one of [71]-[75] and [98], wherein the abiraterone decanoate is characterized as having no detectable amount of ethyl prasterone decanoate.

[78] The pharmaceutical composition of any one of [71]-[77] and [98], wherein the pharmaceutical composition is characterized as having a viscosity of less than 0.1 Pa*s, such as about 0.05 Ps*s or lower.

[79] The pharmaceutical composition of any one of [71]-[78] and [98], wherein the pharmaceutical composition is characterized as having a glide force of about 1-10 N when measured using a 21 G, 1.5 inch needle, and/or about 2-15 N when measured using a 23 G, 1.5 inch needle, and/or about 30-150 N when measured using a 27 G, 1.5 inch needle.

[80] The pharmaceutical composition of any one of [71]-[79] and [98], wherein the pharmaceutical composition is characterized as having no more than 1000 particles having a size of 10 m or greater, and no more than 300 particles having a size of 25 m or greater, when measured according to USP <788> and/or <789>.

[81] The pharmaceutical composition of any one of [71]-[80] and [98], wherein the pharmaceutical composition is characterized as having less than 100 EU/ml, such as less than 25 EU/ml of bacterial endotoxins measured according to USP <85>.

[82] A substantially pure abiraterone decanoate, characterized as having a Palladium content of less than 50 ppm, wherein abiraterone decanoate has the following structure:

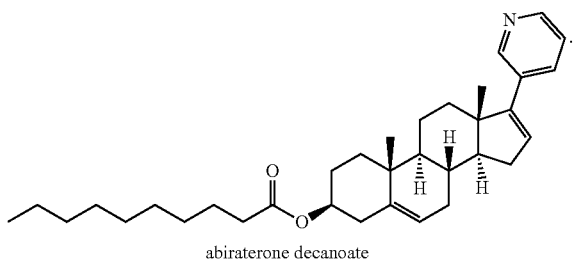

abiraterone decanoate

[83] The substantially pure abiraterone decanoate of [82], having a Palladium content of less than 10 ppm.

[84] The substantially pure abiraterone decanoate of [82] or [83], characterized as having a purity by weight of at least 95%, preferably, at least 98%, such as about 98.5%, about 99%, about 99.5%, or higher.

[85] The substantially pure abiraterone decanoate of any one of [82]-[84], characterized as having less than 1% (e.g., less than 0.5% by weight, such as less than 0.3%, less than 0.2%, or less than 0.1%) by weight of ethyl prasterone decanoate having the formula:

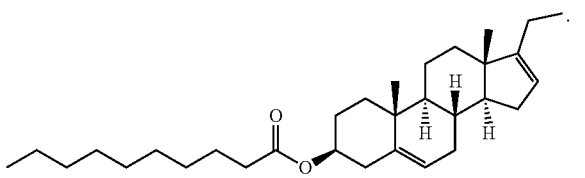

[86] The substantially pure abiraterone decanoate of any one of [82]-[85], which is in a crystalline form, such as the crystalline Form A of any of [108]-[113].

[87] The substantially pure abiraterone decanoate of any one of [82]-[86], which conforms to the specification shown in Table D.

[88] A method for preparing a pharmaceutical composition comprising a) mixing the substantially pure abiraterone decanoate of any one of [82]-[87] with a pharmaceutically acceptable carrier (e.g., any of those described herein) to form a mixture; and optionally b) sterilizing the mixture formed in a).

[89] The method of [88], wherein the pharmaceutically acceptable carrier comprises a pharmaceutically acceptable oil (e.g., any of those described herein) and optionally a pharmaceutically acceptable solvent (e.g., any of those described herein).

[90] The method of [89], wherein the pharmaceutically acceptable oil comprises a vegetable oil, castor oil, corn oil, sesame oil, cottonseed oil, peanut oil, poppy seed oil, tea seed oil, or soybean oil.

[91] The method of [89] or [90], wherein the optional pharmaceutically acceptable solvent comprises benzyl alcohol and/or benzyl benzoate.

[92] The method of any one of [88]-[91], wherein the pharmaceutically acceptable carrier comprises corn oil, benzyl alcohol, and benzyl benzoate.

[93] The method of any one of [88]-[92], wherein the abiraterone decanoate is present at a concentration of about 50 mg/mL to about 300 mg/mL.

[94] The method of any one of [88]-[93], wherein the pharmaceutical composition comprises, for each milliliter, (a) the substantially pure abiraterone decanoate in its basic form, in an amount of about 100 mg to about 300 mg (e.g., about 100 mg, about 120 mg, about 150 mg, about 180 mg, about 200 mg or about 250 mg); (b) benzyl alcohol in an amount of about 50 mg to about 150 mg (e.g., about 75 mg, about 100 mg, or about 125 mg); (c) benzyl benzoate in an amount of about 100 mg to about 300 mg (e.g., about 100 mg, about 150 mg, about 200 mg, or about 250 mg); and (d) corn oil, q.s. to 1 milliliter.

[95] The method of any one of [88]-[93], wherein the pharmaceutical composition comprises, for each milliliter, (a) the substantially pure abiraterone decanoate in its basic form, in an amount of about 180 mg; (b) benzyl alcohol in an amount of about 50 mg to about 150 mg (e.g., about 75 mg, about 100 mg, or about 125 mg); (c) benzyl benzoate in an amount of about 100 mg to about 300 mg (e.g., about 100 mg, about 150 mg, about 200 mg, or about 250 mg); and (d) corn oil, q.s. to 1 milliliter.

[96] The method of any one of [88]-[93], wherein the pharmaceutical composition comprises, for each milliliter, (a) the substantially pure abiraterone decanoate in its basic form, in an amount of about 200 mg; (b) benzyl alcohol in an amount of about 50 mg to about 150 mg (e.g., about 75 mg, about 100 mg, or about 125 mg); (c) benzyl benzoate in an amount of about 100 mg to about 300 mg (e.g., about 100 mg, about 150 mg, about 200 mg, or about 250 mg); and (d) corn oil, q.s. to 1 milliliter.

[97] The method of any one of [88]-[96], wherein the pharmaceutical composition comprises benzyl alcohol and benzyl benzoate, and the weight ratio of benzyl alcohol to benzyl benzoate in the pharmaceutical composition ranges from about 2:1 to about 1:5 (e.g., about 1:1 to 1:3, such as about 1:2).

[98] The pharmaceutical composition produced by the method according to any one of [88]-[97].

[99] The method of any one of [1]-[70], wherein the pharmaceutical composition is selected from any one of [71]-[81] and [98].

[100] A method of preparing crystalline Form A of abiraterone decanoate, the method comprising: a) dissolving the abiraterone decanoate in a first solvent to form a first solution; b) adding activated carbon to the first solution; c) removing the activated carbon to form a second solution; and d) crystallizing the abiraterone decanoate from the second solution to form the crystalline Form A of abiraterone decanoate, wherein abiraterone decanoate has the following structure:

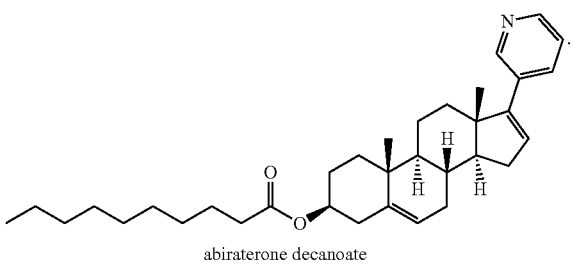

abiraterone decanoate

[101] The method of [100], wherein the crystallizing step d) comprises cooling the second solution, reducing the amount of the first solvent, and/or adding an antisolvent in which abiraterone decanoate has a lower solubility than in the first solvent.

[102] The method of [100] or [101], wherein the first solvent is selected from acetone, dioxane, 1-propanol, methyl tert-butyl ether, isopropyl ether, t-butanol, chloroform, ethyl acetate, nitromethane, dimethyl acetamide, tetrahydrofuran, dimethyl formamide, diethyl ether, 2-butanol, isopropyl acetate, ethanol, methanol, toluene, acetonitrile, heptane, 2-propanol, 2-butanone, 2-methyl tetrahydrofuran, a combination of methanol and tetrahydrofuran, a combination of methanol and chloroform, a combination of acetonitrile and t-butanol, and a combination of acetonitrile and 2-propanol.

[103] The method of [102], wherein the first solvent is selected from ethyl acetate, ter-butanol, chloroform, isopropyl ether, tetrahydrofuran, 2-propanol, acetonitrile, 2-butanone, heptane, toluene, and methanol, wherein the crystallizing step d) comprises cooling the second solution and/or reducing the amount of the first solvent.

[104] The method of [100] or [101], wherein the first solvent is acetone.

[105] The method of any one of [101]-[104], wherein the antisolvent is water.

[106] The method of any one of [101]-[105], wherein the ratio of the volumes of the antisolvent to the first solvent in the second solution ranges from about 1:50 to about 1:10.

[107] The method of [100], which is substantially the same as the process described in Example 1B herein.

[108] The crystalline Form A of abiraterone decanoate, prepared by the method according to any one of [100]-[107], which is substantially free of Form B and Form C of abiraterone decanoate, e.g., no detectable amount of Form B and Form C by XRPD.

[109] The crystalline Form A of abiraterone decanoate according to [108], which is substantially pure.

[110] The crystalline Form A of abiraterone decanoate according to [108] or [109], characterized as having a Palladium content of less than 50 ppm, such as less than 10 ppm.

[111] The crystalline Form A of abiraterone decanoate according to any one of [108]-[110], characterized as having a purity by weight of at least 95%, preferably, at least 98%, such as about 98.5%, about 99%, about 99.5%, or higher.

[112] The crystalline Form A of abiraterone decanoate according to any one of [108]-[111], characterized as having less than 1% (e.g., less than 0.5% by weight, such as less than 0.3%, less than 0.2%, or less than 0.1%) by weight of ethyl prasterone decanoate having the formula:

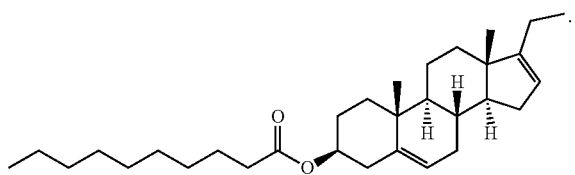

[113] The crystalline Form A of abiraterone decanoate according to any one of [108]-[112], which conforms to the specification shown in Table D.

[114] A pharmaceutical composition comprising abiraterone decanoate in crystalline Form A.

[115] A pharmaceutical composition comprising abiraterone decanoate in crystalline Form B.

[116] A pharmaceutical composition comprising abiraterone decanoate in crystalline Form C.

Embodiments of the present disclosure can fulfill a long felt need in the field of sex hormone-dependent disorders and oncology including the treatment of a sex hormone dependent or androgen receptor driven cancer such as prostate cancer. Embodiments of the present disclosure can also fulfill a long felt need in the field of treating syndromes due to androgen excess syndrome and/or due to glucocorticoid excess such as hypercortisolemia. Embodiments of the present disclosure can overcome major disadvantages and deficiencies of prior art formulations (including commercially-available oral dosage forms) of abiraterone acetate, by providing long-acting, sustained release depot-based parenteral formulations of abiraterone prodrugs, methods of producing the same, methods of treatment using the same, and kits for convenient administration of the formulations to subjects in need of therapy for various disorders including prostate cancer.

There has thus been outlined, rather broadly, features in order that the detailed description thereof that follows may be better understood, and in order that the present contribution to the art may be better appreciated. There are, of course, additional features that will be described further hereinafter. Indeed, it is to be understood that both the foregoing general description and the following detailed description are exemplary and explanatory and are intended to provide further explanation of the disclosure.

In this respect, before explaining at least one embodiment in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those persons skilled in the art will appreciate that the conception upon which this disclosure is based can readily be utilized as a basis for the designing of other formulations, methods, systems, kits, and compositions for carrying out the several purposes of the present disclosure. It is important, therefore, that equivalent constructions insofar as they do not depart from the spirit and scope of the present disclosure, are included in the present disclosure.

The accompanying drawings are included to provide a further understanding and are incorporated in and constitute a part of this specification, illustrate several embodiments, and together with the description explain the principles.

BRIEF DESCRIPTION OF THE DRAWINGS

FIG. 3 shows a representative analysis of a batch of high purity abiraterone decanoate.

DETAILED DESCRIPTION

Figure 1:
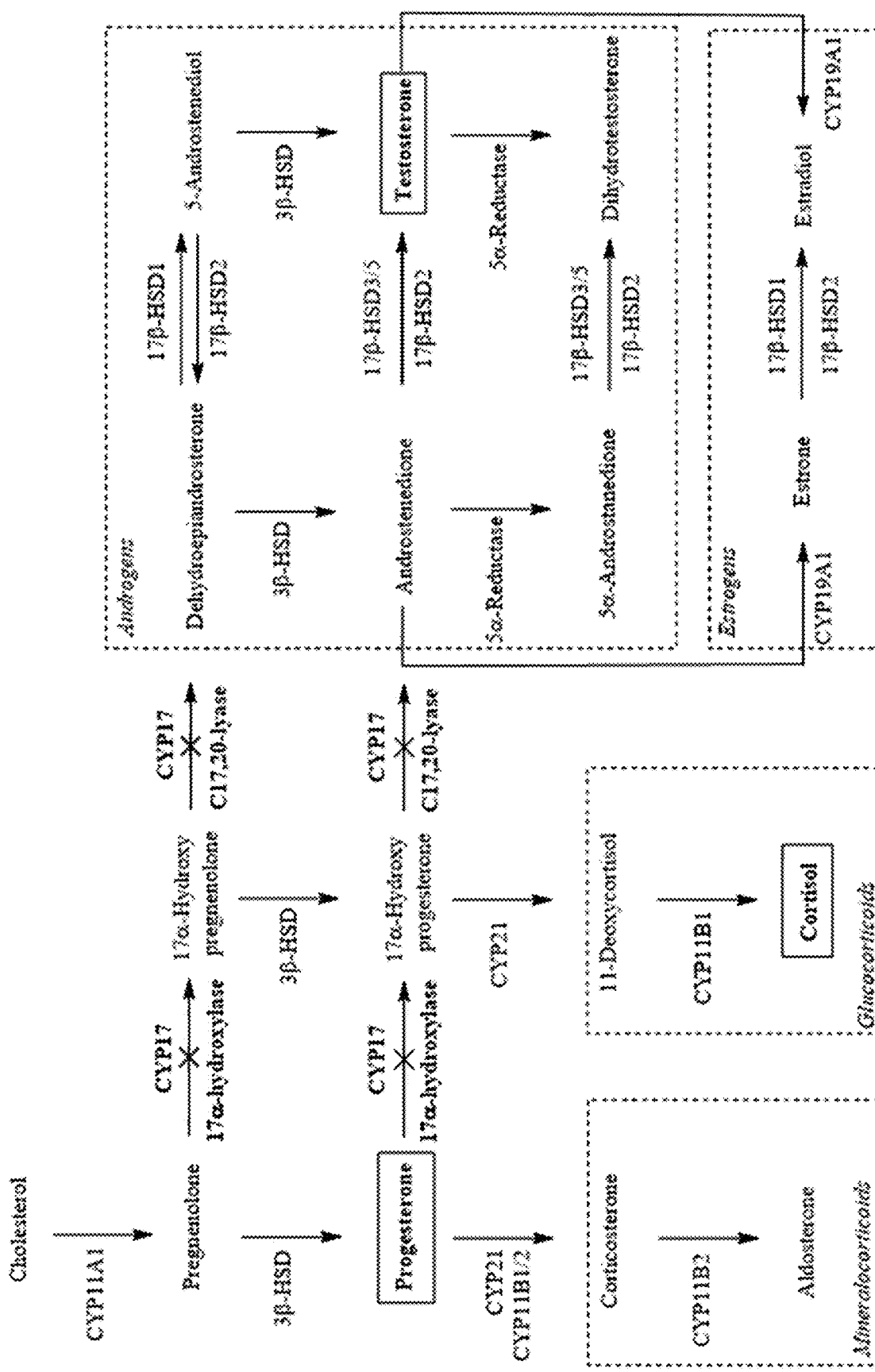
FIG. 1 presents biochemical pathways showing the effects of CYP17A1 inhibition on the synthesis of androgens, estrogens, glucocorticoids, progesterone, and mineralocorticoids.

In a broad aspect, the present disclosure relates to novel methods for modulating serum steroid hormone levels in a subject in need thereof and for treating or preventing a disease or disorder associated with such steroid hormones as well as abiraterone prodrugs and formulations useful for the methods. Embodiments of the present disclosure are based, in part, on that abiraterone prodrugs can be administered to a subject at a dosing frequency of once a week or once in more than a week to achieve sustained inhibition of CYP17A1 activities. Embodiments of the present disclosure are also based, in part, on the unexpected discovery that administering an abiraterone prodrug to a subject can achieve a sustained reduction of serum androgen levels without the need to castrate the subject or administer to the subject another drug in an amount effective in reducing serum androgen levels.

As further detailed herein and described in part in U.S. Pat. No. 10,792,292 B2, and U.S. Provisional Application No. 63/073,502, the methods herein can be advantageous over existing methods in many aspects, including but not limited to a fast and sustained reduction of serum testosterone, no need for castration, reduced or no liver toxicity compared to methods using oral abiraterone acetate formulations, improved bioavailability, elimination of the food effect associated with oral abiraterone acetate formulation, reduced pill burden, better patient compliance, decreased dosing frequency, sustained stable blood levels of active drug, reduced $C_{max}$, which can reduce associated side effects, etc.

Accordingly, in various embodiments, the present disclosure provides novel methods for modulating serum steroid hormone levels, such as for reducing testosterone levels, novel methods for treating or preventing diseases or disorders mediated by or associated with such steroids, such as sex hormone dependent or androgen receptor driven cancers, and/or abiraterone prodrugs and formulations useful for the methods.

Methods of Treatment

In some embodiments, the present disclosure provides a method of treating a disease or disorder described herein in a subject in need thereof. The method typically comprises parenterally administering to the subject, such as a non-castrated subject, a therapeutically effective amount of pharmaceutical composition comprising an abiraterone prodrug (e.g., an abiraterone lipophilic ester), which can be effective in inhibiting CYP17A1 and can modulate various steroid hormone levels in the subject, such as androgens, estrogens, glucocorticoids, progesterone, and mineralocorticoids.

The methods herein are advantageous over those using oral abiraterone acetate in many aspects. For example, compared to oral abiraterone acetate formulation, parenterally administering the pharmaceutical compositions herein can provide increased bioavailability, elimination of the food effect, reduced pill burden, less frequent dosing frequency, and sustained effective blood plasma levels of abiraterone, e.g., continuous plasma exposures above daily $C_{min}$ levels observed for oral administration of abiraterone acetate, for example, for at least one week, typically, for at least two weeks and up to ten weeks or more following administration of the abiraterone prodrug formulation. As detailed herein, administering abiraterone prodrugs can achieve a sustained inhibition of CYP17A1, see also U.S. Pat. No. 10,792,292 B2, and U.S. Provisional Application No. 63/073,502. In particular, as shown in Example 3 of this disclosure, a single administration of a representative abiraterone prodrug, abiraterone decanoate, at a dose of 10 mg/kg, 30 mg/kg, or 100 mg/kg, to chemically castrated monkeys, provided a sustained CYP17A1 inhibition, as evidenced by the sustained increase of progesterone level and reduction of cortisol, dihydrotestosterone and testosterone levels for up to 70 days or more. It was also shown that prolonged PD effects were observed even after abiraterone plasma concentration dropped below 1 ng/mL in the 10 mg/kg dosing group. Without wishing to be bound by theories, these prolonged PD effects observed may in part due to the slow-, tight-binding of CYP17A1 by abiraterone, which may have effectively achieved irreversible inhibition of CYP17A1, see e.g., Cheong E. J. Y., et al. *J. Pharmacol. Exp. Ther.* 374:438-451 (2020). Thus, abiraterone prodrugs and abiraterone prodrug formulations can be advantageously used for inhibiting CYP17A1 activity, reducing glucocorticoids levels, such as cortisol levels, reducing sex hormone levels such as androgen and/or estrogen levels, and/or treating disorders associated with high glucocorticoids levels, such as cortisol levels, and/or treating disorders due to high sex hormone levels such as androgen and/or estrogen levels.

As also detailed in the Examples section herein, the present disclosure unexpectedly shows that administration of abiraterone prodrugs can also lead to a sustained reduction of testosterone in the subject within a few days following the first administration of the prodrug without the need for castration or another drug that is effective in lowering testosterone levels. In particular, intramuscular administration of abiraterone decanoate to non-castrated monkeys, at several doses (20, 60, or 200 mg/kg/dose) administered every two weeks, achieved a sustained reduction of serum androgen levels, including testosterone, androstenedione, dehydroepiandrosterone, and dihydrotestosterone, etc. within 15 days post the first administration. The same sustained reduction was also observed in a separate study in rats, where it was found that a single intramuscular dose of abiraterone decanoate achieved a sustained reduction of testosterone up to 168 hours (last time point tested). Without wishing to be bound by theories, it is believed that the intramuscular administration of the abiraterone prodrug resulted in both a sustained effective blood plasma levels of abiraterone and favorable tissue distribution of abiraterone and abiraterone prodrug, such as to the testes, which may contribute to the observed effects on serum steroids that are not achieved by oral abiraterone acetate formulations (e.g., Zytiga®). Because the methods herein do not rely on castration to achieve a desired testosterone level, it is advantageous to use the methods herein at least for treating subjects who do not wish to be castrated and/or who are sensitive to or otherwise intolerant with gonadal testosterone suppressing drugs.

The present disclosure further shows that administering abiraterone prodrugs are generally well tolerated, for example, no liver toxicity was observed from intramuscular administration of abiraterone decanoate at the tested doses. As such, the methods herein can also advantageously treat subjects suffering from hepatic impairment, such as moderate to severe hepatic impairment (Child-Pugh Class B or C), prior to the administering of the abiraterone prodrug.

Accordingly, in some embodiments, the present disclosure provides a method of treating a disease or disorder described herein in a non-castrated subject in need thereof, the method comprising parenterally administering to the subject a therapeutically effective amount of a pharmaceutical composition comprising an abiraterone prodrug (e.g., an abiraterone lipophilic ester). The term "castration", "castrate(d)", and the alike, as used herein should be understood as encompassing all forms of castration, including surgical and chemical castrations.

In some embodiments, the present disclosure provides a method of treating a disease or disorder described herein in a subject in need thereof, the method comprising parenterally administering to the subject a therapeutically effective amount of a pharmaceutical composition comprising an abiraterone prodrug (e.g., an abiraterone lipophilic ester), wherein the subject suffers from hepatic impairment, such as moderate to severe hepatic impairment (Child-Pugh Class B or C), prior to the administering of the abiraterone prodrug.

Typically, in the methods herein, another drug that is effective in lowering serum and/or gonadal testosterone level, is not administered to the subject concurrently with the administration of the abiraterone prodrug, during the treatment with the abiraterone prodrug, or otherwise interfering with the treatment with the abiraterone prodrug. For example, in some embodiment, the subject is not treated with a gonadal testosterone suppressing drug, other than the administered abiraterone prodrug, in an amount effective to reduce serum testosterone level in the subject. In some embodiment, the subject is not treated with a gonadotropin-releasing hormone antagonist and/or agonist in an amount effective to reduce serum testosterone level in the subject. In some embodiment, the subject is not treated with any gonadal testosterone suppressing drug other than the administered abiraterone prodrug. In some embodiments, the subject is not treated with any gonadotropin-releasing hormone antagonist and/or agonist. In some embodiments, the subject is not treated with a drug selected from buserelin, leuprolide, deslorelin, fertirelin, histrelin, gonadorelin, lecirelin, goserelin, nafarelin, peforelin and triptorelin. In some embodiments, the subject is not treated with a drug selected from abarelix, cetrorelix, degarelix, ganirelix, elagolix, linzagolixa, and relugolix. In some embodiments, the subject can be sensitive to or otherwise intolerant with a gonadotropin-releasing hormone antagonist and/or agonist.

In some embodiments according to the methods herein, a glucococorticoid replacement therapy (e.g., administering a glucocorticoid, such as hydrocortisone, prednisone, prednisolone, methylprednisolone, or dexamethasone) is not desired. For example, a glucocorticoid may be contraindicated for the subject, who may have an underlying condition, such as diabetics. In some embodiments, the method can also be characterized in that the subject is not treated with a glucocorticoid replacement therapy. In some embodiments, the subject is not treated with an agent selected from hydrocortisone, prednisone, prednisolone, methylprednisolone, and dexamethasone. In some embodiments, the methods herein can comprise administering to the subject a mineralocorticoid receptor antagonist, such as eplerenone. For example, in any of the embodiments herein when glucococorticoid replacement therapy is not desired and/or not administered, the method can comprise administering to the subject a mineralocorticoid receptor antagonist, such as eplerenone.

Various diseases or disorders are suitable to be treated with the methods herein. For example, in some embodiments, the disease or disorder can be a sex hormone-dependent benign or malignant disorder, an androgen receptor drive cancer, a syndrome due to androgen excess, and a syndrome due to glucocorticoid excess. In some embodiments, the hormone-dependent benign or malignant disorders can be androgen-dependent disorders and estrogen-dependent disorders such as androgen or estrogen-dependent cancers. In some embodiments, the sex hormone-dependent benign or malignant disorder can be prostate cancer or breast cancer. In some embodiments, the sex hormone-dependent benign or malignant disorder is CRPC or CSPC. In some embodiments, the sex hormone-dependent benign or malignant disorder can be metastatic CRPC or metastatic CSPC. In some embodiments, the sex hormone-dependent benign or malignant disorder can also be ovarian cancer, bladder cancer, hepatocellular carcinoma, or lung cancer. Various non-oncologic syndromes due to androgen excess and/or due to glucocorticoid excess such as hypercortisolemia can also be treated with the methods herein, for example, syndromes due to androgen excess such as endometriosis, polycystic ovary syndrome, classical or nonclassical congenital adrenal hyperplasia, precocious puberty, hirsutism, etc., and/or syndromes due to cortisole excess such as Cushing's syndrome, Cushing's disease, etc.

In some specific embodiments, the methods herein are for treating a sex hormone dependent or androgen receptor driven cancer. In some embodiments, the sex hormone dependent or androgen receptor driven cancer can be androgen receptor positive salivary duct carcinoma, or androgen receptor positive glioblastoma multiforme. In some embodiments, the sex hormone dependent or androgen receptor driven cancer is prostate cancer (e.g., any of those described herein). Prostate cancer suitable to be treated with the methods herein is not particularly limited and include without limitation any of those prostate cancer for which abiraterone or its derivatives (particularly abiraterone acetate) has been approved for marketing (e.g., in the U.S. or Europe) or for which abiraterone or its derivatives (e.g., abiraterone acetate) is or has been in a clinical trial, such as those trials registered in the website clinicaltrials.gov as of the filing date of this application. For example, in some embodiments, the prostate cancer can be primary/localized prostate cancer (newly diagnosed or early stage), advanced prostate cancer (e.g., after castration for recurrent prostate cancer, locally advanced prostate cancer, etc.), recurrent prostate cancer (e.g., prostate cancer which was not responsive to a primary therapy), non-metastatic castration-resistant prostate cancer, metastatic prostate cancer, metastatic castration-resistant prostate cancer (CRPC), or hormone-sensitive prostate cancer. In some embodiments, the prostate cancer is a localized prostate cancer, e.g., a high risk localized prostate cancer. In some embodiments, the subject having prostate cancer is characterized as having a rising amount of prostate specific antigen, e.g., following radical prostatectomy. In some embodiments, the prostate cancer is a metastatic castration-sensitive prostate cancer, non-metastatic castration-sensitive prostate cancer, non-metastatic castration-resistant prostate cancer, or metastatic castration-resistant prostate cancer. In some embodiments, the prostate cancer is a newly diagnosed high risk metastatic hormone sensitive prostate cancer. In some embodiments, the prostate cancer is a metastatic CRPC (mCRPC), wherein the subject is asymptomatic or mildly symptomatic after failure of androgen deprivation therapy in whom chemotherapy is not yet clinically indicated. In some embodiments, the prostate cancer is a metastatic CRPC (mCRPC), wherein the subject's disease has progressed on or after a taxane-based chemotherapy regimen, such as docetaxel-based or cabazitaxel-based chemotherapy regimen. In some embodiments, the prostate cancer is a refractory prostate cancer. As used herein and unless otherwise specified, the phrase "refractory prostate cancer" means prostate cancer that is not responding to an anti-cancer treatment or prostate cancer that is not responding sufficiently to an anti-cancer treatment. Refractory prostate cancer can also include recurring or relapsing prostate cancer. As used herein and unless otherwise specified, the phrase "relapsing prostate cancer" means prostate cancer that was at one time responsive to an anti-cancer treatment but has become no longer responsive to such treatment or is no longer responding sufficiently to such treatment. As used herein and unless otherwise specified, the phrase "recurring (or recurrent) prostate cancer" means prostate cancer that has returned after a patient has been earlier diagnosed with prostate cancer, undergone treatment or had been previously diagnosed as cancer-free.

In some embodiments, the methods herein can also be used for treating breast cancer. Breast cancer suitable to be treated with the methods herein is not particularly limited. For example, in some embodiments, the breast cancer can be molecular apocrine HER2-negative breast cancer, metastatic breast cancer, such as ER+ metastatic breast cancer, ER+ and HER2 negative breast cancer, AR+ triple negative breast cancer, etc.

In some embodiments, a disease or disorder is associated with 21-hydroxylase deficiency can also be treated with the methods herein.

In some embodiments, the methods herein can be used for treating subjects, such as non-castrated subjects, having a cancer, such as prostate cancer, breast cancer, adrenal cancer, leukemia, lymphoma, myeloma, Waldenstöm's macroglobulinemia, monoclonal gammopathy, benign monoclonal gammopathy, heavy chain disease, bone and connective tissue sarcoma, brain tumors, thyroid cancer, pancreatic cancer, pituitary cancer, eye cancer, vaginal cancer, vulvar cancer, cervical cancer, uterine cancer, ovarian cancer, esophageal cancer, stomach cancer, colon cancer, rectal cancer, liver cancer, gallbladder cancer, cholangiocarcinoma, lung cancer, testicular cancer, penal cancer, oral cancer, skin cancer, kidney cancers, Wilms' tumor and bladder cancer.

In some embodiments, the method herein can include treating the subject with one or more additional therapies. For example, in some embodiments, the subject is further treated a radiation therapy. In some embodiments, the method is for treating prostate cancer and includes a combination therapy, which further comprises administering to the subject one or more additional therapies, e.g., as described herein under the section titled Combination Treatment for Prostate Cancer as described herein below. Non-limiting examples of useful additional therapies also include any of those described in [28]-[39] in the Summary section herein.

Subjects suitable to be treated by the methods herein are not particularly limited, which include subjects at various stages of diseases or treatments and other characteristics. For example, in any of the embodiments described herein, unless specified or otherwise contrary, the subject can be a non-castrated subject. In some embodiments, the methods herein can also administer the pharmaceutical composition comprising the abiraterone prodrug to the subject without regard to whether the subject is castrated or not. In some embodiments, the subject has not undergone a prostatectomy. In some embodiments, the subject can be characterized as suffering from hepatic impairment, such as moderate to severe hepatic impairment (Child-Pugh Class B or C), prior to the administering of the abiraterone prodrug. In some embodiments, the subject can be characterized as being sensitive to or otherwise intolerant with a gonadotropin-releasing hormone antagonist and/or agonist. In some embodiments, the subject can be characterized as chemotherapy naïve or hormone therapy naïve prior to being administered the pharmaceutical composition herein. However, in some embodiments, the subject can also be treated with chemotherapy or hormone therapy prior to being administered the pharmaceutical composition herein. For example, in some embodiments, the subject can have a disease or disorder (e.g., prostate cancer) that has progressed on or after the chemotherapy and/or hormone therapy, such as a taxane-based chemotherapy regimen, for example, docetaxel-based or cabazitaxel-based chemotherapy. In any of the embodiments described herein, unless directly contradictory, the subject can be a human subject.

Suitable pharmaceutical compositions and abiraterone prodrugs for the methods herein are not particularly limited and include any of those described herein, such as any of the abiraterone decanoate formulations described herein, e.g., any of those described in the Summary section, such as [71]-[81] and [98] of the Summary section herein, and any of the abiraterone prodrugs and abiraterone prodrug formulations described in U.S. Pat. No. 10,792,292 B2, and U.S. Provisional Application No. 63/073,502. Typically, the pharmaceutical composition suitable for the methods herein is a long-acting parenteral formulation comprising the abiraterone prodrug. In some embodiments, the long-acting parenteral formulation can be formulated to deliver a therapeutically effective plasma levels of abiraterone over an extended period of time (e.g., at least 1 week, e.g., at least two weeks, at least 3 weeks, at least 4 weeks, and up to six or eight weeks or more, etc.) in the subject, following a single administration. In some embodiments, the therapeutically effective plasma concentration of abiraterone can be a concentration of at least 1 ng/ml, e.g., at least 2 ng/ml, at least 4 ng/ml, at least 8 ng/ml. In some embodiments, the therapeutically effective blood plasma concentration of abiraterone can also be about 0.5 ng/ml or higher. In some embodiments, the therapeutically effective blood plasma concentration of abiraterone can also be about 0.1 ng/ml or higher. In some embodiments, the pharmaceutical composition can be formulated to be administered to the subject to provide a PK profile described herein, such as (a) a blood plasma concentration of abiraterone above 1.0 ng/ml for a period of at least two weeks from a single dose; (b) a single dose or steady state $C_{max}$ of abiraterone between about 5 ng/ml and about 300 ng/ml; or (c) both (a) and (b).

Routes of administration and dosing regimen for the methods herein are also not particularly limited and include any of those described herein. Typically, the pharmaceutical composition can be administered to the subject through an intramuscular injection, intradermal injection, or subcutaneous injection. For example, in some specific embodiments, the pharmaceutical composition is administered to the subject through an intramuscular injection. The parenteral administration herein can in some embodiments be advantageous. For example, in some embodiments, the parenteral administering can be carried out without regard to whether the subject has food, thus, in some embodiments, the abiraterone prodrugs or abiraterone prodrug formulations of the present disclosure can be administered to the subject with or without food. In other words, the fed or fasted status of the subject is not important. This removes the restriction associated with the currently marketed Zytiga® formulation, which states that the medication "must be taken on an empty stomach with water at least 1 hour before or 2 hours after a meal." Therefore, among other advantages, the methods herein can improve patient compliance.

Dosing amounts and frequencies for the methods herein are also not particularly limited and include any of those described herein. Generally, the pharmaceutical composition is administered to the subject once a week or once in more than a week. For example, in some embodiments, the methods herein comprise administering the abiraterone prodrug or abiraterone prodrug formulation herein at a dosing frequency ranging from once a week to once every few months. In some embodiments, the pharmaceutical composition is administered to the subject once a month or once in more than a month, such as once every two months or once every three months. As described herein, a single administration of a representative abiraterone prodrug, abiraterone decanoate, at a dose of 10 mg/kg, 30 mg/kg, or 100 mg/kg, provided a sustained CYP17A1 inhibition for up to 70 days or more in chemically castrated monkeys. This result supports the less frequent dosing schedules described herein. In some particular embodiments, the methods herein can comprise administering the abiraterone prodrug or abiraterone prodrug formulation herein in a dosing frequency ranging from once a month to once every few months, such as once every month, once every two months, once every three months, or even less frequent dosing. The dosing amounts of the abiraterone prodrugs herein (e.g., abiraterone decanoate) for each administration can vary, typically ranging from 0.5 mg/kg to 200 mg/kg, such as about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of a subject. In some embodiments, the administering can provide any of the pharmacokinetic profile described herein, for example, (a) a blood plasma concentration of abiraterone above 1.0 ng/ml for a period of at least two weeks (e.g., up to 10 weeks or beyond) from a single dose; (b) a single dose or steady state $C_{max}$ of abiraterone between about 5 ng/ml and about 300 ng/ml; or (c) both (a) and (b). In some embodiments, the administering can also provide a concentration of abiraterone in a tissue of the subject at least 10 times higher than the blood plasma concentration of abiraterone at 7 days post administration (i.e., at 168 hours from the time of administration), wherein the tissue is selected from liver, lung, testes, inguinal lymph, iliac lymph, adrenal, and prostate.

In some embodiments, in particular in the methods of treating prostate cancer herein, the dosing amount and frequency of the abiraterone prodrugs herein (e.g., abiraterone decanoate) can be adjusted such that the administering provides an effective amount of abiraterone to reduce the serum testosterone level to about 50 ng/dL or below (e.g., about 40 ng/dL or below, about 30 ng/dL or below, about 20 ng/dL or below, about 10 ng/dL or below, etc.) in a non-castrated subject or about 1 ng/dL or below in a castrated subject (e.g., a subject chemically castrated with a GnRH agonist and/or antagonist), within 15 days (e.g., within 7 days, between 7-15 days, etc.) of the first administration of the abiraterone prodrug. For example, in some embodiments, the administering provides an effective amount of abiraterone to reduce the serum testosterone level to about 50 ng/dL or below (e.g., about 40 ng/dL or below, about 30 ng/dL or below, about 20 ng/dL or below, about 10 ng/dL or below, etc.) in a non-castrated subject or about 1 ng/dL or below in a castrated subject, when measured on day 15 after the first administration of the abiraterone prodrug. In some embodiments, the administering provides an effective amount of abiraterone to achieve a sustained reduction of serum testosterone level, such as achieving and maintaining the serum testosterone level at about 50 ng/dL or below (e.g., about 40 ng/dL or below, about 30 ng/dL or below, about 20 ng/dL or below, about 10 ng/dL or below, etc.) in a non-castrated subject or about 1 ng/dL or below in a castrated subject, within 15 days (e.g., within 7 days, between 7-15 days, etc.) of the first administration of the abiraterone prodrug. In some embodiments, the dosing amount and frequency of the abiraterone prodrugs herein (e.g., abiraterone decanoate) can be adjusted such that the administering provides an effective amount of abiraterone to reduce 50% or more, preferably, 75% or more of serum testosterone level from baseline within 15 days (e.g., within 7 days, between 7-15 days, etc.) of the first administration of the abiraterone prodrug. For example, in some embodiments, the administering provides an effective amount of abiraterone to reduce 50% or more, preferably, 75% or more of serum testosterone level from baseline when measured on day 15 after the first administration of the abiraterone prodrug. In some embodiments, the administering provides an effective amount of abiraterone to achieve a sustained reduction of serum testosterone level, such as by 50% or more, 75% or more, from baseline within 15 days (e.g., within 7 days, between 7-15 days, etc.) of the first administration of the abiraterone prodrug. To be clear, the phrase "sustained reduction of serum testosterone level" should be understood as referring to that the serum testosterone levels remain at a reduced level, such as at about 50 ng/dL or below in a non-castrated subject or about 1 ng/dL or below in a castrated subject, or 50% or less compared to baseline, for a sustained period of time, which can be 1 day or longer, 3 days or longer, 7 days or longer, and up to a month, or several months. As exemplified herein, the serum testosterone levels can be reduced in a dose-dependent fashion and at a high dose of 200 mg/kg/dose, serum testosterone levels can be reduced by more than 75% for at least 85 days.

Methods of Reducing Steroid Hormone Levels

Some embodiments of the present disclosure are directed to methods of reducing serum steroid hormone level in a subject in need thereof.

In some particular embodiments, the present disclosure provides a method of reducing serum testosterone level in a subject in need thereof, the method comprising parenterally administering to the subject a pharmaceutical composition comprising an abiraterone prodrug (e.g., an abiraterone lipophilic ester). Typically, in particular when the subject is characterized as having prostate cancer, the administering provides an effective amount of abiraterone to reduce the serum testosterone level to about 50 ng/dL or below (e.g., about 40 ng/dL or below, about 30 ng/dL or below, about 20 ng/dL or below, about 10 ng/dL or below, etc.) in a non-castrated subject or about 1 ng/dL or below in a castrated subject, within 15 days (e.g., within 7 days, between 7-15 days, etc.) of the first administration of the abiraterone prodrug. For example, in some embodiments, the administering provides an effective amount of abiraterone to reduce the serum testosterone level to about 50 ng/dL or below (e.g., about 40 ng/dL or below, about 30 ng/dL or below, about 20 ng/dL or below, about 10 ng/dL or below, etc.) in a non-castrated subject or about 1 ng/dL or below in a castrated subject, when measured on day 15 after the first administration of the abiraterone prodrug. In some embodiments, the administering provides an effective amount of abiraterone to achieve a sustained reduction of serum testosterone level, such as achieving and maintaining the serum testosterone level at about 50 ng/dL or below (e.g., about 40 ng/dL or below, about 30 ng/dL or below, about 20 ng/dL or below, about 10 ng/dL or below, etc.) in a non-castrated subject or about 1 ng/dL or below in a castrated subject, within 15 days (e.g., within 7 days, between 7-15 days, etc.) of the first administration of the abiraterone prodrug. Typically, the administering provides an effective amount of abiraterone to reduce 50% or more, preferably, 75% or more of serum testosterone level from baseline within 15 days (e.g., within 7 days, between 7-15 days, etc.) of the first administration of the abiraterone prodrug. For example, in some embodiments, the administering provides an effective amount of abiraterone to reduce 50% or more, preferably, 75% or more of serum testosterone level from baseline when measured on day 15 after the first administration of the abiraterone prodrug. In some embodiments, the administering provides an effective amount of abiraterone to achieve a sustained reduction of serum testosterone level, such as by 50% or more, 75% or more, from baseline within 15 days (e.g., within 7 days, between 7-15 days, etc.) of the first administration of the abiraterone prodrug.

Subjects suitable to be treated with the methods herein for reducing serum testosterone levels are not particularly limited. For example, in some embodiments, the subject can be a non-castrated subject. In some embodiments, the methods herein can also administer the pharmaceutical composition comprising the abiraterone prodrug to the subject without regard to whether the subject is castrated or not. Typically, in the methods herein, another drug that is effective in lowering serum and/or gonadal testosterone level, is not administered to the subject concurrently with the administration of the abiraterone prodrug, during the treatment with the abiraterone prodrug, or otherwise interfering with the treatment with the abiraterone prodrug. For example, in some embodiment, the subject is not treated with a gonadal testosterone suppressing drug, other than the administered abiraterone prodrug, in an amount effective to reduce serum testosterone level in the subject. In some embodiment, the subject is not treated with a gonadotropin-releasing hormone antagonist and/or agonist in an amount effective to reduce serum testosterone level in the subject. In some embodiment, the subject is not treated with any gonadal testosterone suppressing drug other than the administered abiraterone prodrug. In some embodiments, the subject is not treated with any gonadotropin-releasing hormone antagonist and/or agonist. In some embodiments, the subject is not treated with a drug selected from buserelin, leuprolide, deslorelin, fertirelin, histrelin, gonadorelin, lecirelin, goserelin, nafarelin, peforelin and triptorelin. In some embodiments, the subject is not treated with a drug selected from abarelix, cetrorelix, degarelix, ganirelix, elagolix, linzagolixa, and relugolix. In some embodiments, the subject can be sensitive to or otherwise intolerant with a gonadotropin-releasing hormone antagonist and/or agonist.

The subject in need of reduction of testosterone typically suffers from one or more diseases or disorders mediated or associated with androgens. For example, in some embodiments, the subject is characterized as having a sex hormone dependent cancer or androgen receptor driven cancer, e.g., any of those described herein. In some embodiments, the subject is characterized as having androgen receptor positive salivary duct carcinoma, or androgen receptor positive glioblastoma multiforme. In some embodiments, the subject is characterized as having prostate cancer (e.g., any of those described herein). For example, in some embodiments, the prostate cancer is a localized prostate cancer, e.g., a high risk localized prostate cancer. In some embodiments, the subject has not undergone a prostatectomy. In some embodiments, the subject is further treated with a radiation therapy.

Suitable pharmaceutical compositions and abiraterone prodrugs for the methods herein for reducing serum testosterone level are not particularly limited and include any of those described herein, such as any of the abiraterone decanoate formulations described herein, e.g., any of those described in the Summary section, such as [71]-[81] and [98] of the Summary section herein, and any of the abiraterone prodrugs and abiraterone prodrug formulations described in U.S. Pat. No. 10,792,292 B2, and U.S. Provisional Application No. 63/073,502. Typically, the pharmaceutical composition is a long-acting parenteral formulation comprising the abiraterone prodrug. In some embodiments, the long-acting parenteral formulation can be formulated to deliver effective plasma levels of abiraterone over an extended period of time (e.g., at least 1 week, e.g., at least two weeks, at least 3 weeks, at least 4 weeks, and up to six or eight weeks or more, etc.) to reduce serum testosterone levels (e.g., to about 50 ng/dL or below in a non-castrated subject or about 1 ng/dL or below in a castrated subject, or by 50% or more compared to baseline) in the subject, following a single administration. In some embodiments, the effective plasma concentration of abiraterone can be a concentration of at least 1 ng/ml, e.g., at least 2 ng/ml, at least 4 ng/ml, at least 8 ng/ml. In some embodiments, the effective blood plasma concentration of abiraterone can also be about 0.5 ng/ml or higher. In some embodiments, the effective blood plasma concentration of abiraterone can also be about 0.1 ng/ml or higher. In some embodiments, the pharmaceutical composition can be formulated to be administered to the subject to provide (a) a blood plasma concentration of abiraterone above 1.0 ng/ml for a period of at least two weeks from a single dose; (b) a single dose or steady state $C_{max}$ of abiraterone between about 5 ng/ml and about 300 ng/ml; or (c) both (a) and (b).

Routes of administration and dosing regimen for the methods herein are also not particularly limited and include any of those described herein. Typically, the pharmaceutical composition can be administered to the subject through an intramuscular injection, intradermal injection, or subcutaneous injection. For example, in some specific embodiments, the pharmaceutical composition is administered to the subject through an intramuscular injection. Generally, the pharmaceutical composition is administered to the subject once a week or once in more than a week. For example, in some embodiments, the pharmaceutical composition is administered to the subject once a month or once in more than a month, such as once every two months or once every three months.

In some embodiments, the present disclosure also provides a method of inhibiting CYP17A1 activity such as inhibiting 17α-hydroxylase activity and 17,20-lyase activity, the method comprising administering to a subject in need thereof any of the abiraterone prodrugs or abiraterone prodrug formulations of the present disclosure. In some embodiments, the subject is a non-castrated subject. In some embodiments, the subject suffers from a sex hormone-dependent benign or malignant disorder, e.g., as described herein. In some embodiments, the subject suffers from a syndrome due to androgen excess and/or a syndrome due to glucocorticoid excess such as hypercortisolemia, e.g., as described herein. In some embodiments, the subject suffers from a sex hormone dependent cancer or androgen receptor driven cancer described herein. Suitable pharmaceutical compositions, subjects, dosing regimen, and routes of administrations for the method include any of those described herein in any combination, such as any of those described in connection with the methods shown in the Summary section herein.

In some embodiments, the present disclosure provides a method of reducing the level of glucocorticoids (e.g., cortisol) in a subject in need thereof, the method comprising administering to the subject any of the abiraterone prodrugs or abiraterone prodrug formulations of the present disclosure. In some embodiments, the subject is a non-castrated subject. In some embodiments, the subject suffers from a syndrome due to glucocorticoid excess such as hypercortisolemia as described herein, such as Cushing's syndrome or Cushing's disease. Suitable pharmaceutical compositions, subjects, dosing regimen, and routes of administrations for the method include any of those described herein in any combination, such as any of those described in connection with the methods shown in the Summary section herein.

In some embodiments, the present disclosure provides a method of reducing the level of androgens (e.g., testosterone and/or dihydrotestosterone) and/or estrogens in a subject in need thereof, the method comprising administering to the subject any of the abiraterone prodrugs or abiraterone prodrug formulations of the present disclosure. In some embodiments, the subject is a non-castrated subject. In some embodiments, the subject suffers from an androgen receptor driven cancer. In some embodiments, the subject suffers from a syndrome due to androgen excess, such as congenital adrenal hyperplasia (e.g., classical or nonclassical congenital adrenal hyperplasia), endometriosis, polycystic ovary syndrome precocious puberty, hirsutism, etc. In some embodiments, the subject suffers from an androgen and/or estrogen associated cancer, such as prostate cancer or breast cancer. In some embodiments, the subject suffers from a sex hormone dependent cancer described herein. Suitable pharmaceutical compositions, subjects, dosing regimen, and routes of administrations for the method include any of those described herein in any combination, such as any of those described in connection with the methods shown in the Summary section herein.

Abiraterone Prodrugs and Formulations

Various abiraterone prodrugs and abiraterone prodrug formulations are also provided herein, which can be used for the methods herein. For example, in some embodiments, the abiraterone drug can be an abiraterone lipophilic ester, such as an acetate, a propionate, a butanoate, a (vaterate) pentanoate, an isocaproate, a buciclate, a cyclohexanecarboxylate, a phenyl propionate, caproate (hexanoate), an enanthate (heptanoate), a cypionate, an octanoate, a nonanoate, a decanoate, an undecanoate, a dodecanoate, a tridecanoate, a tetradecanoate, a pentadecanoates, or a hexadecanoate of abiraterone. Other suitable abiraterone prodrugs include any of those described in U.S. Pat. No. 10,792,292 B2 and U.S. Provisional Application No. 63/073,502, the content of each of which is herein incorporated by reference in its entirety.

In any of the embodiments described herein, unless specified or otherwise contrary from context, the abiraterone prodrug can be abiraterone decanoate, or a pharmaceutically acceptable salt thereof,

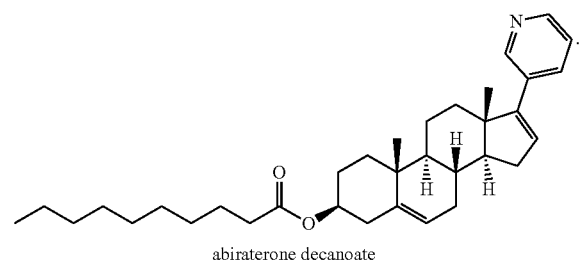

abiraterone decanoate

Typically, the pharmaceutical composition (or alternatively referred to herein as abiraterone prodrug formulation) comprising the abiraterone prodrug is formulated for parenteral administration. For example, in some embodiments, the pharmaceutical composition can be formulated for intramuscular injection, intradermal injection, or subcutaneous injection.

The pharmaceutical composition is generally a non-aqueous formulation, for example, an oil-based formulation, and include a non-aqueous pharmaceutically acceptable carrier (e.g., described herein). The pharmaceutical composition typically comprises the abiraterone prodrug and a pharmaceutically acceptable carrier. The pharmaceutically acceptable carrier is not particularly limited. For example, in some embodiments, the pharmaceutically acceptable carrier comprises a pharmaceutically acceptable oil, such as a pharmaceutically acceptable oil for injection, including oils of vegetable origin or synthetic mono- or diglycerides of fatty acids. In some embodiments, the pharmaceutically acceptable oil can be nature oil, synthetic oil, or semi-synthetic oil, such as fractionated coconut oil and medium-chain triglycerides, such as those sold under the trademark Miglyol. In some embodiments, the pharmaceutically acceptable carrier comprises a triglyceride derived from fatty acids. In some embodiments, the pharmaceutically acceptable carrier comprises a triglyceride derived from long and/or medium chain fatty acids, which can be independently poly-unsaturated, mono-unsaturated, or saturated. As understood by those skilled in the art, medium chain fatty acids typically include 6-12 carbons, such as caprioic acid, caprylic acid, capric acid, lauric acid, etc.; short chain fatty acids typically have fewer than 6 carbons, whereas long-chain fatty acids typically include 13-21 carbons. In some embodiments, the pharmaceutically acceptable carrier comprises a pharmaceutically acceptable oil, which can be selected from vegetable oil, castor oil, corn oil, sesame oil, cottonseed oil, peanut oil (arachis oil), poppy seed oil, tea seed oil, and soybean oil. In some specific embodiments, the pharmaceutically acceptable carrier can comprise corn oil, which includes a triglyceride, in which the fatty acid constituents are primarily linoleic acid, oleic acid, palmitic acid, and stearic acid.

In some embodiments, in addition to the pharmaceutically acceptable oil, the pharmaceutically acceptable carrier can further comprise a pharmaceutically acceptable solvent (or co-solvent if the oil is counted as a solvent), such as an alcohol, ester, acid, etc. In some embodiments, the pharmaceutically acceptable solvent can include benzyl alcohol, benzyl benzoate, ethanol, glycerol, polyethylene glycol, polysorbate 80, acetic acid, and/or ethyl acetate. In some embodiments, the pharmaceutically acceptable solvent can be benzyl alcohol and/or benzyl benzoate. In some embodiments, the pharmaceutically acceptable solvent can be benzyl alcohol. In some embodiments, the pharmaceutically acceptable solvent can be a combination of benzyl alcohol and benzyl benzoate. The solubility of abiraterone prodrugs such as abiraterone decanoate in a pharmaceutically acceptable oil can be significantly enhanced by a combination of benzyl alcohol and benzyl benzoate.

In some embodiments, the pharmaceutically acceptable carrier can comprise the pharmaceutically acceptable oil and the further pharmaceutically acceptable solvent, wherein the pharmaceutically acceptable oil is selected from vegetable oil, castor oil, corn oil, sesame oil, cottonseed oil, peanut oil, poppy seed oil, tea seed oil, and soybean oil, and the further pharmaceutically acceptable solvent comprises benzyl alcohol, benzyl benzoate, or a combination thereof. In some embodiments, the pharmaceutically acceptable carrier comprises corn oil, benzyl alcohol, and benzyl benzoate.

Exemplary Formulations Comprising Abiraterone Decanoate

In some specific embodiments, the pharmaceutical composition comprises abiraterone decanoate having the formula of:

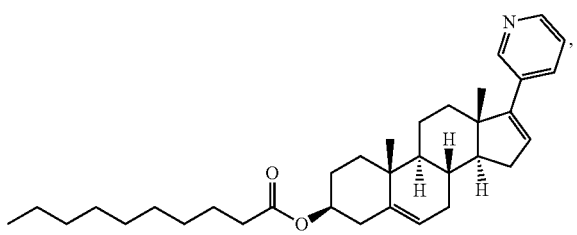

or a pharmaceutically acceptable salt thereof, and a pharmaceutically acceptable carrier. The abiraterone decanoate is typically present in the pharmaceutical composition in its basic form and should be understood as such unless otherwise obvious to the contrary from context. In some embodiments, the abiraterone decanoate can also be in a substantially pure form described herein. For example, the pharmaceutical composition can be prepared from mixing the substantially pure abiraterone decanoate with the pharmaceutically acceptable carrier and optional other ingredients. In some specific embodiments, the substantially pure abiraterone decanoate is in a crystalline form described herein, preferably, crystalline Form A, and the pharmaceutical composition can be prepared from mixing (e.g., dissolving, suspending, or otherwise forming a mixture) the crystalline form (e.g., Form A) with the pharmaceutically acceptable carrier and optional other ingredients.

Abiraterone decanoate is typically prepared in a high purity form, e.g., suitable for pharmaceutical use. In some embodiments, the present disclosure provides abiraterone decanoate in a substantially pure form, such as having a purity of greater than 80%, preferably greater than 90% (e.g., greater than 95%, greater than 97%, greater than 98%, greater than 99%, greater than 99.5%), by weight, by HPLC area, or both. In some embodiments, the abiraterone decanoate can be characterized by a purity by weight and/or by HPLC area of about 95%, about 97%, about 99%, about 99.5%, about 99.9%, or any ranges between the specified values. For example, in some embodiments, the abiraterone decanoate can be characterized by a purity by weight of about 95%, about 97%, about 99%, about 99.5%, about 99.9%, or any ranges between the specified values. In some embodiments, the abiraterone decanoate can also be characterized as having a low palladium content, such as less than 150 ppm, less than 100 ppm, less than 50 ppm, or less than 10 ppm. In some embodiments, the abiraterone decanoate conforms to the specification shown in Table D herein (see Example 1B). Exemplary procedures for preparing the substantially pure abiraterone decanoate are shown in the Examples section. HPLC methods suitable for measuring the purity of the abiraterone decanoate are also described in the Examples section. The substantially pure abiraterone decanoate can be in a solid form (e.g., a crystalline form described herein, preferably, Form A, amorphous form, or a combination thereof) or in a solution, suspension, or another form. For the avoidance of doubt, an abiraterone prodrug formulation comprising the substantially pure abiraterone decanoate herein and one or more other ingredients should be understood as a mixture of the substantially pure abiraterone decanoate herein and the one or more other ingredients, for example, such formulation can be obtained directly or indirectly from mixing (e.g., dissolving, suspending, or otherwise forming a mixture) the substantially pure abiraterone decanoate with the one or more other ingredients, such as pharmaceutically acceptable oil, solvent, etc.

In some specific embodiments, the pharmaceutical composition comprises abiraterone decanoate, a pharmaceutically acceptable oil (e.g., described herein), benzyl alcohol, and benzyl benzoate. In some embodiments, the pharmaceutically acceptable oil is corn oil. In some embodiments, the benzyl alcohol is present in an amount of about 5-10% by volume, the benzyl benzoate is present in an amount of about 10-20% by volume, and corn oil is present in an amount of about 70-85% by volume, with the combined volume of benzyl alcohol, benzyl benzoate, and corn oil being 100%.

The pharmaceutical composition typically includes abiraterone decanoate at a concentration of about 25 mg/ml to about 500 mg/ml. In some embodiments, the abiraterone decanoate can be present in a concentration of about 50 mg/ml, about 100 mg/ml, about 150 mg/ml, about 200 mg/ml, about 250 mg/ml, about 300 mg/ml, about 350 mg/ml, about 400 mg/ml, about 500 mg/ml, or any ranges between the recited values. In some embodiments, the abiraterone decanoate can be present in a concentration of about 100 mg/ml to about 300 mg/ml, such as about 150 mg/ml to about 250 mg/ml, about 200 mg/ml to about 300 mg/ml, etc.

In some embodiments, the pharmaceutical composition can comprise abiraterone decanoate in its basic form, corn oil, benzyl alcohol, and benzyl benzoate. In some embodiments, the abiraterone decanoate is present in the pharmaceutical composition in an amount of about 50-300 mg/mL. In some embodiments, the benzyl alcohol is in an amount of about 50-150 mg/mL. In some embodiments, the benzyl benzoate is in an amount of about 100-300 mg/mL. In some embodiments, the pharmaceutical composition can comprise, for each milliliter, (a) abiraterone decanoate in its basic form, in an amount of about 100 mg to about 300 mg (e.g., about 100 mg, about 120 mg, about 150 mg, about 180 mg, about 200 mg or about 250 mg); (b) benzyl alcohol in an amount of about 50 mg to about 150 mg (e.g., about 75 mg, about 100 mg, or about 125 mg); (c) benzyl benzoate in an amount of about 100 mg to about 300 mg (e.g., about 100 mg, about 150 mg, about 200 mg, or about 250 mg); and (d) corn oil, q.s. to 1 milliliter. In some embodiments, the weight ratio of benzyl alcohol to benzyl benzoate in the pharmaceutical composition ranges from about 2:1 to about 1:5 (e.g., about 1:1 to 1:3, such as about 1:2).

Exemplary Formulations Comprising Substantially Pure Abiraterone Decanoate

In some specific embodiments, the pharmaceutical composition comprises a substantially pure abiraterone decanoate, which has the following formula:

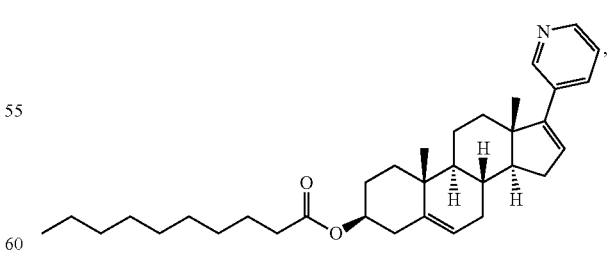

or a pharmaceutically acceptable salt thereof, which is dispersed or dissolved in a pharmaceutically acceptable carrier. In some embodiments, the pharmaceutical composition comprises the substantially pure abiraterone decanoate in its basic form, which is dispersed or dissolved in the pharmaceutically acceptable carrier. In some embodiments, the substantially pure abiraterone decanoate has a purity by weight of at least 95%, preferably, at least 98%, such as about 98.5%, about 99%, about 99.5%, or higher. In some embodiments, the substantially pure abiraterone decanoate can be characterized by a purity by weight and/or by HPLC area of about 95%, about 97%, about 99%, about 99.5%, about 99.9%, or any ranges between the specified values. In some embodiments, the substantially pure abiraterone decanoate can be characterized by a purity by weight of about 95%, about 97%, about 99%, about 99.5%, about 99.9%, or any ranges between the specified values. In some embodiments, the substantially pure abiraterone decanoate can also be characterized as having a low palladium content, such as less than 150 ppm, less than 100 ppm, less than 50 ppm, or less than 10 ppm. Abiraterone is typically synthesized with a step of palladium catalyzed cross-coupling reaction. As such, available abiraterone generally has an undesired level of palladium residue, which may be carried into crude abiraterone decanoate product. As described herein, the present disclosure shows that it is possible to reduce the palladium content of abiraterone decanoate to less than 5 ppm, particularly, 3.7 ppm in Example 1B, by using a process of recrystallization with acetone and water as solvents and activated carbon. In some embodiments, the substantially pure abiraterone decanoate conforms to the specification shown in Table D herein (see Example 1B). In some embodiments, the substantially pure abiraterone decanoate comprises an impurity derived from ethyl prasterone. For example, in some embodiments, the substantially pure abiraterone decanoate comprises ethyl prasterone decanoate having the formula:

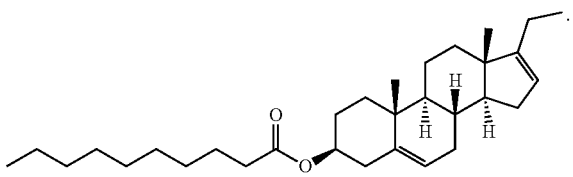

Typically, when present, the substantially pure abiraterone decanoate comprises the ethyl prasterone decanoate in an amount of less than 2% by weight, such as less than 1% by weight, less than 0.5% by weight, such as less than 0.3%, less than 0.2%, or less than 0.1% by weight. The amount of ethyl prasterone decanoate can be readily determined by HPLC methods, such as those descried herein. In some embodiments, the substantially pure abiraterone decanoate can also contain no detectable amount of ethyl prasterone decanoate. Abiraterone starting material is readily available from commercial sources in high purity. Abiraterone starting material obtained from a process using

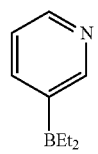

in a cross-coupling reaction to introduce the 3-pyridyl group in abiraterone may contain small amount of impurities which can ultimately be converted into ethyl prasterone. In some embodiments, the substantially pure abiraterone decanoate can be prepared from an abiraterone starting material which has no detectable amount of ethyl prasterone, e.g., those obtained from processes that do not include a cross-coupling with

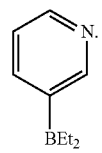

Figure 2A:
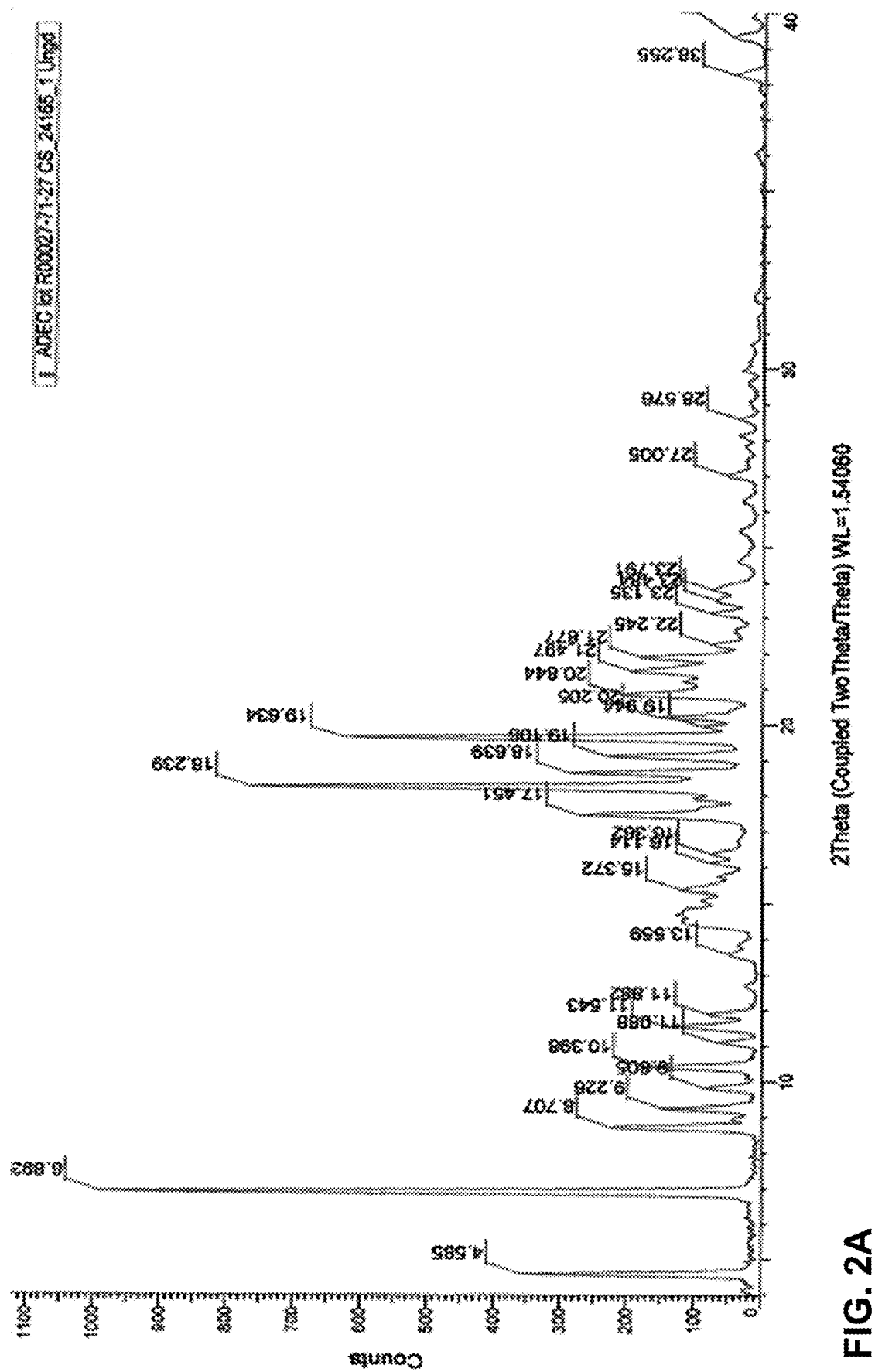
FIG. 2A presents a representative X-ray Powder Diffraction (XRPD) spectrum of the abiraterone decanoate (alternatively abbreviated herein as "AbiDec") solid form prepared in Example 1A, designated as Form A.
Figure 2B:
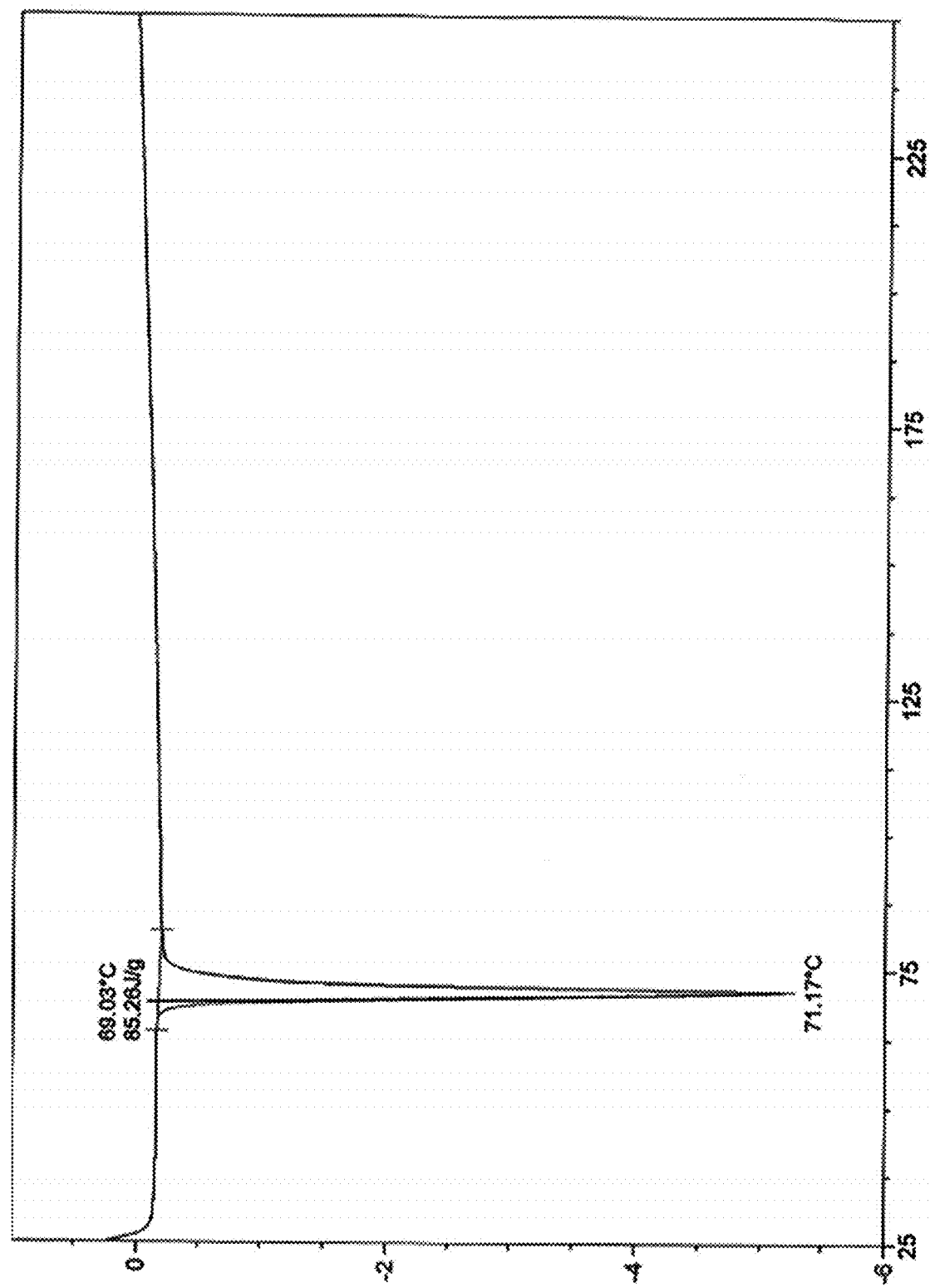
FIG. 2B shows a representative Differential Scanning Calorimetry (DSC) spectrum of the abiraterone decanoate solid form prepared in Example 1A, designated as Form A.

The substantially pure abiraterone decanoate can be in a solid form, such as a crystalline form as described herein. For example, in some embodiments, the substantially pure abiraterone decanoate can be in a crystalline Form A, which can be characterized by an X-Ray Power Diffraction (XRPD) spectrum having one or more (e.g., 1, 2, 3, 4, 5, 6, 7, 8, or 9) of the following peaks: 4.6, 6.9, 8.7, 17.5, 18.3, 18.6, 19.1, 19.6, and 20.8, degrees 2 theta, ±0.2°; a Differential Scanning Calorimetry (DSC) pattern having an endothermic peak with an onset temperature at about 69.0° C.; or a combination thereof. In some embodiments, the crystalline Form A can be characterized by an XRPD spectrum substantially the same as shown in FIG. 2A, for example, the XRPD spectrum shows peaks at the respective diffraction angels (degrees 2 theta, ±0.2°) corresponding to the peaks as shown in FIG. 2A, regardless of their relative intensities. In some embodiments, the crystalline Form A can be characterized by a DSC spectrum substantially the same as shown in FIG. 2B.

In some embodiments, the present disclosure also provides a method of preparing a crystalline Form A of abiraterone decanoate. In some embodiments, the method can include recrystallizing abiraterone decanoate in a suitable solvent, such as acetone and water. In a typical method, the abiraterone decanoate can be first dissolved in a first solvent, such as acetone, at room temperature or under heat (such as about 40° C.), to form a solution; the solution can then be cooled to form a suspension; and optionally, this can then be followed by dilution of the suspension with a second solvent (typically an antisolvent in which abiraterone decanoate has a low solubility), such as water, and stirring for a period of time (such as about 12 hours) to form the crystalline form. The amount of solvent, concentration, etc. can be adjusted by those skilled in the art in view of this disclosure. An exemplary procedure is also shown in Example 1A.

In some embodiments, the present disclosure also provides a method of preparing crystalline Form A of abiraterone decanoate, the method comprising: a) dissolving the abiraterone decanoate in a first solvent to form a first solution; b) adding activated carbon to the first solution; c) removing the activated carbon to form a second solution; and d) crystallizing the abiraterone decanoate from the second solution to form the crystalline Form A of abiraterone decanoate, wherein abiraterone decanoate has the following structure:

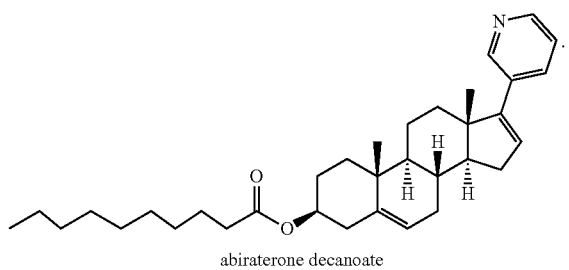

abiraterone decanoate

Typically, the crystallizing step d) comprises cooling the second solution, reducing the amount of the first solvent, and/or adding an antisolvent in which abiraterone decanoate has a lower solubility than in the first solvent. For example, in some embodiments, the crystallizing step d) comprises cooling the second solution, e.g., from about 40° C. to room temperature. In some embodiments, the crystallizing step d) comprises cooling the second solution and reducing the amount of the first solvent. In some embodiments, the crystallizing step d) comprises reducing the amount of the first solvent and adding an antisolvent in which abiraterone decanoate has a lower solubility than in the first solvent. In some embodiments, the crystallizing step d) comprises cooling the second solution, reducing the amount of the first solvent, and adding an antisolvent in which abiraterone decanoate has a lower solubility than in the first solvent.

Various solvents can be suitable as the first solvent. For example, in some embodiments, the first solvent is selected from acetone, dioxane, 1-propanol, methyl tert-butyl ether, isopropyl ether, t-butanol, chloroform, ethyl acetate, nitromethane, dimethyl acetamide, tetrahydrofuran, dimethyl formamide, diethyl ether, 2-butanol, isopropyl acetate, ethanol, methanol, toluene, acetonitrile, heptane, 2-propanol, 2-butanone, 2-methyl tetrahydrofuran, a combination of methanol and tetrahydrofuran, a combination of methanol and chloroform, a combination of acetonitrile and t-butanol, and a combination of acetonitrile and 2-propanol. In some embodiments, the first solvent is selected from selected from ethyl acetate, ter-butanol, chloroform, isopropyl ether, tetrahydrofuran, 2-propanol, acetonitrile, 2-butanone, heptane, toluene, and methanol, wherein the crystallizing step d) comprises cooling the second solution and/or reducing the amount of the first solvent.

In some preferred embodiments, the first solvent can be acetone.

In some preferred embodiments, the antisolvent can be water.

In some preferred embodiments, the crystallizing step d) comprises adding an antisolvent in which abiraterone decanoate has a lower solubility than in the first solvent. In some embodiments, the first solvent is acetone and the antisolvent is water.

When an antisolvent is used, the ratio of the volumes of the antisolvent to the first solvent in the second solution typically ranges from about 1:50 to about 1:10, such as about 1:50, about 1:30, about 1:20, about 1:10, or any ranges in between.

The amount of solvent, concentration, etc. can be adjusted by those skilled in the art in view of this disclosure. An exemplary procedure is also shown in Example 1B. In some embodiments, the method of preparing crystalline Form A of abiraterone decanoate can be substantially the same as the procedures shown in Example 1B.

The crystalline Form A of abiraterone decanoate, prepared by any of the methods herein is also a novel composition of the present disclosure. Typically, the crystalline Form A of abiraterone decanoate prepared according to any of the methods herein can be characterized as being substantially free of Form B and Form C of abiraterone decanoate, e.g., no detectable amount of Form B and Form C by XRPD. Typically, the crystalline Form A of abiraterone decanoate prepared according to any of the methods herein can also be characterized as substantially pure, for example, the crystalline Form A can be characterized as (1) having a Palladium content of less than 50 ppm, such as less than 10 ppm; (2) having a purity by weight of at least 95%, preferably, at least 98%, such as about 98.5%, about 99%, about 99.5%, or higher; (3) having less than 1% (e.g., less than 0.5% by weight, such as less than 0.3%, less than 0.2%, or less than 0.1%) by weight of ethyl prasterone decanoate having the formula:

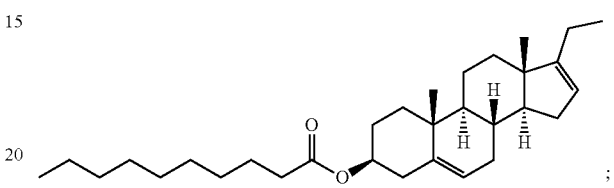

(4) conforming to the specification shown in Table D, or any combinations thereof.

Figure 2C:
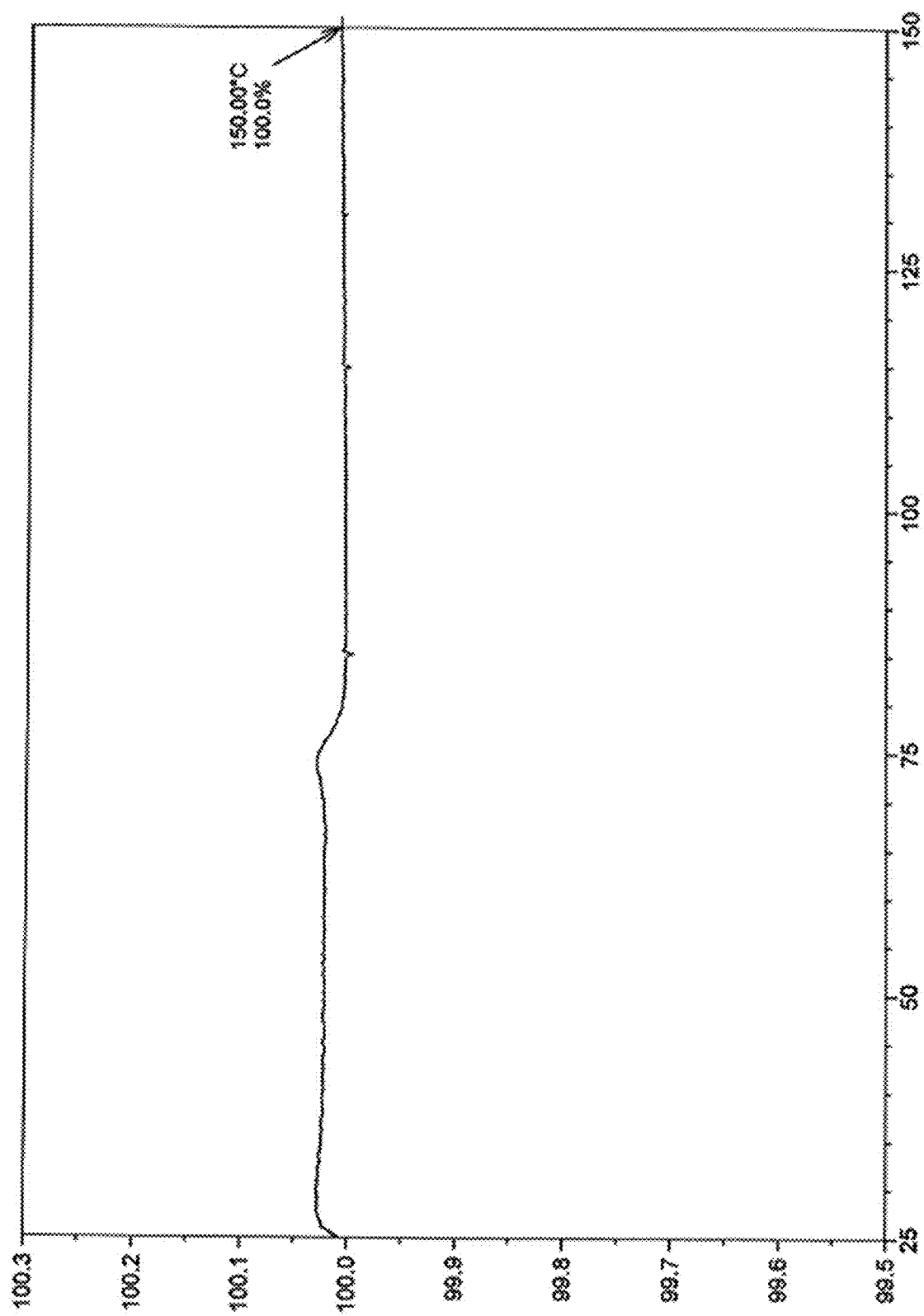
FIG. 2C shows a representative thermogravimetric analysis (TGA) of the abiraterone decanoate solid form prepared in Example 1A, designated as Form A.
Figure 2D:
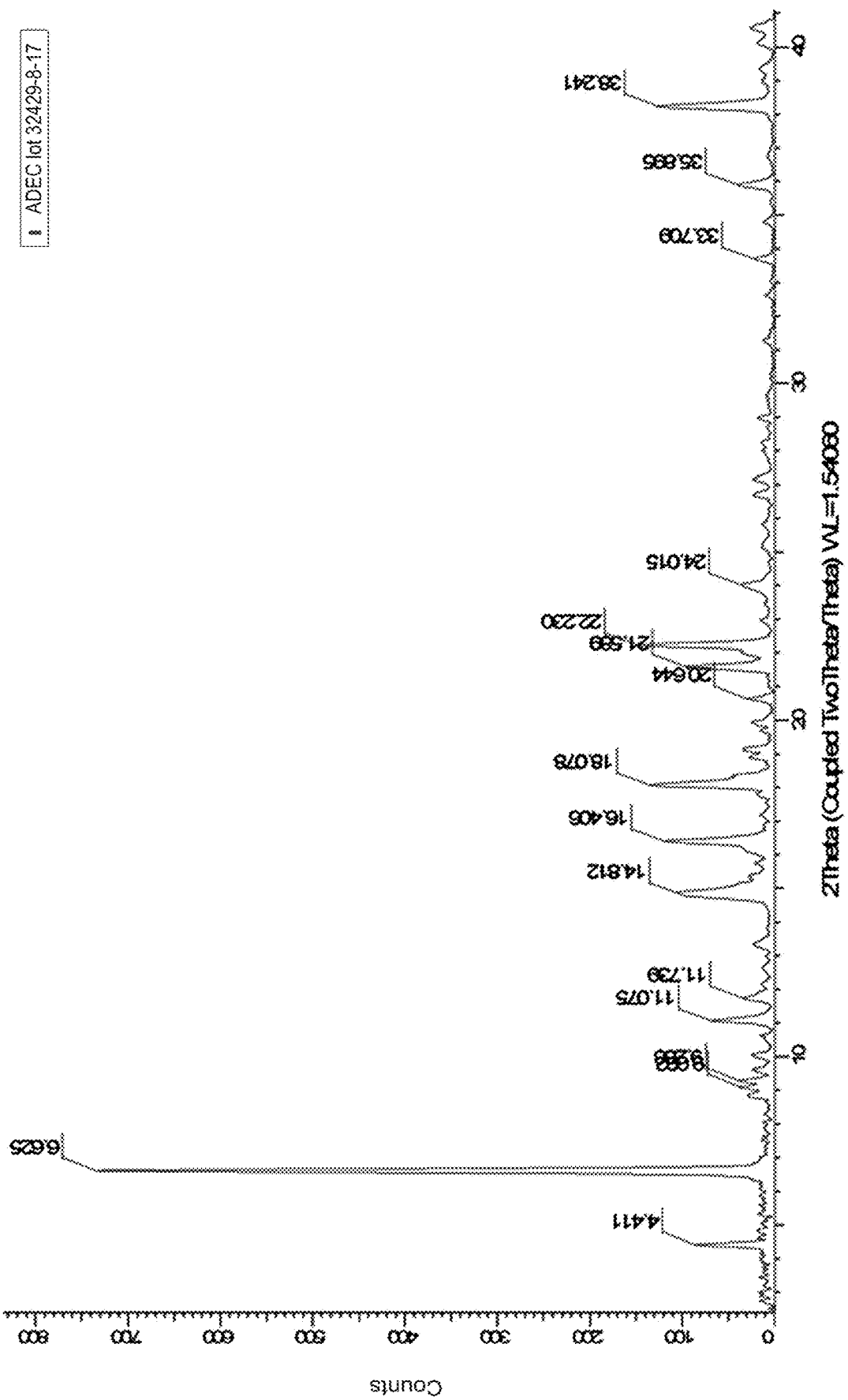
FIG. 2D presents a representative XRPD spectrum of the abiraterone decanoate in Form B.
Figure 2E:
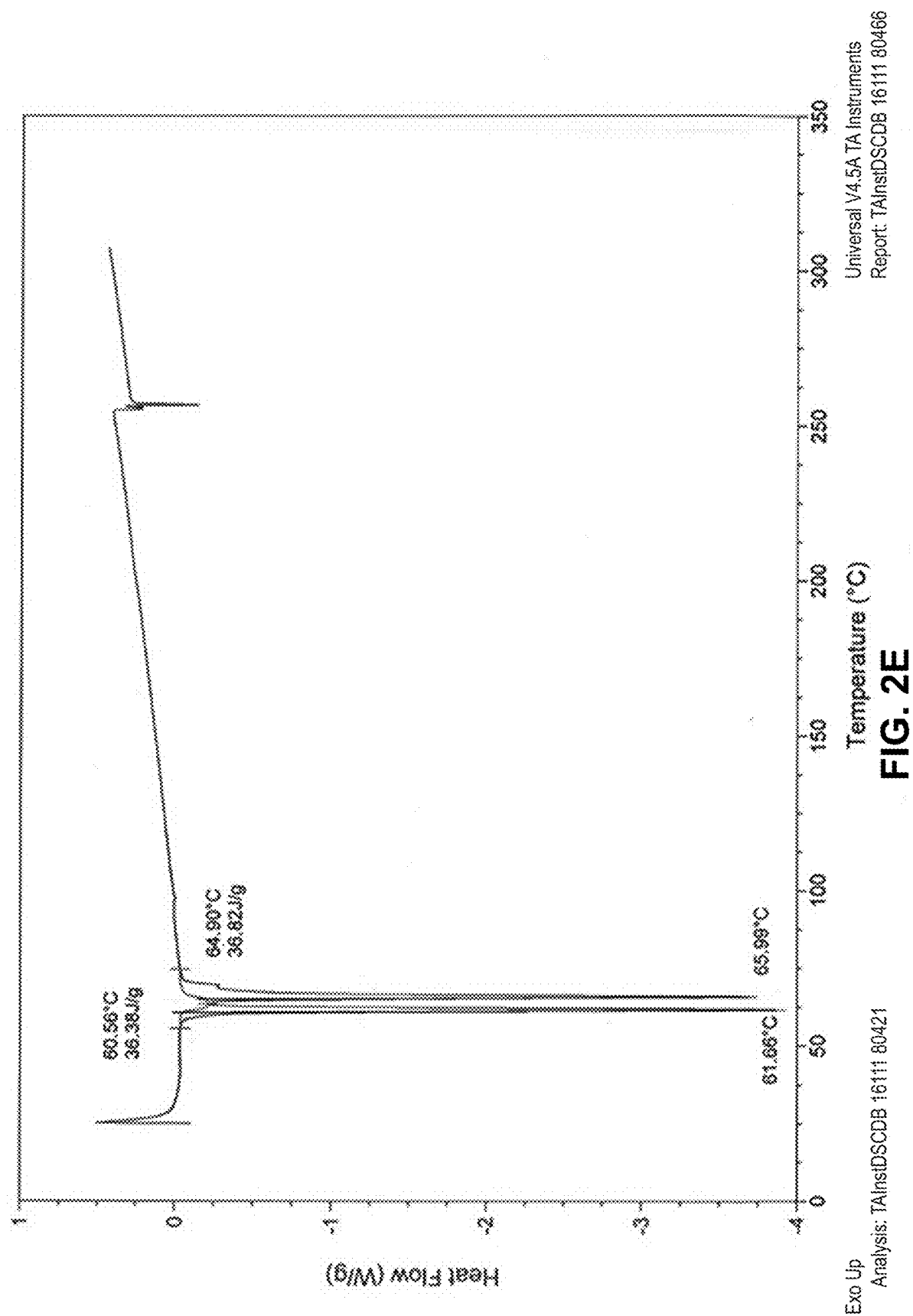
FIG. 2E shows a representative DSC spectrum of the abiraterone decanoate in Form B.

In some embodiments, the present disclosure also provides a crystalline Form B of abiraterone decanoate. In some embodiments, crystalline Form B can be characterized by an X-Ray Power Diffraction (XRPD) spectrum having one or more (e.g., 1, 2, 3, 4, 5, 6, or 7) of the following peaks: 4.4, 6.6, 14.8, 16.4, 18.1, 21.6, and 22.2, degrees 2 theta, ±0.2°; a Differential Scanning Calorimetry (DSC) pattern having two endothermic peaks with onset temperatures at about 60.6° C. and about 64.9° C., respectively; or a combination thereof. In some embodiments, the crystalline Form B can be characterized by an XRPD spectrum substantially the same as shown in FIG. 2D, for example, the XRPD spectrum shows peaks at the respective diffraction angels (degrees 2 theta, ±0.2°) corresponding to the peaks as shown in FIG. 2D, regardless of their relative intensities. In some embodiments, the crystalline Form B can be characterized by a DSC spectrum substantially the same as shown in FIG. 2E. Crystalline Form B can be typically prepared by dissolving abiraterone decanoate in a suitable solvent, such as methanol, ethanol, ethyl acetate, dimethyl acetamide (DMA), methyl tert-butyl ether, 2-propanol, or heptane, to form a solution, and cooling the solution, such as to about −10° C. to about −20° C. to form the crystalline form. Exemplary procedures are shown in Example 1C herein.

Figure 2F:
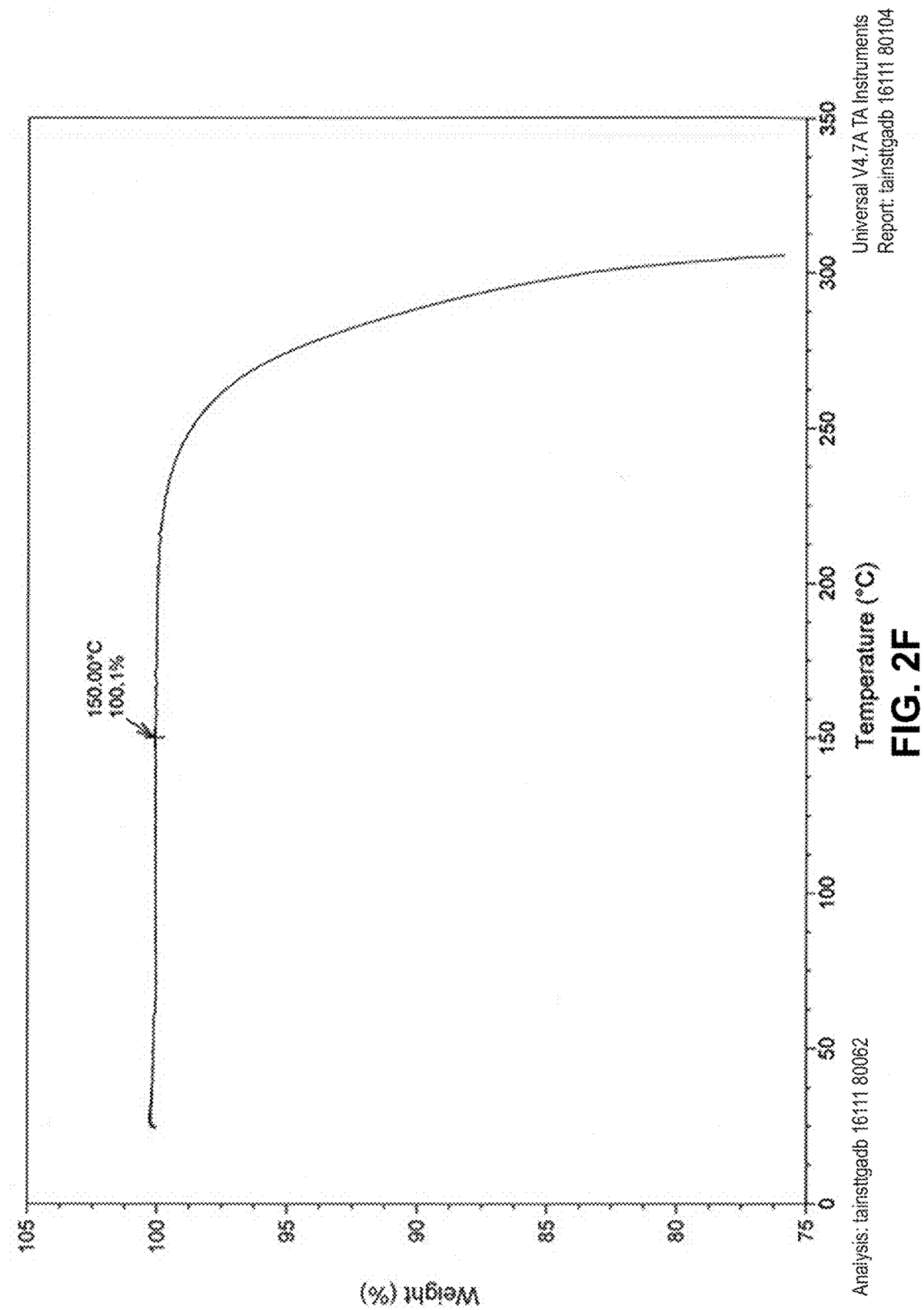
FIG. 2F shows a representative TGA of the abiraterone decanoate in Form B.
Figure 2G:
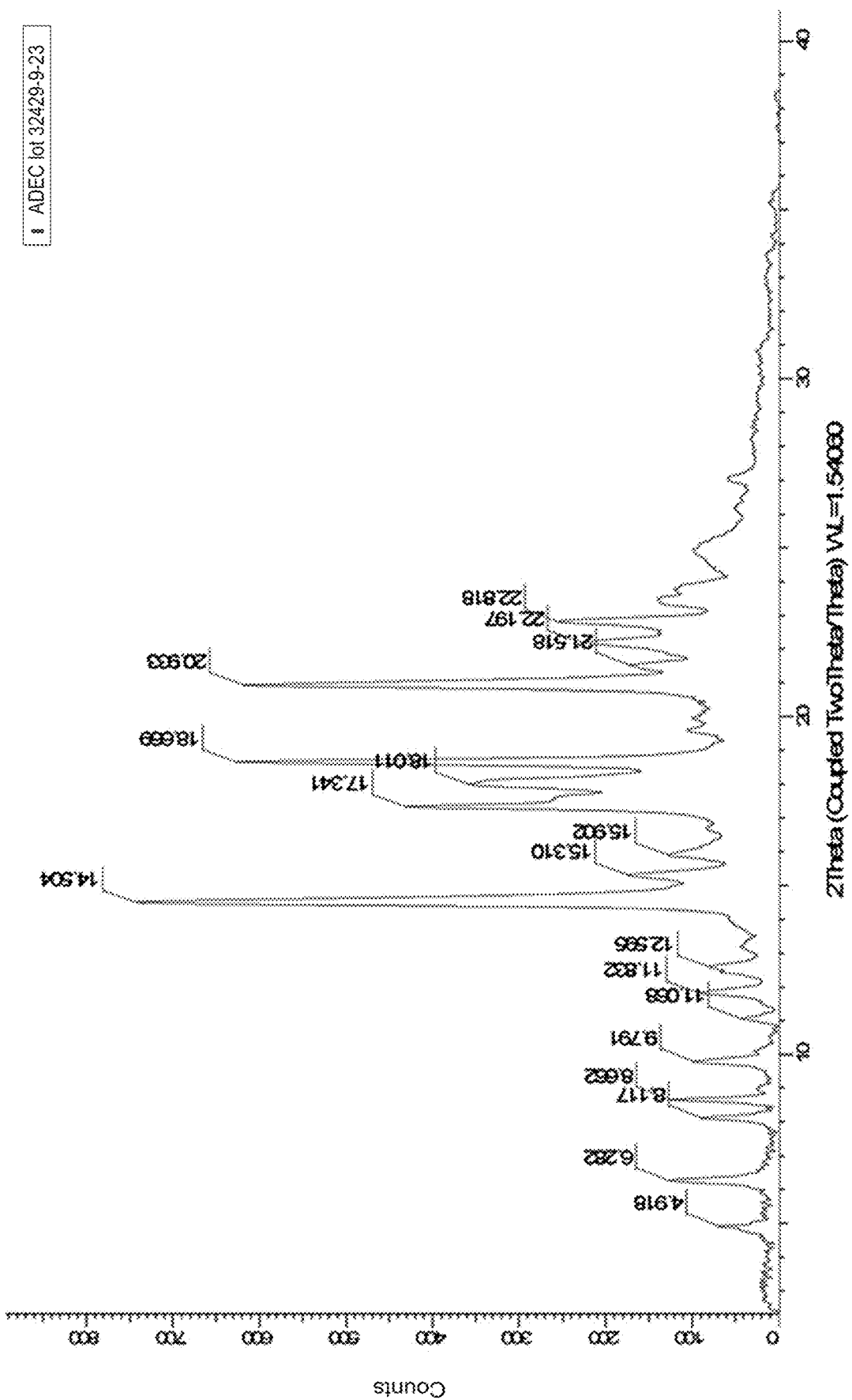
FIG. 2G presents a representative XRPD spectrum of the abiraterone decanoate in Form C.
Figure 2H:
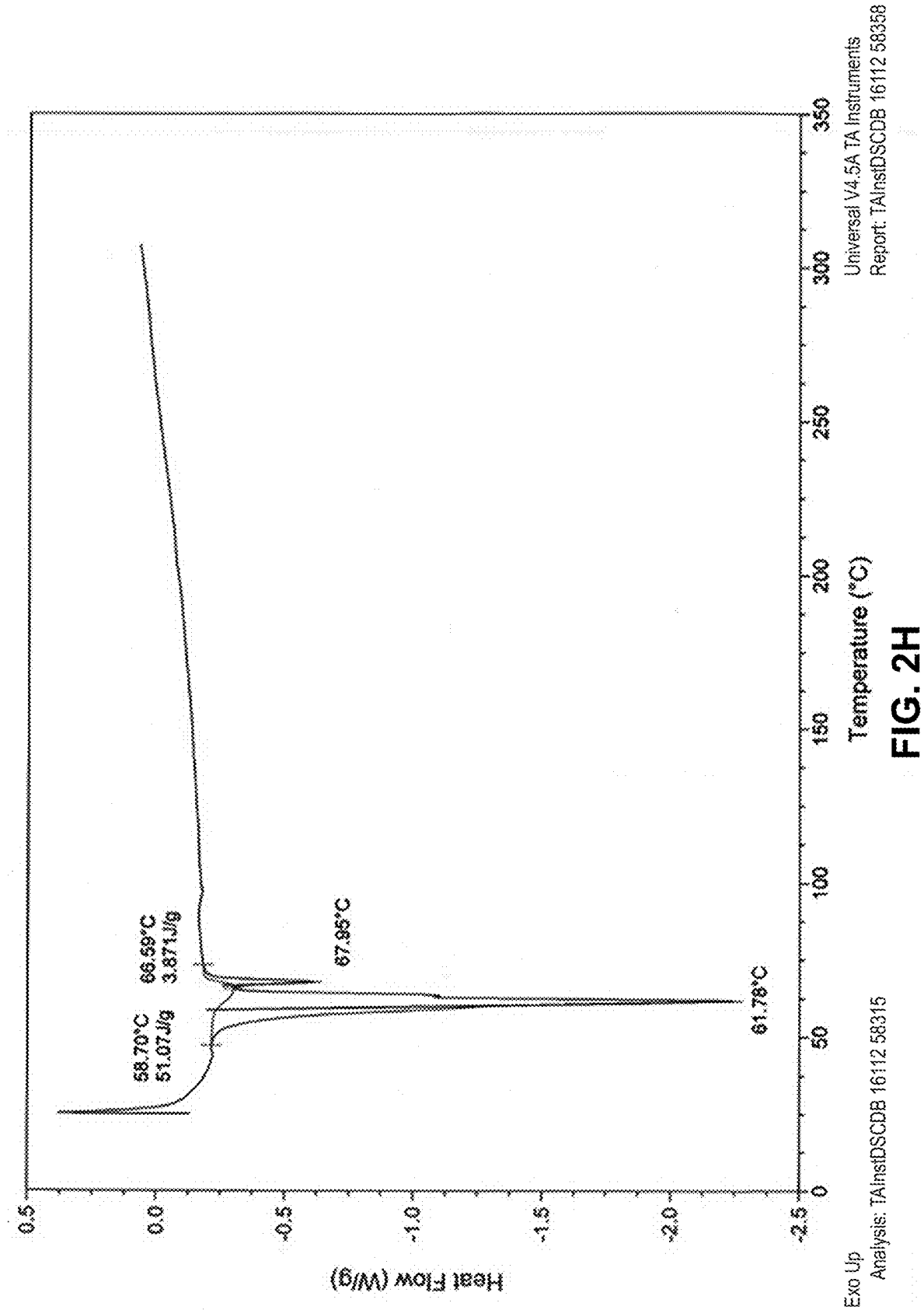
FIG. 2H shows a representative DSC spectrum of the abiraterone decanoate in Form C.

In some embodiments, the present disclosure also provides a crystalline Form C of abiraterone decanoate. In some embodiments, crystalline Form C can be characterized by an X-Ray Power Diffraction (XRPD) spectrum having one or more of the following peaks: 4.9, 6.3, 14.5, and 15.3, degrees 2 theta, ±0.2°; a Differential Scanning Calorimetry (DSC) pattern having two endothermic peaks with onset temperatures at about 58.7° C. and about 66.6° C., respectively; or a combination thereof. In some embodiments, the crystalline Form C can be characterized by an XRPD spectrum substantially the same as shown in FIG. 2G, for example, the XRPD spectrum shows peaks at the respective diffraction angels (degrees 2 theta, ±0.2°) corresponding to the peaks as shown in FIG. 2G, regardless of their relative intensities. In some embodiments, the crystalline Form C can be characterized by a DSC spectrum substantially the same as shown in FIG. 2H. Crystalline Form C can be typically prepared by dissolving abiraterone decanoate in a suitable solvent, such as 1:1 mixture of ethanol and 2-butanone, and reducing the amount of solvent, such as by evaporation, to form the crystalline form. Exemplary procedures are shown in Example 1C herein.

The pharmaceutical compositions herein comprising abiraterone decanoate typically are a solution of the abiraterone decanoate in a suitable vehicle as described herein. Typically, the solution can be prepared by dissolving one or more of the solid forms of abiraterone decanoate, such as crystalline Form A, B, and/or C, in a suitable vehicle. However, in some embodiments, the present disclosure also provides a pharmaceutical composition comprising one or more solid form of abiraterone decanoate. For example, in some embodiments, the pharmaceutical composition can comprise the crystalline Form A described herein. In some embodiments, the pharmaceutical composition can comprise the crystalline Form B described herein. In some embodiments, the pharmaceutical composition can comprise the crystalline Form C described herein.

In some embodiments, the pharmaceutical composition comprising the substantially pure abiraterone decanoate in its basic form, which is dispersed or dissolved in a pharmaceutically acceptable carrier comprising a pharmaceutically acceptable oil (e.g., described herein) and optionally a further pharmaceutically acceptable solvent (e.g., described herein). In some embodiments, the pharmaceutically acceptable oil comprises a triglyceride (e.g., long and/or medium chain triglycerides), and the further pharmaceutically acceptable solvent, if present, comprises an alcohol, ester, and/or acid solvent. In some embodiments, the pharmaceutically acceptable oil is selected from vegetable oil, castor oil, corn oil, sesame oil, cottonseed oil, peanut oil, poppy seed oil, tea seed oil, and soybean oil, and the further pharmaceutically acceptable solvent, if present, comprises benzyl alcohol, benzyl benzoate, or a combination thereof. In some embodiments, the pharmaceutically acceptable carrier comprises corn oil, benzyl alcohol, and benzyl benzoate.

In some specific embodiments, the pharmaceutical composition comprises the substantially pure abiraterone decanoate in its basic form, which is dissolved in a pharmaceutically acceptable oil (e.g., described herein), benzyl alcohol, and benzyl benzoate. In some embodiments, the pharmaceutical composition comprises the substantially pure abiraterone decanoate in its basic form, which is dissolved in corn oil, benzyl alcohol, and benzyl benzoate. In some embodiments, the pharmaceutical composition comprises: (a) the substantially pure abiraterone decanoate in its basic form, at a concentration of about 25 mg/ml to about 500 mg/ml (e.g., about 25 mg/ml, about 50 mg/ml, about 100 mg/ml, about 120 mg/ml, about 150 mg/ml, about 180 mg/ml, about 200 mg/ml, about 250 mg/ml, about 300 mg/ml, about 400 mg/ml, about 500 mg/ml, or any ranges between the recited values, such as about 100 mg/ml to about 300 mg/ml); (b) benzyl alcohol in an amount of about 50 mg to about 150 mg/mL; (c) benzyl benzoate in an amount of about 100 mg to about 300 mg/mL; and (d) a pharmaceutically acceptable oil (e.g., described herein), for example, corn oil, e.g., q.s. to the volume of the pharmaceutical composition. In some specific embodiments, the pharmaceutical composition comprises, for each milliliter, (a) the substantially pure abiraterone decanoate in its basic form, in an amount of about 100 mg to about 300 mg (e.g., about 100 mg, about 120 mg/ml, about 150 mg, about 180 mg/ml, about 200 mg or about 250 mg, or any ranges between the recited values); (b) benzyl alcohol in an amount of about 50 mg to about 150 mg (e.g., about 75 mg, about 100 mg, or about 125 mg, or any ranges between the recited values); (c) benzyl benzoate in an amount of about 100 mg to about 300 mg (e.g., about 100 mg, about 150 mg, about 200 mg, or about 250 mg, or any ranges between the recited values); and (d) corn oil, q.s. to 1 milliliter. In some embodiments, the weight ratio of benzyl alcohol to benzyl benzoate in the pharmaceutical composition ranges from about 2:1 to about 1:5 (e.g., about 1:1 to 1:3, such as about 1:2). In some embodiments, the pharmaceutical composition can be prepared by mixing (e.g., dissolving) the substantially pure abiraterone decanoate with the pharmaceutically acceptable carrier. For example, in some embodiments, the pharmaceutical composition can be prepared by mixing (e.g., dissolving) the substantially pure abiraterone decanoate in its basic form with corn oil, benzyl alcohol, and benzyl benzoate.

The pharmaceutical composition comprising the substantially pure abiraterone decanoate is typically formulated for parenteral administration. For example, in some embodiments, the pharmaceutical composition is formulated for an intramuscular injection, intradermal injection, or subcutaneous injection, e.g., with a desirable viscosity, glide force, number of particulates, endotoxins, etc. In some embodiments, the pharmaceutical composition is characterized as having (1) a viscosity of less than 0.1 Pa*s, such as about 0.05 Ps*s or lower; (2) a glide force of about 1-10 N when measured using a 21 G, 1.5 inch needle, and/or about 2-15 N when measured using a 23 gauge (or 23 G), 1.5 inch needle, and/or about 30-150 N when measured using a 27 G, 1.5 inch needle; (3) no more than 1000 particles having a size of 10 m or greater, and no more than 300 particles having a size of 25 m or greater, when measured according to USP <788> and/or <789>; and/or (4) less than 100 EU/ml, such as less than 25 EU/ml of bacterial endotoxins measured according to USP <85>. Methods for measuring viscosity and glide force are known in the art, which are also exemplified in Example 2 herein. Glide force measurements can be taken using a 5-mL fill for a 5 mL syringe or 2-mL fill for a 3 mL syringe. The USP methods <788>, <789> and <85> referenced herein should be understood as the current version of such methods, which are also known by those skilled in the art.

In any of the embodiments described herein, unless otherwise specified or contrary from context, the pharmaceutical composition (which may be alternatively referred to as abiraterone prodrug formulation) comprising abiraterone decanoate can be any of the pharmaceutical compositions comprising the substantially pure abiraterone decanoate as described herein.

The abiraterone decanoate in the pharmaceutical composition is typically included in a therapeutically effective amount for treating a disease or disorder described herein, such as prostate cancer. In some embodiments, the abiraterone decanoate can be present in the pharmaceutical composition in an amount sufficient to provide a therapeutically effective blood plasma concentration of abiraterone for a period of at least one week, e.g., at least two weeks, at least four weeks, and up to six or eight weeks or more, such as up to ten weeks or more after a single administration to a subject having a sex hormone-dependent benign or malignant disorder, an androgen receptor driven cancer, a syndrome due to androgen excess, and/or a syndrome due to glucocorticoid excess such as hypercortisolemia. In some embodiments, the abiraterone decanoate can be present in the pharmaceutical composition in an amount sufficient to provide a therapeutically effective blood plasma concentration of abiraterone at about 1 ng/ml or higher, such as about 2 ng/ml or higher, about 4 ng/ml or higher, about 5 ng/ml or higher, about 8 ng/ml or higher, etc. for a period of at least one week, e.g., at least two weeks, at least four weeks, and up to six or eight weeks or more, such as up to ten weeks or more after a single administration to a subject having a sex hormone-dependent benign or malignant disorder, an androgen receptor driven cancer, a syndrome due to androgen excess, and/or a syndrome due to glucocorticoid excess such as hypercortisolemia. In some embodiments, the abiraterone decanoate can be present in the pharmaceutical composition in an amount sufficient to provide a therapeutically effective blood plasma concentration of abiraterone at about 0.5 ng/ml or higher for a period of at least four weeks, e.g., at least six weeks and up to eight weeks or more, such as up to ten weeks or more, after a single administration to a subject having a sex hormone-dependent benign or malignant disorder, an androgen receptor driven cancer, a syndrome due to androgen excess, and/or a syndrome due to glucocorticoid excess such as hypercortisolemia. In some embodiments, the abiraterone decanoate can be present in the pharmaceutical composition in an amount sufficient to provide a therapeutically effective blood plasma concentration of abiraterone at about 0.1 ng/ml or higher for a period of at least four weeks, e.g., at least six weeks and up to eight weeks or more, such as up to ten weeks or more, after a single administration to a subject having a sex hormone-dependent benign or malignant disorder, an androgen receptor driven cancer, a syndrome due to androgen excess, and/or a syndrome due to glucocorticoid excess such as hypercortisolemia.

In some specific embodiments, the present disclosure provides a pharmaceutical composition, e.g., unit dosage form, comprising abiraterone decanoate having the formula of:

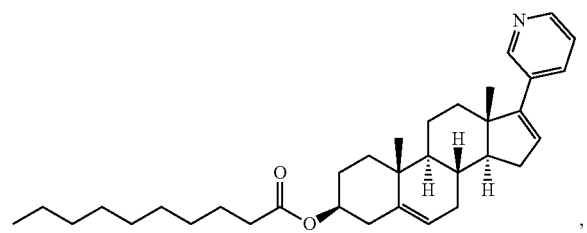

a pharmaceutically acceptable oil, and a pharmaceutically acceptable solvent, wherein the abiraterone decanoate is in its basic form, which is present at a concentration of about 25 mg/ml to about 500 mg/ml, such as about 50 mg/ml, about 100 mg/ml, about 120 mg/ml, about 150 mg/ml, about 180 mg/ml, about 200 mg/ml, about 250 mg/ml, about 300 mg/ml, about 350 mg/ml, about 400 mg/ml, about 500 mg/ml, or any ranges between the recited values, wherein the pharmaceutical composition, e.g., unit dosage form, is formulated for parenteral injection, such as intramuscular injection, intradermal injection, or subcutaneous injection, wherein the pharmaceutical composition, e.g., unit dosage form, comprises the abiraterone decanoate in an amount of about 50 mg to about 5,000 mg, such as about 100 mg, about 350 mg, about 500 mg, about 1000 mg, about 1500 mg, about 2000 mg, about 5000 mg, or any ranges between the recited values. In some embodiments, the pharmaceutical composition can be in a unit dosage form. Typically, depending on the dosing amount, one or more (e.g., 1) of the unit dosage forms can be administered to a subject in need thereof. The pharmaceutically acceptable oil in the pharmaceutical composition, e.g., unit dosage form, can be any of those described herein. For example, in some embodiments, the pharmaceutically acceptable oil is a pharmaceutically acceptable oil for injection, including oils of vegetable origin or synthetic mono- or diglycerides of fatty acids. In some embodiments, the pharmaceutically acceptable oil can be nature oil, synthetic oil, or semi-synthetic oil, such as fractionated coconut oil and medium-chain triglycerides, such as those sold under the trademark Miglyol. In some embodiments, the pharmaceutically acceptable oil can comprise a triglyceride derived from fatty acids. In some embodiments, the pharmaceutically acceptable oil can comprise a triglyceride derived from long and/or medium chain fatty acids, which can be independently poly-unsaturated, mono-unsaturated, or saturated. In some embodiments, the pharmaceutically acceptable oil can be selected from vegetable oil, castor oil, corn oil, sesame oil, cottonseed oil, peanut oil (arachis oil), poppy seed oil, tea seed oil, and soybean oil. In some specific embodiments, the pharmaceutically acceptable oil can comprise corn oil, which includes a triglyceride, in which the fatty acid constituents are primarily linoleic acid, oleic acid, palmitic acid, and stearic acid. The pharmaceutically acceptable solvent in the pharmaceutical composition, e.g., unit dosage form, also include any of those described herein. In some embodiments, the pharmaceutically acceptable solvent (or co-solvent if the oil is counted as a solvent), such as an alcohol, ester, acid, etc. In some embodiments, the pharmaceutically acceptable solvent can include benzyl alcohol, benzyl benzoate, ethanol, glycerol, polyethylene glycol, polysorbate 80, acetic acid, and/or ethyl acetate. In some embodiments, the pharmaceutically acceptable solvent can be benzyl alcohol and/or benzyl benzoate. In some embodiments, the pharmaceutical composition, e.g., unit dosage form, comprises abiraterone decanoate, a pharmaceutically acceptable oil (e.g., described herein), benzyl alcohol, and benzyl benzoate. In some embodiments, the pharmaceutically acceptable oil is corn oil. In some embodiments, the benzyl alcohol is present in an amount of about 5-10% by volume, the benzyl benzoate is present in an amount of about 10-20% by volume, and corn oil is present in an amount of about 70-85% by volume, with the combined volume of benzyl alcohol, benzyl benzoate, and corn oil being 100%. In some embodiments, the abiraterone decanoate is in a substantially pure form as described herein. In some particular embodiments, the pharmaceutical composition comprises: (a) abiraterone decanoate, such as the substantially pure abiraterone decanoate herein, in its basic form, at a concentration of about 25 mg/ml to about 500 mg/ml (e.g., about 25 mg/ml, about 50 mg/ml, about 100 mg/ml, about 120 mg/ml, about 150 mg/ml, about 180 mg/ml, about 200 mg/ml, about 250 mg/ml, about 300 mg/ml, about 400 mg/ml, about 500 mg/ml, or any ranges between the recited values, such as about 100 mg/ml to about 300 mg/ml); (b) benzyl alcohol in an amount of about 50 mg to about 150 mg/mL; (c) benzyl benzoate in an amount of about 100 mg to about 300 mg/mL; and (d) a pharmaceutically acceptable oil (e.g., described herein), in particular, corn oil, e.g., q.s. to the volume of the pharmaceutical composition. In some specific embodiments, the pharmaceutical composition comprises, for each milliliter, (a) abiraterone decanoate, such as the substantially pure abiraterone decanoate herein, in its basic form, in an amount of about 100 mg to about 300 mg (e.g., about 100 mg, about 150 mg, about 200 mg or about 250 mg, or any ranges between the recited values); (b) benzyl alcohol in an amount of about 50 mg to about 150 mg (e.g., about 75 mg, about 100 mg, or about 125 mg, or any ranges between the recited values); (c) benzyl benzoate in an amount of about 100 mg to about 300 mg (e.g., about 100 mg, about 150 mg, about 200 mg, or about 250 mg, or any ranges between the recited values); and (d) corn oil, q.s. to 1 milliliter. In some embodiments, the weight ratio of benzyl alcohol to benzyl benzoate in the pharmaceutical composition ranges from about 2:1 to about 1:5 (e.g., about 1:1 to 1:3, such as about 1:2). In some specific embodiments, the pharmaceutical composition comprises abiraterone decanoate, benzyl alcohol, benzyl benzoate, and corn oil, each in a respective amount (mg per 1 milliliter) substantially the same as that shown in Example 2 of this disclosure.

In some embodiments, the present disclosure provides exemplary abiraterone decanoate formulations as shown in Table C. All numeric values in the table should be understood as preceded by the term "about." The concentration of abiraterone decanoate refers to the amount of abiraterone decanoate in mg per ml of the final formulation, which can be a solution or suspension. The amount of oil (the primary solvent) and co-solvent (benzyl alcohol and/or benzyl benzoate) in the tables is expressed as volume percentage of solvent, which includes both the oil and co-solvent. Suitable oil includes any of the pharmaceutically acceptable oil as described herein, such as corn oil. Optional additional ingredients are not shown in Table C.

TABLE C

Exemplary Abiraterone Decanoate Formulations

| Ingredients | Amount/Concentration | | |
|---|---|---|---|
| | Typical | Exemplary range | More Exemplary Range |
| Abiraterone decanoate | 25 mg/ml to 500 mg/ml | 50 mg/ml to 300 mg/ml; 100 mg/ml to 300 mg/ml | 75 mg/ml to 300 mg/ml, such as 150 mg/ml to about 250 mg/ml |
| Oil (e.g., corn oil, castor oil, sesame oil, peanut oil, cottonseed oil, and/or Miglyol 812) | 30% to 100% of solvent | 50% to 90% of solvent | 60% to 90% of solvent, such as 70% |
| benzyl alcohol | 0% to 20% of solvent | 0% to 15% of solvent | 0% to 10% of solvent, such as 10% |
| benzyl benzoate | 0% to 50% of solvent | 0% to 35% of solvent | 0% to 30% of solvent, such as 20% |

The pharmaceutical composition or unit dosage form herein can be prepared by those skilled in the art in view of the methods disclosed herein. In some embodiments, the present disclosure provides a method for preparing an abiraterone decanoate formulation suitable for parenteral administration to a subject having a sex hormone-dependent benign or malignant disorder, an androgen receptor driven cancer, a syndrome due to androgen excess, and/or a syndrome due to glucocorticoid excess such as hypercortisolemia. In some embodiments, the method comprises mixing (such as dissolving or suspending) abiraterone decanoate, which has the formula of:

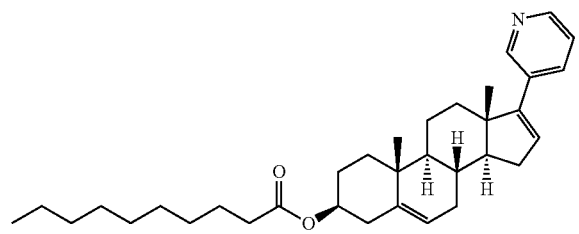

in a pharmaceutically acceptable carrier to form a mixture (such as a solution or suspension). In some embodiments, the abiraterone decanoate is in a substantially pure form as described herein. In some embodiments, the method further comprises sterilizing the mixture (e.g., solution or suspension). In some embodiments, the dissolving or suspending can comprise mixing (e.g., dissolving or suspending) the crystalline form (e.g., Form A) of abiraterone decanoate described herein in the pharmaceutically acceptable carrier. In some embodiments, the mixing (such as dissolving or suspending) can comprise mixing (e.g., dissolving or suspending) the substantially pure abiraterone decanoate described herein in the pharmaceutically acceptable carrier. Suitable pharmaceutically acceptable carriers and amounts, amount of abiraterone decanoate, concentration of abiraterone decanoate, include any of those described herein. For example, in some embodiments, the pharmaceutically acceptable carrier comprises a pharmaceutically acceptable oil and a pharmaceutically acceptable solvent, wherein the pharmaceutically acceptable oil comprises a vegetable oil, castor oil, corn oil, sesame oil, cottonseed oil, peanut oil, poppy seed oil, tea seed oil, or soybean oil, the pharmaceutically acceptable solvent comprises benzyl alcohol and/or benzyl benzoate, and wherein the abiraterone decanoate is present at a concentration of about 50 mg/mL to about 300 mg/mL such as about 100 mg/mL to about 300 mg/mL.

Abiraterone Prodrug of Formula I

In some embodiments, the pharmaceutical composition can comprise an abiraterone prodrug according to any of those described in U.S. Pat. No. 10,792,292 B2, and U.S. Provisional Application No. 63/073,502. For example, in some embodiments, the pharmaceutical composition can include an abiraterone prodrug of Formula I, or a pharmaceutically acceptable salt thereof:

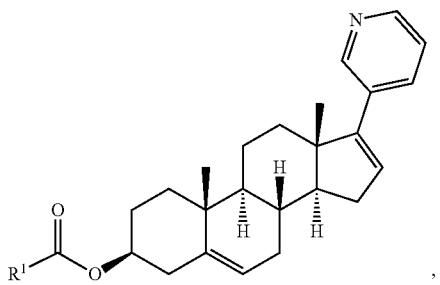

Formula I wherein $R^1$ is $R^{10}$, $O-R^{10}$, or $NHR^{10}$, wherein $R^{10}$ is selected from: a $C_{7-30}$ alkyl; $C_{7-30}$ alkenyl; $C_{7-30}$ alkynyl; an alkyl substituted with a cycloalkyl, which typically has a total number of carbons between 5 and 16; an alkyl substituted with a phenyl, which typically has a total number of carbons between 7 and 16; a cycloalkyl optionally substituted with one or more alkyl, which typically has a total number of carbons between 5 and 16; and a branched C5 or C6 alkyl such as

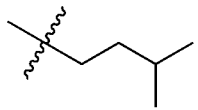

In some preferred embodiments, $R^{10}$ is a $C_{7-30}$ alkyl. As used herein, unless expressly stated to be substituted, an alkyl should be understood as unsubstituted. However, an alkyl can be either linear or branched. In some embodiments, $R^{10}$ can be a linear $C_{7-30}$ alkyl. In some embodiments, $R^{10}$ can be a branched $C_{7-30}$ alkyl. In some embodiments, $R^{10}$ is a linear $C_{7-16}$ alkyl, for example, $R^{10}$ can have a formula $-(CH_2)_n-CH_3$, wherein n is an integer between 6 and 15 (e.g., between 6 and 12, such as 6, 7, 8, 9, 10, 11, or 12). In some embodiments, $R^{10}$ can be a branched $C_{7-16}$ alkyl.

In some embodiments, $R^{10}$ can also be an alkyl substituted with a cycloalkyl. Typically, in such embodiments, $R^{10}$ has a total number of carbons between 5 and 16, i.e., the total number of carbons from the alkyl moiety and the cycloalkyl moiety are between 5 and 16. The cycloalkyl typically is unsubstituted. However, in some embodiments, the cycloalkyl can be optionally substituted, e.g., with one or two lower alkyl (e.g, a $C_{1-4}$ alkyl). In some embodiments, $R^{10}$ can be an alkyl substituted with a $C_{3-6}$ cycloalkyl, which typically has a total number of carbons between 6 and 12. In some embodiments, $R^{10}$ can be a linear alkyl substituted with a $C_{3-6}$ cycloalkyl, for example, $R^{10}$ can have a formula $-(CH_2)_n$-Cy, wherein n is an integer of 1-6 (e.g., 1, 2, 3, 4, 5, or 6), and Cy is a $C_{3-6}$ cycloalkyl (such as cyclopropyl, cyclobutyl, cyclopentyl, or cyclohexyl). In some embodiments, $R^{10}$ can have a formula $-(CH_2)_n$-Cy, wherein n is 1 or 2, and Cy is cyclopentyl or cyclohexyl. In some embodiments, $R^{10}$ can also be a branched alkyl (e.g., branched $C_2$-6) substituted with a $C_{3-6}$ cycloalkyl. As used herein, a branched C2 alkyl should be understood as a 1,1-disubstitued ethyl group, for example, $-CH(CH_3)$-Cy.

In some embodiments, $R^{10}$ can also be an alkyl substituted with a phenyl. Typically, in such embodiments, $R^{10}$ has a total number of carbons between 7 and 16, i.e., the total number of carbons from the alkyl moiety and the phenyl moiety are between 5 and 16. In some embodiments, $R^{10}$ can be a linear alkyl substituted with a phenyl, for example, $R^{10}$ can have a formula $-(CH_2)_n$-Cy, wherein n is an integer of 1-6 (e.g., 1, 2, 3, 4, 5, or 6), and Cy is a phenyl. In some embodiments, $R^{10}$ can have a formula $-(CH_2)_n$-Cy, wherein n is 1 or 2, and Cy is phenyl. In some embodiments, $R^{10}$ can also be a branched alkyl (e.g., branched $C_2$-6) substituted with a phenyl. The phenyl typically is unsubstituted. However, in some embodiments, the phenyl can be optionally substituted, e.g., with one or two lower alkyl (e.g, a $C_{1-4}$ alkyl).

In some embodiments, $R^{10}$ can be a cycloalkyl optionally substituted with one or more alkyl. In such embodiments, $R^{10}$ typically has a total number of carbons between 5 and 16, i.e., the total number of carbons of the cycloalkyl and its optional substituents are between 5 and 16. In some embodiments, $R^{10}$ can be a $C_{3-6}$ cycloalkyl, either unsubstituted or substituted with a $C_{1-4}$ alkyl. In some specific embodiments, $R^{10}$ can be

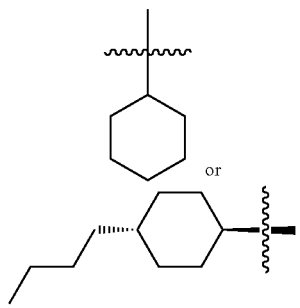

In some embodiments, $R^{10}$ can be a branched C5 or C6 alkyl. In some embodiments, $R^{10}$ can be

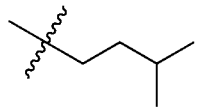

Other branched C5 or C6 alkyls are also suitable.

In some embodiments, $R^{10}$ can be an unsaturated aliphatic group such as a $C_{7-30}$ alkenyl or a $C_{7-30}$ alkynyl.

In some preferred embodiments, the compound of Formula I is an ester of abiraterone, e.g., $R^1$ is $R^{10}$, wherein $R^{10}$ is defined herein. In some embodiments, $R^1$ in Formula I can be a $C_{7-16}$ alkyl, e.g., an alkyl having a formula of $-(CH_2)_n-CH_3$, wherein n is an integer between 6 and 12 (e.g., 6, 7, 8, 9, 10, 11, or 12). In some embodiments, $R^1$ in Formula I can be represented by the formula $-(CH_2)_n$-Cy, wherein n is an integer of 1-6, and Cy is a $C_{3-6}$ cycloalkyl or phenyl, for example, in more specific embodiments, n can be 1 or 2, and Cy is cyclopentyl, cyclohexyl, or phenyl. In some specific embodiments, $R^1$ in Formula I can be

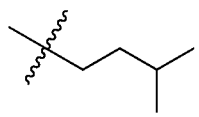

In some specific embodiments, R¹ in Formula I can be

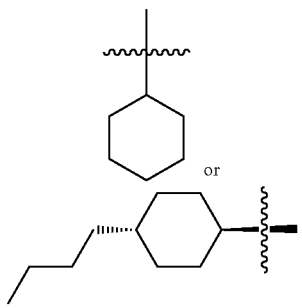

Other suitable groups for R¹ include any of the R¹⁰ defined herein.

In some embodiments, R¹ in Formula I can also be O—R¹⁰ or NHR¹⁰, wherein R¹⁰ is defined herein.

Typically, compounds of Formula I can be present in a formulation in the basic form, for example, in a non-aqueous formulation. However, in some embodiments, pharmaceutically acceptable salts of compounds of Formula I are also useful. Unless specifically referred to as in its salt form or otherwise contradictory from context, the compound of Formula I can be in its basic form in the abiraterone prodrug formulations described herein. In some embodiments, the compound of Formula I can be in a substantially pure form.

Abiraterone Prodrug Formulations

In some embodiments, the pharmaceutical composition comprising the abiraterone prodrug can be an abiraterone prodrug formulation according to any of those described in U.S. Pat. No. 10,792,292 B2, and U.S. Provisional Application No. 63/073,502, which can be used for the methods herein. Typically, the abiraterone prodrugs can be formulated as a parenteral formulation, such as an intramuscular, intradermal, or subcutaneous formulation, and can in some embodiments be formulated to deliver a therapeutically effective plasma concentration of abiraterone over an extended period of time, e.g., for at least 1 week, at least 2 weeks, at least 3 weeks, at least 4 weeks, and up to six or eight weeks or more, such as up to ten weeks or more, etc.

Various abiraterone prodrugs, such as abiraterone esters, carbamates, or carbonates are suitable for compositions and methods of the present disclosure. In some embodiments, the pharmaceutical composition can comprise a compound of Formula I (e.g., any one or more as defined herein), or a pharmaceutically acceptable salt thereof. In some embodiments, the pharmaceutical composition can be formulated for parenteral administration, such as intramuscular injection, intradermal injection, or subcutaneous injection. The pharmaceutical composition typically includes a pharmaceutically acceptable carrier. Suitable carriers include those known in the art, for example, those described in "Remington: The Science and Practice of Pharmacy" (formerly "Remington's Pharmaceutical Sciences," University of the Sciences in Philadelphia, Lippincott, Williams & Wilkins, Philadelphia, Pa. (2005)) and the U.S. Food and Drug Administration's Center for Drug Evaluation and Research's database of inactive ingredients present in FDA-approved drugs. In some embodiments, the pharmaceutically acceptable carrier can be a carrier that is approved for use by the FDA for an intramuscular, intradermal, or subcutaneous drug product, e.g., those listed in the FDA's database of inactive ingredients. In some embodiments, the pharmaceutically acceptable carrier can be any suitable nonaqueous vehicle suitable for injection, such as those described in U.S. Pharmacopeia. In some embodiments, the pharmaceutically acceptable carrier can be a pharmaceutically acceptable oil, e.g., a vegetable oil, castor oil, corn oil, sesame oil, cottonseed oil, peanut oil, poppy seed oil, tea seed oil, or soybean oil. In some embodiments, the pharmaceutically acceptable oil can be oils (e.g., described herein) suitable for use as vehicles for injection, e.g., meeting the criteria as described in the corresponding U.S. Pharmacopeia monograph. In some embodiments, the pharmaceutically acceptable oil can be an oil of vegetable origin suitable for use as vehicles for injection. In some embodiments, the pharmaceutically acceptable oil can be a synthetic oil suitable for use as vehicles for injection, such as a synthetic mono- or diglycerides of fatty acids, e.g., those that are liquid and remain clear when cooled to 10° C. and have an Iodine Value of not more than 140. In some embodiments, the pharmaceutically acceptable oil can be nature oil, synthetic oil, or semi-synthetic oil, such as fractionated coconut oil and medium-chain triglycerides, such as those sold under the trademark Miglyol. In some embodiments, the pharmaceutically acceptable carrier comprises a triglyceride derived from fatty acids. In some embodiments, the pharmaceutically acceptable carrier comprises a triglyceride derived from long and/or medium chain fatty acids, which can be independently poly-unsaturated, mono-unsaturated, or saturated. In some embodiments, two or more different pharmaceutically acceptable oil can be used. In some embodiments, the pharmaceutical composition is a non-aqueous solution or suspension. In some embodiments, the pharmaceutical composition further comprises a pharmaceutically acceptable solvent, such as benzyl alcohol, benzyl benzoate, or a combination thereof. In some embodiments, the compound of Formula I or pharmaceutically acceptable salt thereof can be present in the pharmaceutical composition at a concentration of about 25 mg/ml to about 500 mg/ml (e.g., about 25 mg/ml, about 50 mg/ml, about 100 mg/ml, about 150 mg/ml, about 200 mg/ml, about 250 mg/ml, about 300 mg/ml, about 400 mg/ml, about 500 mg/ml, or any ranges between the recited values).

In some embodiments, the pharmaceutical composition suitable for use in the methods herein can comprise a compound of Formula II, or a pharmaceutically acceptable salt thereof.

Formula II

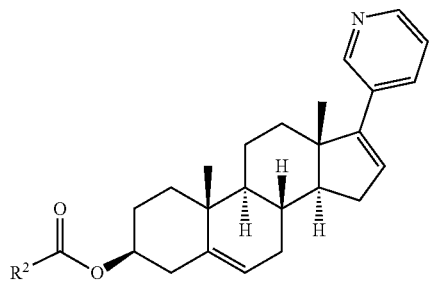

wherein R² is defined herein. In some embodiments, the pharmaceutical composition can be formulated for intramuscular injection, intradermal injection, or subcutaneous injection. In some embodiments, the compound of Formula II or pharmaceutically acceptable salt thereof can be present in the pharmaceutical composition at a concentration of about 25 mg/ml to about 500 mg/ml (e.g., about 25 mg/ml, about 50 mg/ml, about 100 mg/ml, about 150 mg/ml, about 200 mg/ml, about 250 mg/ml, about 300 mg/ml, about 400 mg/ml, about 500 mg/ml, or any ranges between the recited values). In some embodiments, the pharmaceutical composition is a non-aqueous solution or suspension. In some embodiments, the compound of Formula II or pharmaceutically acceptable salt thereof is dissolved or suspended in a pharmaceutically acceptable oil (e.g., described herein), such as a vegetable oil, castor oil, corn oil, sesame oil, cottonseed oil, peanut oil, poppy seed oil, tea seed oil, or soybean oil. In some embodiments, the pharmaceutical composition further comprises a pharmaceutically acceptable solvent, such as benzyl alcohol, benzyl benzoate, or a combination thereof.

Various groups are suitable as $R^2$ in Formula II. In some embodiments, $R^2$ can be selected such that the compound of Formula II is an ester, a carbamate, or a carbonate of abiraterone. In some embodiments, $R^2$ is $R^{20}$, O—$R^{20}$, or NHR$^{20}$, and $R^{20}$ is selected from: a $C_{1-30}$ alkyl; a $C_{2-30}$ alkenyl; a $C_{2-30}$ alkynyl; an alkyl substituted with a cycloalkyl, which typically has a total number of carbons between 4 and 30; an alkyl substituted with a phenyl, which typically has a total number of carbons between 7 and 30; and a cycloalkyl optionally substituted with one or more alkyl, which typically has a total number of carbons between 3 and 30.

In some preferred embodiments, $R^{20}$ is a $C_{1-16}$ alkyl. In some embodiments, $R^{20}$ can be a linear $C_{1-16}$ alkyl. In some embodiments, $R^{20}$ can be a branched $C_{3-16}$ alkyl. In some embodiments, $R^{20}$ can be a branched C5 or C6 alkyl. In some embodiments, $R^{20}$ can be

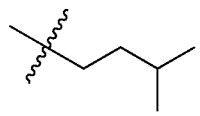

In some embodiments, $R^{20}$ can have a formula —$(CH_2)_n$—$CH_3$, wherein n is an integer between 0 and 12 (e.g., between 6 and 12, such as 6, 7, 8, 9, 10, 11, or 12).

In some embodiments, $R^{20}$ can also be an alkyl substituted with a cycloalkyl. Typically, in such embodiments, $R^{20}$ has a total number of carbons between 4 and 30, such as between 5 and 16 (i.e., the total number of carbons from the alkyl moiety and the cycloalkyl moiety are between 5 and 16). The cycloalkyl typically is unsubstituted. However, in some embodiments, the cycloalkyl can be optionally substituted, e.g., with one or two lower alkyl (e.g, a $C_{1-4}$ alkyl). In some embodiments, $R^{20}$ can be an alkyl substituted with a $C_{3-6}$ cycloalkyl, which typically has a total number of carbons between 6 and 12. In some embodiments, $R^{20}$ can be a linear alkyl substituted with a $C_{3-6}$ cycloalkyl, for example, $R^{20}$ can have a formula —$(CH_2)_n$-Cy, wherein n is an integer of 1-6 (e.g., 1, 2, 3, 4, 5, or 6), and Cy is a $C_{3-6}$ cycloalkyl (such as cyclopropyl, cyclobutyl, cyclopentyl, or cyclohexyl). In some embodiments, $R^{20}$ can have a formula —$(CH_2)_n$-Cy, wherein n is 1 or 2, and Cy is cyclopentyl or cyclohexyl. In some embodiments, $R^{20}$ can also be a branched alkyl (e.g., branched $C_2$-6) substituted with a $C_{3-6}$ cycloalkyl.

In some embodiments, $R^{20}$ can also be an alkyl substituted with a phenyl. Typically, in such embodiments, $R^{20}$ has a total number of carbons between 7 and 30, e.g., between 7 and 16 (i.e., the total number of carbons from the alkyl moiety and the phenyl moiety are between 7 and 16). In some embodiments, $R^{20}$ can be a linear alkyl substituted with a phenyl, for example, $R^{20}$ can have a formula —$(CH_2)_n$ -Cy, wherein n is an integer of 1-6 (e.g., 1, 2, 3, 4, 5, or 6), and Cy is a phenyl. In some embodiments, $R^{20}$ can have a formula —$(CH_2)_n$-Cy, wherein n is 1 or 2, and Cy is phenyl. In some embodiments, $R^{20}$ can also be a branched alkyl (e.g., branched $C_2$-6) substituted with a phenyl. The phenyl typically is unsubstituted. However, in some embodiments, the phenyl can be optionally substituted, e.g., with one or two lower alkyl (e.g, a $C_{1-4}$ alkyl).

In some embodiments, $R^{20}$ can be a cycloalkyl optionally substituted with one or more alkyl. In such embodiments, $R^{20}$ typically has a total number of carbons between 3 and 30, e.g., 5 and 16 (i.e., the total number of carbons of the cycloalkyl and its optional substituents are between 5 and 16). In some embodiments, $R^{20}$ can be a $C_{3-6}$ cycloalkyl, either unsubstituted or substituted with a $C_{1-4}$ alkyl. In some specific embodiments, $R^{20}$ can be

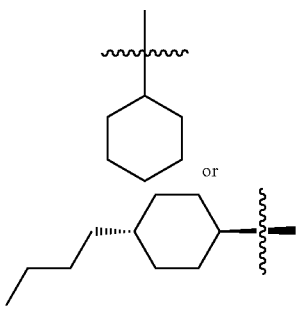

In some embodiments, $R^{20}$ can be an unsaturated aliphatic group such as a $C_{2-30}$ alkenyl or a $C_{2-30}$ alkynyl.

In some preferred embodiments, the compound of Formula II is an abiraterone ester, e.g., $R^2$ is $R^{20}$, wherein $R^{20}$ is defined herein. In some embodiments, $R^2$ in Formula II can be a $C_{1-16}$ alkyl, e.g., an alkyl having a formula of —$(CH_2)_n$—$CH_3$, wherein n is an integer between 0 and 12. In some embodiments, $R^2$ in Formula II can be represented by the formula —$(CH_2)_n$-Cy, wherein n is an integer of 1-6, and Cy is a $C_{3-6}$ cycloalkyl or phenyl, for example, in more specific embodiments, n can be 1 or 2, and Cy is cyclopentyl, cyclohexyl, or phenyl. In some specific embodiments, $R^2$ in Formula II can be

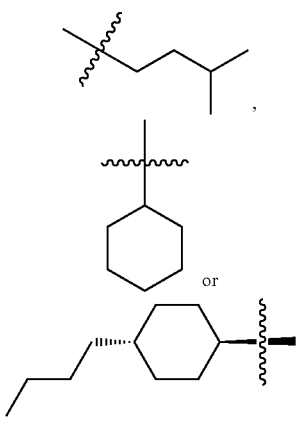

Other suitable groups for $R^2$ include any of the $R^{20}$ defined herein. In some embodiments, the abiraterone ester can be an acetate, a propionate, a butanoate, a (vaterate) pentanoate, an isocaproate, a buciclate, a cyclohexanecarboxylate, a phenyl propionate, caproate (hexanoate), a enanthate (heptanoate), a cypionate, an octanoate, a noncanoate, a decanoate, an undecanoate, a dodecanoate, a tridecanoate, a tetradecanoate, a pentadecanoates, or a hexadecanoate of abiraterone. In some embodiments, the abiraterone ester can be abiraterone acetate, abiraterone propionate, and abiraterone decanoate. In some specific embodiments, the abiraterone ester can be abiraterone pentanoate, abiraterone hexanoate, abiraterone heptanoate, abiraterone decanoate, abiraterone isocaproate, or abiraterone cypionate.

In some embodiments, $R^2$ in Formula II can also be O—$R^{20}$ or NHR$^{20}$, wherein $R^{20}$ is defined herein.

Typically, compounds of Formula II can be present in a formulation in the basic form, for example, in a non-aqueous formulation. However, in some embodiments, pharmaceutically acceptable salts of compounds of Formula II are also useful. Unless specifically referred to as in its salt form or otherwise contradictory from context, the compound of Formula II can be in its basic form in the abiraterone prodrug formulations described herein. In some embodiments, the compound of Formula II can be in a substantially pure form.

The pharmaceutical composition comprising the substantially pure compound of Formula I or II (e.g., abiraterone decanoate) is typically formulated for parenteral administration. For example, in some embodiments, the pharmaceutical composition is formulated for an intramuscular injection, intradermal injection, or subcutaneous injection, e.g., with a desirable viscosity, glide force, number of particulates, endotoxins, etc. In some embodiments, the pharmaceutical composition is characterized as having (1) a viscosity of less than 0.1 Pa*s, such as about 0.05 Ps*s or lower; (2) a glide force of about 1-10 N when measured using a 21 G, 1.5 inch needle, and/or about 2-15 N when measured using a 23 gauge (or 23 G), 1.5 inch needle, and/or about 30-150 N when measured using a 27 G, 1.5 inch needle; (3) no more than 1000 particles having a size of 10 m or greater, and no more than 300 particles having a size of 25 m or greater, when measured according to USP <788> and/or <789>; and/or (4) less than 100 EU/ml, such as less than 25 EU/ml of bacterial endotoxins measured according to USP <85>. Methods for measuring viscosity and glide force are known in the art, which are also exemplified in Example 1 herein. The USP methods <788>, <789> and <85> referenced herein should be understood as the current version of such methods, which are also known by those skilled in the art.

Typically, the abiraterone prodrugs of the present disclosure are formulated as a non-aqueous solution or suspension. In some embodiments, the non-aqueous solution or suspension provides higher levels of abiraterone in the plasma for a longer duration, when compared to an aqueous solution or suspension. For example, as detailed herein, IM injections of an aqueous suspension and a vegetable oil solution of the abiraterone acetate prodrug were evaluated in rats. Surprisingly, it was determined that the vegetable oil solution (but not the aqueous suspension) of abiraterone acetate prodrug gave the highest blood plasma levels and the longest duration of exposure of active drug abiraterone. Accordingly, in some embodiments, the abiraterone prodrug formulations herein can include an abiraterone prodrug of the present disclosure (e.g., compound of Formula I or II) dissolved or dispersed in a pharmaceutically acceptable carrier. In some embodiments, the pharmaceutically acceptable carrier can be any suitable nonaqueous vehicle suitable for injection, such as those described in U.S. Pharmacopeia. In some embodiments, the pharmaceutically acceptable carrier can be a pharmaceutically acceptable oil, e.g., a vegetable oil, castor oil, corn oil, sesame oil, cottonseed oil, peanut oil, poppy seed oil, tea seed oil, or soybean oil. In some embodiments, the pharmaceutically acceptable oil can be oils (e.g., described herein), suitable for use as vehicles for injection, e.g., meeting the criteria as described in the corresponding U.S. Pharmacopeia monograph. In some embodiments, the pharmaceutically acceptable oil can be an oil of vegetable origin suitable for use as vehicles for injection. In some embodiments, the pharmaceutically acceptable oil can be a synthetic oil suitable for use as vehicles for injection, such as synthetic mono- or diglycerides of fatty acids, e.g., those that are liquid and remain clear when cooled to 10° C. and have an Iodine Value of not more than 140. In some embodiments, the pharmaceutically acceptable oil can be nature oil, synthetic oil, or semi-synthetic oil, such as fractionated coconut oil and medium-chain triglycerides, such as those sold under the trademark Miglyol. In some embodiments, the pharmaceutically acceptable carrier comprises a triglyceride derived from fatty acids. In some embodiments, the pharmaceutically acceptable carrier comprises a triglyceride derived from long and/or medium chain fatty acids, which can be independently poly-unsaturated, mono-unsaturated, or saturated. In some embodiments, the pharmaceutically acceptable oil can be any of those that are approved for use by the FDA for an intramuscular, intradermal, or subcutaneous drug product, e.g., those listed in the FDA's database of inactive ingredients. In some specific embodiments, the pharmaceutically acceptable oil is castor oil or corn oil. In some embodiments, two or more different pharmaceutically acceptable oil can be used.

Other ingredients can also be optionally included in the abiraterone prodrug formulations herein. In some embodiments, the abiraterone prodrug formulation can further comprise a pharmaceutically acceptable solvent, such as benzyl alcohol, benzyl benzoate, ethanol, glycerol, polyethylene glycol, polysorbate 80, acetic acid, and ethyl acetate. It was determined that the additives/co-solvents benzyl alcohol and benzyl benzoate had the advantage of increasing the solubility of the prodrugs as well as reducing the viscosity and/or glide force of the solution, see e.g., U.S. Pat. No. 10,792,292 B2, which provided a more concentrated solution that was easier to inject through an acceptable gauge needle for IM injection (e.g., 20-27 gauge such as 22-25 gauge). The co-solvent can be selected based on its ability to reduce the viscosity of the vehicle to allow injection through suitable injection needles or cannula. Benzyl alcohol as an additive in IM or subcutaneous injections also has the advantage that it can act as a local anesthetic at the injection site (Wilson et al. Ann. Emer. Med. 33(5), 495, 1999). In some embodiments, the abiraterone prodrug formulation further comprises benzyl alcohol. In some embodiments, the cosolvent, if present, can be included at a level (e.g., about 0-50% of the solvent, such as about 10%) such that it does not cause irritation (or only minimal or tolerable irritation) at the injection site.

In some embodiments, the abiraterone prodrug formulation can comprise benzyl benzoate as a cosolvent, for example, about 0-50% of the solvent, typically 0-35% or 0-30%, or about 20%. In some embodiments, the abiraterone prodrug formulation can comprise a combination of benzyl alcohol and benzyl benzoate as cosolvents. In some embodiments, the benzyl alcohol can be present in an amount of about 0-20% (e.g., 0-15% or 0-10%, such as about 10%) of the solvent, and benzyl benzoate can be present in an amount of about 0-50% (e.g., 0-35% or 0-30%, such as about 20%)

of the solvent, wherein the balance of the solvent can be any one or more of the pharmaceutically acceptable oil described herein, such as corn oil, castor oil, sesame oil, peanut oil, cottonseed oil, and/or Miglyol 812, etc. The combination of benzyl alcohol and benzyl benzoate were shown to achieve a lower viscosity and glide force, when compared with using just benzyl alcohol or benzyl benzoate. Further, it was unexpectedly found that a representative abiraterone prodrug (abiraterone decanoate) formulation comprising an oil (corn oil, 70%) and benzyl alcohol (10%) and benzyl benzoate (20%) achieved a much higher abiraterone plasma exposure in monkeys when compared with a formulation comprising the same oil vehicle without benzyl benzoate, i.e., corn oil, at 90%, and benzyl alcohol at 10%, which has substantially the same concentration of abiraterone decanoate, and dosed at the same amount.

The solubility of the abiraterone esters can be affected upon adding a co-solvent to the vegetable oil vehicle. In some embodiments, the abiraterone ester is completely dissolved in the composition, and in other embodiments the abiraterone ester is partly dispersed in the composition. In one embodiment, the abiraterone esters are fully dissolved in the vehicle.

The abiraterone prodrug formulations can also contain pharmaceutically acceptable preservatives, polymers, antioxidants, antimicrobials, chelating agents, and other excipients such as citric acid, dextrose, ascorbic acid, benzalkonium chloride, benzoic acid, sodium betadex sulfobutyl ether, calcium chloride, sodium carbomethoxycellulose, chlorobutanol, creatine, croscarmellose, dibasic potassium phosphate, sodium docusate, sodium edetate, glycerin, sodium hyaluronate, hydroxypropyl betadex, lactic acid, lactose, lecithin, maleic acid, mannitol, meglumine, methylcellulose, methylparaben, microcrystalline cellulose, miripitium chloride, momothioglycerol, phenol, poloxamer 188, polyglactin, polysorbate 20, polysorbate 40, polysorbate 80, propylparaben, sodium acetate, sodium benzoate, sodium citrate, sorbitan monolaurate, sorbitol, sucrose, tartaric acid, trisodium citrate, tromantadine, tromethamine, and urea.

The abiraterone prodrug formulations can be sterilized by methods known by persons skilled in the art (for example, gamma irradiation, micron filtration, and autoclaving).

Long-Acting Release of Abiraterone

The abiraterone prodrugs and abiraterone prodrug formulations (e.g., those containing compounds of Formula I or II as described herein) of the present disclosure are typically formulated to provide a long-acting release of abiraterone to a subject in need thereof, such as those having a sex hormone-dependent benign or malignant disorder, an androgen receptor driven cancer, a syndrome due to androgen excess, and/or a syndrome due to glucocorticoid excess such as hypercortisolemia, preferably as a parenteral formulation such as intramuscular, intradermal, or subcutaneous formulation. In some embodiments, the abiraterone prodrugs and abiraterone prodrug formulations (e.g., those containing compounds of Formula I or II as described herein) of the present disclosure can be formulated to deliver therapeutic blood plasma levels of abiraterone over an extended period of time (e.g., at least 1 week, e.g., at least two weeks, at least 3 weeks, at least 4 weeks, and up to six or eight weeks or more, such as up to ten weeks or more, etc.) to subjects having a hormone-dependent benign or malignant disorder, an androgen receptor driven cancer, a syndrome due to androgen excess, and/or a syndrome due to glucocorticoid excess such as hypercortisolemia, following a single administration. In some embodiments, the therapeutic blood plasma concentration of abiraterone can be a concentration of at least 1 ng/ml, e.g., at least 2 ng/ml, at least 4 ng/ml, at least 8 ng/ml. In some embodiments, the therapeutic blood plasma concentration of abiraterone can also be about 0.5 ng/ml or higher. In some embodiments, the therapeutic blood plasma concentration of abiraterone can also be about 0.1 ng/ml or higher.

Unit Dosage Forms

In some embodiments, the abiraterone prodrugs and abiraterone prodrug formulations (e.g., those containing compounds of Formula I or II as described herein) of the present disclosure can be formulated as a unit dosage form. In some embodiments, the unit dosage form can include a sufficient amount of the respective prodrug such that after a single administration (e.g., intramuscular injection) to a subject, e.g., a subject having a sex hormone-dependent benign or malignant disorder (e.g., metastatic CRPC or metastatic CSPC), an androgen receptor driven cancer, a syndrome due to androgen excess, and/or a syndrome due to glucocorticoid excess such as hypercortisolemia, the unit dosage form provides a therapeutically effective blood plasma concentration of abiraterone in the subject for a period of at least two weeks, such as at least 3 weeks, at least 4 weeks, at least 5 weeks, and up to six or eight weeks or more, such as up to ten weeks or more, etc. In some embodiments, the therapeutic blood plasma concentration of abiraterone can be a concentration of at least 1 ng/ml, e.g., at least 2 ng/ml, at least 4 ng/ml, at least 8 ng/ml. In some embodiments, the therapeutic blood plasma concentration of abiraterone can also be about 0.5 ng/ml or higher. In some embodiments, the therapeutic blood plasma concentration of abiraterone can also be about 0.1 ng/ml or higher. In some embodiments, the unit dosage form is a parenteral formulation such as intramuscular, intradermal, or subcutaneous formulation. In some embodiments, the unit dosage form is a non-aqueous solution or suspension. In some embodiments, the unit dosage form comprises the abiraterone prodrug (e.g., compound of Formula I or II) dissolved or suspended in a pharmaceutically acceptable oil, e.g., a vegetable oil such as castor oil, corn oil, sesame oil, cottonseed oil, peanut oil, poppy seed oil, tea seed oil, or soybean oil. In some embodiments, two or more different pharmaceutically acceptable oil can be used in the unit dosage forms. In some embodiments, the unit dosage form can further comprise a pharmaceutically acceptable solvent, e.g., an alcohol, an ester, and/or an acid, such as benzyl alcohol, benzyl benzoate, or a combination thereof. Other suitable ingredients for the unit dosage forms include those described herein.

The abiraterone prodrug (e.g., compound of Formula I or II) is typically present in the unit dosage form at a concentration of about 25 mg/ml to about 500 mg/ml (e.g., about 25 mg/ml, about 50 mg/ml, about 100 mg/ml, about 150 mg/ml, about 200 mg/ml, about 250 mg/ml, about 300 mg/ml, about 400 mg/ml, about 500 mg/ml, or any ranges between the recited values). The amount of abiraterone prodrug in the unit dosage forms can vary, depending on various factors such as the clearance rate of the respective abiraterone prodrug, the intended dosing frequency and the desired plasma levels, etc. Typically, the amount of the abiraterone prodrug can be in the range of about 50 mg to about 2000 mg, which if expressed as equivalent of abiraterone, can typically range from about 25 mg to about 1750 mg. In some embodiments, the amount of the abiraterone prodrug can also be higher, such as in the range of about 50 mg to about 5000 mg. In some embodiments, to achieve a less frequent dosing frequency, such as a once a month, once every two months, or once every three months dosing frequency, the prodrug can be included in the unit dosage form at an amount and/or concentration as high as safely tolerable to a subject user. Typically, the unit dosage form is formulated to have a viscosity suitable for parenteral injection, such as suitable for intramuscular, intradermal, or subcutaneous injection.

In some embodiments, the unit dosage form can be formulated to achieve certain pharmacokinetic (PK) profiles, e.g., a PK profile with a substantially flat curve after an initial rising period. Typically, after the unit dosage form is administered to a subject, during the initial few hours and up to a few days (e.g., 5 days or a week) post administration, the plasma concentration of abiraterone in the subject can be increased, which is then gradually plateaued, see e.g., FIGS. 2-4. In some embodiments, after this initial rising period, the plasma concentration of abiraterone in the subject can be plateaued and can be substantially constant for an extended period of time, for example, for at least a few days (e.g., 2, 3, 4, 5, or 6 days), or for at least 1 week, at least 2 weeks, at least 4 weeks, at least 6 weeks, at least 8 weeks, at least 10 weeks, etc.

In some embodiments, the unit dosage form is suitable for once a month (or once in more than a month, such as once every two months, or once every three months) dosing, and upon a single administration (e.g., intramuscularly) to a subject in need thereof, the unit dosage form achieves a PK profile characterized by one or more of the following: (a) the unit dosage form provides a therapeutically effective blood plasma concentration of abiraterone in the subject for at least 4 weeks, such as up to 6 weeks or 8 weeks, or up to 10 weeks or more; (b) a single dose $C_{max}$ of abiraterone of between about 5 ng/ml and about 300 ng/ml (e.g., between about 50 ng/ml and about 100 ng/ml, about 10 ng/ml and about 100 ng/ml, or between about 15 ng/ml and about 160 ng/ml); (c) no food effect; (d) a single dose $C_{max}$ of abiraterone reduced by at least 30% compared to the $C_{max}$ of abiraterone observed at steady state for a once daily oral dose of Zytiga® at 1000 mg without food; (e) a single dose $C_{min}$ of abiraterone at day 28 post administration between about 1 ng/ml and about 8 ng/ml, or above about 8 ng/ml; (f) the blood plasma concentration of abiraterone remains substantially constant, e.g., for at least 1 week, e.g., between 1 week and 3 weeks, between 1 week and 10 weeks, or between 2 weeks and 8 weeks post administration. In some embodiments, substantially constant for a period of time can mean that the highest concentration observed for any day (i.e., 24 hours) during that time period is no greater than 4-fold, for example, no greater than 2-fold, of the lowest concentration observed for the same day. No food effect should be generally understood as that no significant differences in PK are observed when the unit dosage form is administered to subjects with food or without food, for example, in some embodiments, no food effect can mean that the $C_{max}$ and AUC of abiraterone are substantially the same (e.g., between 80% to 125%) between subjects dosed at a fed state or fasted state. A single dose $C_{max}$ as used herein should be understood as the $C_{max}$ achieved following a single administration to a treatment naïve subject (generally refers to a subject who has not received any abiraterone medication within at least 3 days, such as at least 1 week, prior to the administration and with no observable plasma abiraterone prior to the administration). A single dose $C_{min}$ used herein refers to the minimum concentration observed for a given day following a single administration to a treatment naïve subject, e.g., at day 28 post administration.

In some embodiments, the unit dosage form is suitable for once a month (or once in more than a month, such as once every two months, or once every three months) dosing, and upon administration (e.g., intramuscularly) of the unit dosage form once in a month (or once in more than a month, such as once every two months, or once every three months) to a subject in need thereof, the unit dosage form achieves (a) a steady state $C_{max}$ of abiraterone of between about 5 ng/ml and about 300 ng/ml (e.g., between about 50 ng/ml and about 100 ng/ml, between about 10 ng/ml and about 100 ng/ml, or between about 15 ng/ml and about 160 ng/ml); (b) no food effect; (c) a steady state $C_{max}$ of abiraterone reduced by at least 30% compared to the $C_{max}$ of abiraterone observed at steady state for a once daily oral dose of Zytiga® at 1000 mg without food; (d) a steady state $C_{min}$ of abiraterone between about 1 ng/ml and about 8 ng/ml, or above about 8 ng/ml; and (g) the blood plasma concentration of abiraterone remains substantially constant, e.g., for at least 1 week, e.g., between 1 week and 3 weeks, between 1 week and 10 weeks, or between 2 weeks and 8 weeks post each administration. A steady state $C_{max}$ or $C_{min}$ as used herein should be understood as the $C_{max}$ or $C_{min}$ observed after a steady state is reached, typically following several administrations to a subject.

In some embodiments, the unit dosage form can be packaged in a container such as a vial or ampule. In some embodiments, the unit dosage form can be included in a pre-filled syringe or in a kit with a syringe, such as a disposable syringe. Other packaging and/or containers are also useful, which are known to those skilled in the art. In some embodiments, a kit comprising multiple unit dosage forms described herein is also provided. In some embodiments, the kit can further comprise a syringe. Typically, one or more (such as 1) unit dosage forms are used to satisfy a desired single dosing amount. In some embodiments, the present disclosure provides abiraterone prodrug formulations that allow multiple single uses. In some embodiments, the present disclosure provides abiraterone prodrug formulations that can be subdivided into multiple unit dosage forms.

Exemplary Specific Formulations

In some embodiments, the present disclosure also provides some specific abiraterone prodrug formulations, which can in some embodiments be in a unit dosage form or a multiple unit dosage form. For example, the tables below (Table A and B) show some representative abiraterone ester prodrug formulation in an oil vehicle. All numeric values in the tables should be understood as preceded by the term "about." The concentration of abiraterone prodrug refers to the amount of abiraterone prodrug in mg per ml of the final formulation, which can be a solution or suspension. The amount of oil (the primary solvent) and co-solvent in the tables is expressed as volume percentage of solvent, which includes both the oil and co-solvent. Suitable oil includes any of the pharmaceutically acceptable oil as described herein. Suitable co-solvents also include any of those described herein, e.g., an alcohol, an ester, and/or an acid, such as benzyl alcohol, benzyl benzoate, or a combination thereof, see e.g., Table B. One example of suitable co-solvents is benzyl alcohol. One example of suitable co-solvents is a combination of benzyl alcohol and benzyl benzoate. In some embodiments, no co-solvent is included in the formulation. In some embodiments, the co-solvent does not include benzyl benzoate. Other optional ingredients are described herein.

TABLE A

Exemplary Formulations

| Ingredients | Amount/Concentration | | |
|---|---|---|---|
| | Typical | Exemplary range | More Exemplary Range |
| Abiraterone prodrug (e.g., abiraterone acetate, abiraterone decanoate, abiraterone pentanoate, abiraterone hexanoate, abiraterone heptanoate, abiraterone isocaproate, or abiraterone cypionate) | 25 mg/ml to 500 mg/ml | 50 mg/ml to 300 mg/ml; 100 mg/ml to 300 mg/ml | 75 mg/ml to 300 mg/ml |
| Oil (e.g., castor oil, corn oil) | 50% to 100% of solvent | 70% to 100% of solvent | 80% to 100% of solvent, such as 90% |
| Co-solvent (e.g., benzyl alcohol, benzyl benzoate, or combination thereof) | 0% to 50% of solvent | 0% to 40% or 0% to 30% of solvent | 0% to 30% or 0% to 20% of solvent, such as 10%, or 30% |
| Other optional ingredients | | | |

In some embodiments, the present disclosure provides an abiraterone prodrug formulation comprising the abiraterone prodrug and a pharmaceutically acceptable carrier, wherein the pharmaceutically acceptable carrier comprises a pharmaceutically acceptable oil (e.g., described herein), benzyl alcohol, and benzyl benzoate. In some embodiments, the abiraterone prodrug can be abiraterone decanoate. In some embodiments, the abiraterone prodrug can be abiraterone isocaproate. The pharmaceutically acceptable oil typically comprises a triglyceride derived from fatty acids. In some embodiments, the pharmaceutically acceptable oil can be nature oil, synthetic oil, or semi-synthetic oil, such as fractionated coconut oil and medium-chain triglycerides, such as those sold under the trademark Miglyol. In some embodiments, the pharmaceutically acceptable oil can be selected from vegetable oil, castor oil, corn oil, sesame oil, cottonseed oil, peanut oil (arachis oil), poppy seed oil, tea seed oil, and soybean oil. In some embodiments, the present disclosure provides certain exemplary formulations shown in Table B.

TABLE B

Further Exemplary Formulations

| Ingredients | Amount/Concentration | | |
|---|---|---|---|
| | Typical | Exemplary range | More Exemplary Range |
| Abiraterone prodrug (e.g., abiraterone decanoate or abiraterone isocaproate) | 25 mg/ml to 500 mg/ml | 50 mg/ml to 300 mg/ml; 100 mg/ml to 300 mg/ml | 75 mg/ml to 300 mg/ml, such as 150 mg/ml to about 250 mg/ml |
| Oil (e.g., corn oil, sesame oil, peanut oil, cottonseed oil, and/or Miglyol 812) | 30% to 100% of solvent | 50% to 90% of solvent | 60% to 90% of solvent, such as 70% |
| Co-solvent 1 (e.g., benzyl alcohol) | 0% to 20% of solvent | 0% to 15% of solvent | 0% to 10% of solvent, such as 10% |
| benzyl benzoate | 0% to 50% of solvent | 0% to 35% of solvent | 0% to 30% of solvent, such as 20% |
| Other optional ingredients | | | |

As used herein, when the solvent system of an abiraterone prodrug formulation comprises two or more solvents (including oil), the abiraterone prodrug formulation may be expressed as an abiraterone prodrug solution in the solvent system having x % of an oil and y % of a co-solvent (e.g., 90% corn oil and 10% benzyl alcohol) at a specified concentration. In such expressions, whether or not followed by "v/v," the x % and y % should be understood as based on volume percentages, unless otherwise specified or obviously contrary from context.

Combination Treatment

In some embodiments, the methods herein can comprise administering one or more other drug or agent (for example, another cancer chemotherapeutic drug, hormone replacement drug, or hormone ablation drug) to the subject, either concurrently or sequentially, through the same route or a different route of administration. In some embodiments, the other drug or agent can be a steroid, such as prednisone, prednisolone, and/or methylprednisolone. In some embodiments, the other drug or agent can be a chemotherapy drug, such as paclitaxel, mitoxantrone, and/or docetaxel. Although typically not administered in the methods herein, in some embodiments of the methods herein, the other agent or drug can be a GnRH agonist, such as Leuprolide, deslorelin, goserelin, or triptorelin, e.g., leuprolide acetate (e.g., a long-acting IM injectable formulation). In some embodiments, the other agent or drug can be seocalcitol, bicalutamide, flutamide, a glucocorticoid including, but not limited to, hydrocortisone, prednisone, prednisolone, or dexamethasone. The amount of the other drugs or agents to be administered can vary, typically can be an amount that is effective in treating the respective disease or disorder (e.g., prostate cancer) either alone or in combination with the abiraterone prodrug or abiraterone prodrug formulation of the present disclosure.

Additional suitable other drugs or agents include those described herein. For example, useful other drugs or agents include, but are not limited to, anticancer agents, hormone ablation agents, anti-androgen agents, differentiating agents, anti-neoplastic agents, kinase inhibitors, anti-metabolite agents, alkylating agents, antibiotic agents, immunological agents, interferon-type agents, intercalating agents, growth factor inhibitors, cell cycle inhibitors, enzymes, topoisomerase inhibitors, biological response modifiers, mitotic inhibitors, matrix metalloprotease inhibitors, genetic therapeutics, and anti-androgens.

For example, suitable anti-cancer agents, including but not limited to, acemannan, aclarubicin, aldesleukin, alemtuzumab, alitretinoin, altretamine, amifostine, amsacrine, anagrelide, anastrozole, ancestim, bexarotene, broxuridine, capecitabine, celmoleukin, cetrorelix, cladribine, clotrimazole, daclizumab, dexrazoxane, dilazep, docosanol, doxifluridine, bromocriptine, carmustine, cytarabine, diclofenac, edelfosine, edrecolomab, eflornithine, emitefur, exemestane, exisulind, fadrozole, filgrastim, finasteride, fludarabine phosphate, formestane, fotemustine, gallium nitrate, gemcitabine, glycopine, heptaplatin, ibandronic acid, imiquimod, iobenguane, irinotecan, irsogladine, lanreotide, leflunomide, lenograstim, lentinan sulfate, letrozole, liarozole, lobaplatin, lonidamine, masoprocol, melarsoprol, metoclopramide, mifepristone, miltefosine, mirimostim, mitoguazone, mitolactol, molgramostim, nafarelin, nartograstim, nedaplatin, nilutamide, noscapine, oprelvekin, osaterone, oxaliplatin, pamidronic acid, pegaspargase, pentosan polysulfate sodium, pentostatin, picibanil, pirarubicin, porfimer sodium, raloxifene, raltitrexed, rasburicase, rituximab, romurtide, sargramostim, sizofiran, sobuzoxane, sonermin, suramin, tasonermin, tazarotene, tegafur, temoporfin, temozolomide, teniposide, tetrachlorodecaoxide, thalidomide, thymalfasin, thyrotropin alfa, topotecan, toremifene, trastuzumab, treosulfan, tretinoin, trilostane, trimetrexate, ubenimex, valrubicin, verteporfin, vinorelbine. Suitable anti-androgen agents include but are not limited to bicalutamide, flutamide and nilutamide. Suitable differentiating agents include, but are not limited to, polyamine inhibitors; vitamin D and its analogs, such as, calcitriol, doxercalciferol and seocalcitol; metabolites of vitamin A, such as, ATRA, retinoic acid, retinoids; short-chain fatty acids; phenylbutyrate; and nonsteroidal anti-inflammatory agents. anti-neoplastic agent, including, but not limited to, tubulin interacting agents, topoisomerase inhibitors and agents, acitretin, alstonine, amonafide, amphethinile, amsacrine, ankinomycin, anti-neoplaston, aphidicolin glycinate, asparaginase, baccharin, batracylin, benfluron, benzotript, bromofosfamide, caracemide, carmethizole hydrochloride, chlorsulfaquinoxalone, clanfenur, claviridenone, crisnatol, curaderm, cytarabine, cytocytin, dacarbazine, datelliptinium, dihaematoporphyrin ether, dihydrolenperone, dinaline, distamycin, docetaxel, elliprabin, elliptinium acetate, epothilones, ergotamine, etoposide, etretinate, fenretinide, gallium nitrate, genkwadaphnin, hexadecylphosphocholine, homoharringtonine, hydroxyurea, ilmofosine, isoglutamine, isotretinoin, leukoregulin, lonidamine, merbarone, merocyanlne derivatives, methylanilinoacridine, minactivin, mitonafide, mitoquidone, mitoxantrone, mopidamol, motretinide, N-(retinoyl)amino acids, N-acylated-dehydroalanines, nafazatrom, nocodazole derivative, ocreotide, oquizanocinc, paclitaxel, pancratistatin, pazelliptine, piroxantrone, polyhaematoporphyrin, polypreic acid, probimane, procarbazine, proglumide, razoxane, retelliptine, spatol, spirocyclopropane derivatives, spirogermanium, strypoldinone, superoxide dismutase, teniposide, thaliblastine, tocotrienol, topotecan, ukrain, vinblastine sulfate, vincristine, vindesine, vinestramide, vinorelbine, vintriptol, vinzolidine, and withanolides. a kinase inhibitor including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, SOD mimics or $\alpha_v\beta_3$ inhibitors. Suitable anti-metabolite agents may be selected from, but not limited to, 5-FU-fibrinogen, acanthifolic acid, aminothiadiazole, brequinar sodium, carmofur, cyclopentyl cytosine, cytarabine phosphate stearate, cytarabine conjugates, dezaguanine, dideoxycytidine, dideoxyguanosine, didox, doxifluridine, fazarabine, floxuridine, fludarabine phosphate, 5-fluorouracil, N-(2'-furanidyl)-5-fluorouracil, isopropyl pyrrolizine, methobenzaprim, methotrexate, norspermidine, pentostatin, piritrexim, plicamycin, thioguanine, tiazofurin, trimetrexate, tyrosine kinase inhibitors, and uricytin. Suitable alkylating agents may be selected from, but not limited to, aldo-phosphamide analogues, altretamine, anaxirone, bestrabucil, budotitane, carboplatin, carmustine, chlorambucil, cisplatin, cyclophosphamide, cyplatate, diphenylspiromustine, diplatinum cytostatic, elmustine, estramustine phosphate sodium, fotemustine, hepsul-fam, ifosfamide, iproplatin, lomustine, mafosfamide, mitolactol, oxaliplatin, prednimustine, ranimustine, semustine, spiromustine, tauromustine, temozolomide, teroxirone, tetraplatin and trimelamol. Suitable antibiotic agents may be selected from, but not limited to, aclarubicin, actinomycin D, actinoplanone, adriamycin, aeroplysinin derivative, amrubicin, anthracycline, azino-mycin-A, bisucaberin, bleomycin sulfate, bryostatin-1, calichemycin, chromoximycin, dactinomycin, daunorubicin, ditrisarubicin B, dexamethasone, doxorubicin, doxorubicin-fibrinogen, elsamicin-A, epirubicin, erbstatin, esorubicin, esperamicin-A1, esperamicin-A1b, fostriecin, glidobactin, gregatin-A, grincamycin, herbimycin, corticosteroids such as hydrocortisone, idarubicin, illudins, kazusamycin, kesarirhodins, menogaril, mitomycin, neoenactin, oxalysine, oxaunomycin, peplomycin, pilatin, pirarubicin, porothramycin, prednisone, prednisolone, pyrindanycin A, rapamycin, rhizoxin, rodorubicin, sibanomicin, siwenmycin, sorangicin-A, sparsomycin, talisomycin, terpentecin, thrazine, tricrozarin A, and zorubicin. Non-limiting examples of suitable steroids include hydrocortisone, prednisone, prednisolone, or dexamethasone.

Combination Treatment for Prostate Cancer

Prostate cancer treatments often involve multiple therapies, including for example, radiotherapy, surgery, androgen deprivation therapy, hormone therapy, chemotherapy, immunotherapy, and various drug combinations. A search in the website clinicaltrials.gov identified more than 250 clinical trials with abiraterone/abiraterone acetate listed as an intervention agent, and many of such clinical trials include a combination therapy for treating prostate cancer. As discussed herein, compared to oral abiraterone acetate formulation, the abiraterone prodrugs herein can provide increased bioavailability, elimination of the food effect, reduced pill burden, less frequent dosing frequency, and sustained effective blood plasma levels of abiraterone, and prolonged CYP17A1 inhibition, with sustained increase of progesterone level and reduction of cortisol, dihydrotestosterone, and testosterone levels up to 70 days or more following administration of the abiraterone prodrug formulation. Considering their superior pharmacokinetic and/or pharmacodynamics profiles, the abiraterone prodrugs herein can also be advantageously used in various combination therapies to replace or supplement the oral administration of abiraterone acetate.

Further, the present disclosure shows that administering an abiraterone prodrug to a subject can achieve a sustained reduction of serum androgen levels without the need to castrate the subject or administering to the subject another drug in an amount effective in reducing serum androgen levels. Thus, in any of the embodiments described herein, unless otherwise specified or obviously contrary from context, the methods herein can include the combination treatment that does not treat the subject with a gonadal testosterone suppressing drug, other than the administered abiraterone prodrug, in an amount effective to reduce serum testosterone level in the subject. For example, in some embodiments, the methods herein can include the combination treatment that does not treat the subject with any GnRH angonist and antagonist.

In some embodiments, the present disclosure provides a method of treating prostate cancer (e.g., any of those described herein) in a subject in need thereof, such as a non-castrated subject, with a combination therapy, which comprises administering to the subject a therapeutically effective amount of the abiraterone prodrug (e.g., abiraterone decanoate) or the abiraterone prodrug formulation herein, and one or more additional therapies. The one or more additional therapies can be administered to the subject concurrently or sequentially in any order with administering the abiraterone prodrug or abiraterone prodrug formulation herein, which can be via the same or different route of administration. In some embodiments, the method herein comprises treating the subject with a radiotherapy or surgery. In some embodiments, the method comprises administering to the subject one or more other agents selected from anticancer agents, hormone ablation agents, anti-androgen agents, differentiating agents, anti-neoplastic agents, kinase inhibitors, anti-metabolite agents, alkylating agents, antibiotic agents, immunological agents, interferon-type agents, intercalating agents, growth factor inhibitors, cell cycle inhibitors, enzymes, topoisomerase inhibitors, biological response modifiers, mitotic inhibitors, matrix metalloprotease inhibitors, genetic therapeutics, or combinations thereof. In some embodiments, the method comprises administering to the subject one or more other agents selected from a chemotherapeutic drug, hormone replacement drug, or hormone ablation drug. In some embodiments, the method comprises treating the subject with an androgen deprivation therapy. While many of the combination therapies below are described as in connection with various treatments for prostate cancer, the present disclosure is not so limited. And in some embodiments, the combination therapies described below can also be used in the treatment of other diseases or disorders described herein, such as other cancers described herein.

In more particular embodiments, the combination therapy typically includes administering to the subject a glucocorticoid. For example, in some embodiments, the method comprises administering to the subject one or more agents selected from hydrocortisone, prednisone, prednisolone, methylprednisolone, and dexamethasone. However, in some embodiments, a glucococorticoid replacement therapy (e.g., administering a glucocorticoid, such as hydrocortisone, prednisone, prednisolone, methylprednisolone, or dexamethasone) is not desired. For example, a glucocorticoid may be contraindicated for the subject, who may have an underlying condition, such as diabetics. In some embodiments, the method can also be characterized in that the subject is not treated with a glucocorticoid replacement therapy. In some embodiments, the subject is not treated with an agent selected from hydrocortisone, prednisone, prednisolone, methylprednisolone, and dexamethasone. In some embodiments, the method can comprise administering to the subject a mineralocorticoid receptor antagonist, such as eplerenone. For example, in any of the embodiments herein when glucococorticoid replacement therapy is not desired and/or not administered, the method can can comprise administering to the subject a mineralocorticoid receptor antagonist, such as eplerenone.

The combination therapy for the methods herein can also include, but typically does not include, an androgen deprivation therapy, such as through administering to the subject a gonadotropin-releasing hormone (GnRH) analog. When included, suitable GnRH analogs for the combination therapy are not particularly limited and include both GnRH agonists and GnRH antagonists. For example, in some embodiments, the method can comprise administering to the subject a gonadotropin-releasing hormone (GnRH) agonist, such as buserelin, leuprolide, deslorelin, fertirelin, histrelin, gonadorelin, lecirelin, goserelin, nafarelin, peforelin or triptorelin, and/or a GnRH antagonist, such as abarelix, cetrorelix, degarelix, ganirelix, elagolix, linzagolixa, or relugolix. In some embodiments, the subject is not administered any of the GnRH agonists and GnRH antagonists described herein.

Inhibition of Androgen Receptor Activities

In some embodiments, the combination therapy includes treating the subject to reduce androgen receptor (AR) activities, such as an AR antagonist or an agent otherwise downregulating or inhibiting AR activities.

In some embodiments, the method can include administering to the subject an androgen receptor (AR) antagonist. Various AR antagonists are known in the art, which include without limitation $1^{st}$ and $2^{nd}$-generations AR antagonists, see e.g., Rice, M. A., et al. *Front Oncol.* 9:801 (2019), and third-generation AR antagonists, such as an N-terminal domain inhibitor. In some embodiments, the method comprises administering to the subject a $1^{st}$-generation androgen receptor antagonist, which includes without limitation, proxalutamide, bicalutamide, flutamide, nilutamide, topilutamide, etc. In some embodiments, the method comprises administering to the subject a $2^{nd}$-generation androgen receptor antagonist, which includes without limitation, for example, apalutamide, darolutamide or enzalutamide. In some embodiments, the method comprises administering to the subject apalutamide. In some embodiments, the method comprises administering to the subject enzalutamide. In some embodiments, the method comprises administering to the subject a $3^{rd}$-generation androgen receptor antagonist, such as an N-terminal domain inhibitor. N-terminal domain inhibitors are known in the art. Non-limiting useful examples include any of those described in U.S. Application Publication No. 2020/0123117, the content of which is herein incorporated by reference. It should be noted that in embodiments where an AR antagonist is administered, one or more such antagonists can be administered, which can be selected from $1^{st}$, $2^{nd}$ or $3^{rd}$ AR antagonists alone, or in any combination.

In addition to agents directly targeting androgen receptor, other methods and/or agents that modulate androgen receptor activities, including for example, modulation of upstream kinase activities and/or androgen receptor transcriptional activities, can also be used in the combination therapy herein. For example, in some embodiments, the combination therapy can include administering to the subject one or more upstream kinase modulators, the activation or inhibition of which can reduce AR activities. Such upstream kinases are known in the art, for example, as described in Shah, K. and Bradbury, N. A., *Cancer cell microenviron.* 2(4):doi: 10.14800/ccm.1023 (2015), and Koul H. K. et al. *Genes & Cancer* 4(9-10):342-359 (2013). In some embodiments, the method comprises administering to the subject one or more kinase modulators selected from FLT-3 (FMS-like tyrosine kinase) inhibitors, AXL (anexelekto) inhibitors (e.g., Gilteritinib), CDK (cyclin dependent kinase) inhibitors, such as CDK1, 2, 4, 5, 6, 7, or 9 inhibitors, retinoblastoma (Rb) inhibitors, protein kinase B (AKT) inhibitors, SRC inhibitors, IkappaB kinase 1 (IKK1) inhibitors, PIM-1 modulators, Lemur tyrosine kinase 2 (LMTK2) modulators, Lyn inhibitors, Aurora A inhibitors, ANPK (a nuclear protein kinase) inhibitors, extracellular-signal regulated kinase (ERK) modulators, c-jun N-terminal kinase (JNK) modulators, Big MAP kinase (BMK) modulators, p38 mitogen-activated protein kinases (MAPK) modulators, and combinations thereof. Suitable kinase modulators/inhibitors are not particularly limited, which include any of those known, for example, small molecule drugs, polypeptides including antibodies such as monoclonal antibodies or antigen binding fragments thereof, RNA or DNA based agents.

In some embodiments, the combination therapy can include administering to the subject an agent that downregulates AR or otherwise inhibits AR activities. Without wishing to be bound by theories, AR activities can be affected on the genomic and/or the transcription level of AR itself, or the genomic and/or the transcription level of those upstream targets of AR that play a role in regulating AR activities and those downstream targets that are regulated by AR, using a variety of molecules which interfere with transcription and/or translation (e.g., RNA silencing agents (e.g., antisense, siRNA, shRNA, micro-RNA), Ribozyme and DNAzyme), or on the protein level using e.g., antagonists, enzymes that cleave the polypeptide, small molecules that interfere with the protein's activity (e.g., competitive ligands) and the like.

In some embodiments, downregulation of AR or inhibition of AR activities can be achieved through RNA silencing of a target gene (e.g., AR or suitable upstream and downstream targets of AR as described herein, etc.). As used herein, the phrase "RNA silencing" refers to a group of regulatory mechanisms (e.g., RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In some embodiments, the RNA silencing agent is capable of preventing complete processing (e.g., the full translation and/or expression) of an mRNA molecule through a post-transcriptional silencing mechanism. RNA silencing agents include non-coding RNA molecules, for example, RNA duplexes comprising paired strands, as well as precursor RNAs from which such small non-coding RNAs can be generated. Exemplary RNA silencing agents include double-stranded RNAs (dsRNAs) such as short interfering RNAs (siRNAs), miRNAs and shRNAs. In one embodiment, the RNA silencing agent is capable of inducing RNA interference. In another embodiment, the RNA silencing agent is capable of mediating translational repression. The strands of a double-stranded interfering RNA (e.g., an siRNA) may be connected to form a hairpin or stem-loop structure (e.g., an shRNA or sh-RNA). Thus, as mentioned, the RNA silencing agent of some embodiments of the disclosure may also be a short hairpin RNA (shRNA).

It will be appreciated that the RNA silencing agent of some embodiments of the present disclosure need not be limited to those molecules containing only RNA, but further encompasses chemically modified nucleotides and non-nucleotides.

In some embodiments, the RNA silencing agent provided herein can be functionally associated with a cell-penetrating peptide. As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell.

According to another embodiment, the RNA silencing agent may be a miRNA or a mimic thereof. The term "microRNA", "miRNA", and "miR" are synonymous and refer to a collection of non-coding single-stranded RNA molecules of about 19-28 nucleotides in length, which regulate gene expression. miRNAs are found in a wide range of organisms and have been shown to play a role in development, homeostasis, and disease etiology. The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs).

Downregulation of AR or inhibition of AR activities can also be achieved by gene editing of a target gene (e.g., AR or suitable upstream and downstream targets of AR as described herein, etc.). Gene editing can be performed, for example, with a clustered regularly interspaced short palindromic repeats CRISPR-CAS9 system. CRISPR-CAS9 systems have been described in the literature and can include, for example, CAS9 and a guide RNA. Other gene editing techniques have also been described in the literature and can also be used.

Another agent capable of downregulating a target (e.g., AR or suitable upstream and downstream targets of AR as described herein, etc.) is a DNAzyme molecule capable of specifically cleaving an mRNA transcript or DNA sequence of the target. DNAzymes are single-stranded polynucleotides which are capable of cleaving both single and double stranded target sequences. (Breaker et al., *Chemistry and Biology* 1995; 2:655; Santoro et al., *Proc. Natl. Acad. Sci. USA* 1997; 943:4262.) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions. (Santoro et al., Khachigian, *Curr. Opin. Mol. Ther.* 2002; 4:119-121.)

Downregulation of a target (e.g., AR or suitable upstream and downstream targets of AR as described herein, etc.) can also be affected by using an antisense polynucleotide capable of specifically hybridizing with an mRNA transcript encoding the target.

Another agent capable of downregulating a target (e.g., AR or suitable upstream and downstream targets of AR as described herein, etc.) is a ribozyme molecule capable of specifically cleaving an mRNA transcript encoding a target. Ribozymes are being increasingly used for the sequence-specific inhibition of gene expression by the cleavage of mRNAs encoding proteins of interest. (Welch et al., *Curr. Opin. Biotechnol.* 1998; 9:486-96.)

Another agent capable of downregulating a target (e.g., AR or suitable upstream and downstream targets of AR as described herein, etc.) is any molecule which binds to and/or cleaves the target. Such molecules can be antagonists of the target, or inhibitory peptides of the target.

Another agent which can be used along with some embodiments of the present disclosure to downregulate a target (e.g., AR or suitable upstream and downstream targets of AR as described herein, etc.) is a molecule which prevents target activation and/or substrate binding.

Another agent which can be used along with some embodiments of the present disclosure to downregulate AR or inhibit AR's activities is an androgen receptor degrader, such as those based on PROteolysis TArgeting Chimeric (PROTAC) technology. See, e.g., Kregel, S. et al. *Neoplasia* 22(2):111-119 (2020).

Another agent which can be used along with some embodiments of the present disclosure to downregulate a target (e.g., AR or suitable upstream and downstream targets of AR as described herein, etc.) is to repress or downregulate the activation of the target's transcriptional activity, more particularly, AR's transcriptional activities. For example, such agent can interfere with the nuclear translocation of AR, downregulate the protein level of AR, decrease hormone binding to AR, interfere with recruitment of transcriptional cofactors (e.g., steroid receptor coactivator 1 (SRC1) and transcriptional intermediary factor 2 (TIF2)), interefer with with AR-DNA-binding, e.g., the binding to specific DNA response elements (AREs or, androgen response elements), inhibit AR recruitment to an AR target gene enhancer, and/or inhibit AR-chromatin binding etc. or otherwise inhibit the DNA-binding-dependent or non-DNA-binding-dependent AR signaling pathways. Suitable agents that can inhibit or interfere with AR transcriptional activities include any of those known in the art and any of those agents exemplified herein that are capable of inhibiting or interfering with such activities. For example, certain AR antagonists such as the $1^{st}$ generation AR antagonists (e.g., bicalutamide) are known to inhibit AR transcriptional activities by inhibiting nuclear translocation of AR. Other agents, such as arsenic compounds (e.g., arsenic trioxide), were also known to inhibit AR transcriptional activity. See e.g., Rosenblatt A. E., et al, *Mol. Endocrinol.* 23(3):412-421 (2009).

In some embodiments, the combination therapy can include administering to the subject one or more chemotherapeutic agents. Suitable chemotherapeutic agents include any of those known in the art. In some embodiments, the method comprises administering to the subject a taxane based chemotherapeutic agent (e.g., docetaxel, cabazitaxel, paclitaxel, etc.) and/or platinum based chemotherapeutic agent (e.g., cisplatin, carboplatin, oxaliplatin, etc.).

In some embodiments, the combination therapy can include treating the subject with a radiotherapy. Suitable radiotherapy includes any of those known in the art. In some embodiments, the method comprises treating the subject with stereotactic body radiotherapy or neutron radiation.

In some embodiments, the combination therapy can include treating the subject with Radium-223, e.g., Xofigo (Radium-223 dichloride) injection.

In some embodiments, the combination therapy can include administering to the subject one or more immunotherapies. Suitable immunotherapies include any of those known in the art. In some embodiments, the method comprises administering to the subject Sipuleucel-T. In some embodiments, the method comprises administering to the subject an immune checkpoint inhibitor. For example, in some embodiments, the method comprises administering to the subject an anti-PD-1 antibody, such as pembrolizumab or nivolumab, and/or an anti-PD-L1 antibody, such as avelumab or atezolizumab. In some embodiments, the method comprises administering to the subject an anti-CTLA-4 antibody, such as ipilimumab.

In some embodiments, the combination therapy can include administering to the subject a bispecific T-cell engager (BiTE) therapy, such as blinatumomab or solitomab.

In some embodiments, the combination therapy can include administering to the subject one or more poly ADP ribose polymerase (PARP) inhibitors. In some embodiments, the subject having prostate cancer also has DNA repair defects. In some embodiments, the subject having prostate cancer does not have DNA repair defects. Suitable PARP inhibitors include any of those known in the art. For example, in some embodiments, the method comprises administering to the subject a PARP inhibitor selected from niraparib, rucaparib, olaparib, talazoparib, veliparib, and fluzoparib.

In some embodiments, the combination therapy can include administering to the subject one or more kinase inhibitors. In some embodiments, the subject is characterized as having an abnormal level of the respective kinase. In some embodiments, the kinase inhibitor can reduce the activity of androgen receptor or otherwise beneficial to cancer treatment. Suitable kinase inhibitors include any of those known in the art. For example, in some embodiments, the method comprises administering to the subject a kinase inhibitor selected from sunitinib, dasatinib, cabozantinib, erdafitinib, dovitinib, capivasertib, onvansertib, ipatasertib, afuresertib, alisertib, apitolisib, and opaganib.

In some embodiments, the combination therapy can include administering to the subject one or more bone protecting agents. In such embodiments, typically, the subject is characterized as having prostate cancer (e.g., CRPC) with bone metastasis. Suitable bone protecting agents include any of those known in the art. For example, in some embodiments, the method comprises administering to the subject a bone protecting agent selected from denosumab and zolendronic acid.

In some embodiments, the combination therapy can include administering to the subject one or more additional agents that are useful for treating prostate cancer, by itself or in combination with an abiraterone medication such as the abiraterone prodrugs herein. Such additional agents are not particularly limited. For example, in some embodiments, the method comprises administering to the subject a therapeutic agent selected from 1) an anti-IL23 targeting monoclonal antibody, e.g., tildrakizumab; 2) a selenium, such as sodium selenite; 3) an EZH2 inhibitor, e.g., CPI-1205, GSK2816126, or tazemetostat; 4) a CDK4/6 inhibitor, e.g., palbociclib, ribociclib, abemaciclib; 6) a bromodomain and extra-terminal domain (BET) inhibitor, e.g., CCS1477, INCB057643, alobresib, ZEN-3694, or molibresib (GSK525762); 7) an anti-CD105 antibody, e.g., TRC105 or carotuximab; 8) niclosamide; 9) an A2A receptor antagonist, e.g., AZD4635; 10) a phosphoinositide 3-kinase (PI3K) inhibitor, e.g., AZD-8186, buparlisib, or dactolisib; 11) a further non-steroidal CYP17A1 inhibitor, e.g. seviteronel; 12) an antiprogestogen, e.g., onapristone; 13) navitoclax; 14) an HSP90 inhibitor, e.g., onalespib (AT13387); 15) an HSP27 inhibitor, e.g., OGX-427; 16) a 5-alpha-reductase inhibitor, e.g., dutasteride; 17) metformin; 18) AMG-386; 19) dextromethorphan; 20) theophylline; 21) hydroxychloroquine; and 22) lenalidomide. In some embodiments, the combination therapy can include administering to the subject one or more one or more kinase modulators selected from FLT-3 (FMS-like tyrosine kinase) inhibitors, AXL (anexelekto) inhibitors (e.g., Gilteritinib), CDK (cyclin dependent kinase) inhibitors, such as CDK1, 2, 4, 5, 6, 7, or 9 inhibitors, retinoblastoma (Rb) inhibitors, protein kinase B (AKT) inhibitors, SRC inhibitors, IkappaB kinase 1 (IKK1) inhibitors, PIM-1 modulators, Lemur tyrosine kinase 2 (LMTK2) modulators, Lyn inhibitors, Aurora A inhibitors, ANPK (a nuclear protein kinase) inhibitors, extracellular-signal regulated kinase (ERK) modulators, c-jun N-terminal kinase (JNK) modulators, Big MAP kinase (BMK) modulators, p38 mitogen-activated protein kinases (MAPK) modulators, and combinations thereof. In some embodiments, a cell therapy, such as a T cell mediated cell therapy including central memory T cells, can also be part of the combination therapy.

In some embodiments, the combination therapy can include administering to the subject one or more agents selected from 1) a poly (ADP-ribose) polymerase (PARP) inhibitor including but not limited to olaparib, niraparib, rucaparib, talazoparib; 2) an androgen receptor ligand binding domain inhibitor including but not limited to enzalutamide, apalutamide, darolutamide, bicalutamide, nilutamide, flutamide, ODM-204, TAS3681; 3) an additional inhibitor of CYP17 including but not limited to galeterone, abiraterone, abiraterone acetate; 4) a microtubule inhibitor including but not limited to docetaxel, paclitaxel, cabazitaxel (XRP-6258); 5) a modulator of PD-1 or PD-L1 including but not limited to pembrolizumab, durvalumab, nivolumab, atezolizumab; 6) a gonadotropin releasing hormone agonist including but not limited to cyproterone acetate, leuprolide; 7) a 5-alpha reductase inhibitor including but not limited to finasteride, dutasteride, turosteride, bexlosteride, izonsteride, FCE 28260, SKF105,111; 8) a vascular endothelial growth factor inhibitor including but not limited to bevacizumab (Avastin); 9) a histone deacetylase inhibitor including but not limited to OSU-HDAC42; 10) an integrin alpha-v-beta-3 inhibitor including but not limited to VITAXIN; 11) a receptor tyrosine kinase inhibitor including but not limited to sunitumib; 12) a phosphoinositide 3-kinase inhibitor including but not limited to alpelisib, buparlisib, idealisib; 13) an anaplastic lymphoma kinase (ALK) inhibitor including but not limited to crizotinib, alectinib; 14) an endothelin receptor A antagonist including but not limited to ZD-4054; 15) an anti-CTLA4 inhibitor including but not limited to MDX-010 (ipilimumab); 16) an heat shock protein 27 (HSP27) inhibitor including but not limited to OGX 427; 17) an androgen receptor degrader including but not limited to ARV-330, ARV-110; 18) an androgen receptor DNA-binding domain inhibitor including but not limited to VPC-14449; 19) a bromodomain and extra-terminal motif (BET) inhibitor including but not limited to BI-894999, GSK525762, GS-5829; 20) an androgen receptor N-terminal domain inhibitor including but not limited to a sintokamide; 21) an alpha-particle emitting radioactive therapeutic agent including but not limited to radium 233 or a salt thereof; 22) niclosamide; or related compounds thereof; 23) a selective estrogen receptor modulator (SERM) including but not limited to tamoxifen, raloxifene, toremifene, arzoxifene, bazedoxifene, pipindoxifene, lasofoxifene, enclomiphene; 24) a selective estrogen receptor degrader (SERD) including but not limited to fulvestrant, ZB716, OP-1074, elacestrant, AZD9496, GDC0810, GDC0927, GW5638, GW7604; 25) an aromitase inhibitor including but not limited to anastrazole, exemestane, letrozole; 26) selective progesterone receptor modulators (SPRM) including but not limited to mifepristone, lonaprison, onapristone, asoprisnil, lonaprisnil, ulipristal, telapristone; 27) a glucocorticoid receptor inhibitor including but not limited to mifepristone, COR108297, COR125281, ORIC-101, PT150; 28) CDK4/6 inhibitors including palbociclib, abemaciclib, ribociclib; 29) HER2 receptor antagonist including but not limited to trastuzumab, neratinib; and 30) a mammalian target of rapamycin (mTOR) inhibitor including but not limited to everolimus, temsirolimus.

The combination therapy herein is not particularly limited to any specific numbers of additional therapies. For example, in addition to administering the abiraterone prodrug or abiraterone prodrug formulation herein and an optional glucocorticoid such as hydrocortisone, prednisone, prednisolone, methylprednisolone, and dexamethasone, the combination therapy typically can include additional 1, 2, 3, 4, 5, 6, or more therapies described herein. For example, in some embodiments, the combination therapy can include one additional therapy, e.g., any one of those described herein, for example, a GnRH agonist, a GnRH antagonist, an androgen receptor antagonist, a chemotherapy, a PARP inhibitor, a kinase inhibitor, an immunotherapy, a radiation therapy, surgery, an androgen deprivation therapy, etc. In some embodiments, the combination therapy can include two or more additional therapies described herein. For example, in some particular embodiments, the combination therapy can include administering to the subject a PARP inhibitor and an androgen deprivation therapy. In some embodiments, the combination therapy can include administering to the subject a GnRH agonist and a radiation therapy. In some embodiments, the combination therapy can include administering to the subject a GnRH agonist, a chemotherapeutic agent, and a radiation therapy. In some embodiments, the combination therapy can include administering to the subject an androgen receptor antagonist (e.g., $1^{st}$, $2^{nd}$ and/or $3^{rd}$ generation AR antagonist), a GnRH agonist, and optionally a radiation therapy, a chemotherapeutic agent, indomethacin, or 5-alpha reductase inhibitor. In some embodiments, the combination therapy can include administering to the subject an androgen receptor antagonist (e.g., $1^{st}$, $2^{nd}$ and/or $3^{rd}$ generation AR antagonist) and a radiation therapy. In some embodiments, the combination therapy can include administering to the subject an androgen receptor antagonist (e.g., $1^{st}$, $2^{nd}$ and/or $3^{rd}$ generation AR antagonist) and a chemotherapeutic agent. In some embodiments, the combination therapy can include administering to the subject an androgen receptor antagonist (e.g., $1^{st}$, $2^{nd}$ and/or $3^{rd}$ generation AR antagonist) and an anti-CTLA4 antibody. It should be understood that these combinations discussed are examples of useful combinations, which are in no way limiting, and other combinations of the additional therapies described herein are allowed. However, in preferred embodiments, the combination therapy does not include administering to the subject a GnRH agonist, a GnRH antagonist, an androgen deprivation therapy, and/or does not include castration of the subject.

In any of the combination therapies described herein, unless otherwise specified or contrary from context, the method can comprise administering abiraterone decanoate as described herein or the pharmaceutical composition comprising the abiraterone deconoate as described herein, in combination with the one or more additional therapies.

It should be noted that in some embodiments, the method of treating prostate cancer (e.g., any of those described herein) herein is not in conjunction with a combination therapy. For example, the method comprises administering to the subject a therapeutically effective amount of the abiraterone prodrug (e.g., abiraterone decanoate) or the abiraterone prodrug formulation herein, without the one or more additional therapies described herein.

Dosing Regimen

The abiraterone prodrugs and formulations of the present disclosure can generally provide a long-acting release of abiraterone to a subject user. This long-acting release profile allows administering abiraterone to a subject user at a low dosing frequency, such as once a week, once a month, once every two months, once every three months, or even less frequently, which can improve patient compliance and reduce pill burdens.

In some embodiments, the methods herein can have a dosing regimen of once a week or once in more than a week. Typically, the dosing frequency can range from once a week to once every few months, such as from once a week to once every eight weeks, or from once a week to once every three months, e.g., once a month, once every two months, or once every three months. In some embodiments, the dosing amount for each dose is about 50 mg to about 5000 mg (e.g., about 500 mg, about 1000 mg, about 1500 mg, about 2000 mg, about 5000 mg, or any ranges between the recited values) of abiraterone prodrug. In some embodiments, the dosing amount of abiraterone prodrug for each dose is about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of a subject. In some embodiments, the methods herein can comprise administering to the subject in need thereof an abiraterone prodrug or abiraterone prodrug formulation of the present disclosure, once a week, or once in more than a week, such as once in two weeks, once in a month, wherein the administering provides a therapeutically effective plasma concentration (e.g., as described herein, such as 0.5 ng/ml and above, 1 ng/ml and above, 8 ng/ml and above, or 8.4 ng/ml and above) of abiraterone in the subject for a prolong period of time, such as more than 1 week, more than 2 weeks, more than 3 weeks, more than 4 weeks, and up to six or eight weeks or more, such as up to ten weeks or more etc. In some embodiments, the administering can provide a single dose $C_{max}$ of abiraterone between about 5 ng/ml and about 300 ng/ml (e.g., between about 50 ng/ml and about 100 ng/ml, between about 10 ng/ml and about 100 ng/ml, or between about 15 ng/ml and about 160 ng/ml). In some embodiments, the administering can provide a steady state $C_{max}$ of abiraterone between about 5 ng/ml and about 300 ng/ml (e.g., between about 50 ng/ml and about 100 ng/ml, between about 10 ng/ml and about 100 ng/ml, or between about 15 ng/ml and about 160 ng/ml). In some embodiments, the administering can provide a single dose $C_{min}$ of abiraterone between about 1 ng/ml and about 8 ng/ml, or above about 8 ng/ml such as above 8.4 ng/ml, at each day from day 1 to day 7, or day 1 to day 14, or day 1 to day 21, day 1 to day 28, or day 1 to day 70, or day 7 to day 70 post administration. In some embodiments, the administering can provide a steady state $C_{min}$ of abiraterone between about 1 ng/ml and about 8 ng/ml, or above about 8 ng/ml such as above 8.4 ng/ml.

Abiraterone prodrugs suitable for use for a once a week or once in more than a week dosing methods above include those described herein. In some embodiments, the abiraterone prodrug can be a lipophilic ester of abiraterone described herein, for example, an acetate, a propionate, a butanoate, a (vaterate) pentanoate, an isocaproate, a buciclate, a cyclohexanecarboxylate, a phenyl propionate, caproate (hexanoate), a enanthate (heptanoate), a cypionate, an octanoate, a noncanoate, a decanoate, an undecanoate, a dodecanoate, a tridecanoate, a tetradecanoate, a pentadecanoates, and a hexadecanoate. In some preferred embodiments, the abiraterone prodrug can be a compound of Formula I, for example, a compound of Formula I, wherein $R^1$ is a $C_{7-16}$ alkyl, e.g., an alkyl having a formula of —$(CH_2)_n$—$CH_3$, wherein n is an integer between 6 and 12 (e.g., n is 6, 7, 8, 9, 10); or $R^1$ is represented by the formula —$(CH_2)_n$-Cy, wherein n is an integer of 1-6, and Cy is a $C_{3-6}$ cycloalkyl or phenyl, for example, in more specific embodiments, n can be 1 or 2, and Cy is cyclopentyl, cyclohexyl, or phenyl; or $R^1$ is

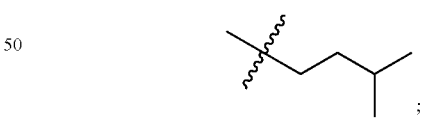

or $R^1$ is

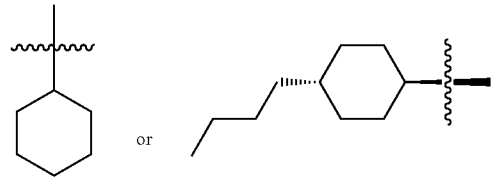

In some embodiments, the abiraterone prodrug can be a compound of Formula II, wherein $R^2$ in Formula II can be a $C_{1-16}$ alkyl, e.g., an alkyl having a formula of —$(CH_2)_n$—$CH_3$, wherein n is an integer between 0 and 12; or $R^2$ in Formula II can be represented by the formula —$(CH_2)_n$-Cy, wherein n is an integer of 1-6, and Cy is a $C_{3-6}$ cycloalkyl or phenyl, for example, in more specific embodiments, n can be 1 or 2, and Cy is cyclopentyl, cyclohexyl, or phenyl; or $R^2$ in Formula II can be

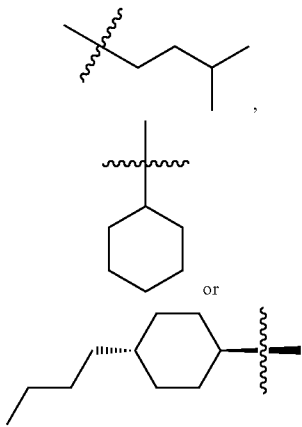

In any of the embodiments described herein, unless otherwise specified or directly contradictory from context, the abiraterone prodrug can be abiraterone decanoate.

In some embodiments, a once a month or once in more than a month dosing is desired, e.g., the dosing frequency ranges from once a month to once every few months, such as from once a month to once every two months, or from once a month to once every three months. In such embodiments, the abiraterone prodrug needs to not only release abiraterone slowly but also to release abiraterone in a sufficient plasma concentration such that it can be beneficial to the subject user. The once a month or once in more than a month dosing is typically a parenteral administration, such as intramuscularly, intradermally, or subcutaneously. In any of the embodiments herein, unless directly contradictory, the administration can be an intramuscular administration.

The abiraterone prodrugs and abiraterone prodrug formulations of the present disclosure can be administered to a subject in need thereof as the only source of abiraterone. However, in some embodiments, other abiraterone medications/formulations are not excluded. For example, in some embodiments, the administering herein can be combined, either concurrently or sequentially in any order, with an oral administration of abiraterone acetate, such as the Zytiga® formulation. In some embodiments, the subject can use the abiraterone prodrugs and abiraterone prodrug formulations as a supplement to an existing abiraterone therapy. Moreover, the administering herein is not limited to administering a single abiraterone prodrug or abiraterone prodrug formulation of the present disclosure. In some embodiments, two or more abiraterone prodrugs and abiraterone prodrug formulations of the present disclosure can be administered to the subject.

In some embodiments, prior to a once a month or once in more than a month dosing, the methods herein can include an initial treatment period with a higher dosing frequency, such as a once a week or once in two weeks dosing. The initial treatment period can include administering the same abiraterone prodrug or a different abiraterone medication such as a different abiraterone prodrug. Typically, the initial treatment period can be used to achieve a blood plasma concentration of abiraterone of about 1 ng/ml to about 8 ng/ml or above about 8 ng/ml, prior to the once a month or once in more than a month dosing described herein. However, in some embodiments, the methods herein do not include such initial treatment period.

As discussed herein, the abiraterone prodrugs and abiraterone prodrug formulations of the present disclosure have many advantages over the currently marketed Zytiga® product. For example, administering the abiraterone prodrugs and abiraterone prodrug formulations of the present disclosure to a subject typically results in reduced $C_{max}$ of abiraterone (e.g., reduced by at least 30% compared to the $C_{max}$ of abiraterone observed at steady state for a once daily oral dose of Zytiga® at 1000 mg without food).

Thus, in some embodiments, the present disclosure provides a method of treating subjects having side effects related to high abiraterone exposure, such as having abiraterone $C_{max}$ related side effects, the method comprising administering abiraterone prodrugs and abiraterone prodrug formulations of the present disclosure to the subject, wherein the administering reduces the side effects when compared to administering of a once daily oral dose of Zytiga® at 1000 mg without food. Suitable routes of administration, dosing amounts, frequencies include those described herein. Various side effects or adverse effects are described in the Zytiga® prescribing information approved by the FDA, see e.g., the February 2018 or June 2019 version. In some embodiments, the present disclosure provides a method of treating subjects who are also administered a drug, the metabolism of which is inhibited by abiraterone, for example, drugs that are CYP2D6 and/or CYP2C8 substrates, the method comprising administering to the subject the abiraterone prodrugs and abiraterone prodrug formulations of the present disclosure, wherein the administering reduces the inhibition of the metabolism of the drug when compared to administering of a once daily oral dose of Zytiga® at 1000 mg without food. In some embodiments, the present disclosure provides a method of treating a subject who has, or is at risk of having, hypertension, hypokalemia, or fluid retention due to mineralocorticoid excess, the method comprising administering to the subject the abiraterone prodrugs and abiraterone prodrug formulations of the present disclosure, wherein the administering reduces hypertension, hypokalemia, and fluid retention or the risk of hypertension, hypokalemia, and fluid retention when compared to administering of a once daily oral dose of Zytiga® at 1000 mg without food. In some embodiments, the present disclosure provides a method of treating a subject who has, or is at risk of having, adrenocortical insufficiency, the method comprising administering to the subject the abiraterone prodrugs and abiraterone prodrug formulations of the present disclosure, wherein the administering reduces adrenocortical insufficiency or the risk of having adrenocortical insufficiency when compared to administering of a once daily oral dose of Zytiga® at 1000 mg without food. In some embodiments, the present disclosure provides a method of treating a subject who has severe or fatal hepatotoxicity after taking Zytiga®, the method comprising administering to the subject the abiraterone prodrugs and abiraterone prodrug formulations of the present disclosure, wherein the administering reduces hepatotoxicity. Without wishing to be bound by theories, it is believed that administering the abiraterone prodrugs and abiraterone prodrug formulations of the present disclosure typically results in a reduced, yet efficacious abiraterone exposure and therefore is beneficial for subjects who need a lower dose of abiraterone, e.g., as described above. Suitable dosing regimens, routes of administrations include those described herein.

Exemplary Methods Using Abiraterone Decanoate

In some specific embodiments, the present disclosure also provides a method of treating a sex hormone-dependent benign or malignant disorder, an androgen receptor driven cancer, a syndrome due to androgen excess, and/or a syndrome due to glucocorticoid excess such as hypercortisolemia, comprising administering to a subject in need thereof, such as a non-castrated subject in need thereof, a therapeutically effective amount of the pharmaceutical composition comprising abiraterone decanoate described herein (e.g., any of those described in the Summary section herein, such as [71]-[81] and [98] of the Summary section herein). The administering is not limited to any particular route. However, the abiraterone decanoate is typically administered parenterally, for example, via an intramuscular injection, intradermal injection, or subcutaneous injection. In some embodiments, the administering is through intramuscular injection. Unlike oral administration of abiraterone acetate, the pharmaceutical composition comprising abiraterone decanoate described herein (e.g., the unit dosage form described herein) can be administered to the subject in need with or without food. In some embodiments, the subject is a non-castrated subject. In some embodiments, the methods herein can also administer the pharmaceutical composition comprising abiraterone decanoate to the subject without regard to whether the subject is castrated or not. In addition, as shown herein, no liver toxicity was observed from intramuscular administration of abiraterone decanoate at the tested doses. As such, the methods herein can also advantageously treat subjects suffering from hepatic impairment, such as moderate to severe hepatic impairment (Child-Pugh Class B or C), prior to the administering of the abiraterone prodrug.

Sex hormone-dependent benign or malignant disorder that can be treated with the methods include any of those described herein such as a sex hormone dependent cancer. In some embodiments, the sex hormone-dependent benign or malignant disorders can be selected from androgen-dependent disorders and estrogen-dependent disorders such as androgen-dependent or estrogen-dependent cancers. In some embodiments, the sex hormone-dependent benign or malignant disorders can be selected from prostate cancer, breast cancer, ovarian cancer, bladder cancer, hepatocellular carcinoma, and lung cancer, etc. In some embodiments, the sex hormone-dependent benign or malignant disorder can be prostate cancer or breast cancer. In some embodiments, the sex hormone-dependent benign or malignant disorder is CRPC or CSPC. In some embodiments, the sex hormone-dependent benign or malignant disorder can be metastatic CRPC or metastatic CSPC. Syndromes due to androgen excess and/or syndromes due to glucocorticoid excess such as hypercortisolemia that can be treated with the methods include any of those described herein. In some embodiments, the method herein can be a method for treating a non-oncologic syndrome in the subject due to androgen excess, such as endometriosis, polycystic ovary syndrome, congenital adrenal hyperplasia (e.g., classical or nonclassical congenital adrenal hyperplasia), precocious puberty, hirsutism, etc. In some embodiments, the method herein can be a method for treating a non-oncologic syndrome due to glucocorticoid (e.g., cortisole) excess, such as Cushing's syndrome or Cushing's disease.

In some specific embodiments, the method is for treating a sex hormone dependent or androgen receptor driven cancer, such as prostate cancer (e.g., described herein), androgen receptor positive salivary duct carcinoma, or androgen receptor positive glioblastoma multiforme.

The methods herein can be used in conjunction with one or more additional therapies for the respective disease or disorder. For example, the method can comprise administering one or more other drug or agent (for example, as described herein, such as another cancer chemotherapeutic drug, hormone replacement drug, or hormone ablation drug) to the subject, either concurrently or sequentially, through the same route or a different route of administration. Non-limiting examples of useful additional therapies also include any of those described in [28]-[39] in the Summary section herein.

Typically, in the methods herein, another drug that is effective in lowering serum and/or gonadal testosterone level, is not administered to the subject concurrently with the administration of abiraterone decanoate, during the treatment with abiraterone decanoate, or otherwise interfering with the treatment with abiraterone decanoate. For example, in some embodiment, the subject is not treated with a gonadal testosterone suppressing drug, other than abiraterone decanoate, in an amount effective to reduce serum testosterone level in the subject. In some embodiment, the subject is not treated with a gonadotropin-releasing hormone antagonist and/or agonist in an amount effective to reduce serum testosterone level in the subject. In some embodiment, the subject is not treated with any gonadal testosterone suppressing drug other than abiraterone decanoate. In some embodiments, the subject is not treated with any gonadotropin-releasing hormone antagonist and/or agonist. In some embodiments, the subject is not treated with a drug selected from buserelin, leuprolide, deslorelin, fertirelin, histrelin, gonadorelin, lecirelin, goserelin, nafarelin, peforelin and triptorelin. In some embodiments, the subject is not treated with a drug selected from abarelix, cetrorelix, degarelix, ganirelix, elagolix, linzagolixa, and relugolix. In some embodiments, the subject can be sensitive to or otherwise intolerant with a gonadotropin-releasing hormone antagonist and/or agonist.

As discussed herein, abiraterone is a 17α-hydroxylase/C17,20-lyase (CYP17) inhibitor, which can lead to reduction in biosynthesis of androgens (such as testosterone), reduction in glucocorticoids (such as cortisol), and a mineralocorticoid excess (e.g., increase in progesterone). Adrenal insufficiency has also been noted to be associated with abiraterone therapy, such as Zytiga®. Intramuscular administration of a pharmaceutical composition comprising abiraterone decanoate herein was shown to provide an effective plasma level of abiraterone and inhibit CYP17A1 in vivo for a prolonged period of time, with an increase in progesterone level and a reduction in cortisol level.

In some embodiments, the method herein (e.g., treating a prostate cancer, or treating classical or nonclassical congenital adrenal hyperplasia) can comprise administering to the subject an agent that offsets the reduction of glucocorticoid(s) associated with the administration of abiraterone decanoate as described herein. In some embodiments, the method can comprise administering to the subject in need an agent effective in treating one or more symptoms associated with adrenal insufficiency, such as acute stress, fatigue, etc. In some specific embodiments, the method can comprise administering to the subject a steroid, such as a corticosteroid. In some embodiments, the method can comprise administering to the subject a glucocorticoid. In some specific embodiments, the method also comprises administering to the subject prednisone, prednisolone, and/or methylprednisolone. In some specific embodiments, the method comprises administering to the subject hydrocortisone, prednisone, prednisolone, methylprednisolone, and/or dexamethasone. In some embodiments, the method also comprises administering to the subject an agent effective in treating cortisol deficiency, for example, hydrocortisone, prednisone, prednisolone, methylprednisolone, and/or dexamethasone. In any such embodiments, the agent can be administered to the subject either concurrently or sequentially in any order, via a same or different route of administration. However, in some embodiments, a glucococorticoid replacement therapy (e.g., administering a glucocorticoid, such as hydrocortisone, prednisone, prednisolone, methylprednisolone, or dexamethasone) is not desired. For example, a glucocorticoid may be contraindicated for the subject, who may have an underlying condition, such as diabetics. In some embodiments, the method can also be characterized in that the subject is not treated with a glucocorticoid replacement therapy. In some embodiments, the subject is not treated with an agent selected from hydrocortisone, prednisone, prednisolone, methylprednisolone, and dexamethasone. In some embodiments, the method can comprise administering to the subject a mineralocorticoid receptor antagonist, such as eplerenone. For example, in any of the embodiments herein when glucococorticoid replacement therapy is not desired and/or not administered, the method can comprise administering to the subject a mineralocorticoid receptor antagonist, such as eplerenone. In some embodiments, the method is for treating prostate cancer and includes a combination therapy, which further comprising administering to the subject one or more additional therapies, e.g., as described herein under the section titled Combination Treatment for Prostate Cancer. Non-limiting examples of useful additional therapies also include any of those described in [28]-[39] in the Summary section herein.

In some embodiments, the methods herein can be characterized by a dosing frequency of once a week or even less frequent. Typically, the dosing frequency can range from once a week to once every few months, such as from once a week to once every three months months, or from once a week to once every eight weeks, such as once a month, once every two months, or once every three months. In some embodiments, the method comprises administering to the subject the pharmaceutical composition comprising abiraterone decanoate (e.g., the unit dosage form described herein) once a week, once in two weeks, once in three weeks, once a month, or once in more than a month such as once every two months, or once every three months. In some embodiments, the method comprises administering to the subject the pharmaceutical composition comprising abiraterone decanoate (e.g., the unit dosage form described herein) once in two weeks, once a month, or once in more than a month, e.g., once every two months, or once every three months. In some embodiments, the dosing amount for each dose is about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoate. In some embodiments, the dosing amount of abiraterone decanoate for each dose is about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of a subject. In some embodiments, the administering is via intramuscular injection. In some embodiments, the administering of a single dose provides a therapeutically effective blood plasma concentration of abiraterone a period of at least one week, e.g., at least two weeks, such as at least three weeks, at least four weeks, and up to six or eight weeks or more, such as up to ten weeks or more, etc. In some embodiments, the administering of a single dose provides a blood plasma concentration of abiraterone above 1.0 ng/ml (e.g., between about 1 ng/ml and about 8 ng/ml, or about 2 ng/ml or higher, about 4 ng/ml or higher, about 5 ng/ml or higher, or about 8 ng/ml or higher) for a period of at least one week, e.g., at least two weeks, such as at least 3 weeks, at least four weeks, and up to six or eight weeks or more, such as up to ten weeks or more, etc. In some embodiments, the administering provides a steady state $C_{min}$ of abiraterone above 1.0 ng/ml (e.g., between about 1 ng/ml and about 8 ng/ml, about 2 ng/ml or higher, about 4 ng/ml or higher, about 5 ng/ml or higher, or about 8 ng/ml or higher). In some embodiments, the administering provides a single dose or steady state $C_{max}$ of abiraterone between about 5 ng/ml and about 300 ng/ml, such as about 5 ng/ml, about 10 ng/ml, about 15 ng/ml, about 20 ng/ml, about 30 ng/ml, about 50 ng/ml, about 60 ng/ml, about 100 ng/ml, about 150 ng/ml, about 160 ng/ml, or any ranges recited between the values, for example, about 10-30 ng/ml, about 20-60 ng/ml, about 15-160 ng/ml or about 50-100 ng/ml. In some embodiments, the administering can also provide a concentration of abiraterone in a tissue of the subject at least 10 times higher than the blood plasma concentration of abiraterone at 7 days post administration (i.e., at 168 hours from the time of administration), wherein the tissue is selected from liver, lung, testes, inguinal lymph, iliac lymph, adrenal, and prostate. In some embodiments, the abiraterone decanoate formulation can be administered to the subject in need thereof as the only source of abiraterone. However, in some embodiments, the abiraterone decanoate formulation can also be administered to the subject in need thereof as a supplement to another abiraterone therapy.

In some embodiments, in particular in the methods of treating prostate cancer herein, the dosing amount and frequency of abiraterone decanoate can be adjusted such that the administering provides an effective amount of abiraterone to reduce the serum testosterone level to about 50 ng/dL or below (e.g., about 40 ng/dL or below, about 30 ng/dL or below, about 20 ng/dL or below, about 10 ng/dL or below, etc.) in a non-castrated subject or about 1 ng/dL or below in a castrated subject, within 15 days (e.g., within 7 days, between 7-15 days, etc.) of the first administration of the abiraterone decanoate. For example, in some embodiments, the administering provides an effective amount of abiraterone to reduce the serum testosterone level to about 50 ng/dL or below (e.g., about 40 ng/dL or below, about 30 ng/dL or below, about 20 ng/dL or below, about 10 ng/dL or below, etc.) in a non-castrated subject or about 1 ng/dL or below in a castrated subject, when measured on day 15 after the first administration of the abiraterone decanoate. In some embodiments, the administering provides an effective amount of abiraterone to achieve a sustained reduction of serum testosterone level, such as achieving and maintaining the serum testosterone level at about 50 ng/dL or below (e.g., about 40 ng/dL or below, about 30 ng/dL or below, about 20 ng/dL or below, about 10 ng/dL or below, etc.) within 15 days (e.g., within 7 days, between 7-15 days, etc.) in a non-castrated subject or about 1 ng/dL or below in a castrated subject, of the first administration of the abiraterone decanoate. In some embodiments, the dosing amount and frequency of abiraterone decanoate can be adjusted such that the administering provides an effective amount of abiraterone to reduce 50% or more, preferably, 75% or more of serum testosterone level from baseline within 15 days (e.g., within 7 days, between 7-15 days, etc.) of the first administration of the abiraterone decanoate. For example, in some embodiments, the administering provides an effective amount of abiraterone to reduce 50% or more, preferably, 75% or more of serum testosterone level from baseline when measured on day 15 after the first administration of the abiraterone decanoate. In some embodiments, the administering provides an effective amount of abiraterone to achieve a sustained reduction of serum testosterone level, such as by 50% or more, 75% or more, from baseline within 15 days (e.g., within 7 days, between 7-15 days, etc.) of the first administration of the abiraterone decanoate.

In some specific example, the present disclosure provides a method of treating prostate cancer, the method comprising administering to a subject in need thereof, such as a non-castrated subject in need thereof, abiraterone decanoate (e.g., substantially pure abiraterone decanoate herein) via intramuscular injection, intradermal injection, or subcutaneous injection, once a week or once in more than a week, such as once a month or once in more than a month, such as once every two months or once every three months, with each dose at about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoateor with each dose of abiraterone decanoate at about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of the subject. In some embodiments, the abiraterone decanoate is administered via intramuscular injection. In some embodiments, the prostate cancer is CRPC or CSPC. In some embodiments, the prostate cancer is metastatic CRPC or metastatic CSPC. Suitable prostate cancers that can be treated with the method also include any of those described herein. For example, in some embodiments, the prostate cancer is a localized prostate cancer. In some embodiments, the subject has not undergone a prostatectomy. In some embodiments, the method of treating prostate cancer includes a combination therapy, which further comprising administering to the subject one or more additional therapies, e.g., as described herein under the section titled Combination Treatment for Prostate Cancer. For example, in some embodiments, the subject is treated with a radiation therapy.

In some specific example, the present disclosure provides a method of treating prostate cancer, the method comprising administering to a subject in need thereof, such as a non-castrated subject in need thereof, the pharmaceutical composition comprising abiraterone decanoate (e.g., substantially pure abiraterone decanoate herein) as described herein (e.g., the unit dosage form described herein) via intramuscular injection, intradermal injection, or subcutaneous injection, once a week or once in more than a week, such as once a month or once in more than a month, such as once every two months, once every three months, with each dose at about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoate or with each dose of abiraterone decanoate at about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of the subject. In some embodiments, the pharmaceutical composition is administered via intramuscular injection. In some embodiments, the prostate cancer is CRPC or CSPC. In some embodiments, the prostate cancer is metastatic CRPC or metastatic CSPC. Suitable prostate cancers that can be treated with the method also include any of those described herein. For example, in some embodiments, the prostate cancer is a localized prostate cancer. In some embodiments, the subject has not undergone a prostatectomy. In some embodiments, the method of treating prostate cancer includes a combination therapy, which further comprising administering to the subject one or more additional therapies, e.g., as described herein under the section titled Combination Treatment for Prostate Cancer. For example, in some embodiments, the subject is treated with a radiation therapy. Non-limiting examples of useful additional therapies also include any of those described in [28]-[39] in the Summary section herein.

In some specific example, the present disclosure provides a method of treating prostate cancer, the method comprising administering to a subject in need thereof, such as a non-castrated subject in need thereof, the unit dosage form described herein via intramuscular injection, intradermal injection, or subcutaneous injection, once a week or once in more than a week, such as once a month or once in more than a month, such as once every two months or once every three months, with each dose at about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoate or with each dose of abiraterone decanoate at about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of the subject. In some embodiments, the unit dosage form is administered via intramuscular injection. In some embodiments, the prostate cancer is CRPC or CSPC. In some embodiments, the prostate cancer is metastatic CRPC or metastatic CSPC. Suitable prostate cancers that can be treated with the method also include any of those described herein. For example, in some embodiments, the prostate cancer is a localized prostate cancer. In some embodiments, the subject has not undergone a prostatectomy. In some embodiments, the method of treating prostate cancer includes a combination therapy, which further comprising administering to the subject one or more additional therapies, e.g., as described herein under the section titled Combination Treatment for Prostate Cancer. For example, in some embodiments, the subject is treated with a radiation therapy.

In some specific example, the present disclosure provides a method of treating a sex hormone dependent or androgen receptor driven cancer, the method comprising administering to a subject in need thereof, such as a non-castrated subject in need thereof, abiraterone decanoate (e.g., substantially pure abiraterone decanoate herein) via intramuscular injection, intradermal injection, or subcutaneous injection, once a week or once in more than a week, such as once a month or once in more than a month, such as once every two months or once every three months, with each dose at about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoate or with each dose of abiraterone decanoate at about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of the subject. In some embodiments, the abiraterone decanoate is administered via intramuscular injection. In some embodiments, the sex hormone dependent or androgen receptor driven cancer is androgen receptor positive salivary duct carcinoma, or androgen receptor positive glioblastoma multiforme. In some embodiments, the sex hormone dependent or androgen receptor driven cancer is a prostate cancer described herein.

In some specific example, the present disclosure provides a method of treating a localized prostate cancer, the method comprising administering to a subject in need thereof, such as a non-castrated subject in need thereof, abiraterone decanoate (e.g., substantially pure abiraterone decanoate herein) via intramuscular injection, intradermal injection, or subcutaneous injection, once a week or once in more than a week, such as once a month or once in more than a month, such as once every two months or once every three months, with each dose at about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoateor with each dose of abiraterone decanoate at about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of the subject, wherein the subject has not undergone a prostatectomy. In some embodiments, the abiraterone decanoate is administered via intramuscular injection. In some embodiments, the subject is treated with a radiation therapy.

In some specific embodiments, the present disclosure also provides a method of treating breast cancer in a subject in need thereof, such as a non-castrated subject in need thereof, the method comprising administering to the subject the pharmaceutical composition comprising abiraterone decanoate described herein (e.g., the unit dosage form described herein) via intramuscular injection, intradermal injection, or subcutaneous injection, once a week or once in more than a week, such as once a month or once in more than a month, such as once every two months or once every three months, with each dose at about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoate or with each dose of abiraterone decanoate at about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of the subject. In some embodiments, the breast cancer can be molecular apocrine HER2-negative breast cancer, metastatic breast cancer, such as ER+ metastatic breast cancer, ER+ and HER2 negative breast cancer, AR+ triple negative breast cancer, etc. In some embodiments, the method further comprising administering to the subject an aromatase inhibitor, e.g., exemestane.

In some specific embodiments, the present disclosure also provides a method of treating 21-hydroxylase deficiency in a subject in need thereof, such as a non-castrated subject in need thereof, the method comprising administering to the subject the pharmaceutical composition comprising abiraterone decanoate described herein (e.g., the unit dosage form described herein) via intramuscular injection, intradermal injection, or subcutaneous injection, once a week or once in more than a week, such as once a month or once in more than a month, such as once every two months or once every three months, with each dose at about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoate or with each dose of abiraterone decanoate at about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of the subject.

In some specific embodiments, the present disclosure also provides a method of delivering abiraterone to a subject in need thereof, such as a non-castrated subject in need thereof, the method comprising administering to the subject the pharmaceutical composition comprising abiraterone decanoate described herein (e.g., the unit dosage form described herein) via intramuscular injection, intradermal injection, or subcutaneous injection, once a week or once in more than a week, such as once a month or once in more than a month, such as once every two months or once every three months, with each dose at about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoate or with each dose of abiraterone decanoate at about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of the subject. In some embodiments, the pharmaceutical composition is administered via intramuscular injection. In some embodiments, the subject suffers from a hormone-dependent benign or malignant disorder, an androgen receptor driven cancer, a syndrome due to androgen excess, and/or a syndrome due to glucocorticoid excess such as hypercortisolemia, e.g., as described herein.

In some specific embodiments, the present disclosure also provides a method of inhibiting CYP17A1 activity in a subject in need thereof, such as a non-castrated subject in need thereof, the method comprising administering to the subject the pharmaceutical composition comprising abiraterone decanoate described herein (e.g., the unit dosage form described herein) via intramuscular injection, intradermal injection, or subcutaneous injection, once a week or once in more than a week, such as once a month or once in more than a month, such as once every two months or once every three months, with each dose at about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoate or with each dose of abiraterone decanoate at about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of the subject. In some embodiments, the pharmaceutical composition is administered via intramuscular injection. In some embodiments, the subject suffers from a sex hormone-dependent benign or malignant disorder, e.g., as described herein. In some embodiments, the subject suffers from a syndrome due to androgen excess and/or a syndrome due to glucocorticoid excess such as hypercortisolemia, e.g., as described herein.

In some specific embodiments, the present disclosure also provides a method of reducing the level of glucocorticoids (e.g., cortisol) in a subject in need thereof, such as a non-castrated subject in need thereof, the method comprising administering to the subject the pharmaceutical composition comprising abiraterone decanoate described herein (e.g., the unit dosage form described herein) via intramuscular injection, intradermal injection, or subcutaneous injection, once a week or once in more than a week, such as once a month or once in more than a month, such as once every two months or once every three months, with each dose at about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoate or with each dose of abiraterone decanoate at about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of the subject. In some embodiments, the pharmaceutical composition is administered via intramuscular injection. In some embodiments, the subject suffers from a hypercortisolemia as described herein, such as Cushing's syndrome or Cushing's disease.

In some specific embodiments, the present disclosure also provides a method of reducing the level of androgens (e.g., testosterone and/or dihydrotestosterone) and/or estrogens in a subject in need thereof in a subject in need thereof, such as a non-castrated subject in need thereof, the method comprising administering to the subject the pharmaceutical composition comprising abiraterone decanoate described herein (e.g., the unit dosage form described herein) via intramuscular injection, intradermal injection, or subcutaneous injection, once a week or once in more than a week, such as once a month or once in more than a month, such as once every two months or once every three months, with each dose at about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoate or with each dose of abiraterone decanoate at about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of the subject. In some embodiments, the pharmaceutical composition is administered via intramuscular injection. In some embodiments, the subject suffers from a syndrome due to androgen excess, such as congenital adrenal hyperplasia (e.g., classical or nonclassical congenital adrenal hyperplasia), endometriosis, polycystic ovary syndrome precocious puberty, hirsutism, etc. In some embodiments, the subject suffers from an androgen and/or estrogen associated cancer, such as prostate cancer or breast cancer. In some embodiments, the subject suffers from an androgen receptor driven cancer, such as those described herein.

In some specific embodiments, the present disclosure also provides a method of reducing serum testosterone level in a subject in need thereof in a subject in need thereof, such as a non-castrated subject in need thereof, the method comprising administering to the subject the pharmaceutical composition comprising abiraterone decanoate described herein (e.g., the unit dosage form described herein) via intramuscular injection, intradermal injection, or subcutaneous injection, once a week or once in more than a week, such as once a month or once in more than a month, such as once every two months or once every three months, with each dose at about 50 mg to about 5000 mg (e.g., about 100 mg, about 350 mg, about 500 mg, about 1000 mg, about 1500 mg, about 2000 mg, about 5000 mg, or any ranges between the recited values) of abiraterone decanoate or with each dose of abiraterone decanoate at about 0.5 mg/kg to about 200 mg/kg (e.g., about 0.5 mg/kg, about 1 mg/kg, about 5 mg/kg, about 10 mg/kg, about 20 mg/kg, about 30 mg/kg, about 50 mg/kg, about 90 mg/kg, about 100 mg/kg, about 200 mg/kg, or any ranges between the recited values) of body weight of the subject. In some embodiments, the pharmaceutical composition is administered via intramuscular injection. In some embodiments, in particular when the subject is characterized as having prostate cancer, the administering provides an effective amount of abiraterone to reduce the serum testosterone level to about 50 ng/dL or below (e.g., about 40 ng/dL or below, about 30 ng/dL or below, about 20 ng/dL or below, about 10 ng/dL or below, etc.) in a non-castrated subject or about 1 ng/dL or below in a castrated subject, within 15 days (e.g., within 7 days, between 7-15 days, etc.) of the first administration of the abiraterone decanoate. For example, in some embodiments, the administering provides an effective amount of abiraterone to reduce the serum testosterone level to about 50 ng/dL or below (e.g., about 40 ng/dL or below, about 30 ng/dL or below, about 20 ng/dL or below, about 10 ng/dL or below, etc.) in a non-castrated subject or about 1 ng/dL or below in a castrated subject, when measured on day 15 after the first administration of the abiraterone decanoate. In some embodiments, the administering provides an effective amount of abiraterone to achieve a sustained reduction of serum testosterone level, such as achieving and maintaining the serum testosterone level at about 50 ng/dL or below (e.g., about 40 ng/dL or below, about 30 ng/dL or below, about 20 ng/dL or below, about 10 ng/dL or below, etc.) in a non-castrated subject or about 1 ng/dL or below in a castrated subject, within 15 days (e.g., within 7 days, between 7-15 days, etc.) of the first administration of the abiraterone decanoate. In some embodiments, the administering provides an effective amount of abiraterone to reduce 50% or more, preferably, 75% or more of serum testosterone level from baseline within 15 days (e.g., within 7 days, between 7-15 days, etc.) of the first administration of the abiraterone decanoate. For example, in some embodiments, the administering provides an effective amount of abiraterone to reduce 50% or more, preferably, 75% or more of serum testosterone level from baseline when measured on day 15 after the first administration of the abiraterone decanoate. In some embodiments, the administering provides an effective amount of abiraterone to achieve a sustained reduction of serum testosterone level, such as by 50% or more, 75% or more, from baseline within 15 days (e.g., within 7 days, between 7-15 days, etc.) of the first administration of the abiraterone decanoate. In some embodiments, the subject suffers from a sex hormone dependent cancer or androgen receptor driven cancer as described herein.

In any of the embodiments described herein, unless specified or otherwise contrary, the abiraterone decanoate can be formulated in a pharmaceutical composition, which comprises, for each milliliter, (a) abiraterone decanoate in its basic form, in an amount of about 100 mg to about 300 mg (e.g., about 100 mg, about 120 mg, about 150 mg, about 180 mg, about 200 mg or about 250 mg); (b) benzyl alcohol in an amount of about 50 mg to about 150 mg (e.g., about 75 mg, about 100 mg, or about 125 mg); (c) benzyl benzoate in an amount of about 100 mg to about 300 mg (e.g., about 100 mg, about 150 mg, about 200 mg, or about 250 mg); and (d) corn oil, q.s. to 1 milliliter. In some embodiments, the weight ratio of benzyl alcohol to benzyl benzoate in the pharmaceutical composition ranges from about 2:1 to about 1:5 (e.g., about 1:1 to 1:3, such as about 1:2). In some embodiments, the pharmaceutical composition is characterized as having (1) a viscosity of less than 0.1 Pa*s, such as about 0.05 Ps*s or lower; (2) a glide force of about 1-10 N when measured using a 21 G, 1.5 inch needle, and/or about 2-15 N when measured using a 23 gauge (or 23 G), 1.5 inch needle, and/or about 30-150 N when measured using a 27 G, 1.5 inch needle; (3) no more than 1000 particles having a size of 10 m or greater, and no more than 300 particles having a size of 25 m or greater, when measured according to USP <788> and/or <789>; and/or (4) less than 100 EU/ml, such as less than 25 EU/ml of bacterial endotoxins measured according to USP <85>. Methods for measuring viscosity and glide force are known in the art, which are also exemplified in Example 2 herein. The USP methods <788>, <789> and <85> referenced herein should be understood as the current version of such methods, which are also known by those skilled in the art. In any of the embodiments described herein, unless specified or otherwise contrary, the abiraterone decanoate can be formulated in a pharmaceutical composition according to any of [71]-[81] and [98] of the Summary section herein. In any of the embodiments described herein, unless specified or otherwise contrary, the abiraterone decanoate can be formulated in a pharmaceutical composition with ingredients on a per milliliter basis according to those shown in Example 2 herein.

Provided herein are formulations, methods, and kits for treating a subject with a sex hormone-dependent benign or malignant disorder such as prostate cancer. Also provided are methods for preparing the formulations useful for treating a subject with a sex hormone-dependent benign or malignant disorder (such as prostate cancer), an androgen receptor driven cancer, a syndrome due to androgen excess, and/or a syndrome due to glucocorticoid excess such as hypercortisolemia. Reference will now be made in detail to representative embodiments, examples of which are illustrated in the accompanying drawings.

The term "subject" as used herein means, but is not limited to, an animal or human in need of or capable of receiving chemotherapy for a sex hormone-dependent benign or malignant disorder such as, for example, an androgen-dependent disorder or an estrogen-dependent disorder (including prostate cancer and breast cancer), an androgen receptor driven cancer, an animal or human in need of or capable of receiving therapy for non-oncologic syndromes due to androgen excess, such as endometriosis, polycystic ovary syndrome, congenital adrenal hyperplasia (e.g., classical or nonclassical congenital adrenal hyperplasia), precocious puberty, hirsutism, etc., and/or due to glucocorticoid excess such as hypercortisolemia, such as Cushing's syndrome or Cushing's disease. In preferred embodiments, the subject is a human subject.

The term "other drug or agent" as used herein (when, for example, referring to prior, simultaneous, and post-administration of at least one other drug or agent with at least one abiraterone prodrug formulation) means at least one other compound, formulation, molecule, biologic, or the like, capable of enhancing the efficacy of the formulation(s), decreasing an undesirable side effect(s) of the formulation(s), or improving the treatment of the particular disorder. Any suitable routes of administration of such "other drug or agent" can be used, for example, oral administration, parenteral administration, etc. A person skilled in the art of treating a subject having a sex hormone-dependent benign or malignant disorder (such as an androgen-dependent disorder or an estrogen-dependent disorder), an androgen receptor driven cancer, syndromes due to androgen excess syndrome, and/or syndromes due to glucocorticoid excess such as hypercortisolemia would know and understand how to choose and use such "other drug or agent" for the intended purpose(s).

The formulations can optionally be administered via a modified-release device or method. The term "modified-release" as used herein should be understood as encompassing delayed release, prolonged or extended release, sustained release, or a targeted release, etc. For example, in some embodiments, the modified release device or method can further prolong the release of abiraterone of the prodrugs and formulations of the present disclosure. In some embodiments, the modified release device or method can also include any device or method capable of releasing an agent or product (for example, a drug or a biologic) at a time later than immediately following its administration (and can include, for example, implants). Various modified release devices have been described (Stubbe et al., *Pharm. Res.* 21:1732, 2004) and could be applicable to the representative embodiments. Modified-release devices and methods can be identified and employed without undue experimentation by a person skilled in the art after consideration of all criteria and use of best judgment on the subject's behalf.

The formulations and agents of the embodiments are administered in a pharmacologically or physiologically acceptable and effective amount to reduce or eliminate the presence, for example, of prostate tumor tissue and abnormal or malignant prostate cells in a subject presenting with prostate cancer. Similarly, the formulations and agents of the embodiments are administered alone or in combination with other therapeutic agents or therapeutic modalities (for example, radiotherapy and surgery) in prophylactically or therapeutically effective amounts, which are to be understood as amounts meeting the intended prophylactic or therapeutic objectives and providing the benefits available from administration of such formulations and agents.

The terms "effective amount," "effective dose," and "therapeutic blood plasma concentration" as used herein mean, but are not limited to, an amount, dose, or concentration capable of treating, delaying, slowing, inhibiting, or eliminating the onset, existence or progression of a disorder, disease or condition. For example, an "effective amount," "effective dose," or "therapeutic blood plasma concentration" is capable of reducing or eliminating the presence of prostate tumor tissue and abnormal or malignant prostate cells in a subject presenting with prostate cancer, which is sufficient to cure (partly or completely) illness or prevent the onset or further spread of disorder, disease or condition. For further example, an effective amount of formulation refers to the amount administered alone or in combination with other therapeutic agents or therapeutic modalities (for example, radiotherapy and surgery) to achieve clinically significant reduction in tumor burden. A person skilled in the art would understand when a clinically significant reduction in tumor burden (or improvement of a sex hormone-dependent benign or malignant disorder or another disorder or syndrome described herein) has occurred following administration of a formulation. An "effective amount," "effective dose," or "therapeutic blood plasma concentration" is understood to be an amount, dose, or concentration not critically harmful to the subject and, in any case, where any harmful side effects are outweighed by benefits. By way of example only, an effective amount or dose of an abiraterone prodrug formulation means an amount capable of attaining blood plasma concentrations of at least 1 ng/ml, e.g., at least 1 ng/ml, at least 2 ng/ml, at least 4 ng/ml, or at least 8 ng/ml, of abiraterone in the subject following parenteral administration of the prodrug formulation, and the efficacious blood plasma concentrations are attained for at least one week, e.g., at least two weeks (for example, four, six, eight or more weeks) following administration.

In general, the dosage ranges for administration of the formulation according to the present disclosure are those that produce the desired effect(s). The useful dosage to be administered will vary depending on the age, weight, and health of the subject treated, the mode, route, and schedule of administration, the response of the individual subject, and the type or staging of prostate cancer (or severity of a sex hormone-dependent benign or malignant disorder or another symdrome or disorder described herein) against which treatment with the formulation is sought. The dosage will also vary with the nature or the severity of the primary tumor and other underlying conditions, with epidemiologic conditions, with the concomitant use of other active compounds, and the route of administration. In addition, the dosage will be determined by the existence of any adverse side effects such as local hypersensitivity, systemic adverse effects, and immune tolerance.

An effective dose of the formulations (and other agent(s)) can be determined without undue experimentation (for example, by pharmacokinetic studies) by a person skilled in the art after consideration of all criteria and use of best judgment on the patient's behalf (and will most often be contingent upon the particular formulation utilized). The dosage to be administered will depend upon the particular case, but in any event, it is the amount sufficient to induce clinical benefit against, or improvement of, a sex hormone-dependent benign or malignant disorder (such as prostate cancer), an androgen receptor driven cancer, a syndrome due to androgen excess, and/or a syndrome due to glucocorticoid excess such as hypercortisolemia.

The formulations and agents of the embodiments can, optionally, be administered in combination with (or can include) one or more pharmaceutically acceptable carriers, diluents, or excipients. Formulations, administration techniques, pharmaceutical compositions, methods of preparing pharmaceutical compositions, and pharmaceutically acceptable carriers, diluents, and excipients are known in the art and are described, for example, in "Remington: The Science and Practice of Pharmacy" (formerly "Remington's Pharmaceutical Sciences," University of the Sciences in Philadelphia, Lippincott, Williams & Wilkins, Philadelphia, Pa. (2005)), the disclosure of which is hereby incorporated by reference. A person skilled in the art can use known injectable, physiologically acceptable sterile solutions. For preparing a ready-to-use solution for parenteral injection or infusion, aqueous isotonic solutions, for example, saline, phosphate buffered saline (PBS) or corresponding plasma protein solutions, are readily available. The formulations can be present as lyophylisates or dry preparations, which can be reconstituted with a known injectable solution directly before use under sterile conditions, for example, as a kit of parts. In addition, the formulations can include one or more acceptable carriers (which can include, for example, solvents, dispersion media, coatings, adjuvants, stabilizing agents, diluents, preservatives, antibacterial and antifungal agents, isotonic agents, absorption-modifying agents, and the like. "Diluents" can include water, saline, phosphate-buffered saline (PBS), dextrose, ethanol, glycerol, and the like. Isotonic agents can include sodium chloride, dextrose, mannitol, sorbitol, and lactose, among others. Stabilizers include albumin and alkali salts of ethylenediaminetetraacetic acid, among others.

Any suitable route of administration can be employed for providing a subject with an effective amount/dosage of formulation and agents according to the representative embodiments. A suitable route of administration can be determined readily by a person skilled in the art of pharmacology, immunology, medicine, oncology, or the like without undue experimentation. However, it is anticipated that the formulations are primarily suitable for parenteral administration such as via IM injection, intradermal injection, or subcutaneous injection.

The abbreviations used herein have their conventional meaning within the chemical and biological arts.

Headings and subheadings are used for convenience and/or formal compliance only, do not limit the subject technology, and are not referred to in connection with the interpretation of the description of the subject technology. Features described under one heading or one subheading of the subject disclosure may be combined, in various embodiments, with features described under other headings or subheadings. Further it is not necessarily the case that all features under a single heading or a single subheading are used together in embodiments.

As used herein, the term "about" modifying an amount related to the disclosure refers to variation in the numerical quantity that can occur, for example, through routine testing and handling; through error in such testing and handling; through differences in the manufacture, source, or purity of ingredients/materials employed in the disclosure; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

It is also meant to be understood that a specific embodiment of a variable moiety herein may be the same or different as another specific embodiment having the same identifier.

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987. The disclosure is not intended to be limited in any manner by the exemplary listing of substituents described herein.

As used herein, the term "alkyl" as used by itself or as part of another group refers to a straight- or branched-chain saturated aliphatic hydrocarbon. In some embodiments, the alkyl can include one to thirty carbon atoms (i.e., $C_{1-30}$ alkyl or alternatively expressed as $C_1$-$C_{30}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is a straight chain $C_{1-16}$ alkyl group. In another embodiment, the alkyl group is a branched chain $C_{3-16}$ alkyl group. To be clear, when a range of carbon numbers is listed, it encompasses each individual integer within the range and sub-ranges between such integers as would be understood by those skilled in the art. For example, "$C_{7-16}$" herein encompasses, $C_7$, $C_8$, $C_9$, $C_{10}$, $C_{11}$, $C_{12}$, $C_{13}$, $C_{14}$, $C_{15}$, $C_{16}$, $C_{7-16}$, $C_{7-15}$, $C_{7-14}$, $C_{7-13}$, $C_{7-12}$, $C_{7-11}$, $C_{7-10}$, $C_{7-9}$, $C_{7-8}$, $C_{8-16}$, $C_{8-15}$, $C_{8-14}$, $C_{8-13}$, $C_{8-12}$, $C_{8-11}$, $C_{8-10}$, $C_{8-9}$, $C_{9-16}$, $C_{9-15}$, $C_{9-14}$, $C_{9-13}$, $C_{9-12}$, $C_{9-11}$, $C_{9-10}$, $C_{10-16}$, $C_{10-15}$, $C_{10-14}$, $C_{10-13}$, $C_{10-12}$, $C_{10-11}$, $C_{11-16}$, $C_{11-15}$, $C_{11-14}$, $C_{11-13}$, $C_{11-12}$, $C_{12-16}$, $C_{12-15}$, $C_{12-14}$, $C_{12-13}$, $C_{13-16}$, $C_{13-15}$, $C_{13-14}$, $C_{14-16}$, $C_{14-15}$, and $C_{15-16}$. Other ranges as described herein such as "number of carbons between 5 and 16" etc. should be understood similarly.

As used herein, the term "cycloalkyl" as used by itself or as part of another group refers to saturated and partially unsaturated (e.g., containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is a $C_{3-8}$ cycloalkyl group. In another embodiment, the cycloalkyl group is a $C_{3-6}$ cycloalkyl group. "Cycloalkyl" also includes ring systems wherein the cycloalkyl ring, as defined above, is fused with one or more aryl or heteroaryl groups wherein the point of attachment is on the cycloalkyl ring, and in such instances, the number of carbons continue to designate the number of carbons in the cycloalkyl ring system. Non-limiting exemplary cycloalkyl groups include cyclopropyl, cyclobutyl, cyclopentyl, cyclohexyl, cycloheptyl, cyclooctyl, norbornyl, decalin, adamantyl, cyclopentenyl, and cyclohexenyl.

As used herein, the term "alkenyl" as used by itself or as part of another group refers to a straight- or branched-chain aliphatic hydrocarbon containing one or more (e.g., 1, 2, or 3) carbon-to-carbon double bonds. In one embodiment, the alkenyl group is a $C_{2-16}$ alkenyl group.

As used herein, the term "alkynyl" as used by itself or as part of another group refers to a straight- or branched-chain aliphatic hydrocarbon containing one or more (e.g., 1, 2, or 3) carbon-to-carbon triple bonds. In one embodiment, the alkynyl has one carbon-carbon triple bond. In one embodiment, the alkynyl group is a $C_{2-16}$ alkynyl group.

As used herein, the term "abiraterone prodrug(s) of the present disclosure" refers to any of the compounds described herein according to Formula I or II, a lipophilic ester of abiraterone prodrug, isotopically labeled compound(s) thereof (e.g., deuterium enriched compounds), possible stereoisomers thereof (including diastereoisomers, enantiomers, and racemic mixtures), tautomers thereof, conformational isomers thereof, and/or pharmaceutically acceptable salts thereof (e.g., acid addition salt such as HCl salt). Hydrates and solvates of the prodrugs of the present disclosure are considered compositions of the present disclosure, wherein the prodrug(s) is in association with water or solvent, respectively. Some of the prodrugs of the present disclosure can also exist in various polymorphic forms or amorphous forms. The prodrugs described herein include those compounds that readily undergo chemical changes under physiological conditions to provide active abiraterone. Additionally, prodrugs can be converted by chemical or biochemical methods in an ex vivo environment. As used herein, the term "abiraterone prodrug formulation(s) of the present disclosure" refers to any of the pharmaceutical composition or formulation comprising any one or more of the abiraterone prodrugs of the present disclosure, for example, any of the formulations prepared in Example 2. In any of the embodiments described herein, unless directly contradictory from context, the abiraterone prodrug of the present disclosure can be abiraterone decanoate. In any of the embodiments described herein, unless directly contradictory from context, the abiraterone prodrug formulation of the present disclosure can be any of the pharmaceutical composition comprising abiraterone decanoate as described herein.

The abiraterone prodrugs of the present disclosure can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, oxygen, and nitrogen, include, but are not limited to $^2H$, $^3H$, $^{13}C$, $^{14}C$, $^{15}N$, and $^{18}O$. Compounds that contain other isotopes of these and/or other atoms are within the scope of this disclosure.

Solid and dashed wedge bonds indicate stereochemistry as customary in the art.

The following examples are provided for illustration purposes only and are in no way intended to limit the scope of the claimed subject matter.

Example 1A. Large Scale Preparation of Abiraterone Decanoate from Decanoic Acid

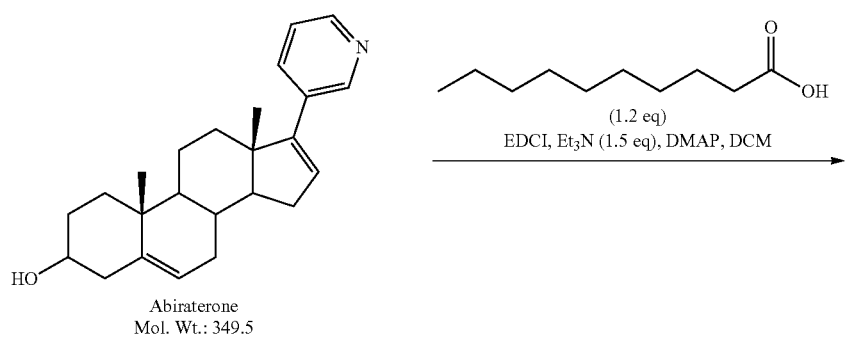

Abiraterone
Mol. Wt.: 349.5

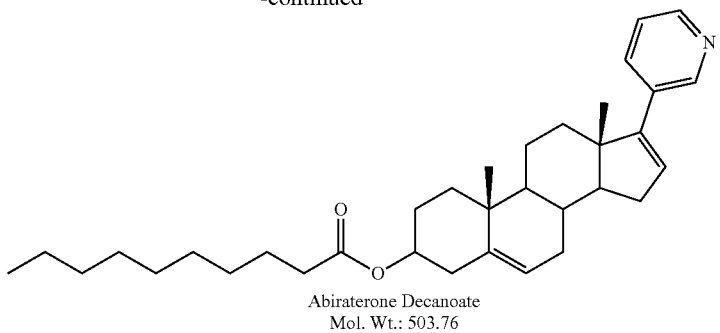

Abiraterone Decanoate
Mol. Wt.: 503.76

To a suspension of Abiraterone (381.9 g, 1.09 mol) in dichloromethane (3500 mL) was added triethylamine (165 g, 1.64 mol) and a catalytic amount of DMAP (13.35 g, 0.109 mol). Decanoic acid (225 g, 1.31 mol) as a solution in dichloromethane (500 mL) was added to the suspension, followed by EDCI (293 g, 1.53 mol) and the reaction then agitated for 19 h at 20-25° C.

10 wt % aq $NaH_2PO_4$ (4000 mL) was then added and the reaction was agitated for 20 min. The organic layer was separated and extracted with 10 wt % aq $NaH_2PO_4$ (2000 mL) and brine (2000 mL). The organic layer was solvent exchanged with acetonitrile (4750 mL) and concentrated to 3100 g keeping temperature of bath <40° C. The suspension was diluted with acetonitrile (900 g). The solids were isolated by filtration to afford 510 g of crude abiraterone decanoate.

510 g of the crude abiraterone decanoate was dissolved in acetone (4000 mL) at 40° C. The solution was filtered through a filter paper. The filtrate was transferred to a 12 L 3-neck flask, diluted to 5100 g and reheated to 40° C. to form a solution. The solution was cooled slowly to 20° C. to form a suspension. This was diluted with water (1020 mL) and agitated at RT overnight. The solid was filtered and the flask was rinsed with the filtrate and transferred to filter funnel. The wet cake was transferred to drying tray and dried at 40-45° C. in vacuum oven overnight to obtain 457.1 g (90% yield) as white solid, the crystalline form of this solid is designated as Form A. $^1$H NMR (CDCl$_3$, 400 MHz): d$_H$ 8.62 (d, 1H, J=1.9 Hz), 8.31 (dd, 1H, J=4.9, 1.6 Hz), 7.64 (dt, 1H, J=7.9, 1.9 Hz), 7.21 (ddd, 1H, J=8.0, 4.9, 0.8 Hz), 6.01-5.97 (m, 1H), 5.44-5.40 (m, 1H), 4.68-4.58 (m, 1H), 2.39-2.23 (m, 3H), 2.27 (t, 2H, J=7.6 Hz), 2.12-2.00 (m, 3H), 1.91-1.54 (m, 10H), 1.49 (dt, 1H, J=11.9, 5.1 Hz), 1.35-1.23 (m, 12H), 1.20-1.07 (m, 2H), 1.08 (s, 3H), 1.05 (s, 3H), 0.88 (t, 3H, J=6.8 Hz). Elemental Analysis, theoretical (corrected for 0.055% moisture level): C, 81.0%; H, 9.8%; N, 2.8%; found: C, 81.1%; H, 10.2%; N, 2.8%. Differential Scanning Calorimetry (DSC) pattern of this solid shows an endothermic peak with an onset temperature at about 69.0° C., see FIG. 2B.

The abiraterone decanoate obtained in this example was determined to have a purity of 99.7% by weight using a HPLC method. For HPLC analysis, abiraterone decanoate samples were prepared in methanol at a concentration of 0.05 mg/mL (for assay analysis) or 5 mg/mL (for impurity analysis). The HPLC conditions are the following: HPLC column: Halo C8 (2.7 um, 100×3.0 mm); injection volume: 5 uL; Column Temperature: 40° C.; Sample Temperature: ambient; Detection: 210 nm; Mobile Phase: 25 mM Ammonium Acetate, pH 8.0 (MPA) and 95/5 acetonitrile/tetrahydrofuran (MPB); Flow Rate: 0.6 ml/min; Gradient: starting with 65/35 MPA/MPB, in 35 minutes, reaching to 100% MPB, hold at 100% MPB until 40 minutes, at 40.10 minute, back to 65/35 MPA/MPB, and hold at 65/35 MPA/MPB until end at 45 minutes.

The white solid obtained in this example was also characterized by X-Ray Powder Diffraction (XRPD) and Differential Scanning Calorimetry (DSC). XRPD was conducted with Bruker's D8 Discover X-rat diffractometer, with Theta\theta vertical goniometer, using Vantec-500 as detector. Standard conditions: voltage 40 kV, current 40 mA, radiation, Cu, temperature, ambient, X-ray source exit slit size, 0.5 mm pinhole, snout collimator, 0.5 mm, sample holder, ground quartz plate. Operating conditions: detector distance, 30 cm, Chi integration range, 4- to 40-degree 20, count time, 120 seconds/frame, # of frames: 3, Theta 1 position, 4 degree, Theta 2 position, 4 degree, Frame width, 12, scan axis, coupled. Software used include GADDs software, General Area Detector Diffraction System, version 4.1.50; and DIFFRAC. EVA, version 4.0. DSC was performed with TA Instruments Q2000 (Thermal Advantage V 5.0.0—qualified), with a sample size of 2-10 mg, heating range from 25° C. to 250° C. at a heating rate of 10° C./min. Representative XRPD and DSC spectra are shown in FIGS. 2A-2B. A thermogravimetric analysis (TGA) was also performed on this sample. TGA was performed with TA Instruments TGA Q500 (Thermal Advantage V5.2.5—qualified), with a sample size of 5-20 mg, heating range from 25° C. to 150° C. at a heating rate of 10° C./min. A representative TGA trace is shown in FIG. 2C.

Example 1B. Preparation of High Purity Abiraterone Decanoate

This example shows a process of purifying abiraterone decanoate to remove residue palladium. Abiraterone decanoate used for this Example was prepared using similar procedures as shown in Example 1A.

Crude abiraterone decanoate (7.17 kg) was dissolved in acetone (142 kg) at room temperature. Activated carbon (1.43 kg) was added and the resulting slurry stirred at room temperature for 4 hours. The mixture was filtered to remove the activated carbon and the solids were washed with acetone (142 kg). The combined acetone filtrates were concentrated by vacuum distillation at 40° C. The concentrated filtrates, which contained about 72 L acetone, were then cooled to 20° C. and water (4.3 kg) was slowly added. The mixture was stirred at 20° C. for 12 hours and the abiraterone decanoate was collected by filtration. The product was washed with 1:1 acetone/water (7.2 kg) and dried under vacuum at 40° C. to yield 5.524 kg of pure abiraterone decanoate (Form A). Analytical data are consistent with those described in Example 1A. A representative certificate of analysis of the obtained abiraterone decanoate is shown in Table D below. Purity of the obtained abiraterone decanoate was analyzed using HPLC Method 1, see details in Example 2 below.

TABLE D

| Specification and Analysis of Abiraterone Decanoate | | |
|---|---|---|
| Test Method | Specifications | Result |
| Appearance | White to yellow solid | White Solid |
| Identification by IR-ATR | Sample spectrum is consistent with Abiraterone Decanoate reference standard spectrum | Conforms |
| Abiraterone Decanoate Content by HPLC (% w/w) | 98-102 (dried basis) | 99.6 |
| Related Substances by HPLC (% w/w) | | |
| Abiraterone | NMT 0.5 | nd |
| Ethylprasterone Decanoate | NMT 0.5 | 0.4 |
| Any Unspecified Impurity | NMT 0.1 | nd |
| Total Impurities | NMT 1.0 | 0.4 |
| Residual Solvents by Gas Chromatography (ppm) | | |
| Dichloromethane | NMT 600 | 181 |
| Acetonitrile | NMT 410 | nd |
| Acetone | NMT 5000 | nd |
| Residual EDU (EDCI coupling reagent by-product) by LC-MS (% w/w) | NMT 0.15 | <0.05 |
| Residual Decanoic Acid by Gas Chromatography (ppm) | NMT 5000 | NT |
| Triethylamine by Ion Chromatography (% w/w) | NMT 0.5 | <0.1 |
| Palladium by ICP (ppm) | NMT 10 | 3.7 |
| Water by Karl Fischer (% w/w) | NMT 1.0 | 0.12 |
| Residue on Ignition (% w/w) | NMT 0.5 | <0.05 |
| Physical Form by XRPD | Report Results | Crystalline |
| Microbial Enumeration by USP <61> | | |
| Total Aerobic Microbial Count (TAMC) CFU/g | ≤100 | <50 |
| Total Combined Yeasts and Molds (TYMC) CFU/g | ≤10 | <50 |
| Bacterial Endotoxins by USP <85> EU/g | ≤350 | <51.4 |

Notes:
nd = not detected.
NT = Not Tested.
NMT = No More Than

The crude abiraterone decanoate contained 130 ppm Pd. Recrystalization from just acetone/water lowered the Pd level to 120 ppm. However, by using the process described in this example, the final abiraterone decanoate can be purified to have a Pd content of only 3.7 ppm.

Example 1C. Polymorph Screening of Abiraterone Decanoate

A polymorph screening study was also carried out for abiraterone decanoate. In addition to Form A, as shown in Example 1A, two other polymorphs of abiraterone decanoate were identified, namely Form B and Form C.

Crystallization by cooling at −15° C.: about 30 mg abiraterone decanoate was dissolved in the minimum volume of solvent. Samples were heated at 50° C. for 1 hr if not completely dissolved. Placed samples in a freezer and filtered (if a precipitate was visible) after 2 days. The results using this crystallization method are shown in Table E1 below:

TABLE E1

| Results from Crystallization by Cooling | | |
|---|---|---|
| Solvent | Appearance | Form |
| Ethanol | White solid | B |
| Dichloromethane | * | * |
| THF | * | * |
| DMF | White solid | A + B |
| Ethyl acetate | White solid | B |
| DMA | White solid | B |
| Isopropyl ether | White solid | A |
| Acetone | White solid | A |
| 1-Propanol | White solid | A + B |
| Chloroform | * | * |
| Trifluoroethanol | * | * |
| 2-Butanol | White solid | A + B |
| Diethyl ether | White solid | A |
| MTBE | White solid | B |
| Corn oil/benzyl alcohol (1:1) | Solvent freezes | * |
| Benzyl alcohol | * | * |
| 2-Propanol | White solid | B |
| Heptane | White solid | B |
| Toluene | * | * |
| Methanol | White solid | B |
| 2-Butanone | White solid | A |
| Acetonitrile | White solid | A + B |

*No solid recovered

Evaporation from binary 1:1 solvent mixtures: about 25 mg abiraterone decanoate dissolved in about 10 mL total volume of solvent. Samples were evaporated under a 1 psi nitrogen purge. The results using this crystallization method are shown in Table E2 below:

TABLE E2

Results from Evaporation from Solvents

| Solvent 1 | Solvent 2 | Appearance | Form |
|---|---|---|---|
| MTBE | Chloroform | Glass | — |
| MTBE | Acetone | Glass | — |
| Toluene | Heptane | Glass | — |
| Toluene | Dioxane | Glass | — |
| Dichloromethane | Diethyl ether | Glass | — |
| Methanol | THF | White solid | A + B |
| Methanol | Chloroform | White solid | A + B |
| Ethyl acetate | Ethanol | Glass | — |
| 2-Butanol | Heptane | White solid | B |
| 2-Butanone | Ethanol | White solid | C |
| 2-Butanone | Acetonitrile | White solid | B |
| Acetonitrile | t-Butanol | White solid | A + B |
| Acetonitrile | 2-Propanol | White solid | A + B |
| 1-Propanol | Heptane | Glass | — |
| Acetone | Chloroform | Glass | — |

Anti-solvent addition: about 25 mg abiraterone decanoate dissolved in 1-2 mL solvent, followed by the addition of 2-4 mL of anti-solvent. Samples were filtered if they formed a precipitate. The results using this crystallization method are shown in Table E3 below:

TABLE E3

Results from Anti-Solvent Addition

| Solvent | Anti-solvent | Form |
|---|---|---|
| Dichloromethane | ACN/water | * |
| THF | Water | * |
| Ethanol | Water | A + B |
| Dioxane | Water | * |
| 2-Butanol | Water | * |
| 1-Propanol | Water | A |
| Acetone | Water | * |
| DMA | Water | * |
| Chloroform | ACN/water | A |
| Trifluoroethanol | Water | A |
| t-Butanol | Water | A |
| DMF | Water | * |
| Ethyl acetate | ACN/water | A + B |
| Corn oil/benzyl alcohol (1:1) | ACN/water | * |
| Benzyl alcohol | ACN/water | A + B |
| Benzyl benzoate | ACN/water | * |
| 2-Butanone | Water | A |
| Toluene | ACN/water | * |
| Methanol | Water | A + B |
| 2-Propanol | Water | A |

*Either no precipitate formed or not enough solid recovered

Solvent recrystallization from single solvent: abiraterone decanoate was recrystallized using various solvents. The scale of the recrystallization experiments was approximately 2-10 mL. Saturated solutions were prepared by agitating excess abiraterone decanoate in contact with the various solvent systems at the saturation temperature. If solids did not completely dissolve in the solvent, the mother liquor was separated from the residual solids by filtration. The mother liquor was then heated above the saturation temperature to dissolve any remaining solids. The temperature of each solution was then adjusted to the growth temperature and a controlled nitrogen shear flow was introduced to begin solvent evaporation. The recrystallization conditions for the solvent based panels used during the study are summarized in Tables E4-E5. XRD analysis was carried out.

TABLE E4

Summary of Fast Evaporation Experiments from Single Solvent Systems at Ambient Temperature

| Solvent | Form |
|---|---|
| Dioxane | A |
| 1-Propanol | A |
| MTBE | A |
| Isopropyl ether | A + C |
| t-Butanol | A |
| Chloroform | A |
| Acetone | A |
| Ethyl acetate | A |
| Nitromethane | A |
| DMA | A |
| THF | A |
| DMF | A |
| Diethyl ether | A |
| 2-Butanol | A |
| Isopropyl acetate | A + C |
| Ethanol | A |
| Water | * |
| Methanol | A |
| Toluene | A + C |
| Acetonitrile | A |
| Heptane | A |
| 2-Propanol | A + B |
| 2-Butanone | A |
| 2-Methyl THF | A |

*No solids recovered

TABLE E5

Summary of Fast Evaporation Experiments from Single Solvent Systems at 55° C.

| Solvent | Form |
|---|---|
| Ethyl acetate | A |
| 1-Propanol | Glass |
| Ethanol | Glass |
| t-Butanol | A |
| Chloroform | A |
| Isopropyl ether | A |
| 2-Butanol | Glass |
| Dioxane | Glass |
| THF | A |
| DMF | Glass |
| DMA | Glass |
| 2-Propanol | A |
| Acetonitrile | A |
| 2-Butanone | A |
| Heptane | A |
| Toluene | A |
| Methanol | A |
| Water | * |
| 2-Methyl THF | Glass |

*No solids recovered

Non-competitive slurry experiments: The non-competitive slurry experiments were performed by exposing abiraterone decanoate in Form A to solvents and agitating the resulting suspensions for one week at ambient temperature. The solids were filtered and analyzed by XRD to determine the resulting form(s). The solvents used in this study include: water, acetonitrile, isopropyl ether/acetonitrile (1:4), 2-butanol/water (1:1), 1-propanol/water (1:1), t-butanol/water (1:1), ethanol/water (1:1), THF/water (1:1), acetone/water (1:1), dioxane/water (1:1), 2-butanone/water (1:1), methanol, DMF/water (1:1), ethyl acetate/water (1:1), and heptane. Based on their X-ray scattering behavior, all of the non-competitive slurry experiments resulted in no change from the starting material.

A competitive study was also carried out. Competitive slurries: about 20 mg abiraterone decanoate suspended in 1-2 mL solvent. Samples were stirred for 3 days and filtered. The results from the competitive studies are shown in Table E6 below:

TABLE E6

Results from Competitive Slurries

| Solvent | Starting Forms | Final Form |
|---|---|---|
| Acetonitrile | A + B | A |
|  | A + C | A |
|  | B + C | A |
| Methanol | A + B | A |
|  | A + C | * |
|  | B + C | * |

*No solid recovered - not enough material and solubility too high

Characterization of Forms: Solids generated from the solvent based recrystallization panels were analyzed by powder XRD. To mitigate preferred grain effects, a two dimensional detection system was used to collect all the XRD screening data. The two dimensional detector integrates along the concentric Debye cones which helps reduce pattern variation. If bright spots appear in the conical rings, it indicates strong preferred grain effects that can lead to considerable variability in the observed diffraction patterns including changes in peak intensities. Some samples of abiraterone decanoate exhibited preferred grain effects based on the appearance of the scattering behavior.

The results of this analysis revealed the material exists as at least 3 primary polymorphs. The observed forms were designated as Forms A, B, and C.

After classifying the data into different forms based on diffraction behavior, each form was studied to determine if other properties of the forms could be differentiated. The characterization of each form began by comparing the diffraction data representative of each form with that from the other forms. This was generally followed by NMR, DSC, and TGA.

The initial material used in this study was Form A, which is consistent with the representative characterization data shown in Example 1A, see also summary table E7 below.

Form B was obtained in a variety of crystallization experiments, particularly those carried out at low temperature (−10 to −20° C.). The characteristic diffraction behavior of this form is shown in a representative XRPD spectrum, FIG. 2D. The $^1$H NMR spectrum of Form B shows no organic impurities and is consistent with the expected structure of ADEC. Representative DSC and TGA spectra of Form B are shown in FIGS. 2E and 2F.

Figure 2I:
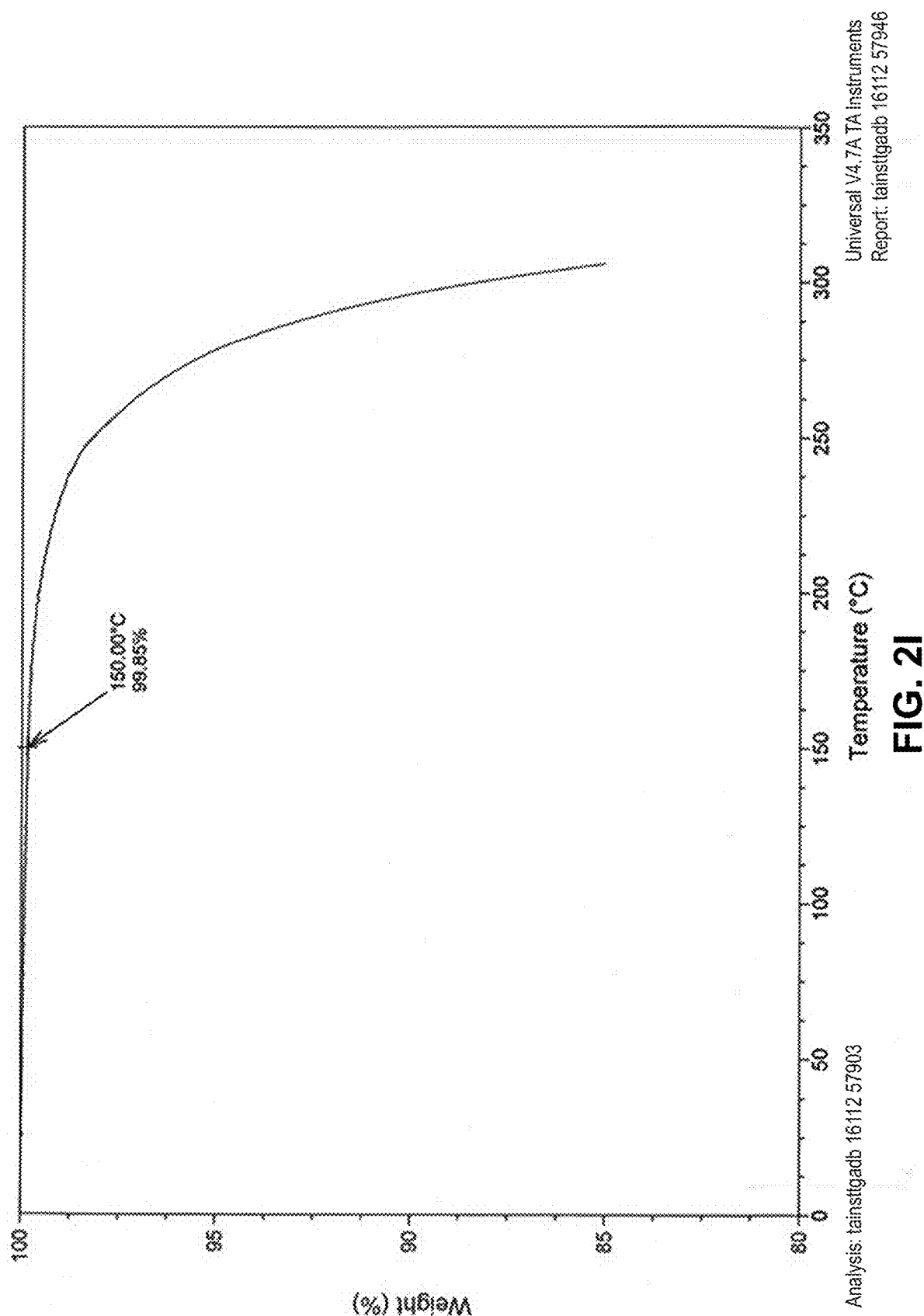
FIG. 2I shows a representative TGA of the abiraterone decanoate in Form C.

Form C was obtained by evaporation from a 1:1 mixture of ethanol and 2-butanone. The characteristic diffraction behavior of this form is shown in a representative XRPD spectrum, FIG. 2G. It should be noted that the diffractogram obtained for the one "pure" Form C sample shows significant overlap with Form A at higher diffraction angles and therefore may contain some Form A. The $^1$H NMR spectrum of Form C shows no organic impurities and is consistent with the expected structure of ADEC. Representative DSC and TGA spectra of Form C are shown in FIGS. 2H and 2I.

Table E7 below summarizes representative analysis of abiraterone decanoate Forms A, B, and C.

TABLE E7

Results Summary of abiraterone decanoate (ADEC) Forms A, B, and C.

| Technique | Property | Form A | Form B | | Form C | |
|---|---|---|---|---|---|---|
| XRD | Crystalline? | Yes | Yes | | Yes* | |
| TGA | Wt % loss @ 150° C. | 0.0 | 0.2 | | 0.0 | |
| DSC | Endotherm | $1^{st}$ | $1^{st}$ | $2^{nd}$ | $1^{st}$ | $2^{nd}$ |
|  | Onset (° C.) | 67.3 | 60.6 | 64.9 | 58.7 | 66.6 |
|  | Peak Max (° C.) | 69.8 | 61.7 | 66.0 | 61.8 | 68.0 |
|  | ΔH (J/g) | 80.0 | 36.4 | 36.8 | 51.1 | 3.9 |
| NMR | Consistent with ADEC structure? |  | Yes | | | |
|  | Residual solvents |  | Not detected | | | |
| DVS | Max H$_2$O uptake (wt %) |  | N/A-non-hygroscopic | | | |

*May contain some Form A

The polymorph screen recrystallization experiments produced either Forms A, B, C, or a mixture of forms. Form A is expected to be thermodynamically stable form under ambient conditions based on the non-competitive and competitive slurry experiments.

Example 2. Preparation of Abiraterone Decanoate Formulations

Approximately a half of the required amount of corn oil was added to a suitable container (~1,750 ml). The required amount of benzyl alcohol (360 g) was weighed and added to the corn oil. The required amount of benzyl benzoate (720 g) was weighed and added to the corn oil. This mixture was mixed using an appropriate mixer (e.g., shaft mixer) for a minimum of 10 minutes or until all the benzyl alcohol and benzyl benzoate was in solution. The appropriate amount of the abiraterone decanoate (720 g) was weighed out and added to the solution of corn oil/benzyl alcohol/benzyl benzoate and mixed using an appropriate mixer (e.g., shaft mixer) for a minimum of 30 minutes or until all the abiraterone decanoate was in solution. The resulting solution was than diluted to its final volume (3,600 ml) with corn oil to make a solution with the composition given below:

TABLE 1A

Ingredients of Abiraterone Decanoate Formulation

| Ingredient | Amount (mg) per mL | Amount (grams) for a 3.6 L batch* |
|---|---|---|
| Abiraterone Decanoate | 200 | 720 |
| Benzyl Alcohol | 100 | 360 |
| Benzyl Benzoate | 200 | 720 |
| Corn Oil | QS to 1 mL | QS to 3,600 mL |

*This is a representative batch size and the batch size can vary based on the amount of drug product needed.

Drug Substance Analysis: The abiraterone decanoate used for preparing the formulations above was obtained from a process similar to those described in Example 1A, except without the recrystallization step. The abiraterone decanoate typically has a purity of 99% by weight (as measured by HPLC) or higher. A typical batch of abiraterone decanoate has a quality as shown in FIG. 3, using HPLC Method 1. Based on such, the assigned purity of such abiraterone decanoate batch is about 99.4% by weight, calculated by the following method: 100%−(% HPLC impurities+% Karl Fischer Moisture+% residue solvents). The HPLC method used for measuring the purity of abiraterone decanoate can be HPLC Method 1: Separation is performed with an Advanced Materials Technology Halo C8 reversed phase column using dimensions of 3.0×100 mm and a particle size of 2.7 μm. A linear gradient program (20 minutes) is used with mobile phases consisting of a 25 mM aqueous ammonium acetate buffer and a mixture of methanol and acetonitrile (see gradient profile below in Table 1B). Working standard and sample solutions are prepared in a methanol diluent. The typical injection volume is 5 μL and the detection wavelength is 210 nm.

TABLE 1B

Gradient Profile of HPLC Method 1

| Time (min) | Mobile Phase A (%) | Mobile Phase B (%) |
|---|---|---|
| 0 | 50 | 50 |
| 20 | 5 | 95 |
| 25 | 5 | 95 |
| 25.1 | 50 | 50 |
| 30 | 50 | 50 |

Mobile Phase A: 25 mM Ammonium Acetate in 90% water, 10% Methanol
Mobile Phase B: 25 mM Ammonium Acetate in 90% acetonitrile, 10% Methanol Under sterile conditions the final solution is then sterilized by passing the solution through a 0.22-micron PVDF filter using a standard pump system (e.g., peristaltic pump) and placed into to sterile vials (219 vials, 15 ml fill volume). The filled vials are sealed with a rubber stopper and then capped to ensure the integrity of the final product. The fill volume and size of the vial can vary based on the dose to be manufactured.

Analytical Methods of Abiraterone Decanoate Formulation

Assay, related substances, and identification by retention time of the abiraterone decanoate formulation were conducted using a reversed phase high performance liquid chromatographic analytical method, HPLC Method 2. HPLC Method 2: separation is performed with an XBridge Shield RP18 reversed phase column using dimensions of 4.6×100 mm and a particle size of 3.5 μm. A linear gradient program (25 minutes) is used with mobile phases consisting of a 40 mM aqueous ammonium bicarbonate buffer and a mixture of methanol and acetonitrile (see gradient profile below in Table 1C). Working standard and sample solutions are prepared in isopropyl alcohol diluent. The typical injection volume is 10 μL and the detection wavelength is 254 nm.

TABLE 1C

Gradient Profile of HPLC Method 2

| Time (min) | Mobile Phase A (%) | Mobile Phase B (%) |
|---|---|---|
| 0 | 100 | 0 |
| 25 | 0 | 100 |
| 35 | 0 | 100 |
| 35.1 | 100 | 0 |
| 40 | 100 | 0 |

Mobile Phase A: 50:25:25 40 mM Ammonium Bicarbonate Buffer: MeOH:ACN
Mobile Phase B: 50:50 MeOH:ACN Glide Force Determination: The analytical method is performed using a tensile and compression testing instrument (eg. Lloyd press or equivalent), with a 250N load cell and Nexygen Plus materials testing software. Two separate syringe/needle configurations were used for the analytical measurements (5-mL Luer-Lok syringe configured with a 23 gauge (23 G) 1.5-inch thin wall precision glide needle and a 5-mL Luer-Lok syringe configured with a 27 gauge (27 G) 1.5 inch regular wall precision glide needle. The glide force measurements are taken using a 5-mL sample size and a constant compression rate.

Viscosity: The analytical method is performed using a Malvern Kinexus Lab+ viscometer instrument with rSpace Rheometry software. The following parameters were developed for the viscosity measurements of the drug product:

Bob Geometry: C25 DIN Splined
Cup Geometry: C25 DIN AL
Analysis Temp: 20.0° C.
Manual Gap: 1.0 mm
Shear Rate: 50 s$^{-1}$
Test time: 1 minute
Sampling Interval: 15 seconds Particulates: The number of particles in the drug products was measured according to the current version of USP<788> and/or <789>.

Bacterial Endotoxins: The bacterial endotoxins test was performed according to the current version of USP<85>.

Analytical Results

The table below shows the analytical results using the methods above.

TABLE 2

Representative Analytical Results of Abiraterone Decanoate Formulation

| Test Description | Analytical Results |
|---|---|
| Appearance | Clear glass vial with red flip-off cap, metal overseal and rubber stopper containing a clear yellow solution free of visible particulates |
| Identification by HPLC | Conforms |
| Chromatographic Purity by HPLC (% of Label Claim, 200 mg/ml)) | 98.9 |
| Related Substances by HPLC (% w/w) | |
| RRT 1.19 | 0.11 |
| RRT 1.21 | 0.13 |
| RRT 1.39 | 0.12 |
| Total Impurities | 0.4 |
| Viscosity (Pa * s) | 0.05420 |
| Glide Force (N) | |
| 23G 1.5-inch needle | 7.6962 |
| 27G 1.5-inch needle | 70.326 |
| Particulates (HIAC) | |
| Particles ≥10 gm | 352 |
| Particles ≥2.5 gm | 68 |
| Bacterial Endotoxins by USP <85> EU/mL | <25 |

The impurity having a relative retention time of 1.19 was determined to be

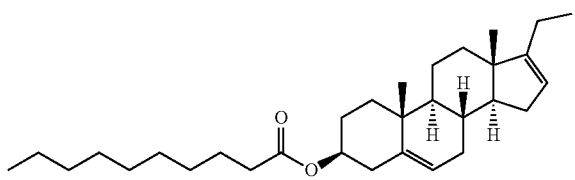

Following similar procedures discussed above, abiraterone decanoate formulation having Abiraterone Decanoate a concentration of about 180 mg/mL was also prepared using the abiraterone decanoate prepared according to Example 1B. The ingredients of the 180 mg/mL formulation include the following, for each milliliter: Abiraterone Decanoate, about 180 mg/mL; Benzyl Alcohol, about 100 mg/mL; Benzyl Benzoate, about 200 mg/mL; and Corn oil, q.s. to 1 mL.

The glide force of the 180 mg/mL abiraterone decanoate formulation (see formulation details above) was also tested using two separate syringe/needle configurations: 5-mL Luer-Lok syringe configured with a 23 gauge (23 G) 1.5-inch thin wall precision glide needle and a 5-mL Luer-Lok syringe configured with a 21 gauge (21 G) 1.5-inch regular wall precision glide needle. The glide force measurements are taken using a 5-mL sample size and a constant compression rate. The mean glide forces observed for the 180 mg/mL abiraterone decanoate formulation are the following: 3.2835 (for 21 G, 1.5-inch needle) and 6.7863 (for 23 G, 1.5-inch needle). The glide force measurements were also taken using a 2-mL fill for a 3 mL syringe. Under these settings, the mean glide forces observed for the 180 mg/mL abiraterone decanoate formulation are the following: 1.0957 (for 21 G, 1.5-inch needle) and 2.1481 (for 23 G, 1.5-inch needle).

Both the 200 mg/mL and 180 mg/mL abiraterone decanoate formulations were found to be storage stable at 25° C./60% RH and 40° C./75% RH for at least 3 months.

Example 3. PK/PD Studies of Abiraterone Decanoate in Chemically Castrated Monkeys This study compares a single oral gavage dose of abiraterone acetate with a single intramolecular injection of abiraterone decanoate in chemically castrated, sexually mature male cynomolgus monkeys.

The test materials used for this study are shown in Table 3A below:

TABLE 3A

Description of Test Articles

| Test Article | Description | Concentration |
|---|---|---|
| Leuprolide Acetate | Lupron Depot Suspension | 7.5 mg/ml |
| Abiraterone acetate | methylcellulose A4M (0.5% w/v), Tween 80 (0.1% w/v) and sodium chloride (0.9% w/v). | 1 mg/ml<br>3 mg/ml<br>9 mg/ml |
| Abiraterone Decanoate | corn oil with 10% benzyl alcohol (w/v) and 20% benzyl benzoate (w/v) (see Example 2) | 200 mg/ml |

The dosing schedules in this study followed those shown in Table 3B below:

TABLE 3B

Description of Dosing Schedules

| Group No. | Dose Route | Test Material | Dose Level | Study Dosing Days | Dose Volume[a] (mL/kg) | Dose Concentration (mg/mL) | Main Study Males |
|---|---|---|---|---|---|---|---|
| 1 | IM | Lupron[b] | 0.3 mg/kg | 1, 30, 57, | 0.04 | 7.5 | 3 |
| 2 | | | | 85 and | 0.04 | 7.5 | 3 |
| 3 | | | | 113 | 0.04 | 7.5 | 3 |
| 1 | PO | Abiraterone | 5 mg/kg | 29 | 5 | 1 | c |
| 2 | | Acetate | 15 mg/kg | | | 3 | c |
| 3 | | | 45 mg/kg | | | 9 | c |
| 1 | IM | Abiraterone | 10 mg/kg | 43 | 0.05 | 200 | c |
| 2 | | Decanoate | 30 mg/kg | | 0.15 | | c |
| 3 | | | 100 mg/kg | | 0.5 | | c |
| 1 | IM | Dexamethasone | 0.5 mg/kg | 105[a] | 0.25 | 2 | c |
| 2 | | | | | | | c |
| 3 | | | | | | | c |
| 1 | IM | Methylprednisolone | 1.29 mg/kg | 120, 127 | 0.016 | 80 | c |
| 2 | | Acetate | | and 134 | | | c |
| 3 | | | | | | | c |

PO = Oral Gavage; IM = Intramuscular.

[a]Based on the most recent body weight measurement.

[b]Animals will be pretreated with Lupron Depot (leuprolide acetate for depot suspension), a gonadal testosterone suppression drug, via intramuscular injection on Days 1, 30, 57, 85 and 113.

[c]The same animals will be administered a single Oral gavage dose of Abiraterone Acetate on Day 29; followed by a single intramuscular injection of Abiraterone Decanoate on Day 43. A dexamethasone dose will be administered on Day 105 (16 hours +/− 30 minutes prior to the start of serial sampling on Day 106).

The dose levels of abiraterone acetate and decanoate are based on the prodrugs, not the equivalent doses of abiraterone, for example, the 10 mg/kg abiraterone decanoate dose shown in the table is about 6.9 mg/kg, if expressed as abiraterone equivalent dose.

Figure 4A:
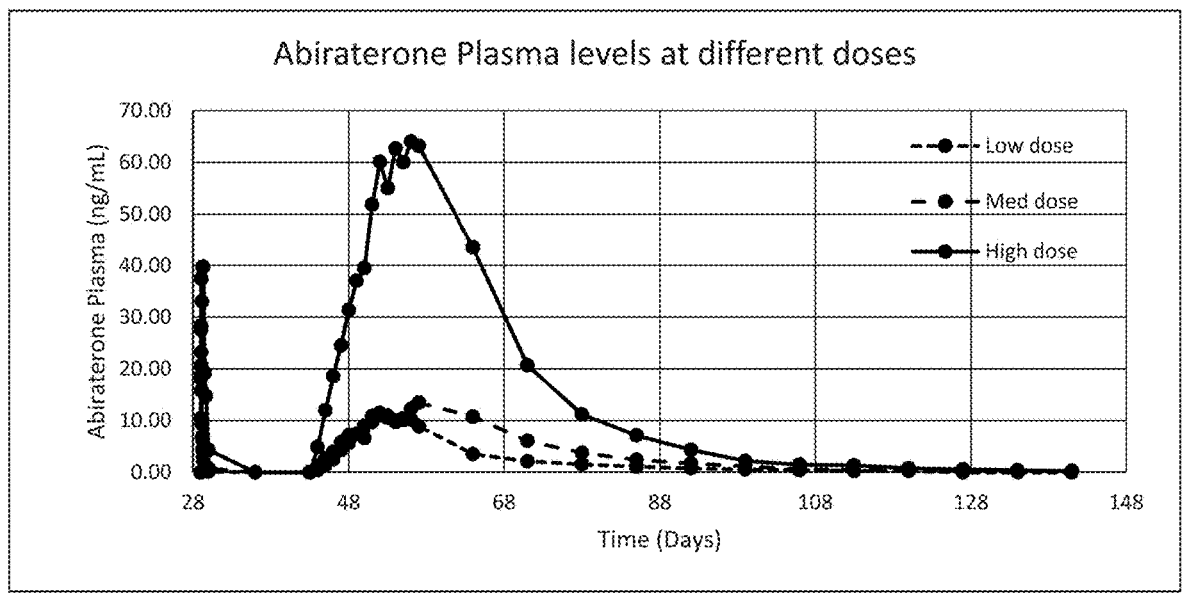
FIG. 4A shows mean abiraterone plasma concentration versus time profile data following a single oral dosing of abiraterone acetate (5 mg/kg, 15 mg/kg, and 45 mg/kg) on day 29 and single IM injection of abiraterone decanoate (10 mg/kg, 30 mg/kg, and 100 mg/kg) on day 43 in chemically castrated, sexually mature male cynomolgus monkeys.
Figure 4B:
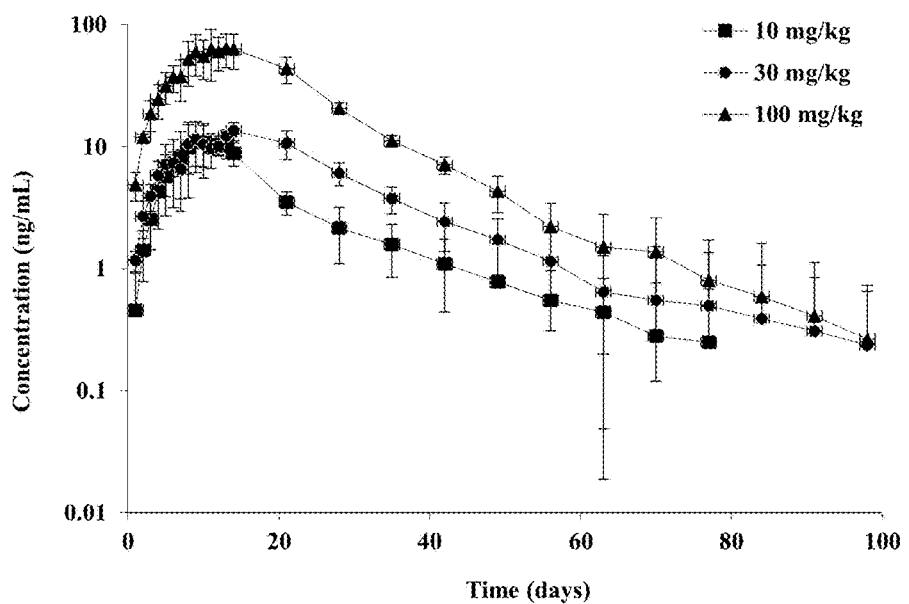
FIG. 4B shows mean abiraterone plasma concentration versus time profile data following a single IM injection of abiraterone decanoate (10 mg/kg, 30 mg/kg, and 100 mg/kg) in chemically castrated, sexually mature male cynomolgus monkeys up to 98 days post injection.
Figure 5A:
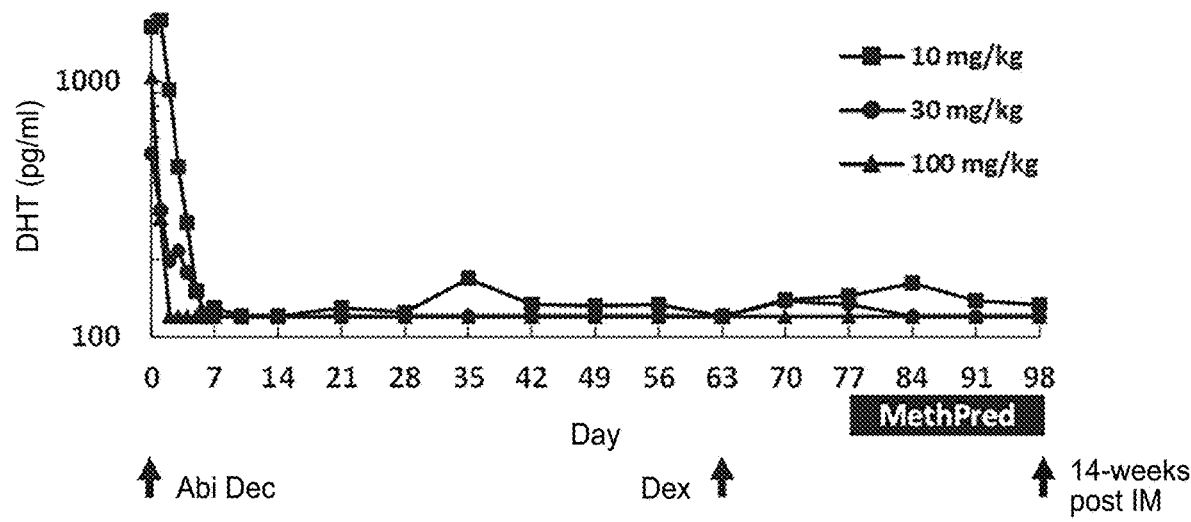
FIG. 5A shows dihydrotestosterone levels (figure label DHT) versus time profile data following a single IM injection of abiraterone decanoate (10 mg/kg, 30 mg/kg, and 100 mg/kg) in chemically castrated, sexually mature male cynomolgus monkeys and up to 98 days post injection. Dexamethasone (Dex) and Methylprednisolone Acetate (MethPred) were also administered according to the schedule shown in Example 3.
Figure 5B:
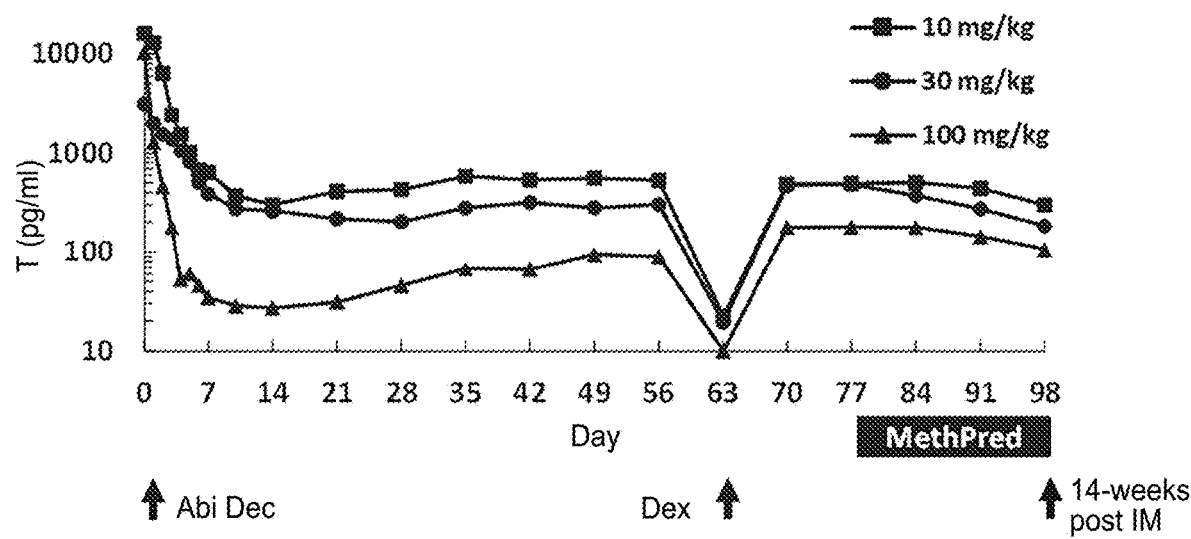
FIG. 5B shows testosterone levels (figure label T) versus time profile data following a single IM injection of abiraterone decanoate (10 mg/kg, 30 mg/kg, and 100 mg/kg) in chemically castrated, sexually mature male cynomolgus monkeys and up to 98 days post injection. Dexamethasone (Dex) and Methylprednisolone Acetate (MethPred) were also administered according to the schedule shown in Example 3.
Figure 5C:
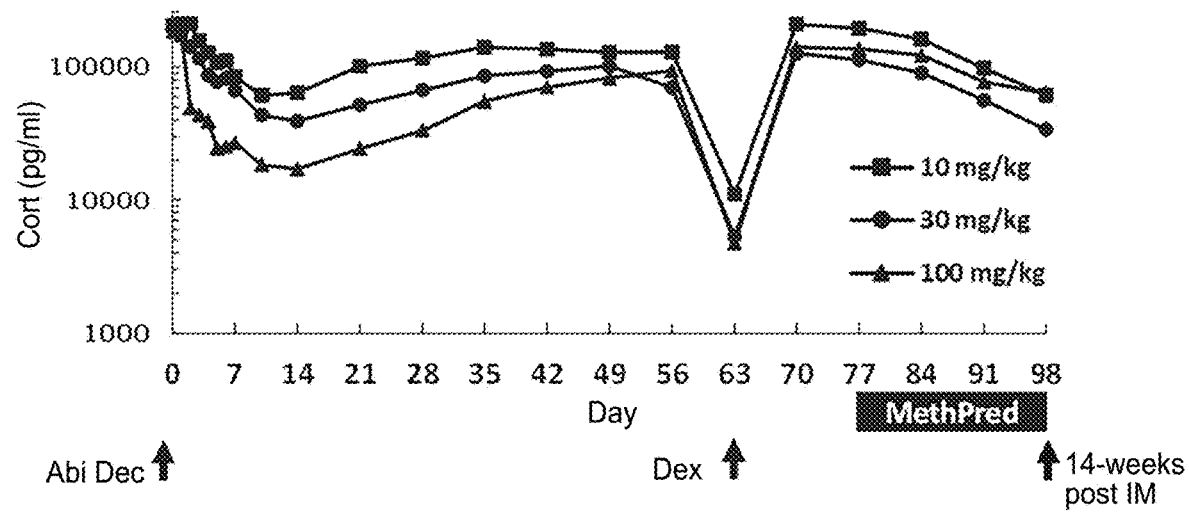
FIG. 5C shows cortisol levels (figure label Cort) versus time profile data following a single IM injection of abiraterone decanoate (10 mg/kg, 30 mg/kg, and 100 mg/kg) in chemically castrated, sexually mature male cynomolgus monkeys and up to 98 days post injection. Dexamethasone (Dex) and Methylprednisolone Acetate (MethPred) were also administered according to the schedule shown in Example 3.
Figure 5D:
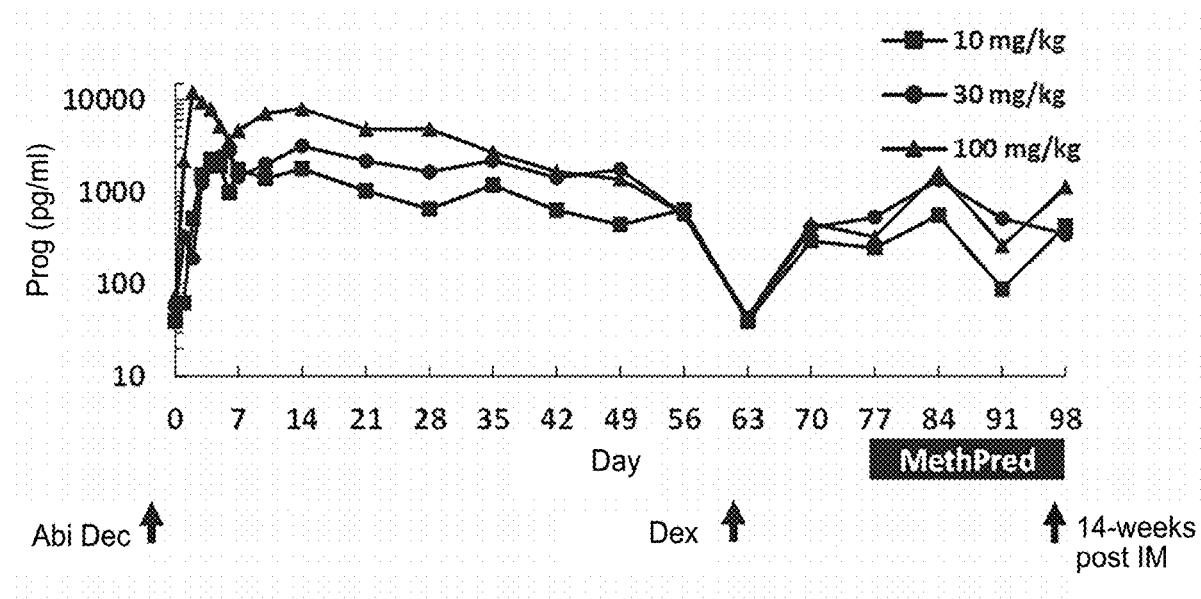
FIG. 5D shows progesterone levels (figure label Prog) versus time profile data following a single IM injection of abiraterone decanoate (10 mg/kg, 30 mg/kg, and 100 mg/kg) in chemically castrated, sexually mature male cynomolgus monkeys and up to 70 days post injection. Dexamethasone (Dex) and Methylprednisolone Acetate (MethPred) were also administered according to the schedule shown in Example 3.
Figure 6A:
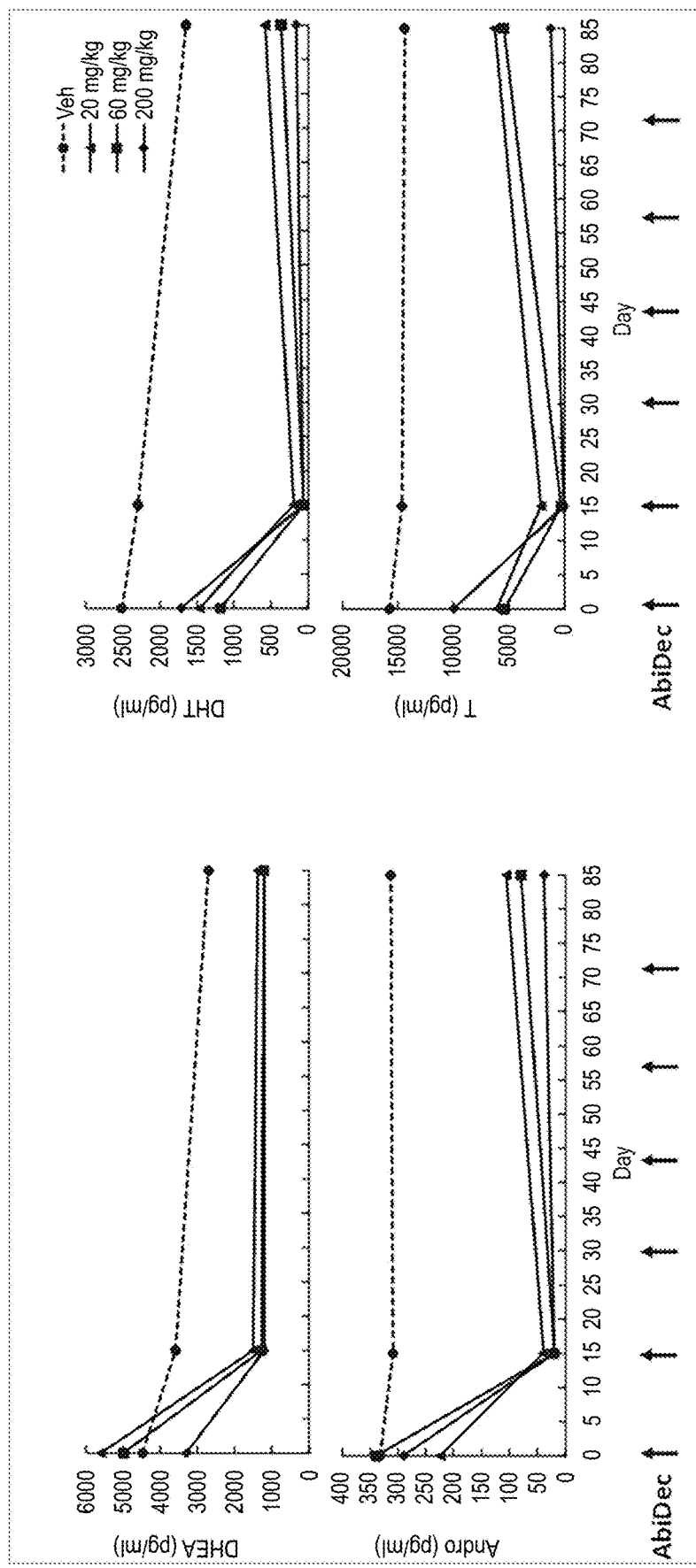
FIG. 6A shows serum androgen levels (dehydroepiandrosterone, androstenedione, testosterone, or dihydrotestosterone) versus time profile data following IM injection of vehicle or abiraterone decanoate (20 mg/kg, 60 mg/kg, and 200 mg/kg) administered every two weeks in gonadally intact, sexually mature, male cynomolgus monkeys up to 85 days post the first injection. Note: Day 0 in the figure notes the sample collected on Day −1 of the study; andro=androstenedione; DHEA=dehydroepiandrosterone; DHT=dihydrotestosterone; T=testosterone.
Figure 6B:
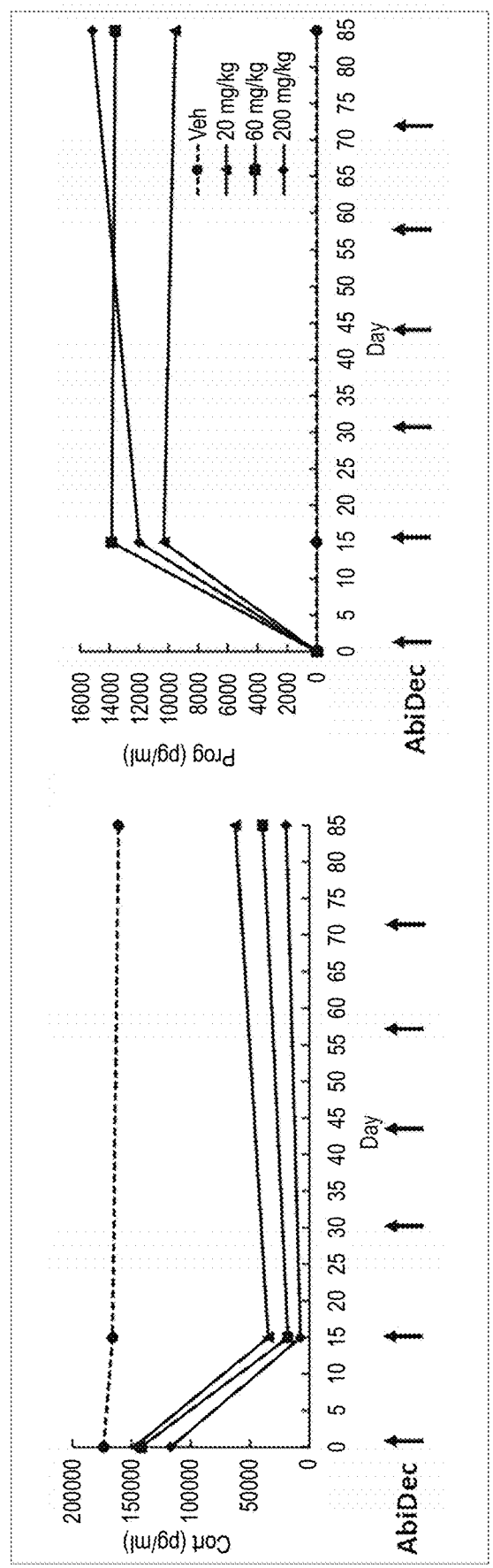
FIG. 6B shows serum cortisol and progesterone levels versus time profile data following IM injection of vehicle or abiraterone decanoate (20 mg/kg, 60 mg/kg, and 200 mg/kg) administered every two weeks in gonadally intact, sexually mature, male cynomolgus monkeys up to 85 days post the first injection. Note: Day 0 in the figure notes the sample collected on Day −1 of the study; cort=cortisol; prog=progesterone.
Figure 6C:
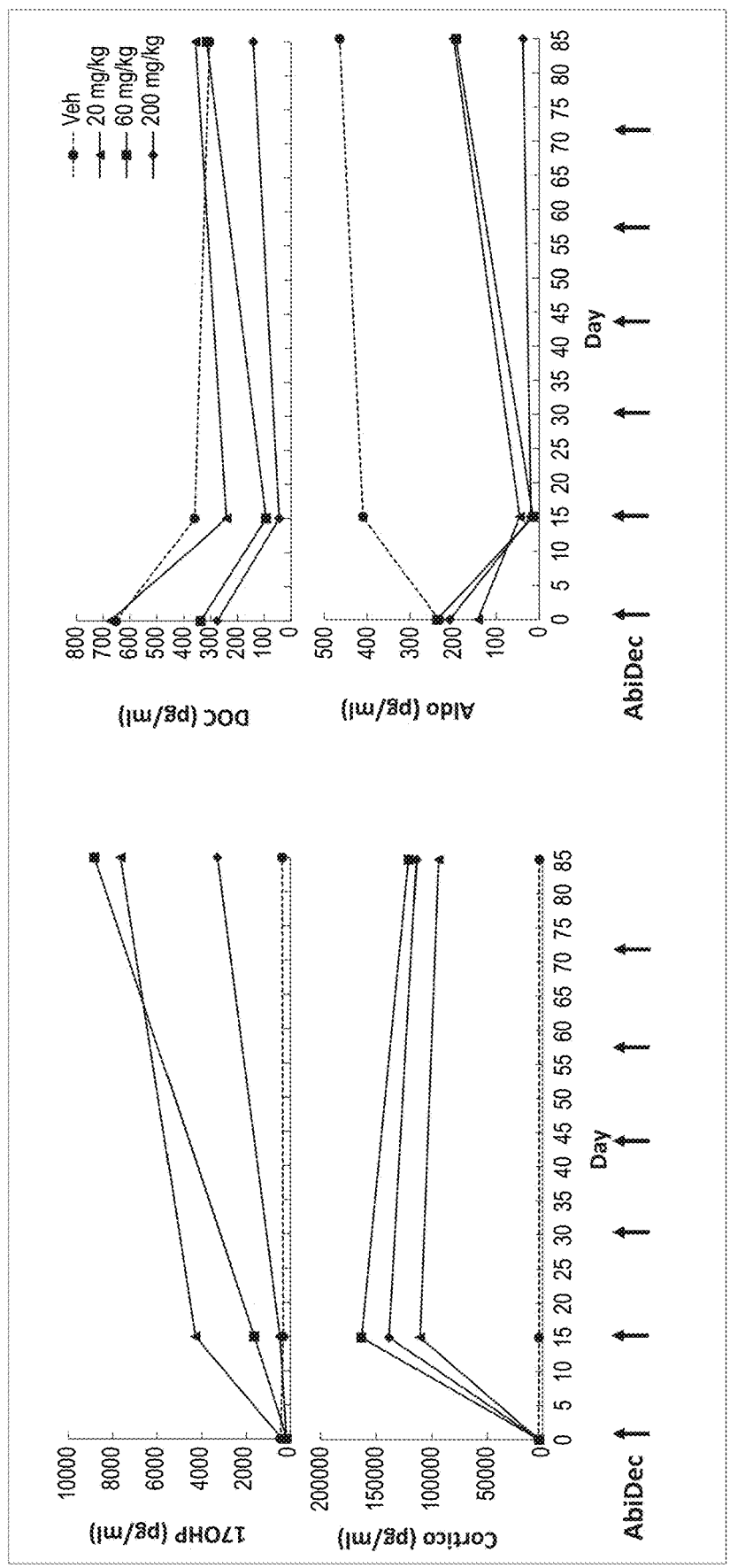
FIG. 6C shows serum cortisol and progesterone levels versus time profile data following IM injection of vehicle or abiraterone decanoate (20 mg/kg, 60 mg/kg, and 200 mg/kg) administered every two weeks in gonadally intact, sexually mature, male cynomolgus monkeys up to 85 days post the first injection. Note: Day 0 in the figure notes the sample collected on Day −1 of the study; 17OHP=17OH-progesterone; aldo=aldosterone; cortico=corticosterone; DOC=deoxycorticosterone.
Figure 7A:
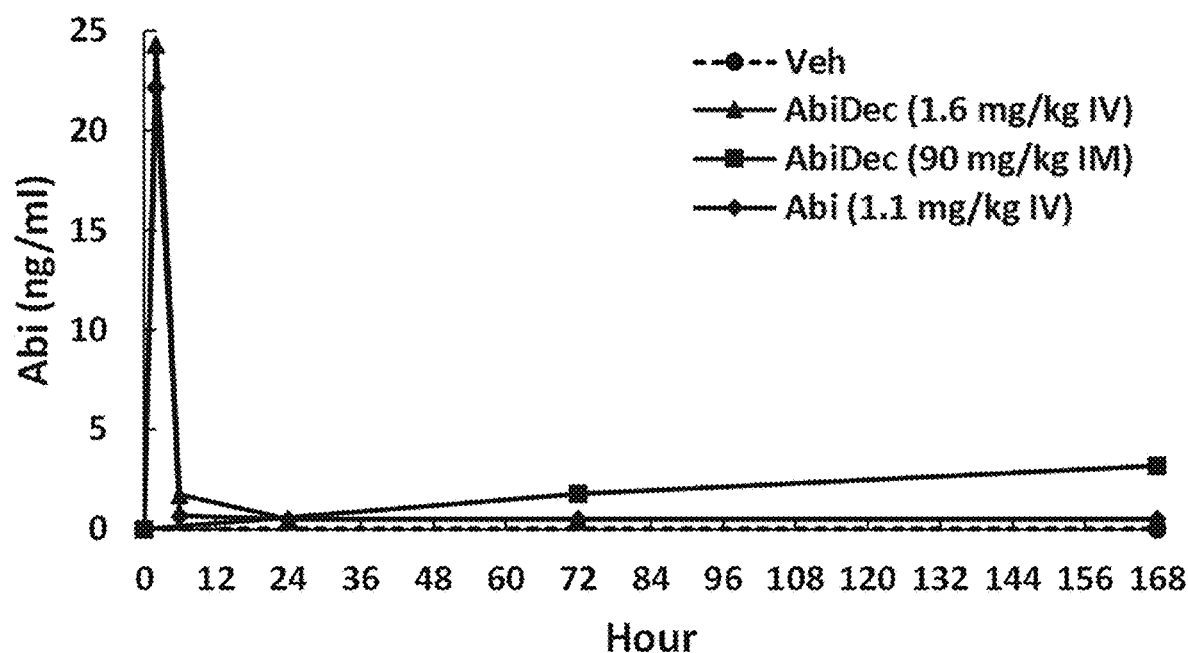
FIG. 7A shows mean abiraterone plasma concentration versus time profile data following a single IM injection of abiraterone decanoate (90 mg/kg) in rats, strain, CD® [Crl:CD® (SD)] and up to 168 hours post administration.
Figure 7B:
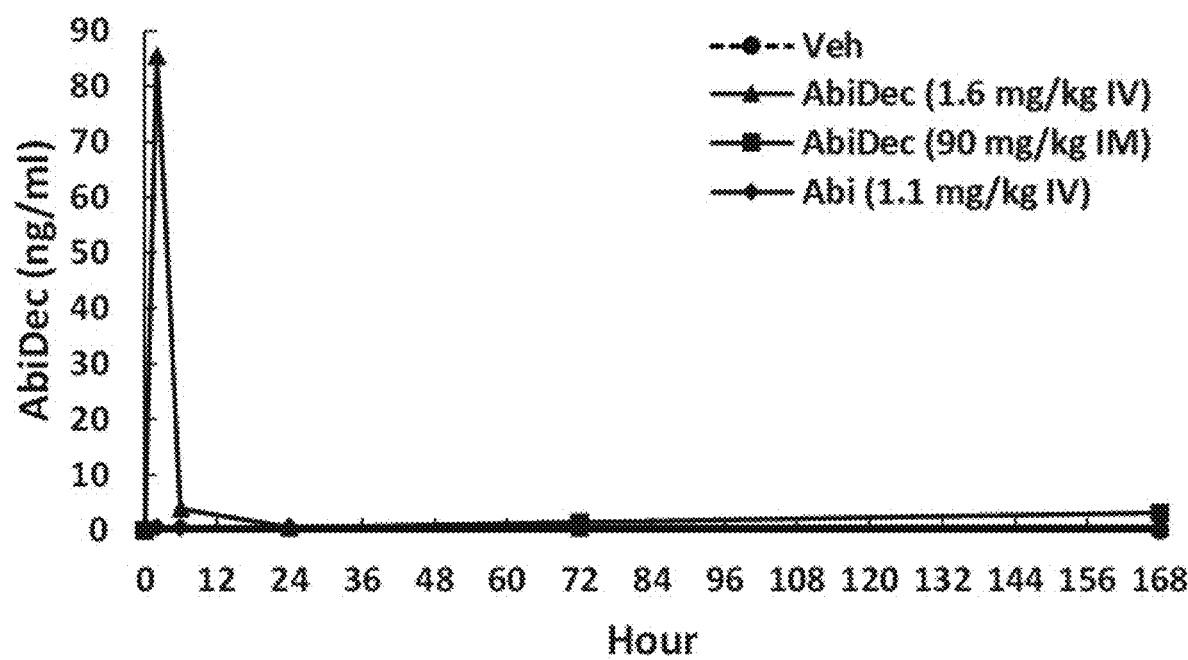
FIG. 7B shows mean abiraterone decanoate plasma concentration versus time profile data following a single IM injection of abiraterone decanoate (90 mg/kg) in rats, strain, CD@[Crl:CD®(SD)] and up to 168 hours post administration.
Figure 7C:
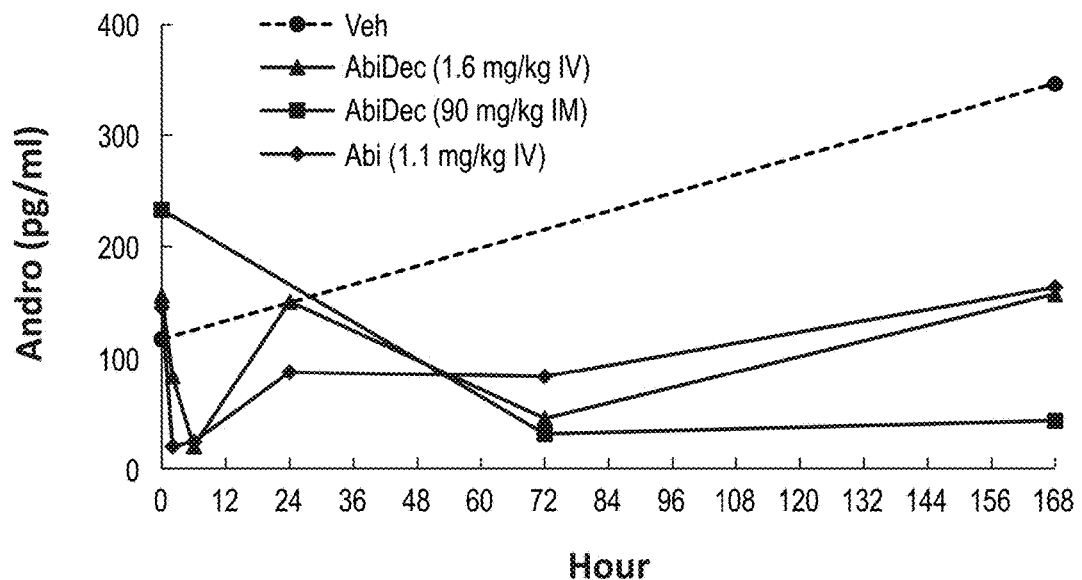
FIG. 7C shows mean serum androstenedione (figure label, Andro) levels versus time profile data following a single IV injection of abiraterone (1.1 mg/kg), or abiraterone decanoate (1.6 mg/kg), or a single IM injection of vehicle or abiraterone decanoate (90 mg/kg) in rats, strain, CD® [Crl:CD®(SD)] and up to 168 hours post administration.
Figure 7D:
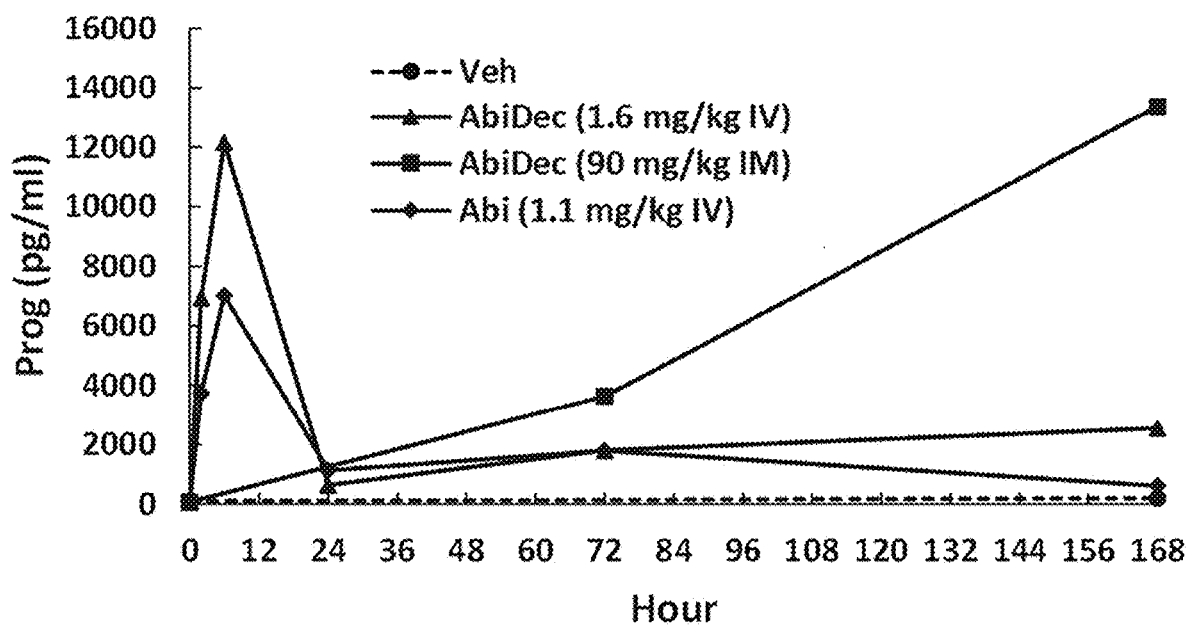
FIG. 7D shows mean serum progesterone (figure label, Prog) levels versus time profile data following a a single IV injection of abiraterone (1.1 mg/kg), or abiraterone decanoate (1.6 mg/kg), or a single IM injection of vehicle or abiraterone decanoate (90 mg/kg) in rats, strain, CD® [Crl:CD®(SD)] and up to 168 hours post administration.
Figure 7E:
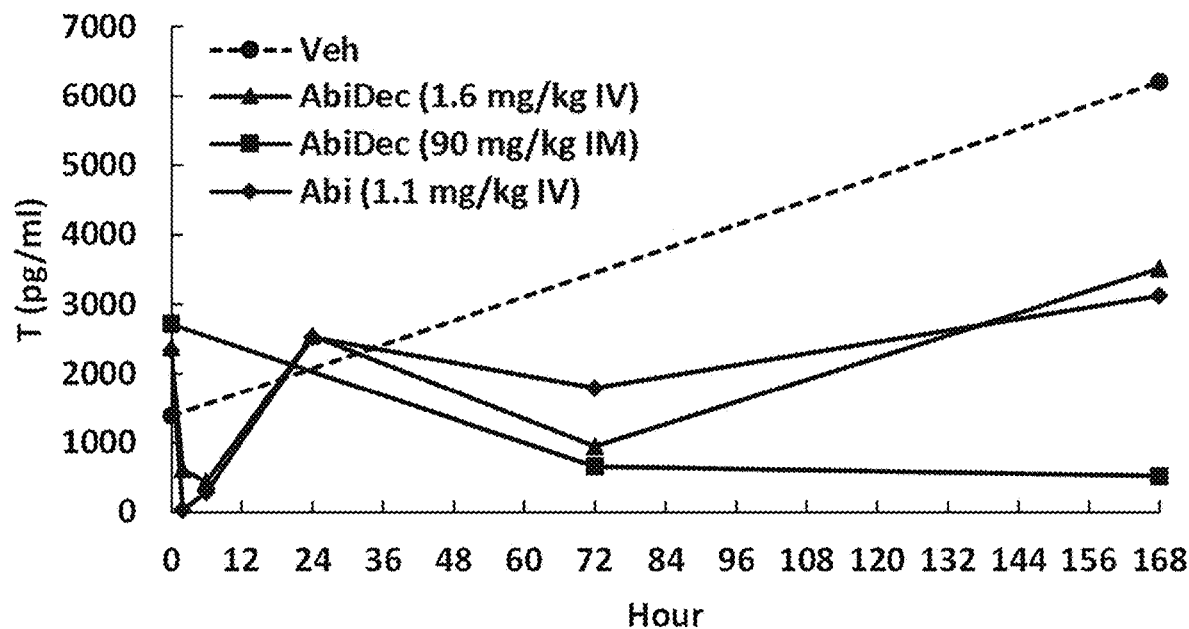
FIG. 7E shows mean serum testosterone (figure label, T) levels versus time profile data following a single IV injection of abiraterone (1.1 mg/kg), or abiraterone decanoate (1.6 mg/kg), or a single IM injection of vehicle or abiraterone decanoate (90 mg/kg) in rats, strain, CD@[Crl:CD®(SD)] and up to 168 hours post administration.
Figure 7F:
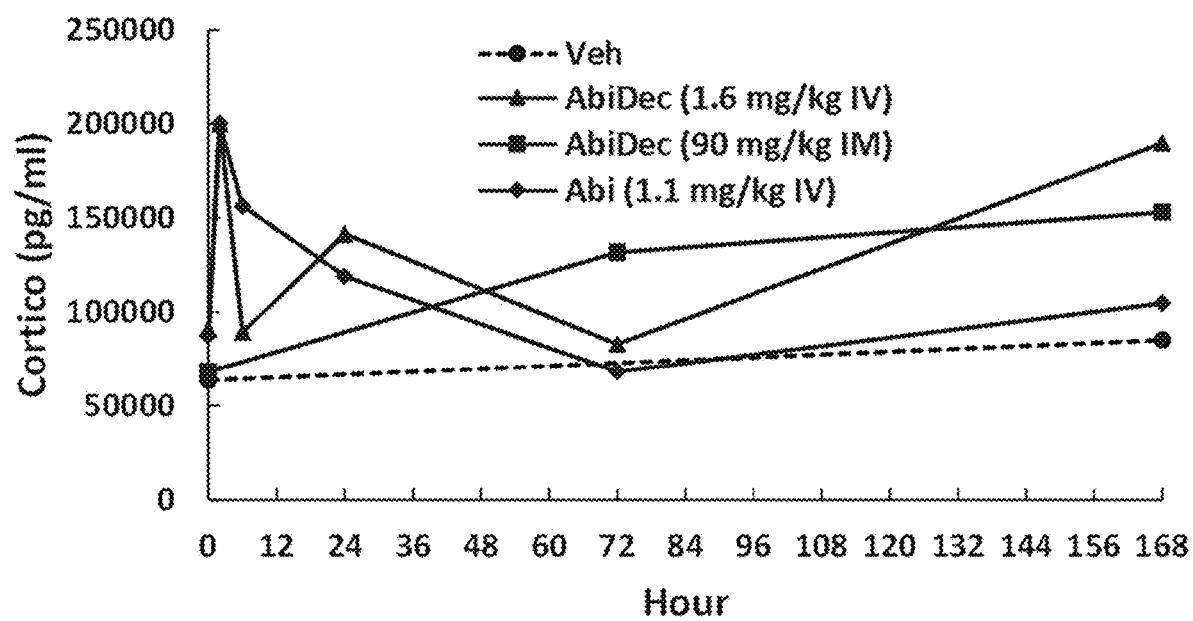
FIG. 7F shows mean serum cortisol (figure label, Prog) levels versus time profile data following a single IV injection of abiraterone (1.1 mg/kg), or abiraterone decanoate (1.6 mg/kg), or a single IM injection of vehicle or abiraterone decanoate (90 mg/kg) in rats, strain, CD@[Crl:CD®(SD)] and up to 168 hours post administration.
Figure 7G:
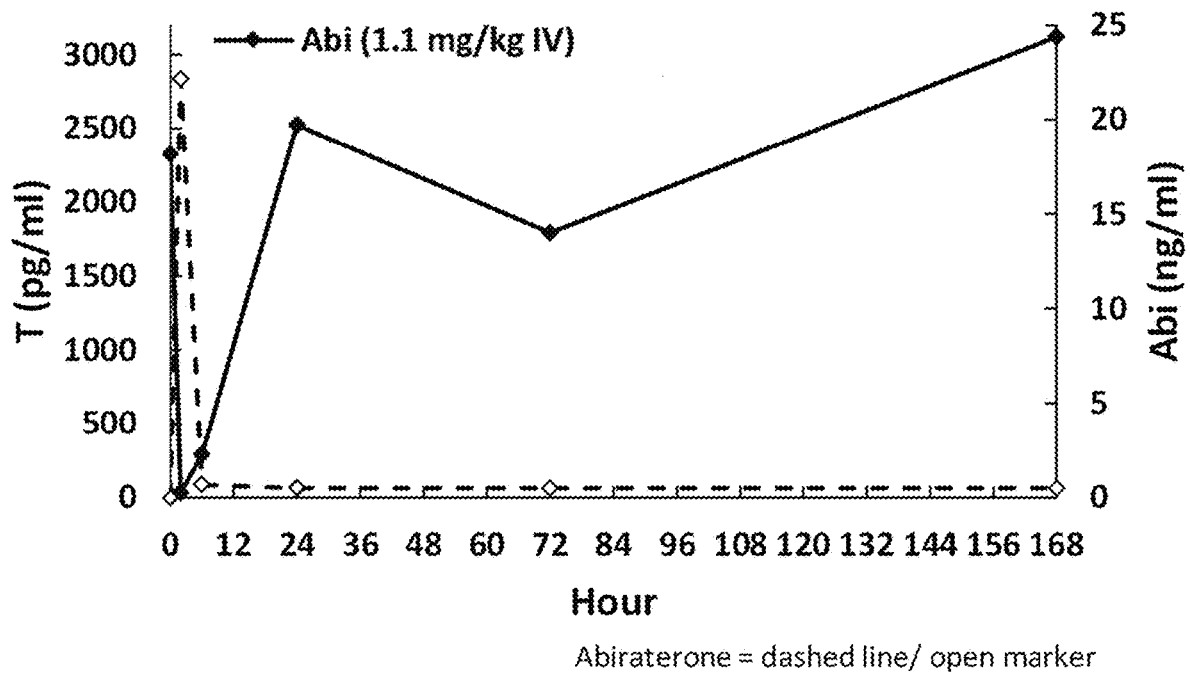
FIG. 7G shows mean serum testosterone (figure label, T) levels versus plasma abiraterone concentrations following a single IV injection of abiraterone (1.1 mg/kg) in rats, strain, CD® [Crl:CD®(SD)] and up to 168 hours post administration.
Figure 7H:
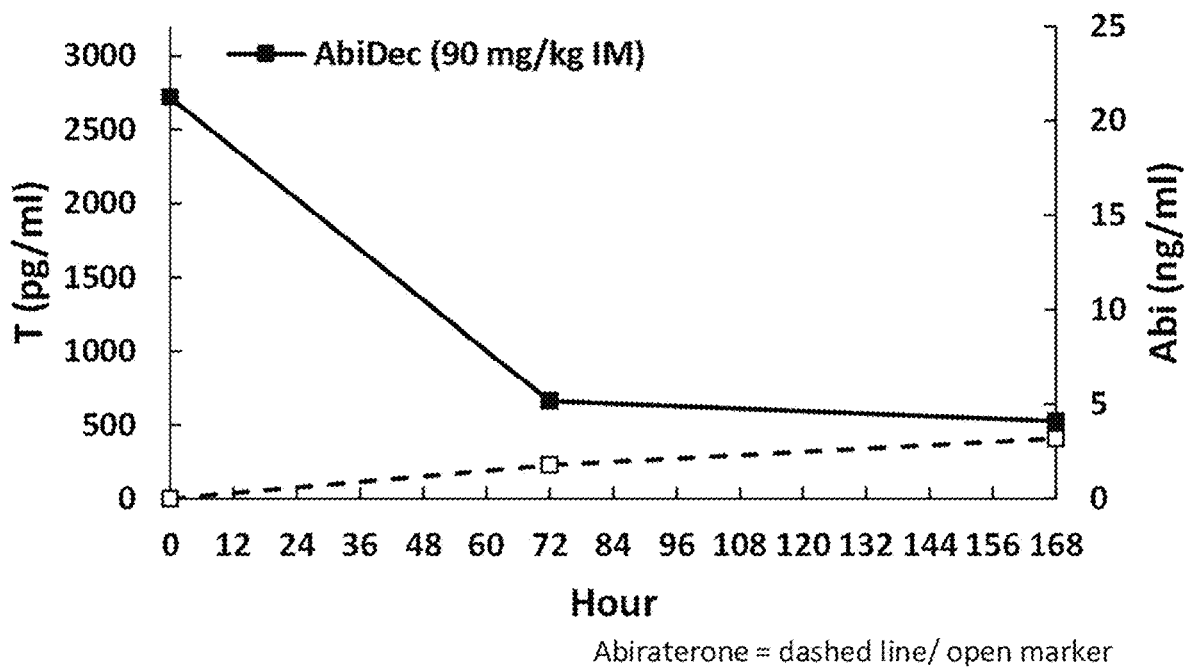
FIG. 7H shows mean serum testosterone (figure label, T) levels versus plasma abiraterone concentrations following a single IM injection abiraterone decanoate (90 mg/kg) in rats, strain, CD® [Crl:CD®(SD)] and up to 168 hours post administration.

PK results obtained from single IM abiraterone decanoate injections are shown in FIGS. 4A and 4B (abiraterone plasma concentration vs. time, up to 98 days post IM injection) and also the tables below (Table 4A-4C, based on time period up to 70 days post IM injection) for each of the 10 mg/kg, 30 mg/kg and 100 mg/kg doses:

TABLE 4A

Abiraterone Plasma Concentration Profile Observed from 10 mg/kg Dose

| Animal | Cmax (ng/mL) | Tmax (day) | AUC0-t (day * ng/mL) | AUC0-∞ (day * ng/mL) | t½ (day) | F (%) |
|---|---|---|---|---|---|---|
| 1001 | 16.2 | 8.00 | 225 | 235 | 14.3 | 180 |
| 1002 | 13.2 | 8.00 | 157 | 166 | 9.75 | 127 |
| 1003 | 11.3 | 13.0 | 212 | 236 | 19.4 | 180 |
| N | 3 | 3 | 3 | 3 | 3 | 3 |
| Mean | 13.6 | 9.67 | 198 | 212 | 14.5 | 162 |
| SD | 2.47 | 2.89 | 36.1 | 40.3 | 4.83 | 30.7 |
| Min | 11.3 | 8.00 | 157 | 166 | 9.75 | 127 |
| Median | 13.2 | 8.00 | 212 | 235 | 14.3 | 180 |
| Max | 16.2 | 13.0 | 225 | 236 | 19.4 | 180 |
| Geometric Mean | 13.4 | 9.41 | 196 | 209 | 13.9 | 160 |
| Geometric CV % | 18.2 | 28.6 | 19.4 | 20.5 | 35.5 | 20.4 |

TABLE 4B

Abiraterone Plasma Concentration Profile Observed from 30 mg/kg Dose

| Animal | Cmax (ng/mL) | Tmax (day) | AUC0-t (day * ng/mL) | AUC0-∞ (day * ng/mL) | t½ (day) | F (%) |
|---|---|---|---|---|---|---|
| 2001 | 11.2 | 14.0 | 281 | 293 | 11.6 | 74.6 |
| 2002 | 13.4 | 14.0 | 285 | 290 | 7.84 | 73.9 |
| 2003 | 16.8 | 9.00 | 449 | 492 | 17.7 | 125 |
| N | 3 | 3 | 3 | 3 | 3 | 3 |
| Mean | 13.8 | 12.3 | 338 | 358 | 12.4 | 91.3 |
| SD | 2.82 | 2.89 | 96.2 | 116 | 4.95 | 29.5 |
| Min | 11.2 | 9.00 | 281 | 290 | 7.84 | 73.9 |
| Median | 13.4 | 14.0 | 285 | 293 | 11.6 | 74.6 |
| Max | 16.8 | 14.0 | 449 | 492 | 17.7 | 125 |
| Geometric Mean | 13.6 | 12.1 | 330 | 347 | 11.7 | 88.4 |
| Geometric CV % | 20.5 | 25.9 | 27.2 | 30.9 | 42.3 | 30.9 |

TABLE 4C

Abiraterone Plasma Concentration Profile Observed from 100 mg/kg Dose

| Animal | Cmax (ng/mL) | Tmax (day) | AUC0-t (day * ng/mL) | AUC0-∞ (day * ng/mL) | t½ (day) | F (%) |
|---|---|---|---|---|---|---|
| 3001 | 53.4 | 13.0 | 1270 | 1330 | 15 | 102 |
| 3002 | 53.8 | 9.00 | 1200 | 1200 | 6.61 | 91.7 |
| 3003 | 95.3 | 11.0 | 1760 | 1770 | 8.56 | 135 |
| N | 3 | 3 | 3 | 3 | 3 | 3 |
| Mean | 67.5 | 11.0 | 1410 | 1430 | 10.1 | 110 |
| SD | 24.1 | 2.00 | 307 | 298 | 4.39 | 22.8 |
| Min | 53.4 | 9.00 | 1200 | 1200 | 6.61 | 91.7 |
| Median | 53.8 | 11.0 | 1270 | 1330 | 8.56 | 102 |
| Max | 95.3 | 13.0 | 1760 | 1770 | 15 | 135 |
| Geometric Mean | 64.9 | 10.9 | 1390 | 1410 | 9.47 | 108 |
| Geometric CV % | 34.2 | 18.6 | 21 | 20.3 | 43.8 | 20.3 |

The PK results above show that the bioavailability of the abiraterone decanoate can be 100%. Also, the single intramuscular administrations provide a prolonged abiraterone plasma exposure up to 98 days or more. For example, even at the 10 mg/kg dose, abiraterone was measurable in the plasma at Day 70. The plasma concentrations of abiraterone at Day 70 day for each of the 30 mg/kg and 100 mg/kg doses range from 1 ng/mL to 10 ng/mL.

The progesterone, cortisol, dihydrotestosterone, and testosterone levels were also analyzed in this study. As shown in FIGS. 5A, 5B, 5C, and 5D, following the single dose IM injections, a long duration of CYP17A1 inhibition, up to 70 days or more, was achieved for all three doses, as evidenced by the sustained increase of progesterone level and reduction of cortisol, dihydrotestosterone, and testosterone level. The effects of administering dexamethasone and methylprednisolone acetate according to the schedule of this Example were also shown in FIGS. 5A, 5B, 5C, and 5D.

The observed PK/PD profiles from the single abiraterone decanoate intramuscular injections in this example further support a dosing regimen with a dosing frequency of once a month or once in more than a month, such as once in two months, or once in 3 months.

Example 4. A 13-Week Intramuscular Toxicity Study of Abiraterone Decanoate in Male Cynomolgus Monkeys with a 28-Day Recovery Period This example studies the potential toxicity of the test article, abiraterone decanoate, when administered once every two weeks as an intramuscular injection for 13 weeks in male cynomolgus monkeys and evaluates the potential reversibility of any findings. In addition, the toxicokinetic characteristics (TK) of abiraterone decanoate and abiraterone, as well as the effects of abiraterone decanoate treatment on serum hormone levels, and adrenocorticotropic hormone (ACTH) and luteinizing hormone (LH) levels in plasma and serum, respectively, were determined.

The study design was as follows:

TABLE 5A

Experimental Design

| Group No. | Test Material | Dose Level (mg/kg/dose) | No. of Dose Sites | Dose Volume/ Site[a] (mL/kg) | Dose Concentration (mg/mL) | No. of Main Study Males | No. of Recovery Study Males |
|---|---|---|---|---|---|---|---|
| 1 | Vehicle Control | 0 | 4 | 0.25 | 0 | 4 | 2 |
| 2 | Abiraterone Decanoate | 20 | 1 | 0.10 | 200 | 4 | — |

TABLE 5A-continued

Experimental Design

| Group No. | Test Material | Dose Level (mg/kg/dose) | No. of Dose Sites | Dose Volume/Site[a] (mL/kg) | Dose Concentration (mg/mL) | No. of Main Study Males | No. of Recovery Study Males |
|---|---|---|---|---|---|---|---|
| 3 | Abiraterone Decanoate | 60 | 2 | 0.15 | 200 | 4 | — |
| 4 | Abiraterone Decanoate | 200 | 4 | 0.25 | 200 | 4 | 2 |

No = Number; "—" = Not applicable.
[a]Based on the most recent body weight measurement.

Test system/animals: gonadally intact, sexually mature, male cynomolgus monkeys. Administration of Test Materials: The vehicle control and test article were administered once every 2 weeks for 13 weeks (Days 1, 15, 29, 43, 57, and 71) during the study via intramuscular injection. The abiraterone decanoate formulation used in this example has the same ingredient as those shown in Example 2, and contains corn oil, benzyl alcohol (10% w/v), and benzyl benzoate (20% w/v). The dose levels were 20, 60, or 200 mg/kg/dose and administered at a dose volume of 0.10, 0.15, and 0.25 mL/kg/site, respectively. The control group received the vehicle control in the same manner as the treated groups at a dose volume of 0.25 mL/kg/site.

The vehicle control and test article formulations were administered via bolus intramuscular injection into the epaxial muscles of the lumbar back. Animals at 0 and 200 mg/kg/dose were dosed in 4 dose sites, animals at 20 mg/kg/dose were dosed in 1 dose site, and animals at 60 mg/kg/dose were dosed in 2 dose sites. The needle (23-gauge, ⅝-inch) was inserted perpendicular to the skin surface. The location of the injection site was documented for each dose. In addition, each injection site was marked with a single large dot at the exact site of needle insertion, for purposes of erythema and swelling evaluation. Each injection site was remarked at least once weekly and prior to necropsy. The skin over the epaxial muscle was shaved free of hair at least 48 hours prior to dose administration.

Individual doses were based on the most recent body weights. Formulations were warmed at 35° C. (±5° C.) for at least 1 hour prior to dosing.

Sample Collection for LH Analysis (Serum): Blood samples (approximately 2.5 mL) were collected from all animals via the femoral vein for determination of the serum concentrations of LH. The animals were fasted prior to blood collection except one deviation.

TABLE 5B

LH Analysis Sample Collection Schedule

| | Sample Collection Time Points[a] | | | | |
|---|---|---|---|---|---|
| Group No. | Day −1 | Day 8 | Day 15 | Day 78 | Day 85 |
| 1, 2, 3, and 4 | X | X | X | X | X |

X = Samples were collected.
[a]All samples were collected between 06:00 and 07:00 and on dosing days the samples were collected prior to dosing.

Sample Collection for ACTH Analysis (Plasma): Blood samples (approximately 2.5 mL) were collected from all animals via the femoral vein for determination of the plasma concentrations of ACTH. The animals were fasted prior to blood collection except one deviation.

TABLE 5C

ACTH Analysis Sample Collection Schedule

| | Sample Collection Time Points[a] | | | | |
|---|---|---|---|---|---|
| Group No. | Day −1 | Day 8 | Day 15 | Day 78 | Day 85 |
| 1, 2, 3, and 4 | X | X | X | X | X |

X = Samples were collected.
[a]All samples were collected between 06:00 and 07:00 and on dosing days the samples were collected prior to dosing.

Sample Collection for Steroid Hormone Analysis (Serum): Blood samples (approximately 2.5 mL) were collected from all animals via the femoral vein for the steroid hormone analysis. The animals were fasted prior to blood collection.

TABLE 5D

Steroid Hormone Analysis Sample Collection Schedule

| | Sample Collection Time Points[a] | | | | |
|---|---|---|---|---|---|
| Group No. | Day −1 | Day 8 | Day 15 | Day 78 | Day 85 |
| 1, 2, 3, and 4 | X | X | X | X | X |

X = Sample were collected.
[a]All samples were collected between 06:00 and 07:00 and on dosing days the samples were collected prior to dosing.

Individual abiraterone decanoate and abiraterone plasma concentration-time profiles from abiraterone decanoate-treated animals were analyzed using model-independent methods. Toxicokinetic parameters were obtained for each animal on Days 1, 29, and 71. Concentrations less than the lower limit of quantitation (LLOQ=0.5 ng/mL for abiraterone decanoate and abiraterone) were set to 0 for toxicokinetic analysis. A single 144-hour sample was collected outside of the allowable window for timed collections from one Animal on Day 29 and the actual time for this time point was used in the toxicokinetic data analysis. Nominal time was used for graphic representation and concentration table generation. For each animal, the following toxicokinetic parameters were determined: maximum observed plasma concentration ($C_{max}$), time of maximum observed plasma concentration ($T_{max}$), and area under the plasma concentration-time curve (AUC). The AUC from time 0 to 336 hours ($AUC_{0\text{-}336 \ hr}$) and the AUC from time 0 to the time of the final quantifiable sample ($AUC_{Tlast}$) were calculated by the linear trapezoidal method for all animals with at least 3 consecutive quantifiable concentrations.

The following parameters and endpoints were evaluated in this study: mortality, clinical signs, body weights, body weight gains, ophthalmology and electrocardiographic examinations, clinical pathology parameters (hematology, coagulation, clinical chemistry, and urinalysis), LH and ACTH analyses, toxicokinetic parameters, gross necropsy findings, organ weights, and histopathologic examinations. Statistical analyses were performed using Group Pair-wise Comparisons (general ANOVA).

Results:

All animals survived to the scheduled necropsy.

Non-adverse abiraterone decanoate related clinical observations included swelling and/or nodules at the injection sites. No other clinical or veterinary observations were related to the test article.

Non-adverse abiraterone decanoate body weight loss was noted in all groups administered the test article. The body weight loss was not considered adverse as it was an expected pharmacological effect of the test article.

Abiraterone decanoate administration had no effect on ophthalmology findings or qualitative or quantitative ECG parameters.

Abiraterone decanoate administration to cynomolgus monkeys was associated with minimal decreases in albumin concentration in males at ≥20 mg/kg/day, and minimal to mild increases in globulin concentration in individual males at 20 and 200 mg/kg/day that were likely related to an acute phase response associated with inflammation at the injection site and/or minimal to moderate inflammation in the lung. Males at 200 mg/kg/dose also had a minimal increase in red cell distribution width (RDW) and minimal decreases in mean corpuscular volume (MCV) and mean corpuscular hemoglobin (MCH) that indicated increased variability in erythrocyte size with an overall decrease in erythrocyte size. At the end of the recovery phase, alterations in albumin and globulin demonstrated a trend towards resolution in the affected male that continued to the recovery phase; alterations in RDW, MCV and MCH persisted at a similar magnitude.

There were also increases in ACTH concentrations in males at ≥20 mg/kg/dose following abiraterone decanoate administration. Increases in ACTH concentrations were likely a compensatory response to test article-related inhibition of androgen production. There were no clear effects on LH concentrations following abiraterone decanoate administration.

Effects on adrenocorticotropic hormone (ACTH) following abiraterone decanoate administration are detailed in Table 6A.

TABLE 6A

Abiraterone Decanoate-Related Effects on ACTH

| | Group | | |
|---|---|---|---|
| | 2 | 3 | 4 |
| | Dose (mg/kg/dose) | | |
| | 20 | 60 | 200 |
| | Sex | | |
| ACTH | M | M | M |
| Day 8 | 1.72× | 2.55×* | 4.90×* |
| Day 15 | 2.63× | 2.35×* | 5.14×* |
| Day 78 | 2.30×* | 1.33×* | 4.65×* |
| Day 85 | 1.89×* | 1.36×* | 4.66×* |

M = Males
F = Females.
Numerical values indicate fold change of the treated group mean value relative to the pretreatment (Day −1) mean value.
*Mean value statistically different from the control mean at $p < 0.01$.
ACTH—Adrenocorticotropic hormone.

Effects on LH following abiraterone decanoate administration are detailed in Table 6B:

TABLE 6B

Abiraterone Decanoate-Related Effects on LH

| AbiDec (mg/kg) | N | Day −1 | Day 8 | Day 15 | Day 78 | Day 85 |
|---|---|---|---|---|---|---|
| 0 | 6 | 4.25 | 7.33 | 7.90 | 8.69 | 8.63 |
| 20 | 4 | 1.67 | 1.67 | 1.67 | 5.67 | 3.12 |
| 60 | 4 | 2.23 | 2.78 | 2.73 | 7.12 | 7.07 |
| 200 | 6 | 1.67 | 1.98 | 2.33 | 5.04 | 5.27 |

Mean abiraterone decanoate plasma toxicokinetic parameters and abiraterone plasma toxicokinetic parameters are provided in Tables 6C and 6D below.

TABLE 6C

Abiraterone Decanoate Toxicokinetic Parameters on Days 1, 29, and 71 Following Once Every Two Weeks by Intramuscular Injection of 20, 60, and 200 mg/kg Abiraterone Decanoate in Male Monkeys

| Analyte Abiraterone | Dose Level | | |
|---|---|---|---|
| Decanoate | 20 mg/kg | 60 mg/kg | 200 mg/kg |
| $C_{max}$ (ng/ml) | | | |
| Dosing Day 1 | 6.27 | 15.8 | 71.3 |
| Dosing Day 29 | 10.1 | 25 | 95.9 |
| Dosing Day 71 | 7.02 | 13.2 | 66.6 |
| $AUC_{0-336\,h}$ (h*ng/mL)$^a$ | | | |
| Dosing Day 1 | 888 | 2040 | 13100 |
| Dosing Day 29 | 1580 | 4080 | 17400 |
| Dosing Day 71 | 891 | 2190 | 12400 |

$^a$AUC measured over 14 days following dose administration.

TABLE 6D

Abiraterone Toxicokinetic Parameters on Days 1, 29, and 71 Following Once Every Two Weeks by Intramuscular Injection of 20, 60, and 200 mg/kg Abiraterone Decanoate in Male Monkeys

| Analyte Abiraterone | Dose Level | | |
|---|---|---|---|
| | 20 mg/kg | 60 mg/kg | 200 mg/kg |
| $C_{max}$ (ng/ml) | | | |
| Dosing Day 1 | 12.5 | 38.8 | 91.8 |
| Dosing Day 29 | 17.6 | 38.6 | 95.3 |
| Dosing Day 71 | 7.2 | 20.5 | 65.1 |
| $AUC_{0-336\,h}$ (Vng/mL)$^a$ | | | |
| Dosing Day 1 | 2080 | 7600 | 16700 |
| Dosing Day 29 | 4060 | 8680 | 24200 |
| Dosing Day 71 | 1730 | 5200 | 17800 |

$^a$AUC measured over 14 days following dose administration.

Plasma exposures to abiraterone after IM administration of abiraterone decanoate, as measured by $C_{max}$ and AUC, were lower than levels achieved in toxicology studies with abiraterone acetate in cynomolgus monkeys. Anticipated pharmacologically mediated effects due to potent CYP17 inhibition on adrenal and mammary glands, male reproductive organs and thymus were observed following abiraterone decanoate administration which were similar in nature to those induced by oral abiraterone acetate. However, treatment with abiraterone decanoate produced no evidence of the adverse liver effects associated with oral abiraterone acetate administration to monkeys, as evidenced by the absence of findings in clinical pathology and histopathology.

Abiraterone decanoate administration in gonadally intact, sexually mature, male cynomolgus monkeys resulted in potent reductions in circulating androgen levels that appeared dose dependent and were sustained for testosterone through Day 85 in the 200 mg/kg/dose animals. Abiraterone decanoate had a predictable effect on the circulating levels of other steroids measured. See FIGS. 6A-6D. In general, steroids "upstream" of CYP17 hydroxylase/lyase (progesterone, mineralocorticoids) showed elevated serum concentrations; steroids "downstream" of CYP17 enzymes (glucocorticoids, androgens) showed decreased serum concentrations.

TABLE 7A

Serum Steroid Concentrations Before and After Abiraterone Decanoate Administration

| Group | Dose (mg/kg) | Day | | Dehydro-epiandrosterone | Androstene-dione | Testos-terone | Dihydro-testosterone |
|---|---|---|---|---|---|---|---|
| 1 (n = 4) | 0 | -1 | Mean (pg/ml) | 4482 | 333 | 15775 | 2517 |
| | | | SD | 2240 | 98 | 6865 | 578 |
| | | 15 | Mean (pg/ml) | 3592 | 309 | 14646 | 2298 |
| | | | SD | 2652 | 113 | 3783 | 679 |
| | | | CFB (%) | -20% | -7% | -7% | -9% |
| | | 85 | Mean (pg/ml) | 2705 | 313 | 14396 | 1647 |
| | | | SD | 2031 | 113 | 6783 | 590 |
| | | | CFB (%) | -40% | -6% | -9% | -35% |
| 2 (n = 4) | 20 | -1 | Mean (pg/ml) | 5608 | 224 | 6109 | 1466 |
| | | | SD | 4043 | 21 | 3100 | 277 |
| | | 15 | Mean (pg/ml) | 1500 | 39 | 2148 | 195 |
| | | | SD | 247 | 6 | 697 | 94 |
| | | | CFB (%) | -73% | -82% | -65% | -87% |
| | | 85 | Mean (pg/ml) | 1372 | 106 | 6286 | 578 |
| | | | SD | 233 | 37 | 3192 | 269 |
| | | | CFB (%) | -76% | -53% | 3% | -61% |
| 3 (n = 4) | 60 | -1 | Mean (pg/ml) | 4996 | 339 | 5375 | 1178 |
| | | | SD | 2540 | 123 | 1978 | 194 |
| | | 15 | Mean (pg/ml) | 1271 | 20 | 335 | 64 |
| | | | SD | 142 | 0 | 149 | 4 |
| | | | CFB (%) | -75% | -94% | -94% | -95% |
| | | 85 | Mean (pg/ml) | 1200 | 79 | 5453 | 361 |
| | | | SD | 0 | 70 | 5809 | 443 |
| | | | CFB (%) | -76% | -77% | 1% | -69% |
| 4 (n = 4) | 200 | -1 | Mean (pg/ml) | 3302 | 290 | 9963 | 1715 |
| | | | SD | 1411 | 139 | 3439 | 626 |
| | | 15 | Mean (pg/ml) | 1200 | 20 | 100 | 67 |
| | | | SD | 0 | 0 | 58 | 8 |
| | | | CFB (%) | -64% | -93% | -99% | -96% |
| | | 85 | Mean (pg/ml) | 1200 | 39 | 1246 | 165 |
| | | | SD | 0 | 37 | 1588 | 158 |
| | | | CFB (%) | -64% | -87% | -87% | -90% |

CFB = change focus baseline (Day -1)

TABLE 7B

Serum Steroid Concentrations Before and After Abiraterone Decanoate Administration

| Group | Dose (mg/kg) | Day | | Proges-terone | Deoxy-cortisol | Cortico-sterone | Aldos-terone | Cortisol | 17OH-Progesterone |
|---|---|---|---|---|---|---|---|---|---|
| 1 (n = 4) | 0 | -1 | Mean (pg/ml) | 20 | 651 | 3740 | 234 | 173676 | 450 |
| | | | SD | 0 | 366 | 1864 | 178 | 34243 | 202 |
| | | 15 | Mean (pg/ml) | 20 | 360 | 3174 | 410 | 166134 | 328 |
| | | | SD | 0 | 220 | 1310 | 350 | 39409 | 94 |
| | | | CFB (%) | 0% | -45% | -15% | 75% | -4% | -27% |
| | | 85 | Mean (pg/ml) | 20 | 305 | 3052 | 464 | 161016 | 375 |
| | | | SD | 0 | 202 | 1231 | 122 | 15428 | 240 |
| | | | CFB (%) | 0% | -53% | -18% | 99% | -7% | -17% |
| 2 (n = 4) | 20 | -1 | Mean (pg/ml) | 20 | 674 | 3196 | 143 | 147717 | 370 |
| | | | SD | 0 | 974 | 1397 | 55 | 36103 | 537 |
| | | 15 | Mean (pg/ml) | 10328 | 241 | 110635 | 45 | 34897 | 4289 |
| | | | SD | 3082 | 41 | 22043 | 41 | 11034 | 1165 |
| | | | CFB (%) | 51539% | -64% | 3361% | -68% | -76% | 1060% |
| | | 85 | Mean (pg/ml) | 9562 | 357 | 93869 | 199 | 62490 | 7647 |
| | | | SD | 7813 | 60 | 12479 | 375 | 39301 | 4520 |
| | | | CFB (%) | 47710% | -47% | 2837% | 40% | -58% | 1968% |
| 3 (n = 4) | 60 | -1 | Mean (pg/ml) | 20 | 338 | 3032 | 238 | 141723 | 156 |
| | | | SD | 0 | 334 | 1648 | 125 | 30215 | 76 |
| | | 15 | Mean (pg/ml) | 13859 | 93 | 163079 | 14 | 18271 | 1631 |
| | | | SD | 2036 | 50 | 29602 | 7 | 3143 | 516 |
| | | | CFB (%) | 69193% | -72% | 5279% | -94% | -87% | 944% |
| | | 85 | Mean (pg/ml) | 13609 | 315 | 120598 | 194 | 39689 | 8821 |
| | | | SD | 6232 | 240 | 20970 | 215 | 29538 | 8357 |
| | | | CFB (%) | 67947% | -7% | 3878% | -18% | -72% | 5546% |
| 4 (n = 4) | 200 | -1 | Mean (pg/ml) | 20 | 276 | 3184 | 209 | 116735 | 184 |
| | | | SD | 0 | 233 | 3906 | 147 | 46895 | 69 |
| | | 15 | Mean (pg/ml) | 11999 | 44 | 138133 | 19 | 7703 | 474 |
| | | | SD | 5806 | 33 | 11962 | 11 | 4324 | 263 |
| | | | CFB (%) | 59894% | -84% | 4238% | -91% | -93% | 158% |
| | | 85 | Mean (pg/ml) | 15180 | 141 | 113629 | 37 | 19682 | 3296 |

TABLE 7B-continued

Serum Steroid Concentrations Before and After Abiraterone Decanoate Administration

| Group | Dose (mg/kg) | Day | | Progesterone | Deoxycortisol | Corticosterone | Aldosterone | Cortisol | 17OH-Progesterone |
|---|---|---|---|---|---|---|---|---|---|
| | | | SD | 5224 | 121 | 10230 | 54 | 12365 | 4359 |
| | | | CFB (%) | 75799% | −49% | 3468% | −82% | −83% | 1696% |

CFB = change focus baseline (Day −1)

The present study demonstrated a potent suppression of serum androgen concentrations on Day 15 in all dose groups following the initial administration of AbiDec on Day 1 (Table 7A). Testosterone suppression appeared to be dose dependent with a Day 15 within dose group CFB of −87%, −95% and −96% for the 20, 60 and 200 mg/kg dose groups, respectively. Serum testosterone concentrations remained suppressed following repeat AbiDec administration in the 200 mg/kg dose group (−87% decline from baseline) but returned to baseline in the two lower dose groups by Day 85. Unlike testosterone concentrations, the other three androgens evaluated did not demonstrate a similar return to baseline at Day 85 following initial suppression at Day 15. This was most apparent with the adrenal androgen dehydroepiandrosterone (DHEA), which remained suppressed within each dose group at Days 15 and 85. Androstenedione and dihydrotestosterone serum concentrations did increase on Day 85 in the 20 and 60 mg/kg dose groups but were still 53-77% and 61-69% below Day −1, respectively. The increase in androgen concentrations, mainly observed with testosterone, following Day 15 in the two lower dose groups was not unexpected given that the animals were not undergoing chemical castration or glucocorticoid supplementation, both of which would counteract increased gonadal and adrenal drive with LH and ACTH, respectively, following CYP17 inhibition.

In response to AbiDec administration, there was an expected increase in progesterone, produced 'upstream' of CYP17 hydroxylase, and a decrease in cortisol, produced 'downstream' of CYP17 hydroxylase (Conley and Bird, 1997). The greatest CFB was observed in the high-dose AbiDec group and the changes in all dose groups were generally maintained through Day 85.

17OH-progesterone and additional steroid concentrations 'upstream' of CYP17 hydroxylase as well as are presented in Table 7B. 17OH-progesterone, which is produced after CYP17 hydroxylase, but before lyase was increased with AbiDec administration through Day 85. In primate gonads 17OH-progesterone may accumulate with CYP17 lyase inhibition since it is not readily converted to other steroids as seen in the adrenal (Conley and Bird, 1997). With regards to mineralocorticoids, corticosterone concentrations increased with AbiDec administration and there was a commensurate decline in aldosterone and deoxycorticosterone concentrations. These changes are also expected with CYP17 hydroxylase inhibition with corticosterone elevations inhibiting the renin-angiotensin system and subsequent aldosterone decline (Ang et al, 2009).

Overall, AbiDec administration in gonadally intact, sexually mature, male cynomolgus monkeys resulted in potent circulating androgen reductions that appeared to be dose dependent and were sustained for testosterone through Day 85 in the high-dose 200 mg/kg animals.

Following biweekly IM administration of abiraterone decanoate, mean $C_{max}$ and $AUC_{0-336\ hr}$ values of abiraterone decanoate and abiraterone increased with increasing dose in an approximately dose proportional manner on Days 1, 29, and 71. Systemic exposure ($AUC_{0-336\ hr}$) to abiraterone decanoate and abiraterone did not appear to consistently change following repeated administration of abiraterone decanoate. Systemic exposure to abiraterone was approximately 1.8 to 2.7-fold greater that abiraterone decanoate at 20 mg/kg, 2.2 to 3.9-fold greater than abiraterone decanoate at 60 mg/kg and was similar to abiraterone decanoate at 200 mg/kg.

Intramuscular injection of abiraterone decanoate resulted in test article-related microscopic findings in the testes, mammary gland, adrenal gland, and lung at ≥20 mg/kg and in the epididymis, prostate, seminal vesicles, and thymus at ≥60 mg/kg at terminal necropsy. Vehicle-related (corn oil) microscopic findings were observed at the injection site and iliac lymph node at all dose levels, including vehicle controls at terminal necropsy.

Test article-related changes in the male reproductive tract consisted of minimal to moderate germ cell depletion and minimal to mild Leydig cell hypertrophy in the testes; mild to severe reduced luminal sperm and/or minimal to mild increased germ cell debris in the epididymis; mild to moderate prostate gland atrophy; and minimal to mild seminal vesicle atrophy. Correlative macroscopic findings in the male reproductive tract consisted of a single incidence of unilateral small testes at 200 mg/kg. Male reproductive tract findings generally corresponded with decreased absolute and relative testes, epididymis, and prostate gland weights. In the mammary gland, test article-related findings consisted of minimal to mild lobular and/or duct hyperplasia. Findings in the lung consisted of minimal to moderate granulomatous inflammation. Adrenal gland changes consisted of minimal to moderate cortical hypertrophy. A single incidence of macroscopically bilaterally enlarged adrenal glands was observed at 200 mg/kg. In the thymus, test article-related changes consisted of minimal to mild increased lymphocytes. Findings in the adrenal gland and thymus correlated with increased absolute and relative adrenal gland and thymus weights. Test article-related microscopic findings persisted following the recovery period.

Vehicle (corn oil)-related injection site changes consisted of minimal to marked chronic inflammation, minimal to marked fibrosis, minimal to moderate necrosis, minimal to moderate skeletal myofiber degeneration/regeneration, and/or minimal to mild hemorrhage. Vehicle-related microscopic changes in the regional (iliac) lymph node consisted of minimal to moderate granulomatous inflammation. Vehicle-related microscopic changes were still observed at recovery necropsy.

Based on the results of this study biweekly intramuscular injections of abiraterone decanoate at dose levels of 20, 60, and 200 mg/kg/dose were well tolerated. No test article-related veterinary observations, ophthalmology findings or ECG effects were noted. Non-adverse test article related findings included clinical observations at the injection sites, body weight loss, as well as clinical chemistry and hematology related changes that were noted as part of the tissue reaction at the dose site. The pathological findings at 200 mg/kg/dose exceeded the highest non-severely toxic dose. Therefore, in this study, the highest non-severely toxic dose was 60 mg/kg/dose.

Example 5. A Tissue Uptake Study of Abiraterone Decanoate Vs. Abiraterone Following a Single Intravenous or Intramuscular Injection in CD•[CRL:CD®(SD)] Rats The objective of this study is to collect tissue samples for the determination of the uptake of abiraterone decanoate and abiraterone following intravenous (IV) and intramuscular (IM; abiraterone decanoate only) injection. Additionally, blood steroid levels also were evaluated.

Test system/animals: rats, strain, CD® [Crl:CD®(SD)], Charles River Laboratories, Inc. Test article for abiraterone decanoate IM injection: 200 mg/ml in corn oil with 10% benzyl alcohol (w/v) and 20% benzyl benzoate (w/v). Test article for abiraterone decanoate IV injection: 0.385 mg/ml solution in 40% HP-β-CD/25 mM Na phosphate (pH 7.4). Test article for abiraterone IV injection: 0.405 mg/mL solution in 40% HP-β-CD/25 mM Na phosphate (pH 7.4). Vehicle for IM injection: Corn oil with 10% benzyl alcohol (w/v) and 20% benzyl benzoate (w/v). Experimental design is shown in Table 8A below. The study followed the protocols described below.

TABLE 8A

| | | | | Experimental Design: | | |
|---|---|---|---|---|---|---|
| Group | Dose Route | Test Material | Dose Level (mg/kg) | Dose Volume$^a$ (mL/kg) | Dose Concentration (mg/mL) | Main Study$^b$ Mates |
| 1 | IM | Vehicle | 0 | 0.45 | 0 | 4 |
| 2 | IV | Abiraterone Decanoate | 1.6 | 4.2 | 0.385 | 20 |
| 3 | IM | Abiraterone Decanoate | 90 | 0.45 | 200 | 8 |
| 4 | IV | Abiraterone | 1.1 | 2.7 | 0.405 | 20 |

IM = Intramusclar injection; IV = Intravenous Injecton
$^a$Based on the most recent body weight measurement.
$^b$Animals will have a timed necropsy (4 animals/sex/group) at the intervals outlined in section 13.

For intramuscular injections, the test article and vehicle will be administered once as a single intramuscular dose on Day 1 to animals in Groups 1 and 3. Doses will be administered via bolus intramuscular injection into the biceps femoris on the hind legs. The Test article will be warmed at 35° C. (±5°) for at least 1 hour prior to dosing. Individual doses will be based on the most recent body weights.

For IV injections, the test article will be administered once on Day 1 as a single intravenous bolus injection to animals in Groups 2 and 4. The test article will be administered via the tail vein as a bolus intravenous injection (less than 2 minutes). Individual doses will be based on the most recent body weights.

For serum steroid analysis, blood samples were collected from animals in each study group at predose and at terminal necropsy according to the following protocol. Animals were designated for 72 hr and 168 hr necropsy, the animals will be fasted overnight before scheduled blood collections. Plasma samples will be used for ACTH level analysis. Serum samples will be used for LH level analysis and steroid level analysis. Plasma samples will also be collected at various time points and be analyzed for abiraterone decanoate and abiraterone. Representative samples of tissues will be collected and snap frozen and analyzed. Lung, Liver, Adrenal glands, Prostate, Testes (Sample 1 and 2) and lymph nodes tissues will be collected. Lymph node(s) draining administration site(s): Inguinal (Groups 1-4) and Iliac (Groups 1 and 3 only). Lymph node, mandibular and Lymph node mesenteric tissues will also be collected. The Liver, Adrenal glands, Prostate, Testes (Sample 1) and lymph nodes frozen samples will be analyzed for abiraterone decanoate and abiraterone. Table 8B below shows sample collections and analysis for each group.

TABLE 8B

| | | | | | Terminal necropsy | | | | |
|---|---|---|---|---|---|---|---|---|---|
| Group | Formulation | N | Pre-Dose | 2 hr | 6 hr | 24 hr | 72 hr | 168 hr |
| 1 | IM Vehicle | 4 | S | | | | | S*/A/T |
| 2 | IV Abiraterone Decanoate (1.6 mg/kg) (eq. to 1.1 mg/kg Abiraterone) | 4 | S | S*/A/T | | | | |
| | | 4 | S | | S*/A/T | | | |
| | | 4 | S | | | S*/A/T | | |
| | | 4 | S | | | | S*/A/T | |
| | | 4 | S | | | | | S*/A/T |
| 3 | IM Abiraterone Decanoate (90 mg/kg) | 4 | S | | | | S*/A/T | |
| | | 4 | S | | | | | S*/A/T |
| 4 | IV Abiraterone (1.1 mg/kg) | 4 | S | S*/A/T | | | | |
| | | 4 | S | | S*/A/T | | | |
| | | 4 | S | | | S*/A/T | | |
| | | 4 | S | | | | S*/A/T | |
| | | 4 | S | | | | | S*/A/T |

S = Pre-Dose Plasma Sample (steroid analysis), S* = Plasma sample at necropsy (steroid analysis)
A = Plasma Sample (Abiraterone & Abiraterone Decanoate at necropsy)
T = tissue collection at necropsy Results:

The serum steroid levels and plasma concentration of abiraterone and abiraterone decanoate are shown in FIGS. 7A-7H. As shown in the figures, a single intramuscular dose of abiraterone decanoate resulted in potent reductions in circulating androgen levels (androstenedione and testosterone) and increased the levels of progesterone and corticosterone.

Comparison of Abiraterone & Abiraterone Decanoate Plasma vs Tissue concentrations (IV Abiraterone vs IV & IM Abiraterone Decanoate) are shown in the table below:

TABLE 9

Plasma and Tissue Concentrations of Abiraterone and Abiraterone Decanoate

| Tissue | IV Abiraterone (1.1 mg/kg) 2-hr post dose | IV Abiraterone decanoate (1.6 mg/kg) 2-hr post dose | | IM Abiraterone decanoate (90 mg/kg) 7-days post dose | |
|---|---|---|---|---|---|
| | Abiraterone | Abiraterone | Decanoate | Abiraterone | Decanoate |
| Plasma (ng/ml) | 22.2 (1) | 24.3 (1) | 85.5 (1) | 3.2 (1) | 3.1 (1) |
| Liver (ng/g) | 474 (21×)* | 606 (25×) | 1017 (12×) | 194 (60×) | 10.4 (3×) |
| Lung (ng/g) | 281 (13×) | 578 (24×) | 1914 (22×) | 201 (63×) | 735 (237×) |
| Testes (ng/g) | 121 (5×) | 132 (5×) | 14.7 (0.2×) | 48.3 (15×) | 1.3 (0.4×) |
| Inguinal Lymph (ng/g) | 763 (34×) | 273 (11×) | 159 (1.9×) | 591 (185×) | 254 (82×) |
| iliac lymph (ng/g) | | | | 2070 (647×) | 90975 (29,000×) |
| Adrenal (ng/g) | 154 (7×) | 250 (10×) | 277 (3.2×) | 52.1 (16×) | 12.1 (3.9×) |
| Prostate (ng/g) | 238 (11×) | 275 (11×) | 43.0 (0.5) | 88.6 (28×) | 0 |

*Value in parenthesis represent ratio of tissue vs plasma conc for each group.

Figure 8A:
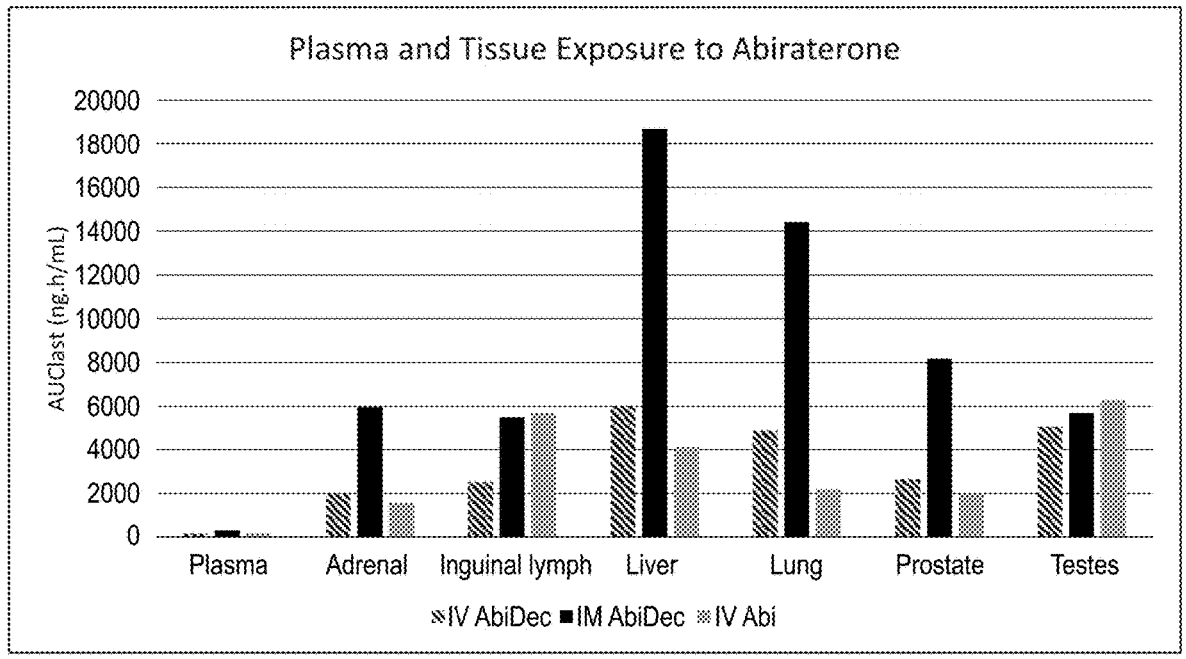
FIG. 8A shows plasma and tissue exposures to abiraterone, expressed in $AUC_{last}$, following a single IV injection of abiraterone (1.1 mg/kg), or abiraterone decanoate (1.6 mg/kg), or a single IM injection of abiraterone decanoate (90 mg/kg) in rats, strain, CD® [Crl:CD®(SD)] and up to 168 hours post administration.
Figure 8B:
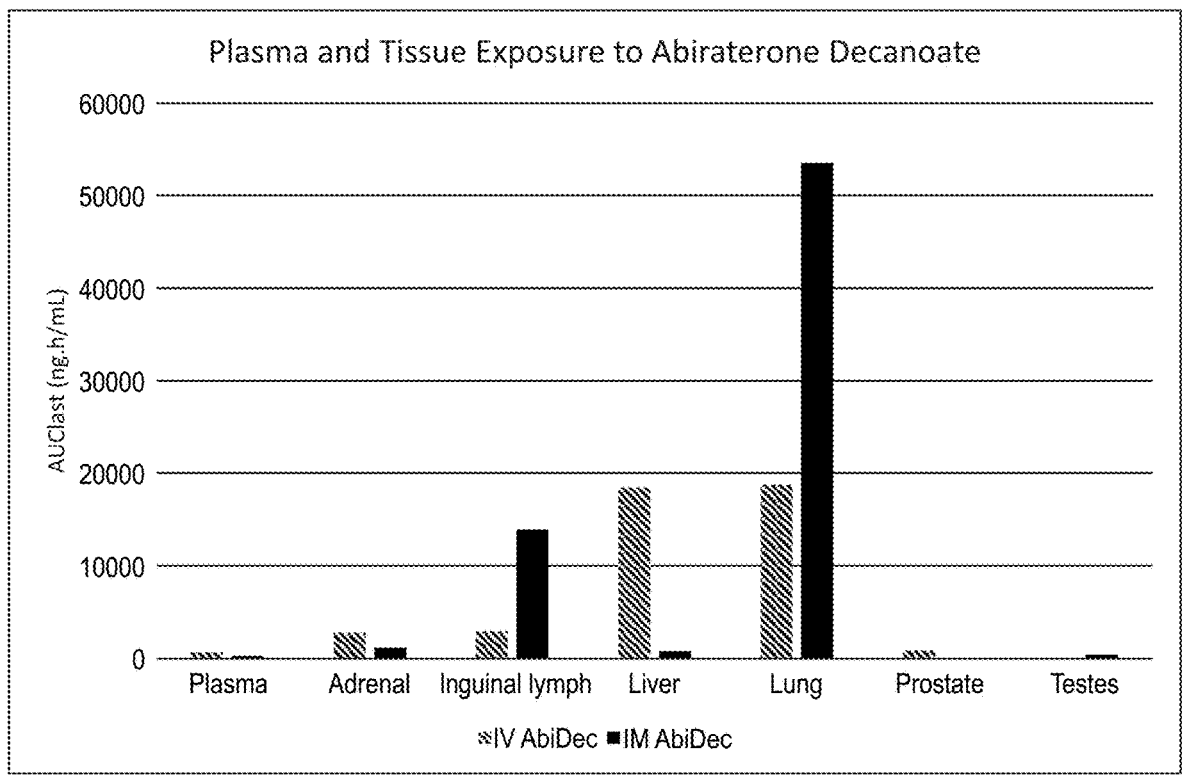
FIG. 8B shows plasma and tissue exposures to abiraterone decanoate, expressed in $AUC_{last}$, following a single IV injection of abiraterone decanoate (1.6 mg/kg), or a single IM injection of abiraterone decanoate (90 mg/kg) in rats, strain, CD® [Crl:CD®(SD)] and up to 168 hours post administration.

Comparisons of plasma and tissue AUC of abiraterone and abiraterone decanoate are shown in FIGS. 8A-8B.

Each reference referred to within this disclosure is hereby incorporated in its respective entirety.

With respect to aspects of the disclosure described as a genus, all individual species are individually considered separate aspects of the disclosure. If aspects of the disclosure are described as "comprising" a feature, embodiments also are contemplated "consisting of" or "consisting essentially of" the feature.

All the various aspects, embodiments, and options described herein can be combined in any and all variations.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, because numerous modifications will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of treating a sex hormone dependent or androgen receptor driven cancer in a non-castrated subject in need thereof, the method comprising parenterally administering to the subject a therapeutically effective amount of a pharmaceutical composition comprising an abiraterone prodrug, and further administering to the subject a bone protecting agent, wherein the subject is characterized as having prostate cancer with bone metastasis.

2. The method of claim 1, wherein the subject is not treated with a gonadotropin-releasing hormone agonist and/or antagonist in an amount effective to reduce serum testosterone level in the subject.

3. The method of claim 1, wherein the subject is not treated with a drug selected from buserelin, leuprolide, deslorelin, fertirelin, histrelin, gonadorelin, lecirelin, goserelin, nafarelin, peforelin and triptorelin.

4. The method of claim 1, wherein the subject is sensitive to or otherwise intolerant with a gonadotropin-releasing hoiinone antagonist and/or agonist.

5. The method of claim 1, wherein the subject is not treated with a glucocorticoid replacement therapy.

6. The method of claim 1, wherein the abiraterone prodrug comprises abiraterone decanoate, or a pharmaceutically acceptable salt thereof,

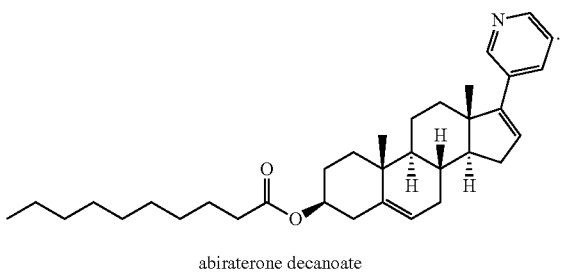

abiraterone decanoate

7. The method of claim 6, wherein the pharmaceutical composition comprises, for each milliliter, (a) abiraterone decanoate in its basic form, in an amount of about 100 mg to about 300 mg; (b) benzyl alcohol in an amount of about 50 mg to about 150 mg; (c) benzyl benzoate in an amount of about 100 mg to about 300 mg; and (d) corn oil, q.s. to 1 milliliter.

8. The method of claim 7, wherein the pharmaceutical composition is characterized as having (1) a viscosity of less than 0.1 Pa*s; (2) a glide force of about 1-10 N when measured using a 21G, 1.5 inch needle, and/or about 2-15 N when measured using a 23G, 1.5 inch needle, and/or about 30-150 N when measured using a 27G, 1.5 inch needle; (3) no more than 1000 particles having a size of 10 µm or greater, and no more than 300 particles having a size of 25 µm or greater, when measured according to USP <788> and/or <789>; and/or (4) less than 100 EU/ml of bacterial endotoxins measured according to USP <85>.

9. The method of claim 1, wherein the subject has not undergone a prostatectomy.

10. The method of claim 1, wherein the subject is further treated with a radiation therapy.

11. The method of claim 1, further comprising administering to the subject one or more agents selected from hydrocortisone, prednisone, prednisolone, methylprednisolone, and dexamethasone.

12. The method of claim 1, further comprising administering to the subject (1) a poly ADP ribose polymerase (PARP) inhibitor; (2) a $1^{st}$-generation androgen receptor antagonist; (3) a $2^{nd}$-generation androgen receptor antagonist; (4) a $3^{rd}$ generation androgen receptor antagonist or an androgen receptor degrader molecule, alone or in combination with one or more $1^{st}$ generation or $2^{nd}$ generation androgen receptor antagonists; (5) a chemotherapeutic agent; (6) an immunotherapy; (7) a bispecific T-cell engager (BiTE) therapy; and/or (8) a kinase inhibitor.

13. The method of claim 1, further comprising administering to the subject a therapeutic agent selected from 1) an anti-IL23 targeting monoclonal antibody; 2) a selenium; 3) an EZH2 inhibitor; 4) a CDK4/6 inhibitor; 6) a bromodomain and extra-terminal domain (BET) inhibitor; 7) an anti-CD105 antibody; 8) niclosamide; 9) an A2A receptor antagonist; 10) a PI3K inhibitor; 11) a further non-steroidal CYP17A1 inhibitor; 12) an anti progestogen; 13) navitoclax; 14) an HSP90 inhibitor; 15) an HSP27 inhibitor; 16) a 5-alpha-reductase inhibitor; 17) metformin; 18) AMG-386; 19) dextromethorphan; 20) theophylline; 21) hydroxychloroquine; and 22) lenalidomide.

14. The method of claim 1, further comprising administering to the subject one or more kinase modulators selected from FLT-3 (FMS-like tyrosine kinase) inhibitors, AXL (anexelekto) inhibitors, CDK (cyclin dependent kinase) inhibitors, retinoblastoma (Rb) inhibitors, protein kinase B (AKT) inhibitors, SRC inhibitors, IkappaB kinase 1 (IKK1) inhibitors, PIM-1 modulators, Lemur tyrosine kinase 2 (LMTK2) modulators, Lyn inhibitors, Aurora A inhibitors, ANPK (a nuclear protein kinase) inhibitors, extracellular-signal regulated kinase (ERIC) modulators, c-jun N-terminal kinase (JNK) modulators, Big MAP kinase (BMK) modulators, p38 mitogen-activated protein kinases (MAPK) modulators, and combinations thereof.

15. The method of claim 1, wherein the subject is chemotherapy naïve or hormone therapy naïve prior to being administered the pharmaceutical composition.

16. The method of claim 1, wherein the administering of the pharmaceutical composition provides an effective amount of abiraterone in the subject to achieve a sustained reduction of serum testosterone level to about 50 ng/dL or below within 15 days of the first administration of the abiraterone prodrug.

17. The method of claim 1, wherein the pharmaceutical composition is administered through an intramuscular injection, intradermal injection, or subcutaneous injection.

18. The method of claim 1, wherein the pharmaceutical composition is administered to the subject once a week or once in more than a week.

19. The method of claim 1, wherein the pharmaceutical composition is administered to the subject with or without food.

20. The method of claim 1, wherein the administering provides (a) a blood plasma concentration of abiraterone above 1.0 ng/ml for a period of at least two weeks from a single dose; (b) a single dose or steady state $C_{max}$ of abiraterone between about 3 ng/ml and about 300 ng/ml; or (c) both (a) and (b).

21. The method of claim 1, wherein the subject suffers from moderate to severe hepatic impairment (Child-Pugh Class B or C), prior to the administering of the abiraterone prodrug.

* * * * *

UNITED STATES PATENT AND TRADEMARK OFFICE
CERTIFICATE OF CORRECTION

| | |
|---|---|
| PATENT NO. | : 11,957,696 B2 |
| APPLICATION NO. | : 17/670712 |
| DATED | : April 16, 2024 |
| INVENTOR(S) | : Matthew J. Sharp and William R. Moore, Jr. |

It is certified that error appears in the above-identified patent and that said Letters Patent is hereby corrected as shown below:

In the Claims

Column 110, Claim 4, Line 47: Please change "hoiinone antagonist and/or agonist" to --hormone antagonist and/or agonist--

Column 111, Claim 13, Line 42: Please change "12) an anti progestogen" to --12) an antiprogestogen--

Column 112, Claim 14, Line 12: Please change "(ERIC)" to --(ERK)--

Signed and Sealed this
Tenth Day of September, 2024

Katherine Kelly Vidal
*Director of the United States Patent and Trademark Office*